United States Patent
Kohler et al.

(10) Patent No.: US 12,409,224 B2
(45) Date of Patent: Sep. 9, 2025

(54) COMPOSITIONS AND METHODS FOR THE TREATMENT OF VEN/AZA RESISTANT ACUTE MYELOID LEUKEMIA

(71) Applicant: The Regents of the University of Colorado, A Body Corporate, Denver, CO (US)

(72) Inventors: Mark Eric Kohler, Denver, CO (US); Haley Simpson, Denver, CO (US); Catherine Danis, Denver, CO (US); Lillie Leach, Denver, CO (US); Amanda Novak, Denver, CO (US)

(73) Assignee: The Regents of the University of Colorado, a body corporate

( * ) Notice: Subject to any disclaimer, the term of this patent is extended or adjusted under 35 U.S.C. 154(b) by 0 days.

(21) Appl. No.: 19/171,465

(22) Filed: Apr. 7, 2025

(65) Prior Publication Data

US 2025/0235535 A1    Jul. 24, 2025

Related U.S. Application Data

(63) Continuation of application No. PCT/US2024/058938, filed on Dec. 6, 2024.

(60) Provisional application No. 63/610,215, filed on Dec. 14, 2023.

(51) Int. Cl.
| | |
|---|---|
| *A61K 40/31* | (2025.01) |
| *A61K 40/11* | (2025.01) |
| *A61K 40/42* | (2025.01) |
| *A61P 35/02* | (2006.01) |
| *C07K 16/28* | (2006.01) |
| *C12N 5/0783* | (2010.01) |

(52) U.S. Cl.
CPC ............ *A61K 40/11* (2025.01); *A61K 40/31* (2025.01); *A61K 40/421* (2025.01); *A61P 35/02* (2018.01); *C07K 16/283* (2013.01); *C12N 5/0636* (2013.01); *C07K 2317/622* (2013.01); *C07K 2319/02* (2013.01); *C07K 2319/03* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,870,287 A | 9/1989 | Cole et al. |
| 5,760,395 A | 6/1998 | Johnstone |
| 5,827,642 A | 10/1998 | Riddell et al. |
| 6,040,177 A | 3/2000 | Riddell et al. |
| 6,797,514 B2 | 9/2004 | Berenson et al. |
| 6,867,041 B2 | 3/2005 | Berenson et al. |
| 6,905,874 B2 | 6/2005 | Berenson et al. |
| 7,378,504 B2 | 5/2008 | Graziano et al. |
| 7,446,190 B2 | 11/2008 | Sadelain et al. |
| 2005/0260186 A1 | 11/2005 | Bookbinder et al. |
| 2006/0104968 A1 | 5/2006 | Bookbinder et al. |
| 2009/0093024 A1 | 4/2009 | Bowers et al. |
| 2013/0287748 A1 | 10/2013 | June et al. |
| 2016/0185861 A1 | 6/2016 | Bedoya et al. |
| 2017/0114111 A1 | 4/2017 | Barth et al. |
| 2020/0308541 A1 | 10/2020 | Ma et al. |

FOREIGN PATENT DOCUMENTS

| | | |
|---|---|---|
| WO | WO 2005/052007 A1 | 6/2005 |
| WO | WO 2012/079000 A1 | 6/2012 |
| WO | WO 2012/129514 A1 | 9/2012 |
| WO | WO 2014/055668 A1 | 4/2014 |
| WO | WO 2023/144412 A1 | 8/2023 |

OTHER PUBLICATIONS

Ausubel et al., "Complementary mutations in an antigenic peptide allow for crossreactivity of autoreactive T-cell clones," Proceedings of the National Academy of Sciences, Dec. 1996, 93(26):15317-22.
Bird et al., "Single-chain antigen-binding proteins," Science, Oct. 1988, 242(4877):423-6.
Denardo et al., "Macrophages as regulators of tumour immunity and immunotherapy," Nature Reviews Immunology, Jun. 2019, 19(6):369, 32 pages.
Doulatov et al., "Revised map of the human progenitor hierarchy shows the origin of macrophages and dendritic cells in early lymphoid development," Nature Immunology, Jul. 2010, 11(7):585-93.
Doulatov et al., "Hematopoiesis: a human perspective," Cell Stem Cell, Feb. 2012, 10(2):120-36.
Fedorov et al., "PD-1-and CTLA-4-based inhibitory chimeric antigen receptors (iCARs) divert off-target immunotherapy responses," Science Translational Medicine, Dec. 2013, 5(215):215ra172, 25 pages.
Feucht et al., "Calibration of CAR activation potential directs alternative T cell fates and therapeutic potency," Nature Medicine, Jan. 2019, 25(1):82, 38 pages.
Guyre et al., "Monoclonal antibodies that bind to distinct epitopes on Fc gamma RI are able to trigger receptor function," Journal of Immunology, Sep. 1989, 143(5):1650-5.
Heijnen et al., "Antigen targeting to myeloid-specific human Fc gamma RI/CD64 triggers enhanced antibody responses in transgenic mice," The Journal of Clinical Investigation, Jan. 1996, 97(2):331-8.
Holliger et al., "Engineered antibody fragments and the rise of single domains," Nature Biotechnology, Sep. 2005, 23(9):1126-36.
Huston et al., "Protein engineering of antibody binding sites: recovery of specific activity in an anti-digoxin single-chain Fv analogue produced in *Escherichia coli*," Proceedings of the National Academy of Sciences, Aug. 1988, 85(16):5879-83.

(Continued)

*Primary Examiner* — Michael D Burkhart
(74) *Attorney, Agent, or Firm* — Fish & Richardson P.C.

(57) ABSTRACT

The disclosure describes T cells that express chimeric antigen receptors (CARs), as well as pharmaceutical compositions comprising T cells and methods of making and using such T cells. Particularly, this disclosure describes T cells expressing a CAR that binds to CD64, and methods of use in treating acute myeloid leukemia.

30 Claims, 55 Drawing Sheets

Specification includes a Sequence Listing.

(56) References Cited

OTHER PUBLICATIONS

Li et al., "Tumor-associated macrophages: potential therapeutic strategies and future prospects in cancer," Journal for Immunotherapy of Cancer, Jan. 2021, 9(1):e001341, 22 pages.
NCBI Accession No. NM_000566.4, "*Homo sapiens* Fc gamma receptor Ia (FCGR1A), transcript variant 2, mRNA," Aug. 17, 2022, 5 pages.
NCBI Accession No. NM_001378804.1, "*Homo sapiens* Fc gamma receptor Ia (FCGR1A), transcript variant 1, mRNA," Aug. 18, 2022, 5 pages.
NCBI Accession No. NM_001378805.1, "*Homo sapiens* Fc gamma receptor Ia (FCGR1A), transcript variant 3, mRNA," Aug. 17, 2022, 5 pages.
NCBI Accession No. NM_001378806.1, "*Homo sapiens* Fc gamma receptor Ia (FCGR1A), transcript variant 4, mRNA," Aug. 17, 2022, 4 pages.
NCBI Accession No. NM_001378807.1, "*Homo sapiens* Fc gamma receptor Ia (FCGR1A), transcript variant 5, mRNA," Aug. 17, 2022, 4 pages.
NCBI Accession No. NM_001378808.1, "*Homo sapiens* Fc gamma receptor Ia (FCGR1A), transcript variant 6, mRNA," Aug. 17, 2022, 4 pages.
NCBI Accession No. NM_001378809.1, "*Homo sapiens* Fc gamma receptor Ia (FCGR1A), transcript variant 7, mRNA," Aug. 18, 2022, 4 pages.
NCBI Accession No. NM_001378810.1, "*Homo sapiens* Fc gamma receptor Ia (FCGR1A), transcript variant 8, mRNA," Aug. 17, 2022, 4 pages.
NCBI Accession No. NM_001378811.1, "*Homo sapiens* Fc gamma receptor Ia (FCGR1A), transcript variant 9, mRNA," Aug. 18, 2022, 4 pages.
Notta et al., "Distinct routes of lineage development reshape the human blood hierarchy across ontogeny," Science, Jan. 2016, 351(6269):aab2116, 22 pages.
Osbourn et al., "Directed selection of MIP-1α neutralizing CCR5 antibodies from a phage display human antibody library," Nature Biotechnology, Aug. 1998, 16(8):778-81.
PCT International Search Report and Written Opinion in International Appln. No. PCT/US2024/058938, mailed on Apr. 30, 2025, 15 pages.
Pei et al., "Monocytic subclones confer resistance to venetoclax-based therapy in patients with acute myeloid leukemia," Cancer Discovery, Apr. 2020, 10(4):536, 31 pages.
Repp et al., "CSF-stimulated PMN in immunotherapy of breast cancer with a bispecific antibody to fcγRI and to HER-2/neu (MDX-210)," Journal of Hematotherapy, Oct. 1995, 4(5):415-21.
Sun et al., "Preclinical evaluation of CD64 as a potential target for CAR-T-cell therapy for acute myeloid leukemia," Journal of Immunotherapy, Feb. 2022, 45(2):67-77.
Valerius et al., "Involvement of the high-affinity receptor for IgG (Fc gamma RI; CD64) in enhanced tumor cell cytotoxicity of neutrophils during granulocyte colony-stimulating factor therapy," Blood, Aug. 1993, 83(3):931-9.
Zoller, "New recombinant DNA methodology for protein engineering," Current Opinion in Biotechnology, Aug. 1992, 3(4):348-54.

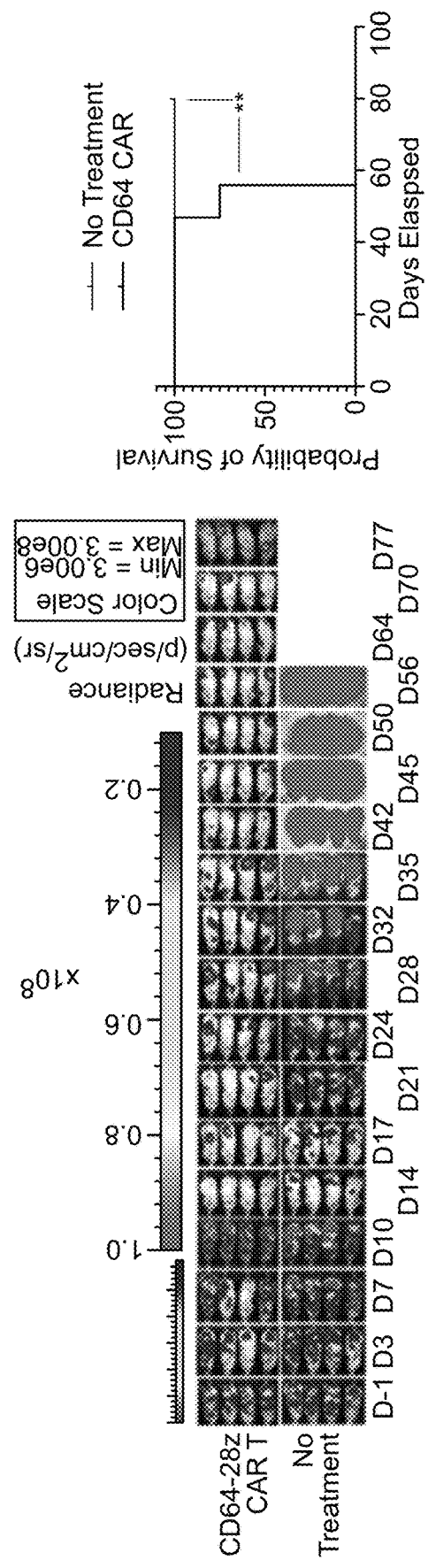
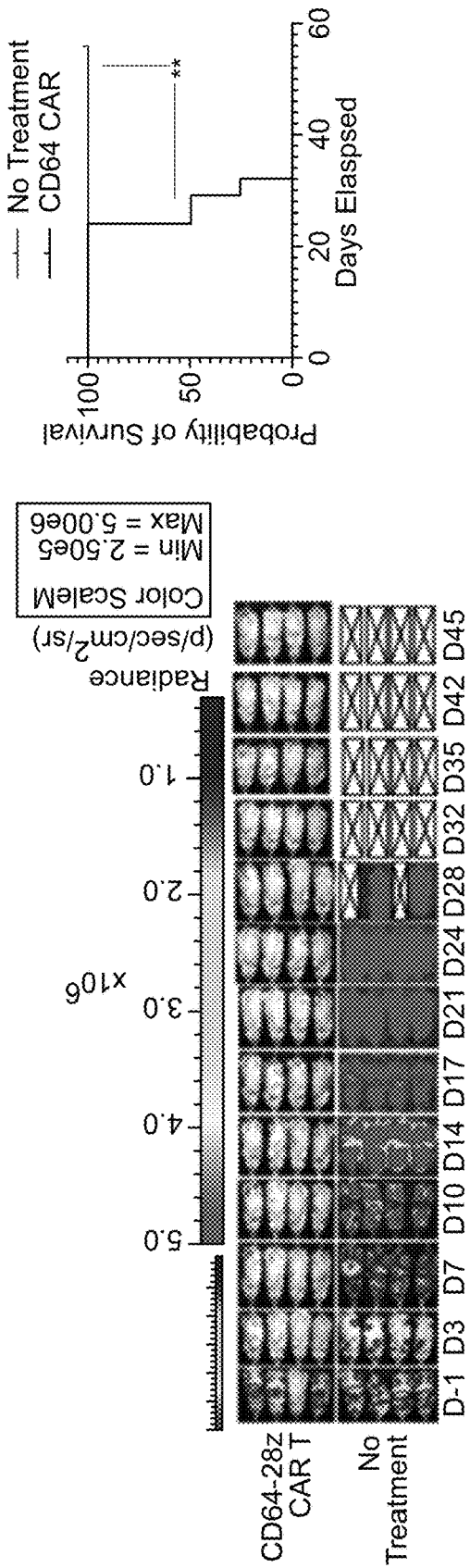
FIG. 2A
FIG. 2B

COMPOSITIONS AND METHODS FOR THE TREATMENT OF VEN/AZA RESISTANT ACUTE MYELOID LEUKEMIA

CROSS-REFERENCE TO RELATED APPLICATIONS

Pursuant to 35 U.S.C. § 119(e) this application is a continuation of International Application PCT/US2024/058938, filed on Dec. 6, 2024, which claims the benefit of U.S. Patent Application Ser. No. 63/610,215, filed on Dec. 14, 2023. The disclosure of the prior applications are considered part of (and are incorporated by reference in) the disclosure of this application.

SEQUENCE LISTING

This application contains a Sequence Listing that has been submitted electronically as an XML file named "58666-0003001_SL_ST26.XML." The XML file, created on Apr. 1, 2025, is 374,316 bytes in size. The material in the XML file is hereby incorporated by reference in its entirety.

BACKGROUND OF THE INVENTION

Acute myeloid leukemia (AML) is a blood cancer in which the bone marrow of a subject makes abnormal myeloblasts, red blood cells, or platelets. AML is one of the most common forms of acute leukemia in adults. The build-up of AML cells in bone marrow and blood can rapidly lead to infection, anemia, excessive bleeding, and death. The BCL-2 inhibitor venetoclax has recently emerged as an important component of therapy for acute myeloid leukemia (AML). The current FDA-approved standard of care for the majority of patients who are too elderly or unfit for aggressive chemotherapy is treatment with venetoclax in combination with a hypomethylating agent, such as azacitidine ("ven/aza treatment") or decitabine. It is estimated that approximately 70% of these patients will achieve complete remission (CR) of their disease upon ven/aza treatment. However, it is estimated that approximately 30% of patients do not respond to treatment with ven/aza and are unable to achieve CR. Furthermore, of those patients that initially achieve a CR, the majority will relapse in the following two years. Thus, there is a need in the art for alternative methods of treating subjects that will not respond to or relapse after treatment with ven/aza.

SUMMARY OF INVENTION

The present disclosure provides polypeptides comprising: a) a first domain comprising an amino acid sequence of one of SEQ ID NO: 1, SEQ ID NO: 2 and SEQ ID NO: 3; b) a second domain comprising an amino acid sequence of SEQ ID NO: 4; c) a third domain comprising an amino acid sequence of SEQ ID NO: 5; d) a fourth domain comprising an amino acid sequence of SEQ ID NO: 6; and e) a fifth domain comprising an amino acid sequence of SEQ ID NO: 7.

In some aspects, the first domain further comprises an amino acid sequence of SEQ ID NO: 23.

In some aspects, the polypeptides comprise an amino acid sequence of one of SEQ ID NO: 11, SEQ ID NO: 12 and SEQ ID NO: 13.

The present disclosure provides polypeptide comprising: a) a first domain comprising an amino acid sequence of one of SEQ ID NO: 1, SEQ ID NO: 2 and SEQ ID NO: 3; b) a second domain comprising an amino acid sequence of SEQ ID NO: 8; c) a third domain comprising an amino acid sequence of SEQ ID NO: 9; d) a fourth domain comprising an amino acid sequence of SEQ ID NO: 10; and e) a fifth domain comprising an amino acid sequence of SEQ ID NO: 7.

In some aspects, the first domain further comprises an amino acid sequence of SEQ ID NO: 23.

In some aspects, polypeptides comprise an amino acid sequence of one of SEQ ID NO: 14, SEQ ID NO: 15 and SEQ ID NO: 16.

The present disclosure provides a nucleic acid molecules comprising nucleic acid sequences encoding a polypeptide of the present disclosure. In some aspects, the nucleic acid molecules comprise a nucleic acid sequence of one of SEQ ID NO: 17-22.

The present disclosure provides vectors comprising the nucleic acid molecules of the present disclosure, preferably wherein the vector is a viral vector, preferably wherein the viral vector is a lentiviral vector.

The present disclosure provides cells comprising the polypeptides of the present disclosure, the nucleic acid molecules of the present disclosure, and/or the vectors of the present disclosure.

In some aspects, the cells are immune cell, preferably wherein the immune cells are T-cells or Natural Killer (NK) cells.

The present disclosure provides populations of the cells of the present disclosure.

The present disclosure provides methods of treating Acute Myeloid Leukemia (AML) in a subject, the method comprising administering the populations of cells of the present disclosure.

In some aspects, the subjects having AML have a population of AML cells that are CD64+.

In some aspects, the subjects having AML have a population of monocytic leukemia stem cells (mLSCs).

In some aspects, the subjects have been previously administered at least one AML-targeting therapy, preferably wherein the AML-targeting therapy comprises the administration of a combination of venetoclax and azacitidine.

In some aspects, the subject has relapsed after treatment with the at least one AML-targeting therapy and/or the subject is resistant to treatment with the at least one AML-targeting therapy.

Any of the above aspects and embodiments, or aspects and embodiments described herein can be combined with any other aspect and embodiment.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers, or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

FIG. 2A-B is a series of graphs showing that CD64-28z CAR T cells (containing the m22 scFv) have in vivo efficacy against CD64+ AML cells lines in xenograft models. A) NSG mice were inoculated with $10^6$ luciferase-expressing THP1 cells via tail vein injection on Day −4. Bioluminescent imagining (BLI) confirmed engraftment of the THP1 cells on Day −1. On Day 0, Mice were either treated with $5 \times 10^6$ CD64-28z CAR T cells or were given no treatment. Leukemia burden was monitored by BLI once to twice weekly and mice were monitored for survival based on the development of predefined endpoints of terminal leukemia. CD64-28z CAR T cells significantly reduced leukemia progression and prolonged survival relative to no treatment. B) NSG mice were inoculated with $10^6$ luciferase-expressing MOLM14 cells via tail vein injection on Day −4. Bioluminescent imagining (BLI) confirmed engraftment of the MOLM14 cells on Day −1. On Day 0, Mice were either treated with $5 \times 10^6$ CD64-28z CAR T cells or were given no treatment. Leukemia burden was monitored by BLI twice weekly, and mice were monitored for survival based on the development of predefined endpoints of terminal leukemia. CD64-28z CAR T cells significantly reduced leukemia progression and prolonged survival relative to no treatment. Statistical analysis of survival in all experiments per Log-Rank analysis with ** representing a p-value of less than 0.01.

Figure 5A:
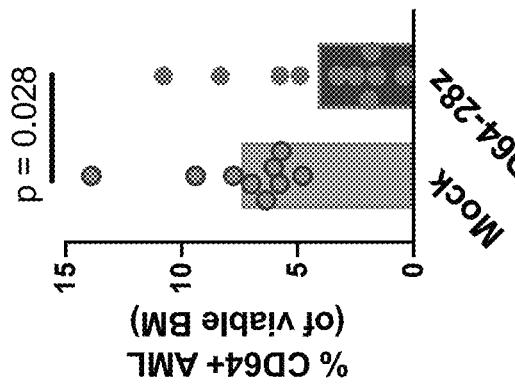
FIG. 5A-D is a series of graphs showing that CD64-28z CAR T cells (containing the m22 scFv) deplete monocytic leukemic stem cells (mLSCs) from patient-derived AML samples. Patient-derived AML samples were obtained from the University of Colorado Biorepository. Predominantly monocytic AML samples (FIG. 5A-5B) and mixed primitive/monocytic AML patient samples (FIG. 5C-5D) were co-incubated with CD64-28z CAR T cells or with matched Mock T cells at an Effector:Target ratio of 1:2 for 24 hours, in vitro. T cells were antibody-depleted and remaining AML cells were injected into NSG-S mice ($10^6$ AML cells/mouse.
Figure 5B:
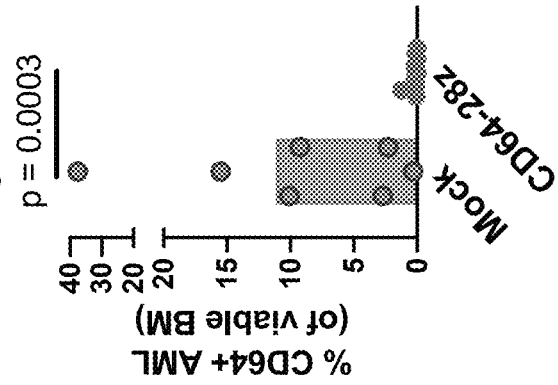
Figure 5C:
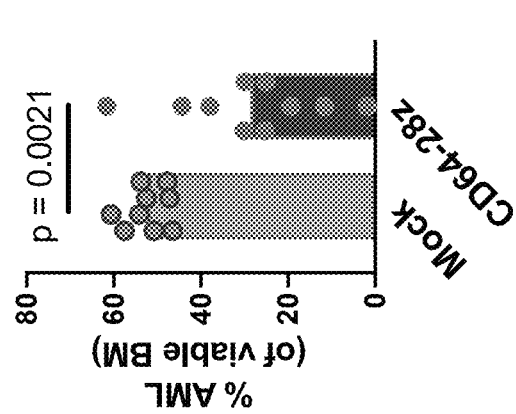
Figure 5D:
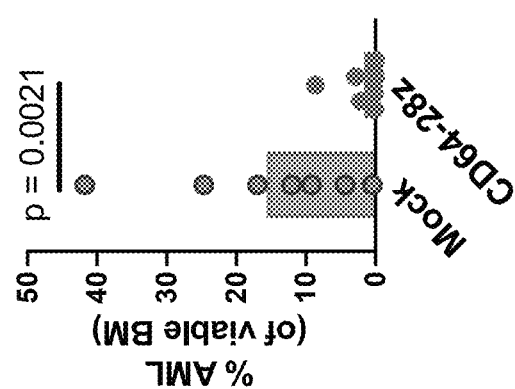

n=7-10 mice/group). AML was allowed to engraft over the next 10 weeks, at which point the mice were taken down and the bone marrow was evaluated by flow cytometry for engraftment of human AML cells and for CD64+ human AML cells. We observed a significant decrease in the engraftment of monocytic AML after pre-incubation with CD64-28z CAR T cells relative to mock T cells (FIG. 5A) with a significant reduction of CD64+ AML cells within the engrafted population (FIG. 5B). We similarly observed a decreased engraftment of mixed primitive/monocytic AML cells after pre-incubation with CD64-28z CAR T cells relative to mock T cells (FIG. 5C) with a significant reduction of CD64+ AML cells as well (FIG. 5D). Collectively, the decreased engraftment of the bulk population and the CD64+ AML cells after ex vivo CAR incubation demonstrates the ability of CD64 CAR T cell to target a mLSC population which carries the engraftment potential of the leukemic population. Statistical comparisons using Mann-Whitney Analysis as indicated.

Figure 6A:
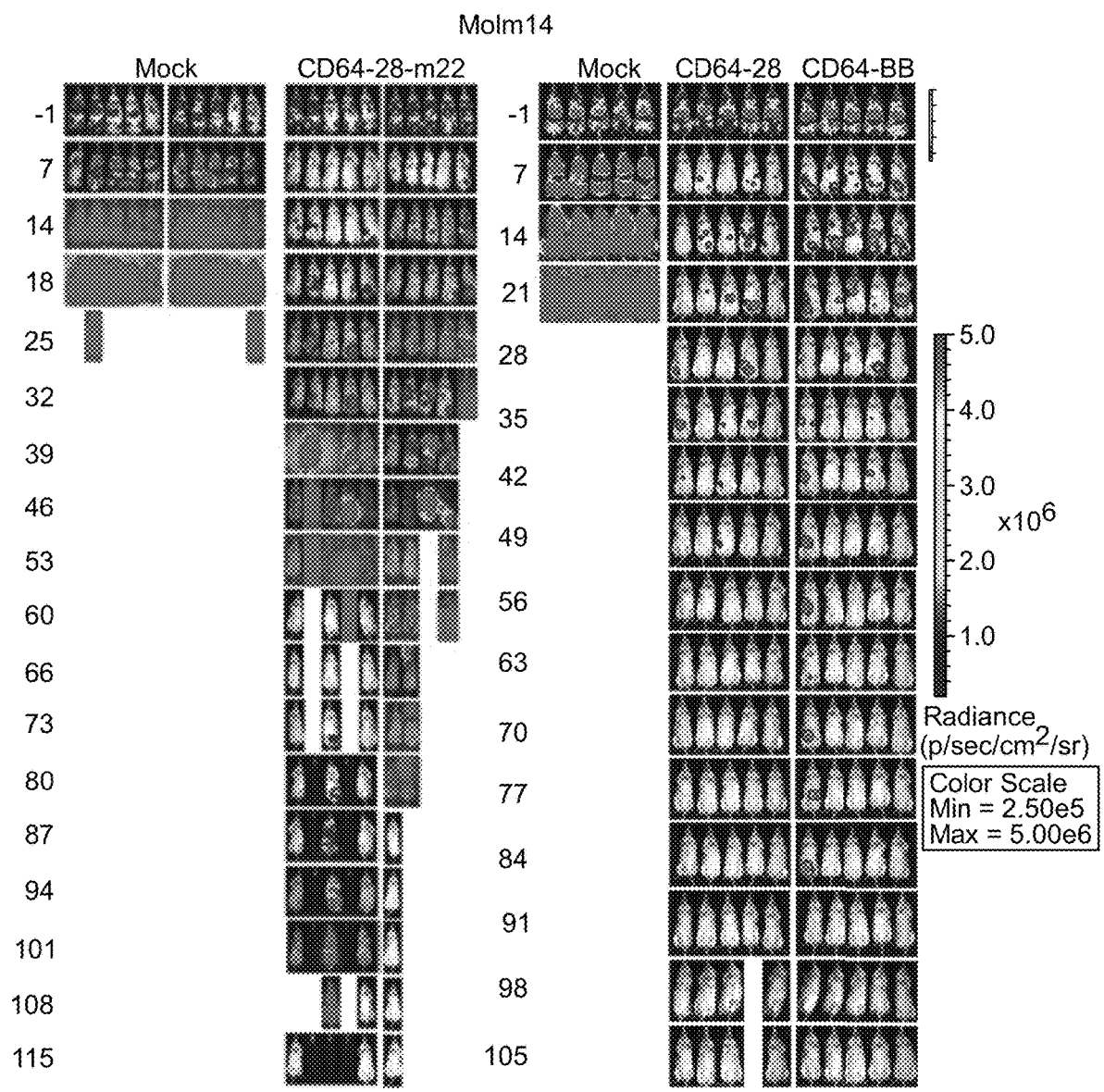
Figure 6B:
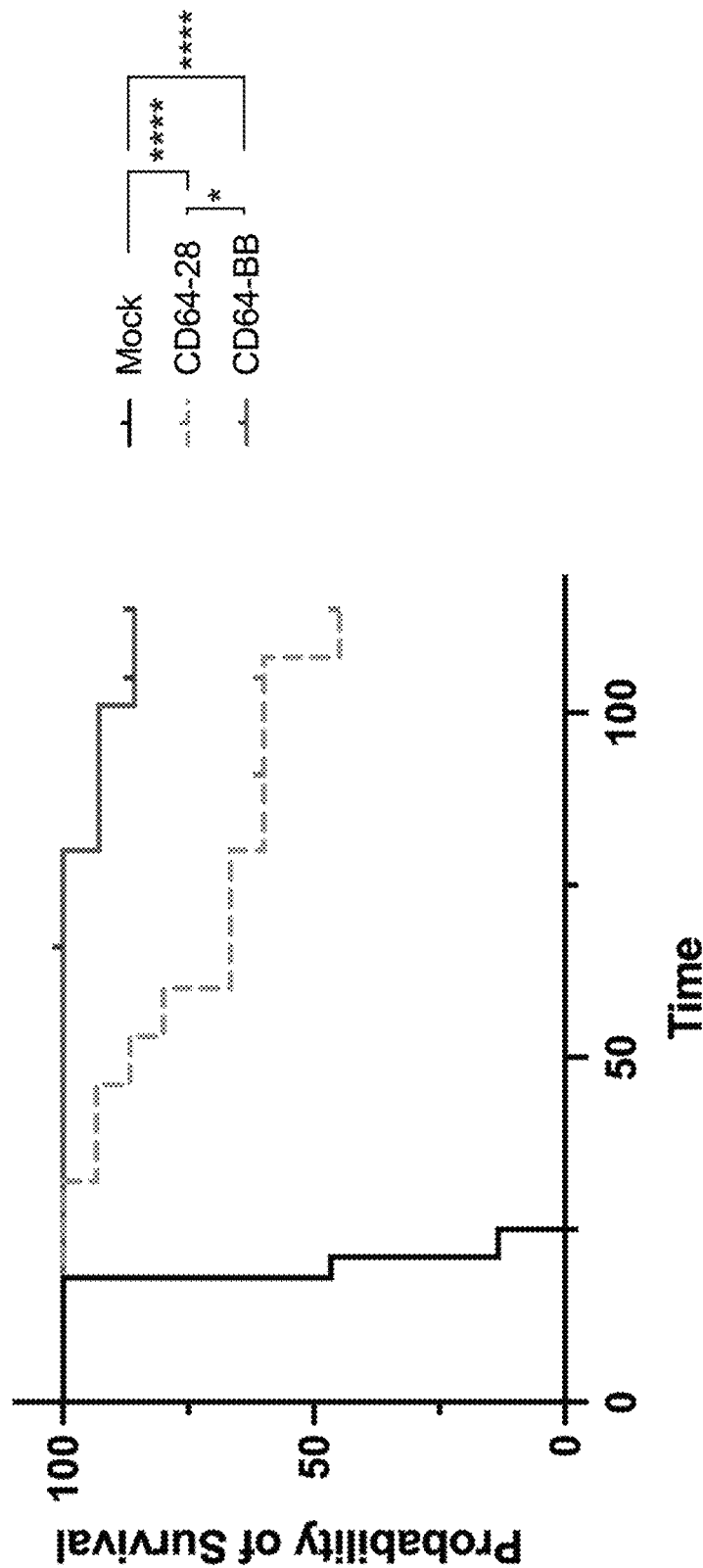
Figure 6C:
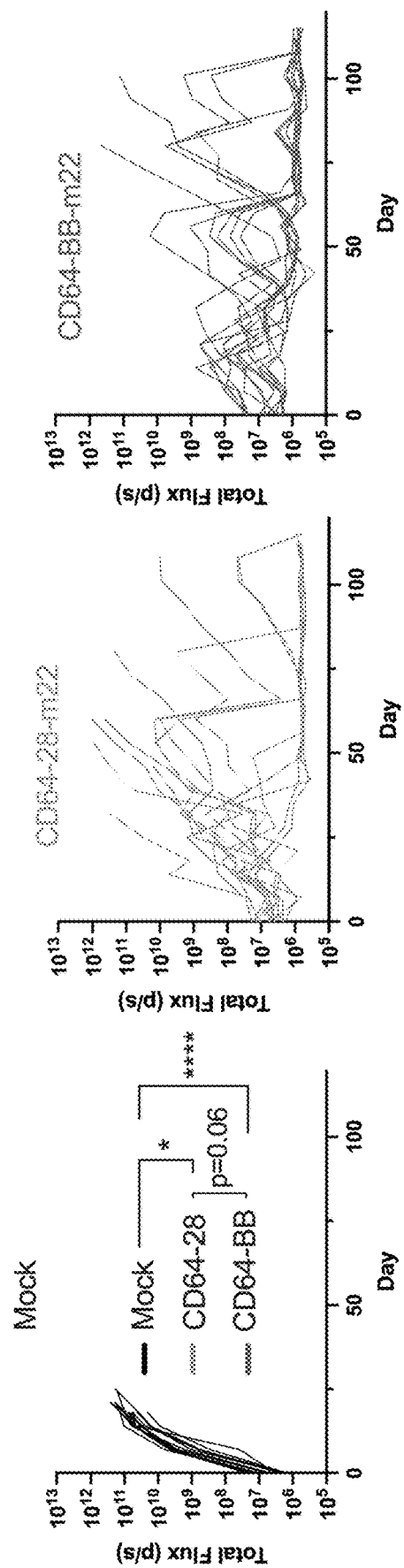

FIG. 6A-C is a series of graphs showing that a CD64 CAR containing the m22 scFv and a 4-1BB costimulatory domain (CD64-BBz) and a CD64 CAR containing the m22 scFv and a CD28 costimulatory domain (CD64-28z) CAR T cells have in vivo efficacy against CD64+AML cells lines in xenograft models. A-B) NSG mice were inoculated with $10^6$ luciferase-expressing MOLM14 cells via tail vein injection on Day −4. Bioluminescent imagining (BLI) confirmed engraftment of the MOLM14 cells on Day −1. On Day 0, Mice were either treated with $3 \times 10^6$ CD64-28z CAR T cells, $3 \times 10^6$ CD64-BBz CAR T cells or an equivalent number of Mock T cells. Mice were treated with Mock or CAR T cells from three independent T cell donors (5 mice per treatment per T cell donor). Leukemia burden was monitored by BLI once to twice weekly (FIG. 6A) and mice were monitored for survival based on the development of predefined endpoints of terminal leukemia (FIG. 6B). Both CD64-28z and CD64-BBz CAR T cells significantly reduced leukemia progression and prolonged survival relative to Mock T cells, with CD64-BBz CAR T cells demonstrating a survival advantage over treatment with CD64-28z CAR T cells. Statistical analysis of survival of each group, combined between donors was performed using Log-Rank analysis whereas *=p-value less than 0.05, and ****=p-value less than 0.0001. C) Quantification of bioluminescent signal as total flux per mouse (photons/second) to quantify leukemia burden in mice over time. Mice treated with CD64-BBz and CD64-28z CAR-T cells demonstrated decreased leukemia burden over time compared to mock treated mice. Statistical analysis by two-way ANOVA where *=p-value less than 0.05, and ****=p-value less than 0.0001. The difference between CD64-28z and CD64-BBz CAR T cell treatment showed a p-value of 0.06 by two-way ANOVA.

Figure 7A:
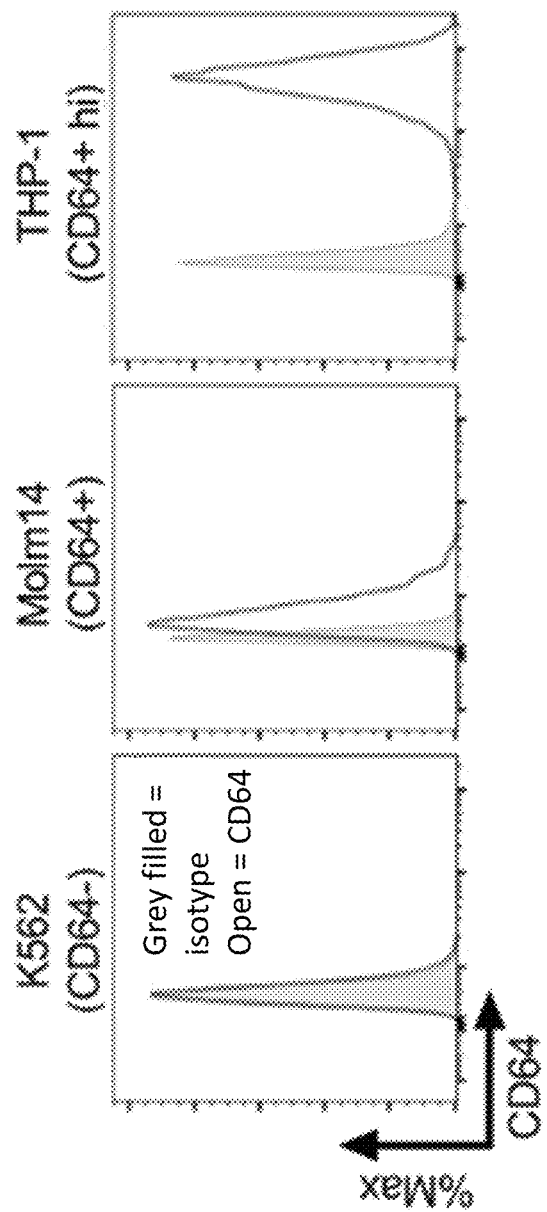
Figure 7B:
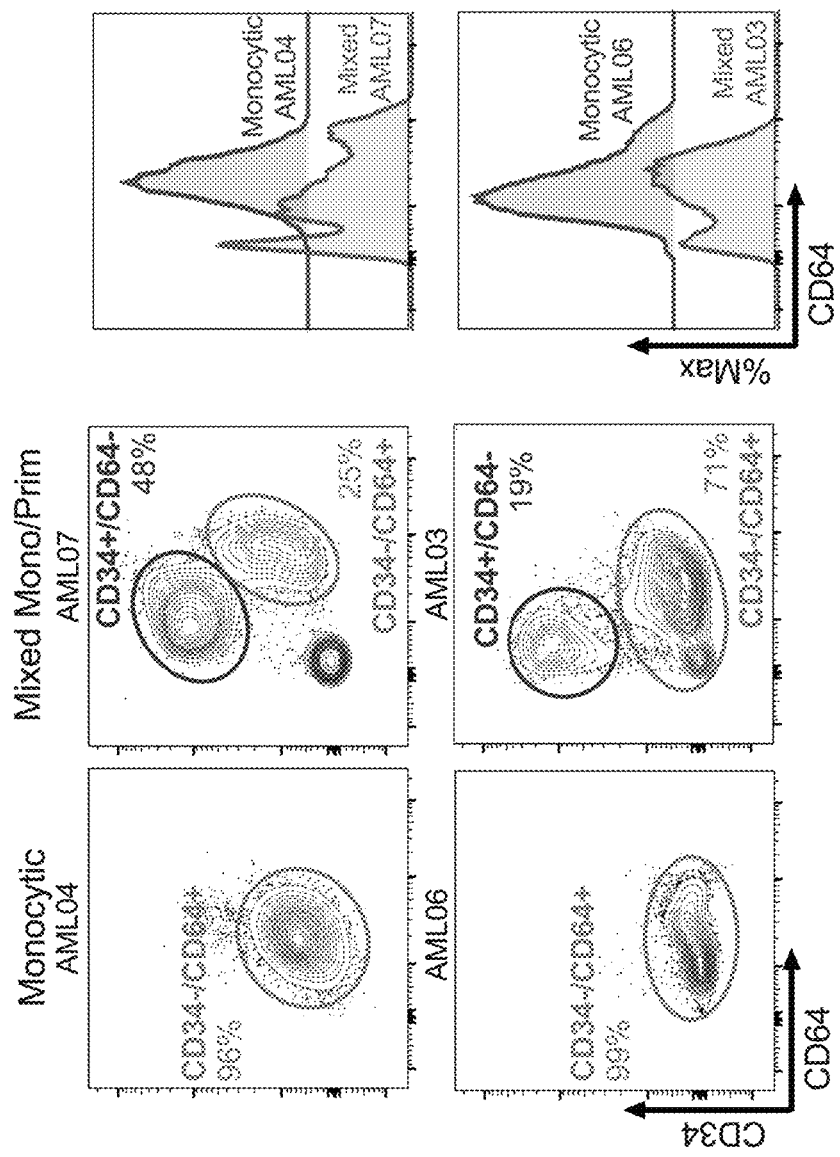

FIG. 7A-B is a series of graphs showing CD64 expression in various leukemia models. A) A series of histograms showing expression of CD64 measured by flow cytometry on K562, MOLM14, and THP-1 AML cell lines. B) A series of histograms and contour plots showing characterization of CD64 expression in primary AML samples.

FIG. 8A-D is a series of diagrams and graphs demonstrating different versions of the CD64 CAR can be expressed in healthy donor T-cells. A) Schematic of exemplary CD64-28-m22, CD64-BB-m22, and CD64-BB-611 CAR constructs. The CD64-28-m22 consists of the m22 scFv, an extracellular and transmembrane (EC/TM) domain derived from CD28, a CD28 costimulatory domain, and the CD3-zeta (CD3z) signaling domain. The CD64-BB-m22 consists of the m22 scFv, an extracellular and transmembrane (EC/TM) domain derived from CD8, a 4-1BB costimulatory domain, and the CD3-zeta (CD3z) signaling domain. The CD64-BB-611 consists of the 611 scFv, an extracellular and transmembrane (EC/TM) domain derived from CD8, a 4-1BB costimulatory domain, and the CD3-zeta (CD3z) signaling domain. B) Histograms showing CD64-28-m22, CD64-BB-m22, and CD64-BB-611 CAR construct transduction efficiency and expression in healthy donor human T cells. C) Graph of CD4 to CD8 T cell ratios in CD64-BB-611, CD64-BB-m22, and CD64-28-m22 CAR T cell populations. D) Bar graph comparing T cell phenotypes in CD64-BB-611, CD64-BB-m22, and CD64-28-m22 CAR T cell populations. Statistical analysis by two-way ANOVA, where =p-value of less than 0.01, *=p-value of less than 0.001 and ****=p-value of less than 0.0001.

Figure 9A:
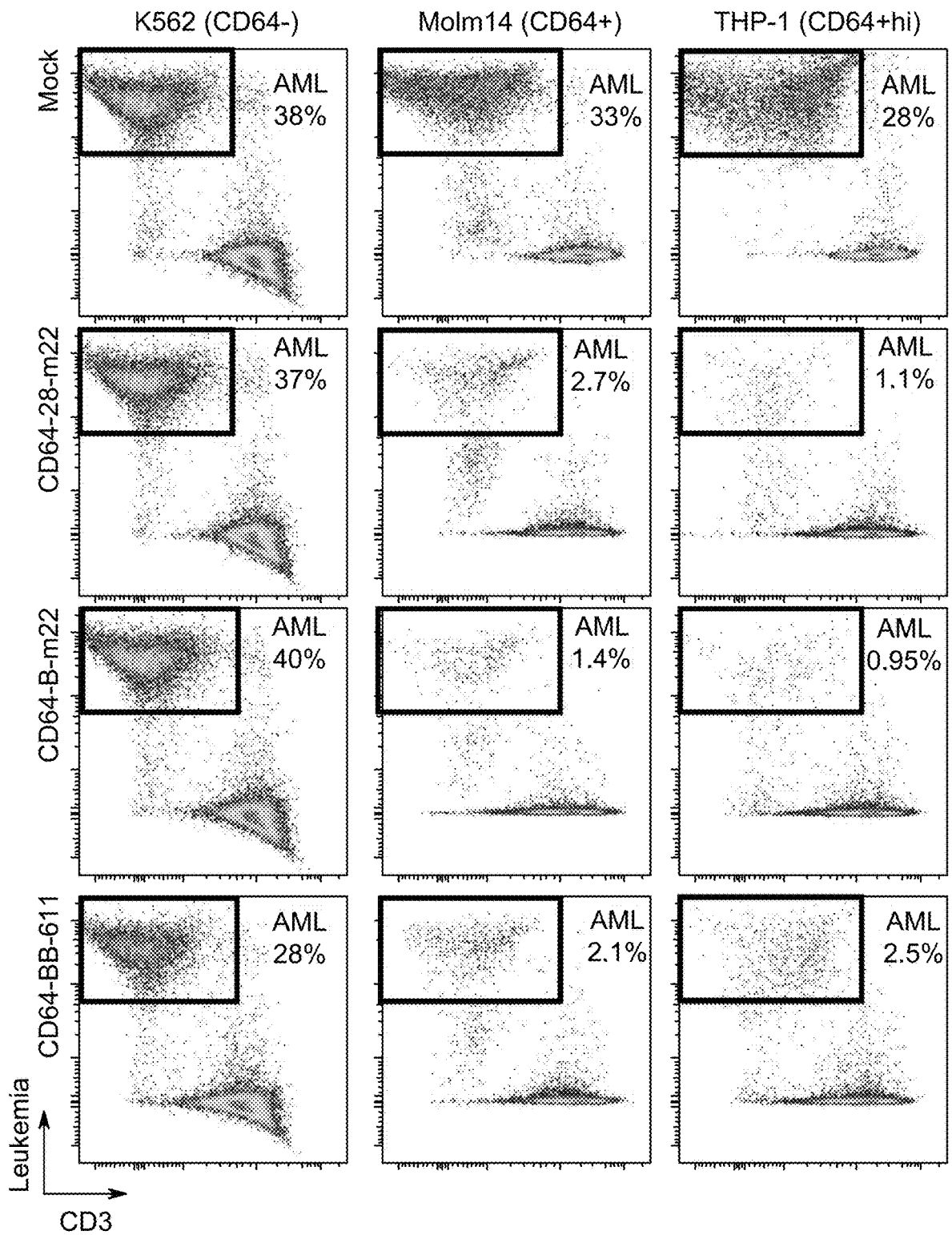

FIG. 9A-E is a series of graphs demonstrating that CD64 CAR T cells are cytotoxic against CD64+ AML cells in vitro. A) Scatter plots of flow cytometry results assessing residual K562, MOLM14, and THP-1 AML cell lines cells after co-culture with CD64-BB-611, CD64-BB-m22, and CD64-28-m22 CAR T cells. B) Quantification of killing of AML cell line cells as shown in FIG. 9A from three replicates at two different E:T ratios showing antigen-dependent cytotoxicity of all CD64 CAR constructs. Statistical analysis by two-way ANOVA, where =p-value of less than 0.01, *=p-value of less than 0.001 and ****=p-value of less than 0.0001. C) Luciferase-based killing assay assessing CD64-BB-611, CD64-BB-m22, and CD64-28-m22 CAR T cell killing of K562, MOLM14, and THP-1 AML cell line cells. Results show each CD64 CAR construct produces antigen-dependent cytotoxicity. D) Scatter plots showing CD64-BB-611, CD64-BB-m22, and CD64-28-m22 CAR T cell reduction of CD64+ AML cells from patient-derived monocytic and mixed monocytic/primitive ("Mixed"). E) Quantification of CD64-BB-611, CD64-BB-m22, and CD64-28-m22 CAR T cell killing of monocytic and mixed monocytic/primitive AML patient samples after 24-hour co-culture at various E:T ratios. Cytotoxicity calculated based on normalization to AML cells co-cultured with equivalent number of Mock T cells at the same E:T ratio and analyzed by flow cytometry at the end of the 24-hour co-culture.

FIG. 1A-F is a series of graphs showing that T cell effector cytokines are released when CD64 CAR T cells engage CD64+ AML cells. A-C) Bar graphs showing antigen-dependent secretion of Interleukin-2 (IL-2) (FIG. 10A), Interferon-gamma (IFNg) (FIG. 10B), and tumor necrosis factor alpha (TNFa) (FIG. 10C) by CD64-BB-m22 and CD64-28-m22, and CD64-BB611 CAR T cells after 24-hour co-culture with the AML cell lines K562, MOLM14, and THP1. D-F) Bar graphs showing antigen-dependent secretion of IL-2 (FIG. 10D), IFNg (FIG. 10E), and TNFa (FIG. 10F) by CD64-BB-m22 and CD64-28-m22, and CD64-BB611 CAR T cells after 24-hour co-culture with patient-derived monocytic or mixed primitive/monocytic AML samples. Statistical analysis throughout FIG. 10 done by two-way ANOVA, where *=p-value of less than 0.05, =p-value of less than 0.01, *=p-value of less than 0.001 and ****=p-value of less than 0.0001.

FIG. 11A-E is a series of graphs showing the manufacturing and efficacy of patient-derived CD64 CAR T cells relative to healthy donor CD64 CAR T cells. A) Line graph showing proliferation of T cells during manufacturing of CD64-BB-m22 CAR T cells. This data demonstrates that patient-derived T cells proliferate with comparable kinetics as healthy donor-derived T cells during CD64-BB-m22 CAR T cell manufacturing. B) Histograms showing CD64-

BB-m22 CAR construct transduction efficiency of T cells from two AML patient donors (pt-AML03 and pt-AML06) as compared to T cells from two health donors (Healthy Donor 42 and 20). C) Bar graph comparing proliferation of patient-derived CD64-BB-m22 CAR T cells and healthy donor-derived CD64-BB-m22 CAR T cells after 24-hour co-culture with MOLM14 AML cells. D) Luciferase killing assay assessing overnight killing of MOLM14 AML cells by two patient-derived CD64-BB-m22 CAR T cell products demonstrating patient-derived CAR T cells are cytotoxic. E) Scatter plots and histograms showing elimination of CD64+ AML cells from monocytic and mixed patient-derived AML samples by autologous patient-derived CD64-BB-m22 CAR T cells.

FIG. 12A-F is a series of bioluminescent images and graphs showing CD64 CAR T cells eliminate CD64+ AML cell lines in xenograft models. A) Bioluminescent images of THP-1 leukemia burden in NSG mice engrafted with $10^6$ THP1 cells on Day −4 and treated with 5×$10^6$ CD64-BB-611, CD64-BB-m22, or CD64-28-m22 (labeled as CD64-28) CAR T cells, or an equivalent dose of Mock T cells from the same T cell donor. This experiment was performed in triplicate with three independent healthy T cell donors. B) Survival analysis of mice treated with CD64-BB-611, CD64-BB-m22, or CD64-28-m22 CAR T cells, or mock-treated control. Both CD64-BB-611 and CD64-BB-m22 CAR T cells significantly reduced leukemia progression and prolonged survival relative to Mock T cell and CD64-28z-m22 CAR T cell treated mice. Statistical analysis of survival of each group, combined between donors was performed using Log-Rank analysis, where =p-value of less than 0.01, *=p-value of less than 0.001 and ****=p-value of less than 0.0001. C) Quantification of bioluminescent signal as total flux per mouse (photons/second) to quantify leukemia burden in mice over time. Mice treated with CD64-BB-m22 and CD64-BB-611 CAR-T cells demonstrated decreased leukemia burden compared to mock treated mice. Statistical analysis by two-way ANOVA, where *=p-value of less than 0.05, =p-value of less than 0.01, *=p-value of less than 0.001 and **=p-value of less than 0.0001. D) Single T-cell donor replicate of data as shown in FIG. 6 with inclusion of treatment with CD64-BB-611 in NSG mice engrafted with MOLM14 leukemia. Bioluminescent imaging of MOLM14 leukemia burden in NSG mouse xenografts models treated with 3×$10^6$ CD64-BB-611, CD64-BB-m22, and CD64-28-m22 CAR T cells as compared to mock-treated control. E) Survival analysis of mice treated with CD64-BB-611, CD64-BB-m22, or CD64-28-m22 CAR T cells, or mock-treated control, showing prolonged survival after treatment with any version of the CD64 CAR compared to Mock T cells. Statistical analysis of survival of each group, combined between donors was performed using Log-Rank analysis, where =p-value of less than 0.01, *=p-value of less than 0.001 and **=p-value of less than 0.0001. F) Quantification of bioluminescent signal as total flux per mouse (photons/second) to quantify leukemia burden in mice over time. Mice treated with CD64-28-m22, CD64-BB-m22, and CD64-BB-611 CAR-T cells demonstrated decreased leukemia burden compared to mock treated mice. Statistical analysis by two-way ANOVA, where *=p-value of less than 0.05, =p-value of less than 0.01, *=p-value of less than 0.001 and ****=p-value of less than 0.0001.

FIG. 13A-F is a series of graphs showing that CD64 CAR T cells persist after clearance of CD64+ leukemia in xenograft models. A) Graphs showing percentage and absolute number of total, CD4+, and CD8+ CD64-BB-m22 and CD64-28-m22 CAR T cells persisting in the bone marrow at 35 days post-infusion and after MOLM14 leukemia clearance. Statistical analysis by Mann-Whitney, where *=p-value of less than 0.05, =p-value of less than 0.01, *=p-value of less than 0.001 and ****=p-value of less than 0.0001. B) Bar graph comparing T cell phenotypes of persisting CD64-BB-m22 and CD64-28-m22 CAR T cells at 35 days post-infusion and MOLM14 leukemia clearance. C) Bar graph showing percentages of persisting CD64-BB-m22 and CD64-28-m22 CAR T cells expressing PD1 and TIM3 exhaustion markers 35 days post-infusion and after MOLM14 leukemia clearance. D) Graphs showing percentage and absolute number of total, CD4+, and CD8+ CD64-BB-611, CD64-BB-m22, and CD64-28-m22 CAR T cells persisting in the bone marrow 105 days after infusion and after MOLM14 leukemia clearance. Statistical analysis by one-way ANOVA, where *=p-value of less than 0.05, =p-value of less than 0.01, *=p-value of less than 0.001 and ****=p-value of less than 0.0001. E) Bar graph comparing T-cell phenotypes of persisting CD64-BB-611, CD64-BB-m22, and CD64-28-m22 CAR T cells 105 days after infusion and after MOLM14 leukemia clearance. Statistical analysis by two-way ANOVA, where *=p-value of less than 0.05. F) Bar graph showing percentages of persisting CD64-BB-611, CD64-BB-m22, and CD64-28-m22 CAR T cells expressing PD1 and TIM3 exhaustion markers 105 days after infusion and after MOLM14 leukemia clearance.

FIG. 14A-E is a series of graphs showing that CD64 CAR T cells exhibit toxicity against monocytes. A) Flow cytometry scatter plots showing the elimination of healthy donor-derived monocytes by CD64-BB-611, CD64-BB-m22, and CD64-28-m22 CAR T cells after overnight co-culture. B) Quantification of monocyte killing in two independent monocyte/T cell donors, in which CD64-28-m22, CD64-BB-m22, CD64-BB-611 CAR T cells were co-cultured with autologous monocytes at various E:T ratios overnight and cytotoxicity of monocytes was calculated by flow cytometry in comparison to Mock T cell negative control. C-E) Bar graphs showing antigen-dependent secretion of IL-2 (FIG. 14C), IFNg, (FIG. 14D), and TNFa (FIG. 14E) by CD64-BB-m22, CD64-28-m22, and CD64-BB-611 CAR T cells after overnight co-culture with monocytes. Three independent healthy T cell donors were used for CAR T cell production (20, 28, and 42). Statistical analysis by two-way ANOVA, where *=p-value of less than 0.05, =p-value of less than 0.01, *=p-value of less than 0.001 and ****=p-value of less than 0.0001.

FIG. 15A-F is a series of graphs that show CD64 CAR T cells in combination with venetoclax and azacitidine additively eliminate CD64+ primary AML ex vivo. A-B) Graphs showing remaining viable AML population (FIG. 15A) and CD33, CD34, and CD64 expression (FIG. 15B) in mixed monocytic/primitive AML cells treated with venetoclax and azacitadine (ven/aza), CD64-BB-m22 CAR T cells, both ven/aza and CD64-BB-m22 CAR T cells, or neither ven/aza or CD64-BB-m22 CAR T cells (DMSO used as negative control for ven/aza and mock T cells used as negative control for CAR T cells). C) Graph showing the quantification of residual CD64+ and CD64−AML cells from a primary mixed monocytic/primitive AML patient sample following treatment with ven/aza, CD64-BB-m22 CAR T cells, both ven/aza and CD64-BB-m22 CAR T cells, or neither ven/aza or CD64-BB-m22 CAR T cells (DMSO/Mock control). D-E) Graphs showing the remaining viable AML population (FIG. 15D) and CD33, CD34, and CD64 expression (FIG. 15E) on these residual AML cells after treatment of a monocytic AML patient sample with ven/aza, CD64-BB-m22 CAR T cells, both ven/aza and CD64-BB-m22 CAR T cells, or neither ven/aza or CD64-BB-m22 CAR T cells (DMSO/Mock control). F) Graph showing the quantification of CD64+ and CD64−AML cells from a primary monocytic AML patient sample after treatment with ven/aza, CD64-BB-m22 CAR T cells, both ven/aza and CD64-BB-m22 CAR T cells, or DMSO and Mock T cell negative controls. Statistical analysis of FIGS. 15C and 15F done by two-way ANOVA, where *=p-value of less than 0.05, =p-value of less than 0.01, *=p-value of less than 0.001 and ****=p-value of less than 0.0001.

DETAILED DESCRIPTION OF THE INVENTION

Acute myeloid leukemia (AML) is a blood cancer that is one of the most commonly diagnosed types of leukemia in adults. There were an estimated 11,000 deaths from AML in the United States in 2020, along with 20,000 newly diagnosed cases. The average age of a person diagnosed with acute myeloid leukemia is about 68, with most cases occurring after the age of 45. However, acute myeloid leukemia is also diagnosed in younger patients, and is the second most common leukemia in children. Prognosis for patients diagnosed with acute myeloid leukemia is generally poor, with a long-term survival of only 40-50% in younger adult patients and a median overall survival of less than one year for older patients. New therapies aimed at supplementing the standard remission induction regimen of cytarabine with intermittent dosing of an anthracycline have not yielded additional clinical benefits. Thus, there exists a need for more specialized and personalized treatment methods, particularly in older patients who are unfit for induction therapy.

Recent research has demonstrated that acute myeloid leukemia exhibits a high level of biological heterogeneity, potentially explaining the difficulty in finding effective therapeutic strategies for the treatment of AML. Furthermore, it has been recently recognized that leukemia stem cells (LSCs), which are capable of giving rise to identical as well as differentiated daughter cells, perpetuate and maintain acute myeloid leukemia and promote disease relapses.

As an alternative to high intensity induction therapy, the current FDA-approved standard of care for elderly patients or patients who are otherwise unfit for aggressive chemotherapy is treatment with a combination of the BCL-2 inhibitor venetoclax and a hypomethylating agent (HMA), such as azacitidine or decitabine. Specifically, treatment with a combination of venetoclax and azacitidine (hereafter referred to as "ven/aza treatment" or "treatment with ven/aza") is estimated to induce a complete remission (CR) of AML in approximately 70% of treated patients. However, this means that approximately 30% of patients do not end up responding to ven/aza treatment and therefore do not achieve complete remission. Furthermore, on average, this remission lasts approximately 18 months with patients ultimately relapsing and dying from leukemia or complications of leukemia-directed therapy. Accordingly, there is a need in the art for new therapies for the treatment of AML, specifically subjects that do not respond to ven/aza treatment or that relapse after treatment with ven/aza.

The present disclosure is based on, inter alia, the discovery that the cell surface protein Cluster of Differentiation 64 ("CD64") can be used to target cellular therapies for the eradication of specific subpopulations of AML cells. Accordingly, the present disclosure provides anti-CD64 cellular immunotherapies for the treatment of AML in a subject.

The present invention generally provides cells, including immune cells (e.g., T cells, B cells, Natural Killer (NK) cells, monocytes, macrophages, or artificially generated cells with immune effector function) derived from a patient, a healthy donor, a differentiated stem cell (including but not limited to induced pluripotent stem cells (iPSC), embryonic stem cells, hematopoietic and/or other tissue specific stem cells), or a non-human source, which are genetically modified to express an antigen recognizing receptor (e.g., chimeric antigen receptor (CAR)) that binds to CD64 and methods of use thereof for the treatment of acute myeloid leukemia in a subject. Immune cell (e.g., T cell) activation is mediated by engagement of CAR molecules to its cognate antigen (i.e., CD64) with signal amplification leading to enhanced persistence, antigen-sensitivity, and efficacy occurring when the CAR is engaged to its respective cognate.

CARs, which are at times referred to as artificial T cell receptors, chimeric T cell receptors (cTCR), T-bodies or chimeric immunoreceptors, are engineered receptors known in the art. They are used primarily to transform immune effector cells, in particular T cells, to provide those cells with a desired antigen specificity and effector response. Adoptive cell therapies using CAR T cells are particularly under investigation in the field of cancer therapy. In these therapies, T cells are removed from a patient, donor or are derived from a stem cell source and engineered to express CARs specific to the antigens found in a particular form of cancer. The CAR T cells, which can then recognize and kill the cancer cells, are reintroduced into the patient whereupon the CAR T cells undergo proliferative expansion, elimination of target antigen-positive cells and, in a minority of patients, transition to a long-lasting, persistent population with retained anti-tumor effector activity.

First generation CARs provide a TCR-like signal from an Immunoreceptor Tyrosine-based Activation Motif (ITAM) containing intracellular signaling domain, most commonly derived from the CD3 zeta (CD3z) molecule, and thereby elicit tumoricidal functions. However, the engagement of CD3z-chain fusion receptors may not suffice to elicit substantial IL-2 secretion and/or T cell proliferation in the absence of a concomitant co-stimulatory signal. In physiological T cell responses, optimal lymphocyte activation requires the engagement of one or more co-stimulatory receptors such as CD28 or 4-1BB. In the setting of suboptimal activation elicited by first generation CARs, T cell activity in vivo is often transient and incapable of controlling the malignancy.

Second (2nd) generation CARs have been constructed to transduce a functional antigen-dependent co-stimulatory signal in human primary T cells in addition to antigen-dependent TCR-like signal, permitting T cell proliferation in addition to tumoricidal activity. Second generation CARs most commonly provide co-stimulation using co-stimulatory domains (synonymously, co-stimulatory signaling regions) derived from CD28 or 4-1BB. The combined delivery of co-stimulation plus a CD3 zeta signal renders 2nd generation CARs superior in terms of function as compared to their first generation counterparts (CD3z signal alone). An example of a 2nd generation CAR is found in U.S. Pat. No. 7,446,190, incorporated herein by reference.

Third (3rd) generation CARs have also been prepared. These combine multiple co-stimulatory domains (synonymously, co-stimulatory signaling regions) with a TCR-like signaling domain in cis, such as CD28+4-1BB+CD3z or CD28+OX40+CD3z, to further augment potency. In the 3rd generation CARs, the co-stimulatory domains are aligned in series in the CAR endodomain and are generally placed upstream of CD3z or its equivalent. In general, however, the results achieved with these third generation CARs have been disappointing, showing only a marginal improvement over 2nd generation configurations, with some 3rd generation CARs being inferior to 2nd generation configurations.

This present invention provides various CARs that engage with CD64. The present disclosure also provides immune cells (e.g., T cells) genetically engineered to express the CARs described herein. As demonstrated in the experimental examples herein, these immune cells comprising the CARs of the present disclosure demonstrate superior activity against acute myeloid leukemia (AML), including AML subtypes that are resistant to treatment with a combination of venetoclax and azacitidine. Thus, the present invention overcomes problems associated with treating the patients that do not end up responding to ven/aza treatment and therefore do not achieve complete remission.

Chimeric Antigen Receptors (CARs) of the Present Disclosure

In some aspects, the present disclosure provides a polypeptide (i.e., a CAR) comprising: a) a first domain; b) a second domain; c) a third domain; d) a fourth domain; and e) a fifth domain. In some aspects, the polypeptide comprises an antigen recognition domain that specifically binds to CD64.

In some aspects of the preceding polypeptides, the first domain can comprise, consist essentially of, or consist of an antigen recognition domain.

In some aspects of the preceding polypeptides, the second domain can comprise, consist essentially of, or consist of a hinge domain.

In some aspects of the preceding polypeptides, the third domain can comprise, consist essentially of, or consist of a transmembrane domain, as described herein.

In some aspects of the preceding polypeptides, the fourth domain can comprise, consist essentially of, or consist of a costimulatory domain, as described herein.

In some aspects of the preceding polypeptides, the firth domain can comprise, consist essentially of, or consist of an activation domain, as described herein.

Antigen Recognition Domains

Antigen recognition domain, (also referred to as an "Antigen recognition moiety") refers to a molecule or portion of a molecule that specifically binds to an antigen. The antigen recognition domains of the present disclosure can specifically bind to CD64.

In some embodiments, the antigen recognition domain of the CAR described herein binds (e.g. specifically binds) to the antigen CD64 described in Table 1. The antigen specific CAR, when expressed on the cell surface, redirects the specificity of immune cells (e.g. T cells) to the respective antigen.

TABLE 1

Target of Antigen Recognition Domains

| | Protein Name | Protein Relevance | UniProt ID | NCBI Accession No. |
|---|---|---|---|---|
| CD64 | high affinity immunoglobulin gamma Fc receptor I; Fc fragment of IgG, high affinity Ia, receptor (CD64); Fc fragment of IgG, high affinity Ia, receptor for (CD64); Fc gamma receptor Ia; Fc-gamma RI; Fc-gamma receptor I A1; IgG Fc receptor I; fc-gamma RIA; fcgammaRIa; Fc fragment of IgG receptor Ia; CD64; FCRI; CD64A; IGFR1 | CD64 is a type of integral membrane glycoprotein known as an Fc receptor that binds monomeric IgG-type antibodies with high affinity. After binding IgG, CD64 interacts with an accessory chain known as the common γ chain (γ chain), which possesses an ITAM motif that is necessary for triggering cellular activation | P12314 | NM_000566 NM_001378804 NM_001378805 NM_001378806 NM_001378807 NM_001378808 NM_001378809 NM_001378810 NM_001378811 |

In some aspects, the antigen recognition domain of a CAR of the present disclosure is an antibody, antibody-like molecule. or fragment thereof and the antigen is a tumor antigen.

In some aspects. the antigen recognition domain of the CARs described herein may recognize an epitope comprising the shared space between one or more antigens. In some embodiments, the antigen recognition domain comprises complementary determining regions (CDRs) of a monoclonal antibody, variable regions of a monoclonal antibody, an scFv, a VH, a VHH, a single domain antibody (e.g., a camelid single domain antibody), an antibody mimetic and/ or antigen binding fragments thereof. In some embodiments, the specificity of the antigen recognition domain is derived from a protein or peptide (e.g., a ligand in a receptor-ligand pair) that specifically binds to another protein or peptide (e.g., a receptor in a receptor-ligand pair). In some embodiments, the antigen recognition domain comprises an aptamer, a T cell receptor (TCR)-like antibody, or a single chain TCR (scTCR). Almost any moiety that binds a given target (e.g., tumor associated antigen (TAA)) with sufficient affinity can be used as an antigen recognition domain. The arrangement of the antigen recognition domain could be multimeric, such as a diabody or multimers. In some embodiments, the multimers can be formed by cross pairing of the variable portion of the light and heavy chains into a diabody.

In some embodiments, the antigen recognition domain of the CARs described herein comprises an antibody mimetic. The term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Exemplary antibody mimetics include, but are not limited to, an affibody, an afflilin, an affimer, an affitin, an alphabody, an anticalin, an avimer (also known as avidity multimer), a DARPin (Designed Ankyrin Repeat Protein), a Fynomer, a Kunitz domain peptide, a monobody and a centyrin.

In some embodiments, the antigen recognition domains of the CARs provided herein comprise a single chain variable fragments (scFv) derived from monoclonal antibodies specific for CD64. Accordingly, the antigen recognition domain of a CAR provided herein can comprise any scFv known in the art to specifically bind CD64. In some embodiments, the antigen recognition domain of the CARs provided herein comprises a fragment of the VH and VL chains of a single-chain variable fragment (scFv) that specifically bind CD64.

In some embodiments, the antigen recognition domain of a CAR provided herein comprises an antibody or an antigen-binding fragment thereof. In some embodiments, the antigen recognition domain of a CAR provided herein comprises a single chain antibody fragment (scFv) comprising a light chain variable domain (VL) and heavy chain variable domain (VH) of a monoclonal anti-CD64 antibody. Optionally, the VH and VL may be joined by a flexible linker, such as a glycine-serine linker or a Whitlow linker. In some embodiments, the antigen binding moiety may comprise VH and VL that are directionally linked, for example, from N to C terminus, VH-linker-VL or VL-linker-VH.

In some embodiments, the antigen recognition domain of a CAR provided herein comprises an scFv whose affinity for CD64 has been optimized to induce cytotoxicity of tumor cells that produce high levels or normal levels of CD64. In some embodiments, the antigen recognition domain of a CAR provided herein comprises an scFv whose affinity for CD64 has been optimized to induce cytotoxicity of tumor cells that produce low levels of CD64.

In some embodiments, the antigen recognition domain of a CAR described herein comprises complementarity determining regions (CDRs) and/or a heavy chain variable domain (VH) and a light chain variable domain (VL) derived from an anti-CD64 antibody.

In some embodiments, the antigen recognition domain of a CAR described herein can comprise, consist essentially of, or consist of an amino acid sequence at least 65%, 70%, 75%, 80%, 85%, 90%, 95%, 96%, 97%, 98%, 99%, or 100% (or any percentage in between) identical to SEQ ID NO: 1, SEQ ID NO: 2, or SEQ ID NO: 3.

The antigen recognition domain of the CARs provided herein may include CDRs and/or VH and VL derived from an anti-CD64 antibody (or antigen binding fragment thereof). Anti-CD64 antibodies of the disclosure can comprise any one of the partial light chain sequences known in the art and/or any one of partial heavy chain sequences known in the art. In some embodiments, the antigen recognition domain of a CAR described herein comprises an scFv comprising a VH and a VL, wherein the VH comprises the amino acid sequence of a VH from an anti-CD64 antibody known in the art, and the VL comprises the amino acid sequence of the corresponding VL known in the art.

In some embodiments, the antigen recognition domain of a CAR described herein comprises an scFv comprising a VH and a VL, wherein the VH comprises a CDRH1, a CDRH2, and a CDRH3 each comprising the amino acid sequence of a CDRH1, a CDRH2, and a CDRH3 of an anti-CD64 antibody known in the art, and wherein the VL comprises a CDRL1, a CDRL2, and a CDRL3 each comprising the amino acid sequence of a CDRL1, a CDRL2, and a CDRL3 of the same anti-CD64 antibody known in the art. Determination of CDR regions is well within the skill of the art. It is understood that in some embodiments, CDRs can be a combination of the Kabat and Chothia CDR (also termed "combined CRs" or "extended CDRs").

In some embodiments, the CDRs are the Kabat CDRs. In other embodiments, the CDRs are the Chothia CDRs. In other embodiments, the CDRs are IMGT CDRs. In other words, in embodiments with more than one CDR, the CDRs may be any of Kabat, Chothia, IMGT combination CDRs, or combinations thereof.

In some embodiments, an antigen recognition domain of a CAR provided herein can include (i) a VH having a CDRH1 having the amino acid sequence set forth in SEQ ID NO:24 (or a derivative of SEQ ID NO:24 with one, two, three, or four amino acid modifications), a CDRH2 having the amino acid sequence set forth in SEQ ID NO:25 (or a derivative of SEQ ID NO:25 with one, two, three, or four amino acid modifications), and a CDRH3 having the amino acid sequence set forth in SEQ ID NO:26 (or a derivative of SEQ ID NO:26 with one, two, three, or four amino acid modifications), and/or (ii) a VL having a CDRL1 having the amino acid sequence set forth in SEQ ID NO:32 (or a derivative of SEQ ID NO:32 with one, two, three, or four amino acid modifications), a CDRL2 having the amino acid sequence set forth in SEQ ID NO:33 (or a derivative of SEQ ID NO:33 with one, two, three, or four amino acid modifications), and a CDRL3 having the amino acid sequence set forth in SEQ ID NO:34 (or a derivative of SEQ ID NO:34 with one, two, three, or four amino acid modifications). Examples of such antigen recognition domains having these CDRs and the ability to bind to CD64 include, without limitation, antigen recognition domains having the VH set forth in SEQ ID NO:31 and the VL set forth in SEQ ID NO:39.

In some embodiments, an antigen recognition domain of a CAR provided herein having (i) a VH having a CDRH1 having the amino acid sequence set forth in SEQ ID NO:24 (or a derivative of SEQ ID NO:24 with one, two, three, or four amino acid modifications), a CDRH2 having the amino acid sequence set forth in SEQ ID NO:25 (or a derivative of SEQ ID NO:25 with one, two, three, or four amino acid modifications), and a CDRH3 having the amino acid sequence set forth in SEQ ID NO:26 (or a derivative of SEQ ID NO:26 with one, two, three, or four amino acid modifications), and/or (ii) a VL having a CDRL1 having the amino acid sequence set forth in SEQ ID NO:32 (or a derivative of SEQ ID NO:32 with one, two, three, or four amino acid modifications), a CDRL2 having the amino acid sequence set forth in SEQ ID NO:33 (or a derivative of SEQ ID NO:33 with one, two, three, or four amino acid modifications), and a CDRL3 having the amino acid sequence set forth in SEQ ID NO:34 (or a derivative of SEQ ID NO:34 with one, two, three, or four amino acid modifications) can include any appropriate framework regions. For example, such an antigen recognition domain can include (i) a VH that includes a framework region 1 having the amino acid sequence set forth in SEQ ID NO:27 (or a derivative of SEQ ID NO:27 with one, two, three, four, five, six, seven, eight, nine, ten, or more amino acid modifications), a framework region 2 having the amino acid sequence set forth in SEQ ID NO:28 (or a derivative of SEQ ID NO:28 with one, two, three, four, five, six, seven, eight, nine, ten, or more amino acid modifications), a framework region 3 having the amino acid sequence set forth in SEQ ID NO:29 (or a derivative of SEQ ID NO:29 with one, two, three, four, five, six, seven, eight, nine, ten, or more amino acid modifications), and a framework region 4 having the amino acid sequence set forth in SEQ ID NO:30 (or a derivative of SEQ ID NO:30 with one, two, three, four, five, six, seven, eight, nine, ten, or more amino acid modifications), and/or (ii) a VL that includes a framework region 1 having the amino acid sequence set forth in SEQ ID NO:35 (or a derivative of SEQ ID NO:35 with one, two, three, four, five, six, seven, eight, nine, ten, or more amino acid modifications), a framework region 2 having the amino acid sequence set forth in SEQ ID NO:36 (or a derivative of SEQ ID NO:36 with one, two, three, four, five, six, seven, eight, nine, ten, or more amino acid modifications), a framework region 3 having the amino acid sequence set forth in SEQ ID NO:37 (or a derivative of SEQ ID NO:37 with one, two, three, four, five, six, seven, eight, nine, ten, or more amino acid modifications), and a framework region 4 having the amino acid sequence set forth in SEQ ID NO:38 (or a derivative of SEQ ID NO:38 with one, two, three, four, five, six, seven, eight, nine, ten, or more amino acid modifications).

In some embodiments, an antigen recognition domain of a CAR provided herein can include (i) a VH that includes an amino acid sequence having at least 90 percent identity to the amino acid sequence set forth in SEQ ID NO:31, and/or (ii) a VL that includes an amino acid sequence having at least 90 percent identity to the amino acid sequence set forth in SEQ ID NO:39. For example, a CAR provided herein can include (i) a VH that includes an amino acid sequence having at least 90, 91, 92, 93, 94, 95, 96, 97, 98, or 99 percent identity to the amino acid sequence set forth in SEQ ID NO:31, and/or (ii) a VL that includes an amino acid sequence having at least 90, 91, 92, 93, 94, 95, 96, 97, 98, or 99 percent identity to the amino acid sequence set forth in SEQ ID NO:39. In some cases, a CAR provided herein can include (i) a VH that includes an amino acid sequence having 100 percent identity to the amino acid sequence set forth in SEQ ID NO:31, and/or (ii) a VL that includes an amino acid sequence having 100 percent identity to the amino acid sequence set forth in SEQ ID NO:39.

In some embodiments, an antigen recognition domain of a CAR provided herein can include (i) a VH that includes an amino acid sequence having at least 90 percent identity to the amino acid sequence set forth in SEQ ID NO:31, provided that the VH includes the amino acid sequences set forth in SEQ ID NOs:24, 25, and 26, and/or (ii) a VL that includes an amino acid sequence having at least 90 percent identity to the amino acid sequence set forth in SEQ ID NO:39, provided that the VL includes the amino acid sequences set forth in SEQ ID NOs:32, 33, and 34. For example, a CAR provided herein can include (i) a VH that includes an amino acid sequence having at least 90, 91, 92, 93, 94, 95, 96, 97, 98, or 99 percent identity to the amino acid sequence set forth in SEQ ID NO:31, provided that the VH includes the amino acid sequences set forth in SEQ ID NOs:24, 25, and 26, and/or (ii) a VL that includes an amino acid sequence having at least 90, 91, 92, 93, 94, 95, 96, 97, 98, or 99 percent identity to the amino acid sequence set forth in SEQ ID NO:39, provided that the VL includes the amino acid sequences set forth in SEQ ID NOs:32, 33, and 34.

In some embodiments, an antigen recognition domain of a CAR provided herein can include (i) a VH having a CDRH1 having the amino acid sequence set forth in SEQ ID NO:40 (or a derivative of SEQ ID NO:40 with one, two, three, or four amino acid modifications), a CDRH2 having the amino acid sequence set forth in SEQ ID NO:41 (or a derivative of SEQ ID NO:41 with one, two, three, or four amino acid modifications), and a CDRH3 having the amino acid sequence set forth in SEQ ID NO:42 (or a derivative of SEQ ID NO:42 with one, two, three, or four amino acid modifications), and/or (ii) a VL having a CDRL1 having the amino acid sequence set forth in SEQ ID NO:48 (or a derivative of SEQ ID NO:48 with one, two, three, or four amino acid modifications), a CDRL2 having the amino acid sequence set forth in SEQ ID NO:49 (or a derivative of SEQ ID NO:49 with one, two, three, or four amino acid modifications), and a CDRL3 having the amino acid sequence set forth in SEQ ID NO:50 (or a derivative of SEQ ID NO:50 with one, two, three, or four amino acid modifications). Examples of such antigen recognition domains having these CDRs and the ability to bind CD64 include, without limitation, antigen recognition domains having the VH set forth in SEQ ID NO:47 and the VL set forth in SEQ ID NO:55.

In some embodiments, an antigen recognition domain of a CAR provided herein having (i) a VH having a CDRH1 having the amino acid sequence set forth in SEQ ID NO:40 (or a derivative of SEQ ID NO:40 with one, two, three, or four amino acid modifications), a CDRH2 having the amino acid sequence set forth in SEQ ID NO:41 (or a derivative of SEQ ID NO:41 with one, two, three, or four amino acid modifications), and a CDRH3 having the amino acid sequence set forth in SEQ ID NO:42 (or a derivative of SEQ ID NO:42 with one, two, three, or four amino acid modifications), and/or (ii) a VL having a CDRL1 having the amino acid sequence set forth in SEQ ID NO:48 (or a derivative of SEQ ID NO:48 with one, two, three, or four amino acid modifications), a CDRL2 having the amino acid sequence set forth in SEQ ID NO:49 (or a derivative of SEQ ID NO:49 with one, two, three, or four amino acid modifications), and a CDRL3 having the amino acid sequence set forth in SEQ ID NO:50 (or a derivative of SEQ ID NO:50 with one, two, three, or four amino acid modifications) can include any appropriate framework regions. For example, such an antigen recognition domain can include (i) a VH that includes a framework region 1 having the amino acid sequence set forth in SEQ ID NO:43 (or a derivative of SEQ ID NO:43 with one, two, three, four, five, six, seven, eight, nine, ten, or more amino acid modifications), a framework region 2 having the amino acid sequence set forth in SEQ ID NO:44 (or a derivative of SEQ ID NO:44 with one, two, three, four, five, six, seven, eight, nine, ten, or more amino acid modifications), a framework region 3 having the amino acid sequence set forth in SEQ ID NO:45 (or a derivative of SEQ ID NO:45 with one, two, three, four, five, six, seven, eight, nine, ten, or more amino acid modifications), and a framework region 4 having the amino acid sequence set forth in SEQ ID NO:46 (or a derivative of SEQ ID NO:46 with one, two, three, four, five, six, seven, eight, nine, ten, or more amino acid modifications), and/or (ii) a VL that includes a framework region 1 having the amino acid sequence set forth in SEQ ID NO:51 (or a derivative of SEQ ID NO:51 with one, two, three, four, five, six, seven, eight, nine, ten, or more amino acid modifications), a framework region 2 having the amino acid sequence set forth in SEQ ID NO:52 (or a derivative of SEQ ID NO:52 with one, two, three, four, five, six, seven, eight, nine, ten, or more amino acid modifications), a framework region 3 having the amino acid sequence set forth in SEQ ID NO:53 (or a derivative of SEQ ID NO:53 with one, two, three, four, five, six, seven, eight, nine, ten, or more amino acid modifications), and a framework region 4 having the amino acid sequence set forth in SEQ ID NO:54 (or a derivative of SEQ ID NO:54 with one, two, three, four, five, six, seven, eight, nine, ten, or more amino acid modifications).

In some embodiments, an antigen recognition domain of a CAR provided herein can include (i) a VH that includes an amino acid sequence having at least 90 percent identity to the amino acid sequence set forth in SEQ ID NO:47, and/or (ii) a VL that includes an amino acid sequence having at least 90 percent identity to the amino acid sequence set forth in SEQ ID NO:55. For example, a CAR provided herein can include (i) a VH that includes an amino acid sequence having at least 90, 91, 92, 93, 94, 95, 96, 97, 98, or 99 percent identity to the amino acid sequence set forth in SEQ ID NO:47, and/or (ii) a VL that includes an amino acid sequence having at least 90, 91, 92, 93, 94, 95, 96, 97, 98, or 99 percent identity to the amino acid sequence set forth in SEQ ID NO:55. In some cases, a CAR provided herein can include (i) a VH that includes an amino acid sequence having 100 percent identity to the amino acid sequence set forth in SEQ ID NO:47, and/or (ii) a VL that includes an amino acid sequence having 100 percent identity to the amino acid sequence set forth in SEQ ID NO:55.

In some embodiments, an antigen recognition domain of a CAR provided herein can include (i) a VH that includes an amino acid sequence having at least 90 percent identity to the amino acid sequence set forth in SEQ ID NO:47, provided that the VH includes the amino acid sequences set forth in SEQ ID NOs:40, 41, and 42, and/or (ii) a VL that includes an amino acid sequence having at least 90 percent identity to the amino acid sequence set forth in SEQ ID NO:55, provided that the VL includes the amino acid sequences set forth in SEQ ID NOs:48, 49, and 50. For example, a CAR provided herein can include (i) a VH that includes an amino acid sequence having at least 90, 91, 92, 93, 94, 95, 96, 97, 98, or 99 percent identity to the amino acid sequence set forth in SEQ ID NO:47, provided that the VH includes the amino acid sequences set forth in SEQ ID NOs:40, 41, and 42, and/or (ii) a VL that includes an amino acid sequence having at least 90, 91, 92, 93, 94, 95, 96, 97, 98, or 99 percent identity to the amino acid sequence set forth in SEQ ID NO:55, provided that the VL includes the amino acid sequences set forth in SEQ ID NOs:48, 49, and 50.

In some embodiments, an antigen recognition domain of a CAR provided herein can include (a) a VH, wherein the VH comprises (i) a CDRH1 that comprises, consists essentially of, or consists of the amino acid sequence set forth in SEQ ID NO:24, (ii) a CDRH2 that comprises, consists essentially of, or consists of the amino acid sequence set forth in SEQ ID NO:25, and (iii) a CDRH3 that comprises, consists essentially of, or consists of the amino acid sequence set forth in SEQ ID NO:26, and/or (b) a VL, wherein the VL comprises (i) a CDRL1 that comprises, consists essentially of, or consists of the amino acid sequence set forth in SEQ ID NO:32, (ii) a CDRL2 that comprises, consists essentially of, or consists of the amino acid sequence set forth in SEQ ID NO:33, and (iii) a CDRL3 that comprises, consists essentially of, or consists of the amino acid sequence set forth in SEQ ID NO:34. As used herein, a "CDRH1 that consists essentially of the amino acid sequence set forth in SEQ ID NO:24" is a CDRH1 that has zero, one, or two amino acid substitutions within SEQ ID NO:24, that has zero, one, two, three, four, or five amino acid residues directly preceding SEQ ID NO:24, and/or that has zero, one, two, three, four, or five amino acid residues directly following SEQ ID NO:24, provided that the CAR maintains its basic ability to bind to CD64. Examples of a CDRH1 that consists essentially of the amino acid sequence set forth in SEQ ID NO:24 include, without limitation, those set forth in Table 2.

TABLE 2

Exemplary CDRH1s that consist essentially of the amino acid sequence set forth in SEQ ID NO: 24.

| Sequence | SEQ ID NO: |
|---|---|
| TGFIFSGYG | 56 |
| CGFIFSGYG | 57 |
| GGFIFSGYG | 58 |
| SSFIFSGYG | 59 |
| SCFIFSGYG | 60 |
| SQFIFSGYG | 61 |
| SNFIFSGYG | 62 |
| STFIFSGYG | 63 |
| SGWIFSGYG | 64 |
| SGFIWSGYG | 65 |
| SGWIWSGYG | 66 |
| SGPIFSGYG | 67 |
| SGFIPSGYG | 68 |
| SGPIPSGYG | 69 |
| SGYIFSGYG | 70 |
| SGFIYSGYG | 71 |
| SGYIYSGYG | 72 |
| SGFLFSGYG | 73 |
| SGFVFSGYG | 74 |
| SGFAFSGYG | 75 |
| SGFMFSGYG | 76 |
| SGFIFTGYG | 77 |
| SGFIFCGYG | 78 |
| SGFIFGGYG | 79 |
| SGFIFSSYG | 80 |
| SGFIFSCYG | 81 |
| SGFIFSTYG | 82 |
| SGFIFSQYG | 83 |
| SGFIFSNYG | 84 |
| SGFIFSGYS | 85 |
| SGFIFSGYC | 86 |
| SGFIFSGYT | 87 |
| SGFIFSGYQ | 88 |
| SGFIFSGYN | 89 |
| SGFIFSGFG | 90 |
| SGFIFSGSG | 91 |
| SGFIFSGTG | 92 |

As used herein, a "CDRH2 that consists essentially of the amino acid sequence set forth in SEQ ID NO:25" is a CDRH2 that has zero, one, or two amino acid substitutions within SEQ ID NO:25, that has zero, one, two, three, four, or five amino acid residues directly preceding SEQ ID NO:25, and/or that has zero, one, two, three, four, or five amino acid residues directly following SEQ ID NO:25, provided that the CAR maintains its basic ability to bind to CD64. Examples of a CDRH2 that consists essentially of the amino acid sequence set forth in SEQ ID NO:25 include, without limitation, those set forth in Table 3.

TABLE 3

Exemplary CDRH2s that consist essentially of the amino acid sequence set forth in SEQ ID NO: 25.

| Sequence | SEQ ID NO: |
|---|---|
| LWYDGSNK | 93 |
| VWYDGSNK | 94 |
| AWYDGSNK | 95 |
| IFYDGSNK | 96 |
| IPYDGSNK | 97 |
| IHYDGSNK | 98 |
| IWFDGSNK | 99 |
| IWSDGSNK | 100 |
| IWTDGSNK | 101 |
| IWYEGSNK | 102 |
| IWYNGSNK | 103 |
| IWYDSSNK | 104 |
| IWYDTSNK | 105 |
| IWYDCSNK | 106 |

TABLE 3-continued

Exemplary CDRH2s that consist essentially of the amino acid sequence set forth in SEQ ID NO: 25.

| Sequence | SEQ ID NO: |
|---|---|
| IWYDNSNK | 107 |
| IWYDQSNK | 108 |
| IWYDGCNK | 109 |
| IWYDGTNK | 110 |
| IWYDGGNK | 111 |
| IWYDGNNK | 112 |
| IWYDGQNK | 113 |
| IWYDGSQK | 114 |
| IWYDGSGK | 115 |
| IWYDGSSK | 116 |
| IWYDGSCK | 117 |
| IWYDGSTK | 118 |
| IWYDGSNR | 119 |
| IWYDGSNH | 120 |

As used herein, a "CDRH3 that consists essentially of the amino acid sequence set forth in SEQ ID NO:26" is a CDRH3 that has zero, one, or two amino acid substitutions within SEQ ID NO:26, that has zero, one, two, three, four, or five amino acid residues directly preceding SEQ ID NO:26, and/or that has zero, one, two, three, four, or five amino acid residues directly following SEQ ID NO:26, provided that the CAR maintains its basic ability to bind to CD64. Examples of a CDRH3 that consists essentially of the amino acid sequence set forth in SEQ ID NO:26 include, without limitation, those set forth in Table 4.

TABLE 4

Exemplary CDRH3s that consist essentially of the amino acid sequence set forth in SEQ ID NO: 26.

| Sequence | SEQ ID NO: |
|---|---|
| VRDTGDRFFDY | 121 |
| LRDTGDRFFDY | 122 |
| IRDTGDRFFDY | 123 |
| AKDTGDRFFDY | 124 |
| AHDTGDRFFDY | 125 |
| ARETGDRFFDY | 126 |
| ARDSGDRFFDY | 127 |
| ARDCGDRFFDY | 128 |
| ARDYGDRFFDY | 129 |
| ARDTQDRFFDY | 130 |
| ARDTCDRFFDY | 131 |
| ARDTTDRFFDY | 132 |
| ARDTSDRFFDY | 133 |
| ARDTGERFFDY | 134 |
| ARDTGDKFFDY | 135 |
| ARDTGDHFFDY | 136 |
| ARDTGDRWFDY | 137 |
| ARDTGDRPFDY | 138 |
| ARDTGDRYFDY | 139 |
| ARDTGDRFWDY | 140 |
| ARDTGDRFPDY | 141 |
| ARDTGDRFYDY | 142 |
| ARDTGDRFFEY | 143 |
| ARDTGDRFFDT | 144 |
| ARDTGDRFFDS | 145 |
| ARDTGDRFFDF | 146 |

As used herein, a "CDRL1 that consists essentially of the amino acid sequence set forth in SEQ ID NO:32" is a CDRL1 that has zero, one, or two amino acid substitutions within SEQ ID NO:32, that has zero, one, two, three, four, or five amino acid residues directly preceding SEQ ID NO:32, and/or that has zero, one, two, three, four, or five amino acid residues directly following SEQ ID NO:32, provided that the CAR maintains its basic ability to bind to CD64. Examples of a CDRL1 that consists essentially of the amino acid sequence set forth in SEQ ID NO:32 include, without limitation, those set forth in Table 5.

TABLE 5

Exemplary CDRL1s that consist essentially of the amino acid sequence set forth in SEQ ID NO: 32.

| Sequence | SEQ ID NO: |
|---|---|
| GSVSSY | 147 |
| NSVSSY | 148 |
| QTVSSY | 149 |
| QCVSSY | 150 |
| QYVSSY | 151 |
| QSASSY | 152 |
| QSLSSY | 153 |
| QSISSY | 154 |
| QSMSSY | 155 |
| QSVTSY | 156 |
| QSVCSY | 157 |
| QSVYSY | 158 |
| QSVSTY | 159 |
| QSVSCY | 160 |
| QSVSYY | 161 |
| QSVSSS | 162 |
| QSVSST | 163 |
| QSVSSF | 164 |

As used herein, a "CDRL2 that consists essentially of the amino acid sequence set forth in SEQ ID NO:33" is a CDRL2 that has zero, one, or two amino acid substitutions within SEQ ID NO:33, that has zero, one, two, three, four, or five amino acid residues directly preceding SEQ ID NO:33, and/or that has zero, one, two, three, four, or five amino acid residues directly following SEQ ID NO:33, provided that the CAR maintains its basic ability to bind to CD64. Examples of a CDRL2 that consists essentially of the amino acid sequence set forth in SEQ ID NO:33 include, without limitation, those set forth in Table 6.

TABLE 6

Exemplary CDRL2s that consist essentially of the amino acid sequence set forth in SEQ ID NO: 33.

| Sequence | SEQ ID NO: |
|---|---|
| EAS | 165 |
| DVS | 166 |
| DLS | 167 |
| DIS | 168 |
| DMS | 169 |
| DAT | 170 |
| DAC | 171 |
| DAY | 172 |

As used herein, a "CDRL3 that consists essentially of the amino acid sequence set forth in SEQ ID NO:34" is a CDRL3 that has zero, one, or two amino acid substitutions within SEQ ID NO:34, that has zero, one, two, three, four, or five amino acid residues directly preceding SEQ ID NO:34, and/or that has zero, one, two, three, four, or five amino acid residues directly following SEQ ID NO:34, provided that the CAR maintains its basic ability to bind to CD64. Examples of a CDRL3 that consists essentially of the amino acid sequence set forth in SEQ ID NO:34 include, without limitation, those set forth in Table 7.

TABLE 7

Exemplary CDRL3s that consist essentially of the amino acid sequence set forth in SEQ ID NO: 34.

| Sequence | SEQ ID NO: |
|---|---|
| NLRSNWPPYT | 173 |
| PLRSNWPPYT | 174 |
| QIRSNWPPYT | 175 |
| QVRSNWPPYT | 176 |
| QARSNWPPYT | 177 |
| QLKSNWPPYT | 178 |
| QLHSNWPPYT | 179 |
| QLRTNWPPYT | 180 |
| QLRCNWPPYT | 181 |
| QLRYNWPPYT | 182 |
| QLRSQWPPYT | 183 |
| QLRSNFPPYT | 184 |
| QLRSNYPPYT | 185 |
| QLRSNPPPYT | 186 |
| QLRSNWFPYT | 187 |
| QLRSNWQPYT | 188 |
| QLRSNWNPYT | 189 |
| QLRSNWPWYT | 190 |
| QLRSNWWPYT | 191 |
| QLRSNWPNYT | 192 |
| QLRSNWPQYT | 193 |
| QLRSNWPPTT | 194 |
| QLRSNWPPST | 195 |
| QLRSNWPPFT | 196 |
| QLRSNWPPYS | 197 |
| QLRSNWPPYC | 198 |
| QLRSNWPPYY | 199 |

In some embodiments, an antigen recognition domain of a CAR provided herein can include (a) a VH, wherein the VH comprises (i) a CDRH1 that comprises, consists essentially of, or consists of the amino acid sequence set forth in SEQ ID NO:0, (ii) a CDRH2 that comprises, consists essentially of, or consists of the amino acid sequence set forth in SEQ ID NO:41, and (iii) a CDRH3 that comprises, consists essentially of, or consists of the amino acid sequence set forth in SEQ ID NO:42, and/or (b) a VL, wherein the VL comprises (i) a CDRL1 that comprises, consists essentially of, or consists of the amino acid sequence set forth in SEQ ID NO:48, (ii) a CDRL2 that comprises, consists essentially of, or consists of the amino acid sequence set forth in SEQ ID NO:49, and (iii) a CDRL3 that comprises, consists essentially of, or consists of the amino acid sequence set forth in SEQ ID NO:50. As used herein, a "CDRH1 that consists essentially of the amino acid sequence set forth in SEQ ID NO:0" is a CDRH1 that has zero, one, or two amino acid substitutions within SEQ ID NO:0, that has zero, one, two, three, four, or five amino acid residues directly preceding SEQ ID NO:0, and/or that has zero, one, two, three, four, or five amino acid residues directly following SEQ ID NO:0, provided that the CAR maintains its basic ability to bind to CD64. Examples of a CDRH 1 that consists essentially of the amino acid sequence set forth in SEQ ID NO:0 include, without limitation, those set forth in Table 8.

TABLE 8

Exemplary CDRH1s that consist essentially of the amino acid sequence set forth in SEQ ID NO: 40.

| Sequence | SEQ ID NO: |
|---|---|
| SYGMH | 200 |
| CYGMH | 201 |
| TYGMH | 202 |
| QYGMH | 203 |

TABLE 8-continued

Exemplary CDRH1s that consist essentially of the amino acid sequence set forth in SEQ ID NO: 40.

| Sequence | SEQ ID NO: |
|---|---|
| NYGMH | 204 |
| GYSMH | 205 |
| GYCMH | 206 |
| GYTMH | 207 |
| GYQMH | 208 |
| GYNMH | 209 |
| GFGMH | 210 |
| GSGMH | 211 |
| GTGMH | 212 |
| GYGIH | 213 |
| GYGLH | 214 |
| GYGVH | 215 |
| GYGAH | 216 |
| GYGCH | 217 |
| GYGMK | 218 |
| GYGMR | 219 |
| GYGMP | 220 |

As used herein, a "CDRH2 that consists essentially of the amino acid sequence set forth in SEQ ID NO:1" is a CDRH2 that has zero, one, or two amino acid substitutions within SEQ ID NO:1, that has zero, one, two, three, four, or five amino acid residues directly preceding SEQ ID NO:1, and/or that has zero, one, two, three, four, or five amino acid residues directly following SEQ ID NO:1, provided that the CAR maintains its basic ability to bind to CD64.

Examples of a CDRH2 that consists essentially of the amino acid sequence set forth in SEQ ID NO:1 include, without limitation, those set forth in Table 9.

TABLE 9

Exemplary CDRH2s that consist essentially of the amino acid sequence set forth in SEQ ID NO: 41.

| Sequence | SEQ ID NO: |
|---|---|
| LIWYDGSNKYYADSVKG | 221 |
| IIWYDGSNKYYADSVKG | 222 |
| AIWYDGSNKYYADSVKG | 223 |
| MIWYDGSNKYYADSVKG | 224 |
| VLWYDGSNKYYADSVKG | 225 |
| VVWYDGSNKYYADSVKG | 226 |
| VAWYDGSNKYYADSVKG | 227 |
| VMWYDGSNKYYADSVKG | 228 |
| VILWYDGSNKYYADSVKG | 229 |
| VIVWYDGSNKYYADSVKG | 230 |
| VIAWYDGSNKYYADSVKG | 231 |
| VIIFYDGSNKYYADSVKG | 232 |
| VIIPYDGSNKYYADSVKG | 233 |
| VIIHYDGSNKYYADSVKG | 234 |
| VIIWFDGSNKYYADSVKG | 235 |
| VIIWSDGSNKYYADSVKG | 236 |
| VIIWTDGSNKYYADSVKG | 237 |
| VIIWYEGSNKYYADSVKG | 238 |
| VIIWYNGSNKYYADSVKG | 239 |
| VIIWYDSSNKYYADSVKG | 240 |
| VIIWYDTSNKYYADSVKG | 241 |
| VIIWYDCSNKYYADSVKG | 242 |
| VIIWYDNSNKYYADSVKG | 243 |
| VIIWYDQSNKYYADSVKG | 244 |
| VIIWYDGCNKYYADSVKG | 245 |
| VIIWYDGTNKYYADSVKG | 246 |
| VIIWYDGGNKYYADSVKG | 247 |
| VIIWYDGNNKYYADSVKG | 248 |
| VIIWYDGQNKYYADSVKG | 249 |
| VIIWYDGSQKYYADSVKG | 250 |
| VIIWYDGSGKYYADSVKG | 251 |
| VIIWYDGSSKYYADSVKG | 252 |
| VIIWYDGSCKYYADSVKG | 253 |
| VIIWYDGSTKYYADSVKG | 254 |

TABLE 9-continued

Exemplary CDRH2s that consist essentially of the
amino acid sequence set forth in SEQ ID NO: 41.

| Sequence | SEQ ID NO: |
|---|---|
| VIIWYDGSNRYYADSVKG | 255 |
| VIIWYDGSNHYYADSVKG | 256 |
| VIWYDGSNKSYADSVKG | 257 |
| VIWYDGSNKTYADSVKG | 258 |
| VIWYDGSNKFYADSVKG | 259 |
| VIWYDGSNKYSADSVKG | 260 |
| VIWYDGSNKYTADSVKG | 261 |
| VIWYDGSNKYFADSVKG | 262 |
| VIWYDGSNKYYVDSVKG | 263 |
| VIWYDGSNKYYLDSVKG | 264 |
| VIWYDGSNKYYIDSVKG | 265 |
| VIWYDGSNKYYMDSVKG | 266 |
| VIWYDGSNKYYAESVKG | 267 |
| VIWYDGSNKYYADCVKG | 268 |
| VIWYDGSNKYYADTVKG | 269 |
| VIWYDGSNKYYADSAKG | 270 |
| VIWYDGSNKYYADSLKG | 271 |
| VIWYDGSNKYYADSIKG | 272 |
| VIWYDGSNKYYADSMKG | 273 |
| VIWYDGSNKYYADSVRG | 274 |
| VIWYDGSNKYYADSVHG | 275 |
| VIWYDGSNKYYADSVKS | 276 |
| VIWYDGSNKYYADSVKT | 277 |
| VIWYDGSNKYYADSVKC | 278 |

As used herein, a "CDRH3 that consists essentially of the amino acid sequence set forth in SEQ ID NO:42" is a CDRH3 that has zero, one, or two amino acid substitutions within SEQ ID NO:42, that has zero, one, two, three, four, or five amino acid residues directly preceding SEQ ID NO:42, and/or that has zero, one, two, three, four, or five amino acid residues directly following SEQ ID NO:42, provided that the CAR maintains its basic ability to bind to CD64. Examples of a CDRH3 that consists essentially of the amino acid sequence set forth in SEQ ID NO:42 include, without limitation, those set forth in Table 10.

TABLE 10

Exemplary CDRH3s that consist essentially of the
amino acid sequence set forth in SEQ ID NO: 42.

| Sequence | SEQ ID NO: |
|---|---|
| ETGDRFFDY | 279 |
| DSGDRFFDY | 280 |
| DCGDRFFDY | 281 |
| DYGDRFFDY | 282 |
| DTQDRFFDY | 283 |
| DTCDRFFDY | 284 |
| DTTDRFFDY | 285 |
| DTSDRFFDY | 286 |
| DTGERFFDY | 287 |
| DTGDKFFDY | 288 |
| DTGDHFFDY | 289 |
| DTGDRWFDY | 290 |
| DTGDRPFDY | 291 |
| DTGDRYFDY | 292 |
| DTGDRFWDY | 293 |
| DTGDRFPDY | 294 |
| DTGDRFYDY | 295 |
| DTGDRFFEY | 296 |
| DTGDRFFDT | 297 |
| DTGDRFFDS | 298 |
| DTGDRFFDF | 299 |

As used herein, a "CDRL1 that consists essentially of the amino acid sequence set forth in SEQ ID NO:48" is a CDRL1 that has zero, one, or two amino acid substitutions within SEQ ID NO:48, that has zero, one, two, three, four, or five amino acid residues directly preceding SEQ ID NO:48, and/or that has zero, one, two, three, four, or five amino acid residues directly following SEQ ID NO:48, provided that the CAR maintains its basic ability to bind to CD64. Examples of a CDRL1 that consists essentially of the amino acid sequence set forth in SEQ ID NO:48 include, without limitation, those set forth in Table 11.

TABLE 11

Exemplary CDRL1s that consist essentially of the
amino acid sequence set forth in SEQ ID NO: 48.

| Sequence | SEQ ID NO: |
|---|---|
| KASQSVSSYLA | 300 |
| HASQSVSSYLA | 301 |
| RVSQSVSSYLA | 302 |
| RLSQSVSSYLA | 303 |
| RISQSVSSYLA | 304 |
| RMSQSVSSYLA | 305 |
| RATQSVSSYLA | 306 |
| RACQSVSSYLA | 307 |
| RAYQSVSSYLA | 308 |
| RASGSVSSYLA | 309 |
| RASNSVSSYLA | 310 |
| RASQTVSSYLA | 311 |
| RASQCVSSYLA | 312 |
| RASQYVSSYLA | 313 |
| RASQSASSYLA | 314 |
| RASQSLSSYLA | 315 |
| RASQSISSYLA | 316 |
| RASQSMSSYLA | 317 |
| RASQVTSYLA | 318 |
| RASQSVCSYLA | 319 |
| RASQSVYSYLA | 320 |
| RASQSVSTYLA | 321 |
| RASQSVSCYLA | 322 |
| RASQSVSYYLA | 323 |
| RASQSVSSSLA | 324 |
| RASQSVSSTLA | 325 |
| RASQSVSSFLA | 326 |
| RASQSVSSYIA | 327 |
| RASQSVSSYVA | 328 |
| RASQSVSSYAA | 329 |
| RASQSVSSYMA | 330 |
| RASQSVSSYLV | 331 |
| RASQSVSSYLL | 332 |
| RASQSVSSYLI | 333 |
| RASQSVSSYLM | 334 |

As used herein, a "CDRL2 that consists essentially of the amino acid sequence set forth in SEQ ID NO:49" is a CDRL2 that has zero, one, or two amino acid substitutions within SEQ ID NO:49, that has zero, one, two, three, four, or five amino acid residues directly preceding SEQ ID NO:49, and/or that has zero, one, two, three, four, or five amino acid residues directly following SEQ ID NO:49, provided that the CAR maintains its basic ability to bind to CD64. Examples of a CDRL2 that consists essentially of the amino acid sequence set forth in SEQ ID NO:49 include, without limitation, those set forth in Table 12.

TABLE 12

Exemplary CDRL2s that consist essentially of the
amino acid sequence set forth in SEQ ID NO: 49.

| Sequence | SEQ ID NO: |
|---|---|
| EASSRAT | 335 |
| DVSSRAT | 336 |
| DLSSRAT | 337 |
| DISSRAT | 338 |
| DMSSRAT | 339 |
| DATSRAT | 340 |

TABLE 12-continued

Exemplary CDRL2s that consist essentially of the
amino acid sequence set forth in SEQ ID NO: 49.

| Sequence | SEQ ID NO: |
|---|---|
| DACSRAT | 341 |
| DAYSRAT | 342 |
| DASTRAT | 343 |
| DASCRAT | 344 |
| DASYRAT | 345 |
| DASSKAT | 346 |
| DASSHAT | 347 |
| DASSRVT | 348 |
| DASSRLT | 349 |
| DASSRIT | 350 |
| DASSRAS | 351 |
| DASSRAC | 352 |
| DASSRAY | 353 |

As used herein, a "CDRL3 that consists essentially of the amino acid sequence set forth in SEQ ID NO:50" is a CDR3 that has zero, one, or two amino acid substitutions within SEQ ID NO:50, that has zero, one, two, three, four, or five amino acid residues directly preceding SEQ ID NO:50, and/or that has zero, one, two, three, four, or five amino acid residues directly following SEQ ID NO:50, provided that the CAR maintains its basic ability to bind to CD64. Examples of a CDRL3 that consists essentially of the amino acid sequence set forth in SEQ ID NO:50 include, without limitation, those set forth in Table 13.

TABLE 13

Exemplary CDR3s that consist essentially of the
amino acid sequence set forth in SEQ ID NO: 50.

| Sequence | SEQ ID NO: |
|---|---|
| NLRSNWPPYT | 354 |
| PLRSNWPPYT | 355 |
| QIRSNWPPYT | 356 |
| QVRSNWPPYT | 357 |
| QARSNWPPYT | 358 |
| QLKSNWPPYT | 359 |
| QLHSNWPPYT | 360 |
| QLRTNWPPYT | 361 |
| QLRCNWPPYT | 362 |
| QLRYNWPPYT | 363 |
| QLRSQWPPYT | 364 |
| QLRSNFPPYT | 365 |
| QLRSNYPPYT | 366 |
| QLRSNPPPYT | 367 |
| QLRSNWFPYT | 368 |
| QLRSNWQPYT | 369 |
| QLRSNWNPYT | 370 |
| QLRSNWPWYT | 371 |
| QLRSNWWPYT | 372 |
| QLRSNWPNYT | 373 |
| QLRSNWPQYT | 374 |
| QLRSNWPPTT | 375 |

TABLE 13-continued

Exemplary CDR3s that consist essentially of the
amino acid sequence set forth in SEQ ID NO: 50.

| Sequence | SEQ ID NO: |
|---|---|
| QLRSNWPPST | 376 |
| QLRSNWPPFT | 377 |
| QLRSNWPPYS | 378 |
| QLRSNWPPYC | 379 |
| QLRSNWPPYY | 380 |

A representative number of antigen recognition domains of the CARs provided herein are further described in Table 14.

TABLE 14

Representative antigen recognition domains

| | SEQ ID NO(s) of: | | | | | |
|---|---|---|---|---|---|---|
| Clone # (type) | CDRHs 1, 2, and 3 | VH domain Framework Regions | VH domain | CDRLs 1, 2, and 3 | VL domain Framework Regions | VL domain |
| #1 (scFv) | 24, 25, 26 | 27, 28, 29, 30 | 31 | 32, 33, 34 | 35, 36, 37, 38 | 39 |
| #2 (scFv) | 40, 41, 42 | 43, 44, 45, 46 | 47 | 48, 49, 50 | 51, 52, 53, 54 | 55 |

Signal Peptides

In some embodiments, any of the CARs provided herein can further comprise a signal peptide (also known in the art as a signal peptide, signal sequence, signal peptide sequence, leader peptide, and leader peptide sequence). In some embodiments, the first domain of the CAR described herein comprises a signal peptide or a leader peptide sequence. Exemplary signal sequences include but are not limited to a CD8a signal sequence or an IgG signal sequence. In some embodiments, the CAR described herein does not comprise a signal peptide.

In some embodiments, the CAR (e.g., the first domain of the CAR) may comprise a human CD8a signal sequence.

In some embodiments, the CAR (e.g., the first recognition domain of the CAR) may comprise a human IgG signal sequence. In some aspects, the hinge domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 23.

Hinge Domains

In some embodiments, a hinge domain (also known in the art as a spacer region or a stalk region) is located between the antigen recognition domain and the transmembrane domain of the CAR. In particular, stalk regions are used to provide more flexibility and accessibility for the extracellular antigen recognition domain. In some embodiments, a hinge domain may comprise up to about 300 amino acids. In some embodiments, the hinge comprises about 10 to about 100 amino acids in length. In some embodiments, the hinge comprises about 25 to about 50 amino acids in length. In some embodiments, the hinge domain establishes an optimal effector-target inter membrane distance. In some embodiments, the hinge domain provides flexibility for antigen recognition domain to bind the target antigen. Any protein that is stable and/or dimerizes can serve this purpose.

A hinge domain may be derived from all or part of naturally occurring molecules, such as from all or part of the extracellular region of CD8α or CD28, or from all or part of an antibody heavy-chain constant region. Alternatively, the hinge domain may be a synthetic sequence that corresponds to a naturally occurring hinge sequence or may be an entirely synthetic hinge sequence.

In some embodiments, the hinge domain is a part of human CD8α chain (e.g., NP_001139345.1). In some embodiments, the hinge domain of CARs described herein comprises a subsequence of CD8α or CD28 either in wild-type form or mutated to avoid Fc-receptor binding in particular the hinge domain of any of an CD8a, or a CD28. In some embodiments, the stalk region comprises a human CD8α hinge or a human CD28 hinge.

In some embodiments, the hinge domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 4.

In some embodiments, the hinge domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 8.

Transmembrane Domains

Suitable transmembrane domains for a CAR disclosed herein have the ability to (a) be expressed at the surface of a cell, which is in some embodiments an immune cell such as, for example a T cell, and/or (b) interact with the ligand-binding domain and intracellular signaling domain for directing cellular response of an immune cell against a predefined target cell. The transmembrane domain can be derived either from a natural or from a synthetic source. The transmembrane domain can be derived from any membrane-bound or transmembrane protein. The transmembrane domains can include the transmembrane region(s) of CD8α and/or CD28. In some embodiments, the transmembrane domain comprises a CD8α transmembrane domain. In some embodiments, the transmembrane domain comprises a CD28 transmembrane domain.

Alternatively, the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the intracellular domain of a CAR. In some embodiments, the linker is a glycine-serine linker.

In some embodiments, the transmembrane domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 5.

In some embodiments, the transmembrane domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 9.

Costimulatory Domains

The intracellular domain of a CAR provided herein may comprise one or more costimulatory domains. The costimulatory domains can include a 4-1BB (CD137) and/or a CD28 costimulatory domain, or a fragment thereof, or a combination thereof. In some embodiments, a CAR described herein comprises a CD28 costimulatory domain or a fragment thereof. In some embodiments, a CAR described herein comprises a 4-1BB (CD137) costimulatory domain or a fragment thereof.

In some embodiments, the costimulatory domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 6.

In some embodiments, the costimulatory domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 10.

Activation Domains

In some embodiments, the activation domain of a CAR disclosed herein is responsible for activation of at least one of the normal effector functions of the immune cell (e.g. T cell) in which the CAR is expressed. The terms "intracellular signaling domain" or "intracellular domain" are used interchangeably and refer to a domain that comprises a co-stimulatory domain and/or an activation domain. The term "effector function" refers to a specialized function of a cell. Effector function of a T-cell, for example, may be cytolytic activity or helper activity including the secretion of cytokines. The term "activation domain" refers to the portion of a protein which transduces the effector function signal and directs the cell to perform a specialized function. While usually an entire activation domain can be employed, in many cases it is not necessary to use the entire chain. To the extent that a truncated portion of the activation domain is used, such truncated portion may be used in place of the intact chain as long as it transduces the effector function signal. The term activation domain is thus meant to include any truncated portion of the activation domain sufficient to transduce the effector function signal. In some embodiments, the activation domain further comprises a signaling domain for T-cell activation. In some instances, the signaling domain for T-cell activation comprises an intracellular domain derived from CD3ξ (CD3zeta; CD3z). In some embodiments, the CAR described herein comprises at least one (e.g., one, two, three, or more) activation domains selected from a CD3ξ or a fragment thereof. In some embodiments, the CAR described herein has an activation domain comprising a domain derived from CD3ξ CD3zeta; CD3z).

In some embodiments, the activation domain of a CAR of the present disclosure can comprise, consist essentially of, or consist of an amino acid sequence having at least 65%, 70%, 75%, 80%, 85%, 90%, 95%, 96%, 97%, 98%, 99%, or 100% (or any percentage in between) identical to SEQ ID NO: 7.

In some embodiments, the CD3zeta activation domain comprises a mutation in an ITAM domain. Examples of mutations in ITAM domains of CD3zeta are provided in Feucht et al., *Nat Med.* 2019; 25(1): 82-88. In some embodiments, each of the two tyrosine residues in one or more of ITAM1, ITAM2, or ITAM3 domains of the CD3zeta activation domain are point-mutated to a phenylalanine residue.

In some embodiments, the CD3zeta activation domain comprises a deletion of one or more of the ITAM1, ITAM2, or ITAM3 domains.

Table 15 provides exemplary amino acid sequences of the domains which can be used in the CARs described herein. In some embodiments, a CAR provided herein comprises one or more domains described in Table 15, or a fragment or portion thereof.

TABLE 15

Exemplary Amino Acid Sequences of CAR Domains

| Exemplary CAR domains | Amino Acid Sequence | SEQ ID NO: |
|---|---|---|
| SIGNAL PEPTIDE | | |
| human CD8alpha signal sequence | MALPVTALLLPLALLLHAARP | 23 |
| HINGES | | |
| human CD8alpha hinge domain | TTTPAPRPPTPAPTIASQPLSLR PEACRPAAGGAVHTRGLDFACD | 4 |
| human CD28 hinge domain | IEVMYPPPYLDNEKSNGTI IHVKGKHLCPSPLFPGPSKP | 8 |
| TRANSMEMBRANE | | |
| human CD8alpha transmembrane domain | IYIWAPLAGTCGVLLLSLVITLYC | 5 |
| human CD28 transmembrane domain | FWVLVVVGGVLACYS LLVTVAFIIFWV | 9 |
| COSTIMULATORY DOMAINS | | |
| human 4-1BB costimulatory domain | KRGRKKLLYIFKQPFMRPVQTT QEEDGCCRFPEEEEGGCEL | 6 |
| human CD28 costimulatory domain | RSKRSRLLHSDYMNMTPRRPG PTRKHYQPYAPPRDFAAYRS | 10 |
| ACTIVATION DOMAINS | | |
| human CD3zeta intracellular signaling domain | RVKFSRSADAPAYQQGQNQLYNE LNLGRREEYDVLDKRRGRDPEM GGKPRRKNPQEGLYNELQKDKMA EAYSEIGMKGERRRGKGHDGLY QGLSTATKDTYDALHMQALPPR | 7 |

Nucleic Acids of the Present Disclosure

Nucleic acids encoding any of the CARs described herein are also provided. Nucleic acids encoding the CAR may be humanized. In some embodiments, the nucleic acid encoding a CAR provided herein is codon-optimized for expression in human cells. In some embodiments, the disclosure provides a full-length CAR cDNA or coding region. Included in the scope of the invention are nucleic acid sequences that encode functional portions of the CAR described herein. Functional portions encompass, for example, those parts of a CAR that retain the ability to recognize target cells, or detect, treat, or prevent a disease, to a similar extent, the same extent, or to a higher extent, as the parent CAR.

Exemplary Anti-CD64 CAR Constructs

Disclosed herein are CARs that specifically bind to CD64. In some embodiments, the CAR comprises an antigen recognition domain that specifically binds human CD64, a hinge domain comprising or consisting of a CD8α hinge domain or a CD28 hinge domain, a transmembrane domain comprising or consisting of a CD8α transmembrane domain or a CD28 transmembrane domain; a costimulatory domain comprising or consisting of a 4-1BB costimulatory domain or a CD28 costimulatory domain; and an intracellular signaling domain comprising or consisting of a CD3zeta activation domain. Also disclosed herein are nucleic acid sequences encoding said CARs. In some embodiments, a T cell or population of T cells described herein is genetically modified to express at least one of the exemplary anti-CD64 CAR constructs described herein.

611 scfv CAR Constructs

An exemplary anti-CD64 CAR, "611-41BBz", amino acid sequence is shown below. (CD8α signal peptide, CD64 scFv (611), CD8α hinge, CD8α transmembrane domain, 4-1BB signaling domain, CD3z signaling domain)

(SEQ ID NO: 11)
*MALPVTALLLPLALLLHAARP*QVQLVEAGGGVVQPGRSLRLSCAASGFI

FSGYGMHWVRQAPGKGLEWVTVIWYDGSNKYYADSVKGRFTISRDNSKN

TLYLQMNSLRAEDTAVYYCARDTGDRFFDYWGQGTLVTVSSGGGGSGGG

GSGGGGSEIVLTQSPATLSLSPGERATLSCRASQSVSSYLAWYQQKPGQ

APRLLIYDASSRATGIPARFGGSGSGTDFTLTISSLEPEDFAVYYCQLR

SNWPPYTFGQGTKLEIKTSTTTPAPRPPTPAPTIASQPLSLRPEACRPA

AGGAVHTRGLDFACD*IYIWAPLAGTCGVLLLSLVITLYC*KRGRKKLLYI*

*FKQPFMRPVQTTQEEDGCSCRFPEEEEGGCEL*SRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPR*

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 11.

An exemplary anti-CD64 CAR, "611-41BBz", polynucleotide sequence is shown below. (CD8α signal peptide, CD64 scFv (611), CD8α hinge, CD8α transmembrane domain, 4-1BB signaling domain, CD3z signaling domain)

(SEQ ID NO: 17)
ATGGCTTTGCCTGTTACAGCTCTGCTGCTGCCCCTGGCTCTGCTT

CTGCATGCTGCTAGACCTCAGGTGCAGCTGGTTGAAGCTGGTGGC

GGAGTTGTGCAGCCTGGCAGATCTCTGAGACTGAGCTGTGCCGCC

AGCGGCTTCATCTTTAGCGGCTATGGCATGCACTGGGTCCGACAG

GCACCTGGCAAAGGCCTGGAATGGGTCACCGTGATTTGGTACGAC

GGCAGCAACAAGTACTACGCCGACAGCGTGAAGGGCAGATTCACC

ATCAGCCGGGACAACAGCAAGAACACCCTGTACCTGCAGATGAAC

AGCCTGAGAGCCGAGGACACCGCCGTGTACTACTGTGCCAGAGAC

ACCGGCGACAGATTCTTCGACTATTGGGGCCAGGGCACCCTCGTG

ACAGTTTCTTCTGGCGGCGGAGGATCTGGCGGAGGTGGAAGCGGA

GGCGGTGGATCTGAAATCGTGCTGACACAGAGCCCCGCCACACTG

TCACTTTCTCCAGGCGAAAGAGCCACACTGAGCTGCAGAGCCTCT

CAGAGCGTGTCCTCTTACCTGGCCTGGTATCAGCAGAAGCCTGGA

CAGGCTCCCCGGCTGCTGATCTACGATGCTTCTAGCAGAGCTACA

GGCATCCCCGCCAGATTTGGCGGCTCTGGCTCTGGCACTGATTTC

ACCCTGACCATAAGCAGCCTGGAACCTGAGGACTTTGCCGTGTAT

TATTGCCAGCTGCGGAGCAACTGGCCTCCTTACACATTTGGCCAG

```
GGGACCAAGCTGGAAATCAAGACTAGTACCACCACACCAGCTCCT

CGGCCACCTACTCCAGCTCCAACAATTGCCAGCCAGCCTCTGTCT

CTGAGGCCCGAAGCTTGTAGACCTGCTGCTGGCGGAGCCGTGCAT

ACAAGAGGACTGGATTTCGCCTGCGACATCTACATCTGGGCCCCT

CTGGCTGGAACATGTGGCGTGCTGCTGCTCAGCCTGGTCATCACC

CTGTACTGCAAGCGGGGCAGAAAGAAGCTGCTGTACATCTTCAAG

CAGCCCTTCATGCGGCCCGTGCAGACCACACAAGAGGAAGATGGC

TGCTCCTGCAGATTCCCCGAGGAAGAAGAAGGCGGCTGCGAGCTG

TCTAGAGTGAAGTTCAGCAGAAGCGCCGACGCTCCTGCCTATCAG

CAGGGACAGAATCAGCTGTACAACGAGCTGAACCTGGGCGCAGA

GAAGAGTACGACGTGCTGGACAAGAGAAGAGGCAGGGACCCTGAG

ATGGGCGGCAAGCCCAGAAGAAAGAACCCTCAAGAGGGCCTGTAT

AATGAGCTGCAGAAAGACAAGATGGCCGAGGCCTACAGCGAGATC

GGAATGAAGGGCGAACGCAGAAGAGGAAAGGGCCACGACGGACTG

TATCAGGGCCTGAGCACAGCCACCAAGGACACCTATGATGCCCTG

CACATGCAGGCACTGCCTCCAAGATGA
```

In some embodiments, the anti-CD64 CAR provided herein is encoded by a polynucleotide sequence comprising, consisting essentially of, or consisting of a nucleic acid sequence having at least 90%, 91%, 92%, 93%, 94%, 95%, 96%, 97%, 98%, 99%, or 100% identity with the nucleic acid sequence of SEQ ID NO: 17.

An exemplary anti-CD64 CAR, "611-CD28z", amino acid sequence is shown below. (CD8α signal peptide, CD64 scFv (611), CD28 hinge, CD28 transmembrane domain, CD28 signaling domain, CD3z signaling domain)

```
                                       (SEQ ID NO: 14)
MALPVTALLLPLALLLHAARPQVQLVEAGGGVVQPGRSLRLSCAA

SGFIFSGYGMHWVRQAPGKGLEWVTVIWYDGSNKYYADSVKGRFT

ISRDNSKNTLYLQMNSLRAEDTAVYYCARDTGDRFFDYWGQGTLV

TVSSGGGGSGGGGSGGGGSEIVLTQSPATLSLSPGERATLSCRAS

QSVSSYLAWYQQKPGQAPRLLIYDASSRATGIPARFGGSGSGTDF

TLTISSLEPEDFAVYYCQLRSNWPPYTFGQGTKLEIKTSGAAAIE

VMYPPPYLDNEKSNGTIIHVKGKHLCPSPLFPGPSKPFWVLVVVG

GVLACYSLLVTVAFIIFWVRSKRSRLLHSDYMNMTPRRPGPTRKH

YQPYAPPRDFAAYRSRVKFSRSADAPAYQQGQNQLYNELNLGRRE

EYDVLDKRRGRDPEMGGKPRRKNPQEGLYNELQKDKMAEAYSEIG

MKGERRRGKGHDGLYQGLSTATKDTYDALHMQALPPR*
```

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 14.

An exemplary anti-CD64 CAR, "611-CD28z", polynucleotide sequence is shown below. (CD8α signal peptide, CD64 scFv (611), CD28 hinge, CD28 transmembrane domain, CD28 signaling domain, CD3z signaling domain)

```
                                       (SEQ ID NO: 18)
ATGGCTTTGCCTGTTACAGCTCTGCTGCTGCCCCTGGCTCTGCTT

CTGCATGCTGCTAGACCTCAGGTGCAGCTGGTTGAAGCTGGTGGC

GGAGTTGTGCAGCCTGGCAGATCTCTGAGACTGAGCTGTGCCGCC

AGCGGCTTCATCTTTAGCGGCTATGGCATGCACTGGGTCCGACAG

GCACCTGGCAAAGGCCTGGAATGGGTCACCGTGATTTGGTACGAC

GGCAGCAACAAGTACTACGCCGACAGCGTGAAGGGCAGATTCACC

ATCAGCCGGGACAACAGCAAGAACACCCTGTACCTGCAGATGAAC

AGCCTGAGAGCCGAGGACACCGCCGTGTACTACTGTGCCAGAGAC

ACCGGCGACAGATTCTTCGACTATTGGGGCCAGGGCACCCTCGTG

ACAGTTTCTTCTGGCGGCGGAGGATCTGGCGGAGGTGGAAGCGGA

GGCGGTGGATCTGAAATCGTGCTGACACAGAGCCCCGCCACACTG

TCACTTTCTCCAGGCGAAAGAGCCACACTGAGCTGCAGAGCCTCT

CAGAGCGTGTCCTCTTACCTGGCCTGGTATCAGCAGAAGCCTGGA

CAGGCTCCCCGGCTGCTGATCTACGATGCTTCTAGCAGAGCTACA

GGCATCCCCGCCAGATTTGGCGGCTCTGGCTCTGGCACTGATTTC

ACCCTGACCATAAGCAGCCTGGAACCTGAGGACTTTGCCGTGTAT

TATTGCCAGCTGCGGAGCAACTGGCCTCCTTACACATTTGGCCAG

GGGACCAAGCTGGAAATCAAGACTAGTGGCGCCGCTGCTATTGAA

GTGATGTACCCTCCTCCTTACCTGGACAACGAGAAGTCCAACGGC

ACCATCATCCACGTGAAGGGCAAGCACCTGTGTCCTTCTCCACTG

TTCCCCGGACCTAGCAAGCCTTTCTGGGTGCTCGTTGTTGTTGGC

GGCGTGCTGGCCTGTTATTCCCTGCTGGTTACCGTGGCCTTCATC

ATCTTTTGGGTCCGAAGCAAGCGGAGCCGGCTGCTGCACAGCGAC

TACATGAACATGACCCCTAGACGGCCCGGACCAACCAGAAAGCAC

TACCAGCCTTACGCTCCTCCTAGAGACTTCGCCGCCTACCGGTCT

AGAGTGAAGTTCAGCAGATCCGCCGACGCTCCTGCCTATCAGCAG

GGACAGAACCAGCTGTACAACGAGCTGAACCTGGGCGAAGAGAA

GAGTACGACGTGCTGGACAAGCGGAGAGGCAGAGATCCTGAGATG

GGCGGCAAGCCCAGACGGAAGAATCCTCAAGAGGGCCTGTATAAT

GAGCTGCAGAAAGACAAGATGGCCGAGGCCTACAGCGAGATCGGA

ATGAAGGGCGAGCGCAGAAGAGGCAAGGGACACGATGGACTGTAC

CAGGGCCTGAGCACCGCCACCAAGGATACCTATGATGCCCTGCAC

ATGCAGGCCCTGCCTCCAAGATGA
```

In some embodiments, the anti-CD64 CAR provided herein is encoded by a polynucleotide sequence comprising, consisting essentially of, or consisting of a nucleic acid sequence having at least 90%, 91%, 92%, 93%, 94%, 95%, 96%, 97%, 98%, 99%, or 100% identity with the nucleic acid sequence of SEQ ID NO: 18.

H22 scfv CAR Constructs

An exemplary anti-CD64 CAR, "H22-41BBz", amino acid sequence is shown below. (CD8α signal peptide, CD64 scFv (H22), CD8α hinge, CD8α transmembrane domain, 4-1B signaling domain, CD3z signaling domain)

(SEQ ID NO: 12)
MALPVTALLLPLALLLHAARPQVQLVESGGGWQPGRSLRLSCSSS
GFIFSDNYMYWVRQAPGKGLEWVATISDGGSYTYYPDSVKGRFTI
SRDNSKNTLFLQMDSLRPEDTGVYFCARGYYRYEGAMDYWGQGTP
VTVSSGGGGSGGGGSGGGGSDIQLTQSPSSLSASVGDRVTITCKS
SQSVLYSSNQKNYLAWYQQKPGKAPKLLIYWASTRESGVPSRFSG
SGSGTDFTFTISSLQPEDIATYYCHQYLSSWTFGQGTKLEIKTST
TTPAPRPPTPAPTIASQPLSLRPEACRPAAGGAVHTRGLDFACDI
YIWAPLAGTCGVLLLSLVITLYC*KRGRKKLLYIFKQPFMRPVQTT*
*QEEDGCSCRFPEEEEGGCEL*SRVKFSRSADAPAYQQGQNQLYNEL
NLGRREEYDVLDKRRGRDPEMGGKPRRKNPQEGLYNELQKDKMAE
AYSEIGMKGERRRGKGHDGLYQGLSTATKDTYDALHMQALPPR*

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 12.

An exemplary anti-CD64 CAR, "H22-41BBz", polynucleotide sequence is shown below. (CD8α signal peptide, CD64 scFv (H22), CD8α hinge, CD8α transmembrane domain, 4-1BB signaling domain, CD3z signaling domain)

(SEQ ID NO: 19)
ATGGCTTTGCCTGTTACAGCTCTGCTGCTGCCCCTGGCTCTGCTT
CTGCATGCTGCTAGACCTCAGGTGCAGCTGGTGGAATCTGGCGGA
GGATGGCAGCCTGGCAGAAGCCTGAGACTGAGCTGTAGCAGCAGC
GGCTTCATCTTCAGCGACAACTACATGTACTGGGTCCGACAGGCC
CCTGGCAAAGGCCTTGAATGGGTCGCCACAATCTCTGACGGCGGC
AGCTACACCTACTATCCCGACTCTGTGAAGGGCAGATTCACCATC
AGCCGGGACAACAGCAAGAATACCCTGTTCCTGCAGATGGACAGC
CTGCGGCCTGAAGATACCGGCGTGTACTTTTGCGCCAGAGGCTAC
TACAGATACGAGGGCGCCATGGACTATTGGGGCCAGGGAACACCT
GTGACCGTTTCTAGCGGCGGAGGTGGAAGCGGAGGCGGAGGTAGT
GGTGGTGGCGGATCTGACATTCAGCTGACACAGAGCCCTAGCAGC
CTGTCTGCCTCTGTGGGCGACAGAGTGACCATCACATGCAAGAGC
AGCCAGAGCGTGCTGTACTCCAGCAACCAGAAGAACTACCTGGCC
TGGTATCAGCAGAAGCCCGGCAAGGCTCCTAAGCTGCTGATCTAC
TGGGCCAGCACCAGAGAAAGCGGCGTGCCAAGCAGATTTTCTGGC
AGCGGCTCTGGCACCGACTTCACCTTCACCATAAGCTCCCTGCAG
CCTGAGGACATTGCCACCTACTACTGCCACCAGTACCTGAGCAGC
TGGACCTTTGGCCAGGGCACCAAGCTGGAAATCAAGACTAGTACC
ACCACACCAGCTCCTCGGCCACCTACTCCAGCTCCAACAATTGCC
AGCCAGCCTCTGTCTCTGAGGCCCGAAGCTTGTAGACCTGCTGCT
GGCGGAGCCGTGCATACAAGAGGACTGGATTTCGCCTGCGACATC
TACATCTGGGCCCCTCTGGCTGGAACATGTGGCGTGCTGCTGCTC

-continued
AGCCTGGTCATCACCCTGTACTGCAAGCGGGGCAGAAAGAAGCTG
CTGTACATCTTCAAGCAGCCCTTCATGCGGCCCGTGCAGACCACA
CAAGAGGAAGATGGCTGCTCCTGCAGATTCCCCGAGGAAGAAGAA
GGCGGCTGCGAGCTGTCTAGAGTGAAGTTCAGCAGAAGCGCCGAC
GCTCCTGCCTATCAGCAGGGACAGAATCAGCTGTACAACGAGCTG
AACCTGGGGCGCAGAGAAGAGTACGACGTGCTGGACAAGAGAAGA
GGCAGGGACCCTGAGATGGGCGGCAAGCCCAGAAGAAAGAACCCT
CAAGAGGGCCTGTATAATGAGCTGCAGAAAGACAAGATGGCCGAG
GCCTACAGCGAGATCGGAATGAAGGGCAACGCAGAAGAGGAAAG
GGCCACGACGGACTGTATCAGGGCCTGAGCACAGCCACCAAGGAC
ACCTATGATGCCCTGCACATGCAGGCACTGCCTCCAAGATGA In some embodiments, the anti-CD64 CAR provided herein is encoded by a polynucleotide sequence comprising, consisting essentially of, or consisting of a nucleic acid sequence having at least 90%, 91%, 92%, 93%, 94%, 95%, 96%, 97%, 98%, 99%, or 100% identity with the nucleic acid sequence of SEQ ID NO: 19.

An exemplary anti-CD64 CAR, "H22-CD28z", amino acid sequence is shown below. (CD8α signal peptide, CD64 scFv (H22), CD28 hinge, CD28 transmembrane domain, CD28 signaling domain, CD3z signaling domain)

(SEQ ID NO: 15)
MALPVTALLLPLALLLHAARPQVQLVESGGGWQPGRSLRLSCSSS
GFIFSDNYMYWVRQAPGKGLEWVATISDGGSYTYYPDSVKGRFTI
SRDNSKNTLFLQMDSLRPEDTGVYFCARGYYRYEGAMDYWGQGTP
VTVSSGGGGSGGGGSGGGGSDIQLTQSPSSLSASVGDRVTITCKS
SQSVLYSSNQKNYLAWYQQKPGKAPKLLIYWASTRESGVPSRFSG
SGSGTDFTFTISSLQPEDIATYYCHQYLSSWTFGQGTKLEIKTSG
AAAIEVMYPPPYLDNEKSNGTIIHVKGKHLCPSPLFPGPSKPFWV
LVVVGGVLACYSLLVTVAFIIFWVRSKRSRLLHSDYMNMTPRRPG
PTRKHYQPYAPPRDFAAYRSRVKFSRSADAPAYQQGQNQLYNELN
LGRREEYDVLDKRRGRDPEMGGKPRRKNPQEGLYNELQKDKMAEA
YSEIGMKGERRRGKGHDGLYQGLSTATKDTYDALHMQALPPR*

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 15.

An exemplary anti-CD64 CAR, "H22-CD28z", polynucleotide sequence is shown below. (CD8α signal peptide, CD64 scFv (H22), CD28 hinge, CD28 transmembrane domain, CD28 signaling domain, CD3z signaling domain)

(SEQ ID NO: 20)
ATGGCTTTGCCTGTTACAGCTCTGCTGCTGCCCCTGGCTCTGCTT
CTGCATGCTGCTAGACCTCAGGTGCAGCTGGTGGAATCTGGCGGA
GGATGGCAGCCTGGCAGAAGCCTGAGACTGAGCTGTAGCAGCAGC

```
GGCTTCATCTTCAGCGACAACTACATGTACTGGGTCCGACAGGCC
CCTGGCAAAGGCCTTGAATGGGTCGCCACAATCTCTGACGGCGGC
AGCTACACCTACTATCCCGACTCTGTGAAGGGCAGATTCACCATC
AGCCGGGACAACAGCAAGAATACCCTGTTCCTGCAGATGGACAGC
CTGCGGCCTGAAGATACCGGCGTGTACTTTTGCGCCAGAGGCTAC
TACAGATACGAGGGCGCCATGGACTATTGGGGCCAGGGAACACCT
GTGACCGTTTCTAGCGGCGGAGGTGGAAGCGGAGGCGGAGGTAGT
GGTGGTGGCGGATCTGACATTCAGCTGACACAGAGCCCTAGCAGC
CTGTCTGCCTCTGTGGGCGACAGAGTGACCATCACATGCAAGAGC
AGCCAGAGCGTGCTGTACTCCAGCAACCAGAAGAACTACCTGGCC
TGGTATCAGCAGAAGCCCGGCAAGGCTCCTAAGCTGCTGATCTAC
TGGGCCAGCACCAGAGAAAGCGGCGTGCCAAGCAGATTTTCTGGC
AGCGGCTCTGGCACCGACTTCACCTTCACCATAAGCTCCCTGCAG
CCTGAGGACATTGCCACCTACTACTGCCACCAGTACCTGAGCAGC
TGGACCTTTGGCCAGGGCACCAAGCTGGAAATCAAGACTAGTGGC
GCCGCTGCTATTGAAGTGATGTACCCTCCTCCTTACCTGGACAAC
GAGAAGTCCAACGGCACCATCATCCACGTGAAGGGCAAGCACCTG
TGTCCTTCTCCACTGTTCCCCGGACCTAGCAAGCCTTTCTGGGTG
CTCGTTGTTGTTGGCGGCGTGCTGGCCTGTTATTCCCTGCTGGTT
ACCGTGGCCTTCATCATCTTTTGGGTCCGAAGCAAGCGGAGCCGG
CTGCTGCACAGCGACTACATGAACATGACCCCTAGACGGCCCGGA
CCAACCAGAAAGCACTACCAGCCTTACGCTCCTCCTAGAGACTTC
GCCGCCTACCGGTCTAGAGTGAAGTTCAGCAGATCCGCCGACGCT
CCTGCCTATCAGCAGGGACAGAACCAGCTGTACAACGAGCTGAAC
CTGGGGAGAAGAGAAGAGTACGACGTGCTGGACAAGCGGAGAGGC
AGAGATCCTGAGATGGGCGGCAAGCCCAGACGGAAGAATCCTCAA
GAGGGCCTGTATAATGAGCTGCAGAAAGACAAGATGGCCGAGGCC
TACAGCGAGATCGGAATGAAGGGCGAGCGCAGAAGAGGCAAGGGA
CACGATGGACTGTACCAGGGCCTGAGCACCGCCACCAAGGATACC
TATGATGCCCTGCACATGCAGGCCCTGCCTCCAAGATGA
```

In some embodiments, the anti-CD64 CAR provided herein is encoded by a polynucleotide sequence comprising, consisting essentially of, or consisting of a nucleic acid sequence having at least 90%, 91%, 92%, 93%, 94%, 95%, 96%, 97%, 98%, 99%, or 100% identity with the nucleic acid sequence of SEQ ID NO: 20.

M22 scfv CAR Constructs

An exemplary anti-CD64 CAR, "M22-41BBz", amino acid sequence is shown below. (CD8α signal peptide, CD64 scFv (M22), CD8α hinge, CD8α transmembrane domain, 4-1BB signaling domain, CD3z signaling domain)

```
                                        (SEQ ID NO: 13)
MALPVTALLLPLALLLHAARPEVQLVESGGGLVKPGGSLRLSCVA

SGFIFSDNYMYWVRQTPEKRLEWVATISDGGSYTYYPDSVKGRFT

ISRDNAKNNLYLQMSSLKSEDTAIYYCARGYYRYEGAMDYWGQGT

SVTVSSGGGGSGGGGSGGGGSNIVMTQSPSSLAVSAGEKVTMSCK

SSQSVLYSSNQKNYLAWYQQKPGQSPKLLIYWASTRESGVPDRFT

GSGSGTDFTLTISSVQAEDLAVYYCHQYLSSWTFGGGTKLEIKTS

TTTPAPRPPTPAPTIASQPLSLRPEACRPAAGGAVHTRGLDFACD

IYIWAPLAGTCGVLLLSLVITLYCKRGRKKLLYIFKQPFMRPVQT

TQEEDGCSCRFPEEEEGGCELSRVKFSRSADAPAYQQGQNQLYNE

LNLGRREEYDVLDKRRGRDPEMGGKPRRKNPQEGLYNELQKDKMA

EAYSEIGMKGERRRGKGHDGLYQGLSTATKDTYDALHMQALPPR*
```

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 13.

An exemplary anti-CD64 CAR, "M22-41BBz", polynucleotide sequence is shown below. (CD8α signal peptide, CD64 scFv (M22), CD8α hinge, CD8α transmembrane domain, 4-1BB signaling domain, CD3z signaling domain)

```
                                        (SEQ ID NO: 21)
ATGGCTCTGCCTGTTACAGCTCTGCTGCTGCCTCTGGCTCTGCTT

CTGCATGCCGCTAGACCTGAGGTGCAGCTGGTTGAATCTGGCGGC

GGACTTGTGAAGCCTGGCGGATCTCTGAGACTGAGCTGTGTGGCC

AGCGGCTTCATCTTCAGCGACAACTACATGTACTGGGTCCGACAG

ACCCCTGAGAAGCGGCTGGAATGGGTCGCCACAATCTCTGATGGC

GGCAGCTACACCTACTATCCCGACAGCGTGAAGGGCAGATTCACC

ATCAGCCGGGACAACGCCAAGAACAACCTGTACCTGCAGATGAGC

AGCCTGAAGTCCGAGGACACCGCCATCTACTACTGCGCCAGAGGC

TACTACAGATACGAGGGCGCCATGGACTATTGGGGCCAGGGAACA

AGCGTGACAGTGTCTAGCGGAGGCGGAGGATCAGGTGGCGGTGGA

TCTGGCGGTGGCGGCTCTAATATCGTGATGACACAGAGCCCTAGC

AGCCTGGCTGTGTCTGCCGGCGAGAAGTGACCATGAGCTGCAAG

AGCAGCCAGAGCGTGCTGTACTCCAGCAACCAGAAGAACTACCTG

GCCTGGTATCAGCAGAAGCCCGGACAGTCTCCCAAGCTGCTGATC

TACTGGGCCAGCACCAGAGAAAGCGGCGTGCCCGATAGATTCACA

GGCAGCGGCTCTGGCACCGACTTCACCCTGACAATCAGCTCTGTG

CAGGCCGAGGATCTGGCCGTGTACTACTGTCACCAGTACCTGAGC

AGCTGGACCTTTGGCGGAGGCACCAAGCTGGAAATCAAGACTAGT

ACCACCACACCAGCTCCTCGGCCACCTACTCCAGCTCAACAATT

GCCAGCCAGCCTCTGTCTCTGAGGCCCGAAGCTTGTAGACCTGCT

GCTGGCGGAGCCGTGCATACAAGAGGACTGGATTTCGCCTGCGAC

ATCTACATCTGGGCCCCTCTGGCTGGAACATGGCGTGCTGCTG

CTCAGCCTGGTCATCACCCTGTACTGCAAGCGGGGCAGAAAGAAG

CTGCTGTACATCTTCAAGCAGCCCTTCATGCGGCCCGTGCAGACC

ACACAAGAGGAAGATGGCTGCTCCTGCAGATTCCCCGAGGAAGAA
```

```
GAAGGCGGCTGCGAGCTGTCTAGAGTGAAGTTCAGCAGAAGCGCC

GACGCTCCTGCCTATCAGCAGGGACAGAATCAGCTGTACAACGAG

CTGAACCTGGGGCGCAGAGAAGAGTACGACGTGCTGGACAAGAGA

AGAGGCAGGGACCCTGAGATGGGCGGCAAGCCCAGAAGAAAGAAC

CCTCAAGAGGGCCTGTATAATGAGCTGCAGAAAGACAAGATGGCC

GAGGCCTACAGCGAGATCGGAATGAAGGGCGAACGCAGAAGAGGA

AAGGGCCACGACGGACTGTATCAGGGCCTGAGCACAGCCACCAAG

GACACCTATGATGCCCTGCACATGCAGGCACTGCCTCCAAGATGA
```

In some embodiments, the anti-CD64 CAR provided herein is encoded by a polynucleotide sequence comprising, consisting essentially of, or consisting of a nucleic acid sequence having at least 90%, 91%, 92%, 93%, 94%, 95%, 96%, 97%, 98%, 99%, or 100% identity with the nucleic acid sequence of SEQ ID NO: 21.

An exemplary anti-CD64 CAR, "M22-CD28z", amino acid sequence is shown below. (CD8α signal peptide, CD64 scFv (M22), CD28 hinge, CD28 transmembrane domain, CD28 signaling domain, CD3z signaling domain)

```
                                       (SEQ ID NO: 16)
MALPVTALLLPLALLLHAARPEVQLVESGGGLVKPGGSLRLSCVA

SGFIFSDNYMYWVRQTPEKRLEWVATISDGGSYTYYPDSVKGRFT

ISRDNAKNNLYLQMSSLKSEDTAIYYCARGYYRYEGAMDYWGQGT

SVTVSSGGGGSGGGGSGGGGSNIVMTQSPSSLAVSAGEKVTMSCK

SSQSVLYSSNQKNYLAWYQQKPGQSPKLLIYWASTRESGVPDRFT

GSGSGTDFTLTISSVQAEDLAVYYCHQYLSSWTFGGGTKLEIKTS

GAAAIEVMYPPPYLDNEKSNGTIIHVKGKHLCPSPLFPGPSKPFW

VLVVVGGVLACYSLLVTVAFIIFWVRSKRSRLLHSDYMNMTPRRP

GPTRKHYQPYAPPRDFAAYRSRVKFSRSADAPAYQQGQNQLYNEL

NLGRREEYDVLDKRRGRDPEMGGKPRRKNPQEGLYNELQKDKMAE

AYSEIGMKGERRRGKGHDGLYQGLSTATKDTYDALHMQALPPR*
```

In some embodiments, the anti-CD64 CAR provided herein may comprise, consist essentially of, or consist of an amino acid sequence having at least 90%, 91%, 92%, 93%, 94%, 95%, 96%, 97%, 98%, 99%, or 100% identity with the amino acid sequence of SEQ ID NO: 16.

An exemplary anti-CD64 CAR, "M22-CD28z", polynucleotide sequence is shown below. (CD8α signal peptide, CD64 scFv (M22), CD28 hinge, CD28 transmembrane domain, CD28 signaling domain, CD3z signaling domain)

```
                                       (SEQ ID NO: 22)
ATGGCTCTGCCTGTTACAGCTCTGCTGCTGCCTCTGGCTCTGCTT

CTGCATGCCGCTAGACCTGAGGTGCAGCTGGTTGAATCTGGCGGC

GGACTTGTGAAGCCTGGCGGATCTCTGAGACTGAGCTGTGTGGCC

AGCGGCTTCATCTTCAGCGACAACTACATGTACTGGGTCCGACAG

ACCCCTGAGAAGCGGCTGGAATGGGTCGCCACAATCTCTGATGGC

GGCAGCTACACCTACTATCCCGACAGCGTGAAGGGCAGATTCACC

ATCAGCCGGGACAACGCCAAGAACAACCTGTACCTGCAGATGAGC

AGCCTGAAGTCCGAGGACACCGCCATCTACTACTGCGCCAGAGGC

TACTACAGATACGAGGGCGCCATGGACTATTGGGGCCAGGGAACA

AGCGTGACAGTGTCTAGCGGAGGCGGAGGATCAGGTGGCGGTGGA

TCTGGCGGTGGCGGCTCTAATATCGTGATGACACAGAGCCCTAGC

AGCCTGGCTGTGTCTGCCGGCGAGAAAGTGACCATGAGCTGCAAG

AGCAGCCAGAGCGTGCTGTACTCCAGCAACCAGAAGAACTACCTG

GCCTGGTATCAGCAGAAGCCCGACAGTCTCCCAAGCTGCTGATC

TACTGGGCCAGCACCAGAGAAAGCGGCGTGCCCGATAGATTCACA

GGCAGCGGCTCTGGCACCGACTTCACCCTGACAATCAGCTCTGTG

CAGGCCGAGGATCTGGCCGTGTACTACTGTCACCAGTACCTGAGC

AGCTGGACCTTTGGCGGAGGCACCAAGCTGGAAATCAAGACTAGT

GGCGCCGCTGCTATTGAAGTGATGTACCCTCCTCCTTACCTGGAC

AACGAGAAGTCCAACGGCACCATCATCCACGTGAAGGGCAAGCAC

CTGTGTCCTTCTCCACTGTTCCCCGGACCTAGCAAGCCTTTCTGG

GTGCTCGTTGTTGTTGGCGGCGTGCTGGCCTGTTATTCCCTGCTG

GTTACCGTGGCCTTCATCATCTTTTGGGTCCGAAGCAAGCGGAGC

CGGCTGCTGCACAGCGACTACATGAACATGACCCCTAGACGGCCC

GGACCAACCAGAAAGCACTACCAGCCTTACGCTCCTCCTAGAGAC

TTCGCCGCCTACCGGTCTAGAGTGAAGTTCAGCAGATCCGCCGAC

GCTCCTGCCTATCAGCAGGGACAGAACCAGCTGTACAACGAGCTG

AACCTGGGGAGAAGAGAAGAGTACGACGTGCTGGACAAGCGGAGA

GGCAGAGATCCTGAGATGGGCGGCAAGCCCAGACGGAAGAATCCT

CAAGAGGGCCTGTATAATGAGCTGCAGAAAGACAAGATGGCCGAG

GCCTACAGCGAGATCGGAATGAAGGGCGAGCGCAGAAGAGGCAAG

GGACACGATGGACTGTACCAGGGCCTGAGCACCGCCACCAAGGAT

ACCTATGATGCCCTGCACATGCAGGCCCTGCCTCCAAGATGA
```

In some embodiments, the anti-CD64 CAR provided herein is encoded by a polynucleotide sequence comprising or consisting of a nucleic acid sequence having at least 90%, 91%, 92%, 93%, 94%, 95%, 96%, 97%, 98%, 99%, or 100% identity with the nucleic acid sequence of SEQ ID NO: 22.

In some embodiments, the genetically engineered cells include additional CARs, including activating or stimulatory CARs, co-stimulatory CARs (see, e.g., PCT Publ. No. WO 2014/055668), and/or inhibitory CARs (iCARs, see, e.g., Fedorov et al., 2013). The CARs generally include an extracellular antigen (or ligand) recognition domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone. For example, once an antigen is recognized by the extracellular antigen recognition domain, the intracellular signaling components transmit an activation signal to the T cell that induces the T cell to destroy a targeted tumor cell.

In embodiments, the CARs described herein contain additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The term "functional variant," as used herein in reference to a CAR, refers to a CAR, a polypeptide, or a protein having substantial or significant sequence identity or similarity to the CAR encoded by a nucleic acid sequence, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized.

As described herein, the amino acid sequences described herein can include amino acid modifications (e.g., the articulated number of amino acid modifications). Such amino acid modifications can include, without limitation, amino acid substitutions, amino acid deletions, amino acid additions, and combinations. In some cases, an amino acid modification can be made to improve the binding and/or contact with an antigen and/or to improve a functional activity of a CAR provided herein. In some cases, an amino acid substitution within an articulated sequence identifier can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution within an articulated sequence identifier can be a non-conservative amino acid substitution. Non-conservative amino acid substitutions can be made by substituting one amino acid residue for another amino acid residue having a dissimilar side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating an amino acid sequence variant (e.g., an amino acid sequence that includes one or more modifications with respect to an articulated sequence identifier) can include site-specific mutagenesis or random mutagenesis (e.g., by PCR) of a nucleic acid encoding the antibody or fragment thereof. See, for example, Zoller, Curr. Opin. Biotechnol. 3: 348-354 (1992). Both naturally occurring and non-naturally occurring amino acids (e.g., artificially-derivatized amino acids) can be used to generate an amino acid sequence variant provided herein.

Immune Cells of the Present Disclosure

The present disclosure provides cells and populations of cells comprising the CAR constructs described above and/or the nucleic acid molecules encoding said CAR constructs.

Accordingly, the present disclosure provides populations of genetically modified immune cells (e.g. T cells) engineered to express a CAR described above and/or a polynucleotide encoding said CAR The immune cells may be T cells (e.g., regulatory T cells, CD4$^+$ T cells, CD8$^+$ T cells, or gamma-delta T cells), NK cells, invariant NK cells, NKT cells, stem cells (e.g., mesenchymal stem cells (MSCs) or induced pluripotent stem (iPSC) cells). In some embodiments, the cells are monocytes or granulocytes, e.g., myeloid cells, macrophages, neutrophils, dendritic cells, mast cells, eosinophils, and/or basophils. Also provided herein are methods of producing and engineering the immune cells and methods of using and administering the cells to a subject, in which case the cells may be autologous or allogeneic. Thus, the immune cells may be used as immunotherapy, such as to target cancer cells.

In some embodiments, the cells comprise one or more nucleic acids introduced via genetic engineering that encode one or more antigen receptors, and genetically engineered products of such nucleic acids. In some embodiments, the nucleic acids are heterologous. In some embodiments, the nucleic acids are not naturally occurring, such as a nucleic acid not found in nature (e.g., chimeric).

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. The isolated immune cells may be used directly, or they can be stored for a period of time, such as by freezing. In some embodiments, the immune cells are isolated from blood, such as peripheral blood or cord blood. In some embodiments, immune cells isolated from cord blood have enhanced immunomodulation capacity, such as measured by CD4-positive or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood. The population of immune cells can be derived from induced pluripotent stem cells (iPSCs) and/or any other stem cell known in the art. In some aspects, the iPSCS and/or stem cells used to derive the population of immune cells can be obtained from a subject in need of therapy or suffering from a disease associate with reduced immune cell activity, thus these IPSCs and/or stem cells will be autologous to the subject in need of therapy. Alternatively, the iPSCs and/or stem cells can be obtained from a donor and therefore be allogeneic to the subject in need of therapy.

When the population of immune cells is obtained from a donor distinct from the subject, the donor is preferably allogeneic, provided the cells obtained are subject-compatible in that they can be introduced into the subject. Allogeneic donor cells are may or may not be human leukocyte antigen (HLA)-compatible. To be rendered subject-compatible, allogeneic cells can be treated to reduce immunogenicity.

T Cells

T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g CD4+ cells), Cytotoxic T cells (also known as TC, cytotoxic T lymphocyte, CTL, T killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Ra+, but they also express large amounts of CD95, IL-2R, CXCR3, and LFA-1, and show numerous functional attributes distinctive of memory cells); (ii) central memory TCM cells express L-selectin and the CCR7, they secrete IL-2, but not IFNg or IL-4, and (iii) effector memory TEM cells, however, do not express L-selectin or CCR7 but produce effector cytokines like IFNg and IL-4), Regulatory T cells (Tregs, suppressor T cells, or CD4+CD25+ regulatory T cells), Natural Killer T cells (NKT) and Gamma Delta T cells.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

CAR Expression Levels

The present disclosure provides a population of engineered T cells, wherein a plurality of the engineered T cells of the population comprise any chimeric stimulatory receptor (CAR) disclosed herein. The present disclosure also provides a composition comprising a population of T cells, wherein a plurality of the T cells of the population comprises a non-naturally occurring CAR comprising, consisting essentially of, or consisting of a chimeric antigen receptor (CAR) comprising an antigen recognition domain that binds to CD64, a transmembrane domain, and an intracellular signaling domain. In some embodiments, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the population comprise any chimeric stimulatory receptor (CAR) disclosed herein. In some embodiments, the CAR polypeptide is expressed at a copy number of at least 1, 2, 3, 4, 5, 6, 7, 8, 9, 10, 20, 30, 40, 50, 60, 70, 80, 90, or 100 copies per cell. In some embodiments, the nucleic acid encoding the CAR is integrated into the genome at a copy number of at least 1, 2, 3, 4, 5, 6, 7, 8, 9, 10, 20, or 30 copies per cell.

In some embodiments, a population of genetically engineered T cells as disclosed herein exhibits T cell functions (e.g., effector functions). In some embodiments, the population is cytotoxic to CD64-expressing cells (e.g., CD64-positive tumor cells, CD64-low tumor cells). Effector function of a T cell, for example, may be cytolytic activity or helper activity including the secretion of cytokines. In some embodiments, the population exhibits one or more T cell effector functions at a level that is least 3-4-fold higher than the functions exhibited by a population of T cells not expressing the CAR.

Methods of Making the Cells of the Present Disclosure

Chimeric antigen receptors may be readily inserted into and expressed by immune cells, (e.g., T cells). In certain embodiments, cells (e.g., immune cells such as T cells) are obtained from a donor subject. In some embodiments, the donor subject is a human patient afflicted with a cancer or a tumor. In other embodiments, the donor subject is a human patient not afflicted with a cancer or a tumor. In some embodiments, an engineered cell is autologous to a subject. In some embodiments, an engineered cell is allogeneic to a subject.

The cell of the present disclosure may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as $CD4^+$, $CD8^+$, $CD28^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD8, CD1 lb, CD14, CD16, CD20, and HLA-DR. In certain embodiments, flow cytometry and cell sorting are used to isolate cell populations of interest for use in the present disclosure.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CCR7, CD3, CD28, CD45RO, CD62L, and CD127 and are negative for granzyme B. In some embodiments, central memory T cells are $CD8^+$. CD45RO+, and CD62L+ T cells. In some embodiments, effector T cells are negative for CCR7, CD28, CD62L, and CD127 and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

Methods of Gene Delivery and Cell Modification

One of skill in the art would be well-equipped to construct a vector through standard recombinant techniques (see, for example, Sambrook et al., 2001 and Ausubel et al, 1996, both incorporated herein by reference) for the expression of the antigen receptors of the present disclosure. Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

Viral Vectors

Viral vectors encoding an antigen receptor, a cytokine, and/or a functional effector element may be provided in certain aspects of the methods of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor mediated-endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

In some embodiments of the methods of the disclosure, introducing a nucleic acid sequence and/or a genomic editing construct into an immune cell ex vivo, in vivo, in vitro or in situ comprises a viral vector. In some embodiments, the viral vector is a non-integrating non-chromosomal vector. Exemplary non-integrating, non-chromosomal vectors include, but are not limited to, adeno-associated virus (AAV), adenovirus, and herpes viruses. In some embodiments, the viral vector is an integrating chromosomal vector. Integrating chromosomal vectors include, but are not limited to, adeno-associated vectors (AAV), lentiviruses, and gamma-retroviruses.

In some embodiments of the methods of the disclosure, introducing a nucleic acid sequence and/or a genomic editing construct into an immune cell ex vivo, in vivo, in vitro, or in situ comprises a combination of vectors. Exemplary, non-limiting vector combinations include viral and non-viral vectors, a plurality of non-viral vectors, or a plurality of viral vectors. Exemplary but non-limiting vectors combinations include: a combination of a DNA-derived and an RNA-derived vector, a combination of an RNA and a reverse transcriptase, a combination of a transposon and a transposase, a combination of a non-viral vector and an endonuclease, and a combination of a viral vector and an endonuclease.

In some embodiments of the methods of the disclosure, genome modification comprising introducing a nucleic acid sequence and/or a genomic editing construct into an immune cell ex vivo, in vivo, in vitro or in situ stably integrates a nucleic acid sequence, transiently integrates a nucleic acid sequence, produces site-specific integration a nucleic acid sequence, or produces a biased integration of a nucleic acid sequence. In some embodiments, the nucleic acid sequence is a transgene.

In some embodiments of the methods of the disclosure, genome modification comprising introducing a nucleic acid sequence and/or a genomic editing construct into an immune cell ex vivo, in vivo, in vitro, or in situ stably integrates a nucleic acid sequence. In some embodiments, the stable chromosomal integration can be a random integration, a site-specific integration, or a biased integration. In some embodiments, the site-specific integration can be non-assisted or assisted. In some embodiments, the assisted site-specific integration is co-delivered with a site-directed nuclease. In some embodiments, the site-directed nuclease comprises a transgene with 5' and 3' nucleotide sequence extensions that contain a percentage homology to upstream and downstream regions of the site of genomic integration. In some embodiments, the transgene with homologous nucleotide extensions enables genomic integration by homologous recombination, microhomology-mediated end joining, or nonhomologous end-joining. In some embodiments the site-specific integration occurs at a safe harbor site. Genomic safe harbor sites are able to accommodate the integration of new genetic material in a manner that ensures that the newly inserted genetic elements function reliably (for example, are expressed at a therapeutically effective level of expression) and do not cause deleterious alterations to the host genome that cause a risk to the host organism. Potential genomic safe harbors include, but are not limited to, intronic sequences of the human albumin gene, the adeno-associated virus site 1 (AAVS1), a naturally occurring site of integration of AAV virus on chromosome 19, the site of the chemokine (C-C motif) receptor 5 (CCR5) gene and the site of the human ortholog of the mouse Rosa26 locus.

In some embodiments, the site-specific transgene integration occurs at a site that disrupts expression of a target gene. In some embodiments, disruption of target gene expression occurs by site-specific integration at introns, exons, promoters, genetic elements, enhancers, suppressors, start codons, stop codons, and response elements. In some embodiments, exemplary target genes targeted by site-specific integration include but are not limited to any immunosuppressive gene, and genes involved in allo-rejection.

In some embodiments, the site-specific transgene integration occurs at a site that results in enhanced expression of a target gene. In some embodiments, enhancement of target gene expression occurs by site-specific integration at introns, exons, promoters, genetic elements, enhancers, suppressors, start codons, stop codons, and response elements.

Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters.

Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively, a replication origin of other extra-chromosomally replicating virus as described above or an autonomously replicating sequence (ARS) can be employed.

Other Methods of Nucleic Acid Delivery

In addition to viral delivery of the nucleic acids encoding the antigen receptor, the following are additional methods of recombinant gene delivery to a given cell, (e.g. an NK cell) and are thus considered in the present disclosure.

Introduction of a nucleic acid, such as DNA or RNA, into the immune cells of the current disclosure may use any suitable methods for nucleic acid delivery for transformation of a cell, as described herein or as would be known to one of ordinary skill in the art. Such methods include, but are not limited to, direct delivery of DNA such as by ex vivo transfection, by injection, including microinjection); by electroporation; by calcium phosphate precipitation; by using DEAE-dextran followed by polyethylene glycol; by direct sonic loading; by liposome mediated transfection and receptor-mediated transfection; by microprojectile bombardment; by agitation with silicon carbide fibers; by *Agrobacterium*-mediated transformation; by desiccation/inhibition-mediated DNA uptake, and any combination of such methods. Through the application of techniques such as these, organelle(s), cell(s), tissue(s) or organism(s) may be stably or transiently transformed.

Generally, the gene transfer system can include a transposon-based or a viral-based integration system.

In some embodiments, the gene transfer system comprises a transposon system. DNA transposons can translocate via a non-replicative "cut-and-paste" mechanism. This mechanism requires recognition of the two inverse terminal repeats (ITRs) by a catalytic enzyme, i.e., transposase, which can cleave its target and consequently release the DNA transposon from its donor template. Upon excision, the DNA transposons may subsequently integrate into the acceptor DNA that is cleaved by the same transposase. In some of their natural configurations, DNA transposons are flanked by two ITRs and may contain a gene encoding a transposase that catalyzes transposition. As would be appreciated by the skilled artisan, transposon systems offer many advantages for nucleic acid integration, e.g., as compared to viral vectors. For example, transposons can carry larger cargos, which can be advantageous for delivering one or more of the CARs, functional effector elements, and/or cytokines disclosed herein to an immune cell (e.g., an NK cell). Further, transposons may comprise, for example, CRISPR tools (e.g., along with cargo), and thereby allow multiplex engineering of a cell.

Methods of Use

In some embodiments, the present disclosure provides methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

Tumors for which the present treatment methods are useful include any malignant cell type, such as those found in a solid tumor or a hematological tumor. In some embodiments, the cancer is acute myeloid leukemia. In some embodiments, the cancer is monocytic acute myeloid leukemia. In some embodiments, the cancer is mixed monocytic/primitive acute myeloid leukemia. In some embodiments, the cancer is a CD64-positive cancer. In some embodiments, the cancer has a low expression of CD64 (e.g. a CD64 low cancer). In some embodiments, the cancer has a low expression of CD64 and is converted to a CD64-positive cancer. In some embodiments, the cancer has a low expression of CD64 (e.g., a CD64 low cancer) prior to treatment with at least one acute myeloid leukemia-targeting treatment (e.g., treatment with venetoclax in combination with a hypomethylating agent, such as azacitidine) but the cancer remaining after treatment with at least one least one acute myeloid leukemia-targeting treatment has higher expression of CD64 (e.g., a CD64-positive cancer). In some embodiments, the cancer has little or no expression of CD64 and is converted to a CD64-positive cancer. In some embodiments, the cancer has little or no expression of CD64 (e.g., a CD64-negative cancer) prior to treatment with at least one acute myeloid leukemia-targeting treatment (e.g., treatment with venetoclax in combination with a hypomethylating agent, such as azacitidine), but the cancer remaining after treatment with at least one least one acute myeloid leukemia-targeting treatment expresses CD64 (e.g., a CD64-positive cancer).

Accordingly, the present disclosure provides methods of treating acute myeloid leukemia in a subject, the method comprising administering to the subject at least one amount of the immune cells of the present disclosure to the subject. The present disclosure provides the immune cells of the present disclosure for use in the treatment of acute myeloid leukemia in a subject. The present disclosure provides the use of the immune cells of the present disclosure in the manufacture of a medicament for the treatment of acute myeloid leukemia in a subject.

Particular embodiments concern methods of treatment of acute myeloid leukemia in a subject in need thereof. Acute myeloid leukemia (AML) is a blood cancer in which the bone marrow of a subject makes abnormal myeloblasts, red blood cells, or platelets. AML is one of the most common forms of acute leukemia in adults. The build-up of AML cells in bone marrow and blood can rapidly lead to infection, anemia, excessive bleeding and death. In some embodiments, the AML has a population of AML cells that are CD64+. In some embodiments, the AML lacks a population of AML cells that are CD64-positive prior to treatment with at least one AML-targeting therapy (e.g., treatment with venetoclax in combination with a hypomethylating agent, such as azacitidine), but the AML has a population of AML cells that are CD64-positive after treatment with at least one AML-targeting therapy. In some embodiments, the AML has a population of monocytic leukemia stem cells (mLSCs). In some embodiments, the subject has been previously administered at least one AML-targeting therapy. In some embodiments, the AML-targeting therapy comprises the administration of a combination of venetoclax and azacitidine. In some embodiments, the subject has relapsed after treatment with the at least one AML-targeting therapy and/or the subject is resistant to treatment with the at least one AML-targeting therapy. In some embodiments, the subject that has been previously administered at least one AML-targeting therapy (e.g., treatment with venetoclax in combination with a hypomethylating agent, such as azacitidine) has a population of AML cells that are CD64-positive, whereas the subject lacked a population of AML cells that were CD64-positive prior to the subject being administered at least one AML-targeting therapy.

In particular aspects, the CD64-specific CARs described herein are administrated to a subject having acute myeloid leukemia (AML). In particular aspects, the CD64-specific CARs described herein are administrated to a subject having a population of AML cells that are CD64+ and/or a population of monocytic leukemia stem cells (mLSCs). In particular aspects, the CD64– specific CARs described herein are administrated to a subject having relapsed after treatment with the at least one AML-targeting therapy and/or the subject is resistant to treatment with the at least one AML-targeting therapy. In particular aspects, the CD64-specific CARs described herein are administrated to a subject having a population of AML cells that are CD64-positive after treatment with at least one AML-targeting therapy (e.g., treatment with venetoclax in combination with a hypomethylating agent, such as azacitidine), whereas the subject lacked a population of AML cells that was CD64-positive prior to treatment with the at least one AML-targeting therapy.

In certain embodiments of the present disclosure, immune cells are delivered to an individual in need thereof, such as an individual that has cancer or an infection. The cells then enhance the individual's immune system to attack or directly attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, 8, 9, 10, 11, or 12 or more weeks.

In yet another embodiment, the subject is the recipient of a transplanted organ or stem cells, and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of venetoclax and azacitidine.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ. It can be the amount necessary to reduce the number of cancer cells in the subject. It can be the amount necessary to increase survival time of the subject.

The immune cell population can be administered in treatment regimens consistent with the disease, for example a single or a few doses over one to several weeks to ameliorate a disease state or periodic doses over an extended time to inhibit disease progression and prevent disease recurrence. The precise dose to be employed in the formulation will also depend on the route of administration, and the seriousness of the disease or disorder. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m². In a certain embodiment, the dose used in the treatment of human subjects ranges from about $3.8 \times 10^9$ to about $3.8 \times 10^{10}$ immune cells/m² (e.g., from about $3.8 \times 10^{10}$ immune cells/m² to about $3.3 \times 10^{10}$, from about $3.8 \times 10^9$ to about $2.8 \times 10^{10}$, from about $3.8 \times 10^9$ to about $2.2 \times 10^{10}$, from about $3.8 \times 10^9$ to about $1.7 \times 10^{10}$, from about $3.8 \times 10^9$ to about $1.4 \times 10^{10}$, from about $3.8 \times 10^9$ to about $1 \times 10^{10}$, from about $3.8 \times 10^9$ to about $7.1 \times 10^9$, from about $7.1 \times 10^9$ to about $3.8 \times 10^{10}$, from about $1 \times 10^{10}$ to about $3.8 \times 10^{10}$, from about $1.4 \times 10^{10}$ to about $3.8 \times 10^{10}$, from about $1.7 \times 10^{10}$ to about $3.8 \times 10^{10}$, from about $2.2 \times 10^{10}$ to about $3.8 \times 10^{10}$, from about $2.8 \times 10^{10}$ to about $3.8 \times 10^{10}$, from about $3.3 \times 10^9$ to about $3.8 \times 10^{10}$, from about $7.1 \times 10^9$ to about $3.3 \times 10^{10}$, from about $1 \times 10^{10}$ to about $2.8 \times 10^{10}$, or from about $1.4 \times 10^{10}$ to about $2.2 \times 10^{10}$). In additional embodiments, a therapeutically effective amount of immune cells can vary from about $5 \times 10^6$ cells per kg body weight to about $7.5 \times 10^8$ cells per kg body weight, such as from about $2 \times 10^7$ cells to about $5 \times 10^8$ cells per kg body weight, or from about $5 \times 10^7$ cells to about $2 \times 10^8$ cells per kg body weight, or from about $5 \times 10^6$ cells per kg body weight to about $1 \times 10^7$ cells per kg body weight. In some embodiments, a therapeutically effective amount of immune cells ranges from about $1 \times 10^5$ cells per kg body weight to about $1 \times 10^9$ cells per kg body weight (e.g., from about $1 \times 10^5$ cells per kg body weight to about $8.8 \times 10^9$, from about $1 \times 10^5$ to about $7.5 \times 10^9$, from about $1 \times 10^{10}$ cells per kg body weight to about $6.3 \times 10^9$, from about $1 \times 10^5$ cells per kg body weight to about $5 \times 10^9$, from about $1 \times 10^5$ cells per kg body weight to about $3.8 \times 10^9$, from about $1 \times 10^5$ cells per kg body weight to about $2.5 \times 10^9$, from about $1 \times 10^5$ cells per kg body weight to about $1.3 \times 10^9$, from about $1.3 \times 10^9$ to about $1 \times 10^{10}$, from about $2.5 \times 10^9$ to about $1 \times 10^{10}$, from about $3.8 \times 10^9$ to about $1 \times 10^{10}$, from about $5 \times 10^9$ to about $1 \times 10^{10}$, from about $6.3 \times 10^9$ to about $1 \times 10^{10}$, from about $7.5 \times 10^9$ to about $1 \times 10^{10}$, from about $1.3 \times 10^9$ to about $8.8 \times 10^9$, from about $2.5 \times 10^9$ to about $7.5 \times 10^9$, or from about $3.8 \times 10^9$ to about $6.3 \times 10^9$). The exact amount of immune cells is readily determined by one of skill in the art based on the age, weight, sex, and physiological condition of the subject. Effective doses can be extrapolated from dose –response curves derived from in vitro or animal model test systems.

The immune cells may be administered in combination with one or more other therapeutic agents for the treatment of the immune-mediated disorder. Combination therapies can include, but are not limited to, one or more antimicrobial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetyls alicylic acid, ibuprofen or naproxen sodium), cytokine antagonists (for example, anti-TNF and anti-IL-6), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; chemokines, interleukins or their inhibitors (e.g., BAFF, IL-2, anti-IL-2R, IL-4, JAK kinase inhibitors); or immune checkpoint inhibitors (e.g., anti-PD1 antibodies, anti-PDL1 antibodies, anti-PDL2 antibodies, anti-LAG3 antibodies, and anti-CTLA4 antibodies) can be administered.

Such additional pharmaceutical agents can be administered before, during, or after administration of the immune cells, depending on the desired effect. This administration of the cells and the agent can be by the same route or by different routes, and either at the same site or at a different site.

Pharmaceutical Compositions

Also provided herein are pharmaceutical compositions and formulations comprising immune cells of the present disclosure (e.g., T cells) and a pharmaceutically acceptable carrier.

In some embodiments, a pharmaceutical composition comprises a dose ranging from about $1\times10^5$ T cells to about $1\times10^9$ T cells (e.g., from about $1\times10^5$ T cells to about $8.75\times10^8$, from about $5\times10^5$ to about $7.5\times10^8$, from about $5\times10^5$ to about $6.25\times10^8$, from about $5\times10^5$ to about $5\times10^8$, from about $5\times10^5$ to about $3.75\times10^8$, from about $5\times10^5$ to about $2.5\times10^8$, from about $5\times10^5$ to about $1.25\times10^8$, from about $1.25\times10^8$ to about $1\times10^9$, from about $2.5\times10^8$ to about $1\times10^9$, from about $3.75\times10^8$ to about $1\times10^9$, from about $5\times10^8$ to about $1\times10^9$, from about $6.25\times10^8$ to about $1\times10^9$, from about $7.5\times10^8$ to about $1\times10^9$, from about $8.75\times10^8$ to about $1\times10^9$, from about $1.25\times10^8$ to about $8.75\times10^8$, from about $2.5\times10^8$ to about $7.5\times10^8$, or from about $3.75\times10^8$ to about $6.25\times10^8$). In some embodiments, the dose is about $1\times10^5$, $\mathbf{1\times10^6}$, $\mathbf{1\times10^7}$, $\mathbf{1\times10^8}$ or $1\times10^9$ T cells. In some embodiments, a pharmaceutical composition comprises a dose ranging from about $5\times10^5$ T cells to about $10\times10^{12}$ T cells (e.g., from about $5\times10^5$ T cells to about $8.75\times10^{11}$, from about $5\times10^5$ to about $7.5\times10^{11}$, from about $5\times10^5$ to about $6.25\times10^{11}$, from about $5\times10^8$ to about $5\times10^{11}$, from about $5\times10^8$ to about $3.75\times10^{11}$, from about $5\times10^{11}$ to about $2.5\times10^{11}$, from about $5\times10^5$ to about $1.25\times10^{11}$, from about $1.25\times10^{11}$ to about $1\times10^{12}$, from about $2.5\times10^{11}$ to about $1\times10^{12}$, from about $3.75\times10^{11}$ to about $1\times10^{12}$, from about $5\times10^{11}$ to about $2.5\times10^{12}$, from about $6.25\times10^{11}$ to about $\times10^{12}$, from about $7.5\times10^{11}$ to about $1\times10^{12}$, from about $8.75\times10^{11}$ to about $1\times10^{12}$, from about $1.25\times10^{11}$ to about $8.75\times10^{11}$, from about $2.5\times10^{11}$ to about $7.5\times10^{11}$, or from about $3.75\times10^{11}$ to about $6.25\times10^{11}$).

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Combination Therapies

In some embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be one or more of the chemotherapeutic agents known in the art.

An immune cell therapy may be administered before, during, after, or in various combinations relative to an additional cancer therapy. The administrations may be in intervals ranging from concurrently to minutes to days to weeks. Various combinations may be employed.

For the example below an immune cell therapy is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, decitabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above. In some embodiments, azacitidine is administered at 75 mgs/m$^2$ subcutaneously.

In some aspects, the immune cells of the present disclosure can be administered in combination with venetoclax. In some aspects, the immune cells of the present disclosure can be administered in combination with azacitidine. In some aspects, the immune cells of the present disclosure can be administered in combination with venetoclax and azacitidine. In some aspects, the immune cells of the present disclosure can be administered after administration of venetoclax and/or azacitidine.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395, 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Dosage Regimens

In one embodiment, the immune effector cells (e.g., T cells) are modified by engineering/introducing chimeric antigen receptors (e.g., anti-CD64 CAR) into said immune effector cells and then infused into a subject. In some embodiments, immune effector cells are modified by engineering/introducing a chimeric receptor, and functional effector element and/or a cytokine into the immune effector cells and then infused within about 0 days, within about 1 day, within about 2 days, within about 3 days, within about 4 days, within about 5 days, within about 6 days or within about 7 days into a subject.

In some embodiments, an amount of modified effector cells is administered to a subject in need thereof and the amount is determined based on the efficacy and the potential of inducing a cytokine-associated toxicity. In another embodiment, the modified effector cells are CAR$^+$ and CD56$^+$ cells. In some embodiments, an amount of modified effector cells comprises about $10^4$ to about $10^{11}$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^5$ modified effector cells/kg. In some cases, an amount of modified effector cells comprises about $10^8$ to about $10^5$ modified effector cells/kg. In some cases, an amount of modified effector cells comprises about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$, about $2\times10^8$, about $3 \times 10^8$, about $4 \times 10^8$, about $5 \times 10^8$, about $6 \times 10^8$, about $7 \times 10^8$, about $8 \times 10^8$, about $9 \times 10^8$, or about $1 \times 10^9$ modified effector cells/kg.

In one embodiment, the modified immune effector cells are targeted to the cancer via regional delivery directly to the tumor tissue. For example, in ovarian or renal cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IV followed by a second dose of modified immune effector cells delivered via IV. In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent doses can be about 0 days to about 30 days (e.g., about 0 days to about 27 days, about 0 to about 24, about 0 to about 21, about 0 to about 18, about 0 to about 15, about 0 to about 12, about 0 to about 9, about 0 to about 6, about 0 to about 3, about 3 to about 30, about 6 to about 30, about 9 to about 30, about 12 to about 30, about 15 to about 30, about 18 to about 30, about 21 to about 30, about 24 to about 30, about 27 to about 30, about 3 to about 27, about 6 to about 24, about 9 to about 21, about 12 to about 18, about 0 to about 6, about 3 to about 9, about 6 to about 12, about 9 to about 15, about 12 to about 18, about 15 to about 21, about 18 to about 24, about 21 to about 27, or about 24 to about 30. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In one embodiment, the duration between the first and second or further subsequent dose can be about 0 months to about 36 months (e.g., about 0 to about 30, about 0 to about 24, about 0 to about 18, about 0 to about 12, about 0 to about 6, about 6 to about 36, about 12 to about 36, about 18 to about 36, about 24 to about 36, about 30 to about 36, about 6 to about 30, about or 12 to about 24). In some embodiments, the duration between the first and second or further subsequent dose can be about: 0, 1, 2, 3, 4, 5, 6, 7, 8, 9 or 10 years. In some embodiments, the duration between the first and second or further subsequent dose can be about 0 years to about 10 years (e.g., about 0 years to about 9 years, about 0 to about 8, about 0 to about 7, about 0 to about 6, about 0 to about 5, about 0 to about 4, about 0 to about 3, about 0 to about 2, about 0 to about 1, about 1 to about 10, about 2 to about 10, about 3 to about 10, about 4 to about 10, about 5 to about 10, about 6 to about 10, about 7 to about 10, about 8 to about 10, about 9 to about 10, about 1 to about 9, about 2 to about 8, about 3 to about 7, about 4 to about 6, about 0 to about 2, about 1 to about 3, about 2 to about 4, about 3 to about 5, about 4 to about 6, about 5 to about 7, about 6 to about 8, about 7 to about 9, or about 8 to about 10).

In another embodiment, a catheter can be placed at the tumor or metastasis site for further administration of 1, 2, 3, 4, 5, 6, 7, 8, 9, 10 doses of modified immune effector cells. In some cases, doses of modified effector cells can comprise about $10^2$ to about $10^9$ modified effector cells/kg (e.g., about $1 \times 10^2$ modified effector cells/kg to about $8.75 \times 10^8$ effector cells/kg, about $1 \times 10^2$ to about $7.5 \times 10^8$, about $1 \times 10^2$ to about $6.25 \times 10^8$, about $1 \times 10^2$ to about $5 \times 10^8$, about $1 \times 10^2$ to about $3.75 \times 10^8$, about $1 \times 10^2$ to about $2.5 \times 10^8$, about $1 \times 10^2$ to about $1.25 \times 10^8$, about $1.25 \times 10^8$ to about $1 \times 10^9$, about $2.5 \times 10^8$ to about $1 \times 10^9$, about $3.75 \times 10^8$ to about $1 \times 10^9$, about $5 \times 10^8$ to about $1 \times 10^9$, about $6.25 \times 10^8$ to about $1 \times 10^9$, about $7.5 \times 10^8$ to about $1 \times 10^9$, about $8.75 \times 10^8$ to about $1 \times 10^9$, about $1.25 \times 10^8$ to about $8.75 \times 10^8$, about $2.5 \times 10^8$ to about $7.5 \times 10^8$, or about $3.75 \times 10^8$ to about $6.25 \times 10^8$). In cases where toxicity is observed, doses of modified effector cells can comprise about $10^2$ to about 10 modified effector cells/kg (e.g., about $1 \times 10^2$ modified effector cells/kg to about $7.5 \times 10^7$ modified effector cells/kg, about $1 \times 10^2$ to about $5 \times 10^4$, about $1 \times 10^2$ to about $2.5 \times 10^4$, about $2.5 \times 10^4$ to about $1 \times 10^4$, about $5 \times 10^4$ to about $1 \times 10^5$, about $7.5 \times 10^4$ to about $1 \times 10^5$, about $2.5 \times 10^4$ to about $7.5 \times 10^4$, or about $4 \times 10^4$ to about $6 \times 10^4$. In some cases, doses of modified effector cells can start at about $10^2$ modified effector cells/kg and subsequent doses can be increased to about: $10^4$, $10^5$, $10^6$, $10^7$, $10^8$ or $10^9$ modified effector cells/kg.

Articles of Manufacture or Kits

An article of manufacture or a kit comprising immune cells is also provided herein. The article of manufacture or kit can further comprise a package insert comprising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags, and syringes. The container may be formed from a variety of materials such as glass, plastic (such as polyvinyl chloride or poly olefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

General Definitions

As used herein, the term "portion" when used in reference to a polypeptide or a peptide refers to a fragment of the polypeptide or peptide. In some embodiments, a "portion" of a polypeptide or peptide retains at least one function and/or activity of the full-length polypeptide or peptide from which it was derived. For example, in some embodiments, if a full-length polypeptide binds a given ligand, a portion of that full-length polypeptide also binds to the same ligand.

The terms "protein" and "polypeptide" are used interchangeably herein.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced into a cell population or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells or is otherwise flanked by a different nucleic acid sequence than that found in nature. The term "exogenous" is used interchangeably with the term "heterologous".

By "expression construct" or "expression cassette" is used to mean a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide, or the protein expressed by said polynucleotide, to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, that when present in a plasmid in a cell is capable of maintaining linked sequences in the plasmid and/or a site at or near where DNA synthesis initiates. As an example, an ori for EBV (Ebstein-Barr virus) includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR. DS or Rep* sequences or any functionally equivalent sequences through nucleic acid modifications or synthetic combination derived therefrom. For example, methods of the present disclosure may also use genetically engineered replication origin of EBV, such as by insertion or mutation of individual elements.

A "gene," "polynucleotide," "coding region," "sequence," "segment," "fragment," or "transgene" that "encodes" a particular protein, is a section of a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein to refer to a nucleotide region comprising a DNA regulatory sequence, wherein the regulatory sequence is derived from a gene that is capable of binding to a RNA polymerase and allowing for the initiation of transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an functional effector element) are connected in such a way as to permit transcription of the nucleic acid molecule. "Operably linked" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of molecules that are not found in a single polypeptide in nature.

The term "homology" refers to the percent of identity between the nucleic acid residues of two polynucleotides or the amino acid residues of two polypeptides. The correspondence between one sequence and another can be determined by techniques known in the art. For example, homology can be determined by a direct comparison of the sequence information between two polypeptides by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two polynucleotide (e.g., DNA), or two polypeptide, sequences are "substantially homologous" to each other when at least about 80%, at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPScs, "iPSCs" or "iPS cells".

An "embryonic stem (ES) cell" is an undifferentiated pluripotent cell which is obtained from an embryo in an early stage, such as the inner cell mass at the blastocyst stage, or produced by artificial means (e.g., nuclear transfer) and can give rise to any differentiated cell type in an embryo or an adult, including germ cells (e.g., sperm and eggs).

"Induced pluripotent stem cells" (iPScs, iPSCs or iPS cells) are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, granulocytes (neutrophils, basophils, eosinophils, and mast cells), erythrocytes, megakaryocytes/platelets, dendritic cells), and lymphoid lineages (T-cells, B cells, NK cells) (see e.g., Doulatov et al., 2012; Notta et al., 2015).

A "multilymphoid progenitor" (MLP) is defined to describe any progenitor that gives rise to all lymphoid lineages (B. T. and NK cells), but that may or may not have other (myeloid) potentials (Doulatov et al., 2010) and is CD45RA$^+$/CD10$^+$/CD7$^+$. Any B, T, and NK progenitor can be referred to as an MLP. A "common myeloid progenitor" (CMP) refers to CD45RA$^+$/CD135$^+$/CD10$^+$/CD7$^+$ cells that can give rise to granulocytes, monocytes, megakaryocytes and erythrocytes.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

As used herein, the term "subject" or "subject in need thereof" refers to a mammal, preferably a human being, male or female at any age that is in need of a therapeutic intervention, a cell transplantation or a tissue transplantation. Typically, the subject is in need of therapeutic intervention, cell or tissue transplantation (also referred to herein as recipient) due to a disorder or a pathological or undesired condition, state, or syndrome, or a physical, morphological or physiological abnormality which is amenable to treatment via therapeutic intervention, cell or tissue transplantation.

As used herein, a "disruption" or "alteration" in reference to a gene refers to a homologous recombination event with a nucleic acid molecule (e.g., an endogenous gene sequence) which results in elimination or reduction of expression of one or more gene products encoded by the subject gene in a cell, compared to the level of expression of the gene product in the absence of the disruption. Exemplary gene products include mRNA and protein products encoded by the subject gene. Alteration in some cases is transient or reversible and in other cases is permanent. Alteration in some cases is of a functional or full-length protein or mRNA, despite the fact that a truncated or nonfunctional product may be produced. In some embodiments herein, gene activity or function, as opposed to expression, is disrupted. Gene alteration is generally induced by artificial methods, i.e., by addition or introduction of a compound, molecule, complex, or composition, and/or by alteration of nucleic acid of or associated with the gene, such as at the DNA level. Exemplary methods for gene alteration include gene silencing, knockdown, knockout, and/or gene alteration techniques, such as gene editing. Examples of gene editing methods include CRISPR/Cas systems, meganuclease systems, Zinc Finger Protein (ZFP) and Zinc Finger Nuclease (ZFN) systems and/or transcription activator-like protein (TAL), transcription activator-like effector protein (TALE) or TALE nuclease protein (TALEN) systems. Examples of gene alteration also include antisense technology, such as RNAi, siRNA, shRNA, and/or ribozymes, which generally result in transient reduction of expression, as well as gene editing techniques which result in targeted gene inactivation or alteration, e.g., by induction of breaks and/or homologous recombination. Examples include insertions, mutations, and deletions. The alterations typically result in the repression and/or complete absence of expression of a normal or "wild-type" product encoded by the gene. Exemplary of such gene alterations are insertions, frameshift and missense mutations, deletions, substitutions, knock-in, and knock-out of the gene or part of the gene, including deletions of the entire gene. Such alterations can occur in the coding region, e.g., in one or more exons, resulting in the inability to produce a full-length product, functional product, or any product, such as by insertion of a stop codon. Such alterations may also occur by alterations in the promoter or enhancer or other region affecting activation of transcription, so as to prevent transcription of the gene. Gene alterations include gene targeting, including targeted gene inactivation by homologous recombination.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "immune response" is a response of a cell of the immune system, such as a NK cell, B cell, or a T cell, or innate immune cell to a stimulus. In one embodiment, the response is specific for a particular antigen (an "antigen-specific response").

As used herein, the term "antigen" is a molecule capable of being bound by an antibody, T cell receptor, Chimeric Antigen Receptor, and or engineered immune receptor. An antigen may generally be used to induce a humoral immune response and/or a cellular immune response leading to the production of B and/or T lymphocytes.

The terms "tumor-associated antigen," "tumor antigen," and "cancer cell antigen" are used interchangeably herein. In each case, the terms refer to proteins, glycoproteins, or carbohydrates that are specifically or preferentially expressed by cancer cells.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies bind to the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

An "autoimmune disease" refers to a disease in which the immune system produces an immune response (for example, a B cell or a T cell response) against an antigen that is part of the normal host (that is, an autoantigen), with consequent injury to tissues. An autoantigen may be derived from a host cell or may be derived from a commensal organism such as the micro-organisms (known as commensal organisms) that normally colonize mucosal surfaces.

The term "Graft-Versus-Host Disease (GVHD)" refers to a common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor. In some embodiments, the GVHD is chronic GVHD (cGVHD).

A "parameter of an immune response" is any particular measurable aspect of an immune response, including, but not limited to, cytokine secretion (IFN-γ, etc.), chemokine secretion, altered migration or cell accumulation, immunoglobulin production, dendritic cell maturation, regulatory activity, number of immune cells and proliferation of any cell of the immune system. Another parameter of an immune response is structural damage or functional deterioration of any organ resulting from immunological attack. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. Similarly, an inhibition or decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease. A statistical test, such as a non-parametric ANOVA, or a T-test, can be used to compare differences in the magnitude of the response induced by one agent as compared to the percent of samples that respond using a second agent. In some examples, $p \leq 0.05$ is significant, and indicates that the chance that an increase or decrease in any observed parameter is due to random variation is less than 5%. One of skill in the art can readily identify other statistical assays of use.

"Treating" or treatment of a disease or condition refers to executing a protocol or treatment plan, which may include administering one or more compositions to a patient (e.g. the anti-CD64 CAR compositions of the present disclosure), in an effort to alleviate signs or symptoms of the disease or the recurrence of the disease. Desirable effects of treatment include decreasing the rate of disease progression, ameliorating or palliating the disease state, and remission, increased survival, improved quality of life or improved prognosis. In addition, "treating" or "treatment" does not require complete alleviation of signs or symptoms, does not require a cure, and specifically includes protocols or treatment plans that have only a marginal effect on the patient.

As used herein, "prevent", "preventing" and the like describe stopping the onset of the disease, condition or disorder, or one or more symptoms or complications thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis or recurrence. Treatment of cancer may also refer to prolonging survival of a subject with cancer.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CHL CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR 1, CDR2, and CDR3, form the "hypervariable region" of an antibody, which is responsible for antigen binding.

"Antibody like molecules" may be for example proteins that are members of the Ig-superfamily which are able to selectively bind a partner.

The terms "fragment of an antibody," "antibody fragment,", "functional fragment of an antibody," and "antigen-binding portion" are used interchangeably herein to mean one or more fragments or portions of an antibody that retain the ability to specifically bind to an antigen (see, generally, Holliger et al. (2005) *Nat. Biotech.* 23(9):1126-29). The antibody fragment desirably comprises, for example, one or more CDRs, the variable region (or portions thereof), the constant region (or portions thereof), or combinations thereof.

Examples of antibody fragments include, but are not limited to, (i) a Fab fragment, which is a monovalent fragment consisting of the VL, VH, CL, and CH1 domains: (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al. (1988), Science 242: 423-6; Huston et al. (1988) *Proc. Natl. Acad. Sci. USA* 85: 5879-83; and Osbourn et al. (1998) *Nat. Biotechnol.* 16: 778-81) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1.

A "chimeric antigen receptor" is also known as an artificial cell receptor, a chimeric cell receptor, or a chimeric immunoreceptor. Chimeric antigen receptors (CARs) are engineered receptors, which graft a selected specificity onto an immune effector cell. CARs typically have an extracellular domain (ectodomain), which comprises an antigen-binding domain and a stalk region, a transmembrane domain and an intracellular (endodomain) domain.

A "stalk region", which encompasses the terms "spacer region" or "hinge domain" or "hinge", is used to link the antigen-binding domain to the transmembrane domain. As used herein, the term "stalk region" generally means any oligonucleotide or polypeptide that functions to link the transmembrane domain to, either the extracellular domain or, the cytoplasmic domain in the polypeptide chain of a CAR. In embodiments, it is flexible enough to allow the antigen-binding domain to orient in different directions to facilitate antigen recognition.

The term "functional portion," when used in reference to a CAR, refers to any part or fragment of a CAR described herein, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 70% identical, about 75% identical, about 80% identical, about 85% identical, about 90% identical, about 95% identical, or about 99% identical to the nucleic acid sequence encoding the parent CAR.

The phrases "pharmaceutical or pharmacologically acceptable" refers to molecular entities and compositions that do not produce an adverse, allergic, or other untoward reaction when administered to an animal, such as a human, as appropriate. For animal (e.g., human) administration, it will be understood that preparations should meet sterility, pyrogenicity, general safety, and purity standards as required, e.g., by the FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "T cell" refers to T lymphocytes, and includes, but is not limited to, γ/δ T cells, α/β T cells, NK T cells, CD4+ T cells and CD8+ T cells. CD4'0 T cells include THO, $T_h1$ and TH2 cells, as well as regulatory T cells ($T_{reg}$). There are at least three types of regulatory T cells: CD4+ CD25+ $T_{reg}$, CD25 $T_H3$ $T_{reg}$, and CD25 $T_R$ 1 $T_{reg}$. "Cytotoxic T cell" refers to a T cell that can kill another cell. The majority of cytotoxic T cells are CD8+ MHC class I-restricted T cells, however some cytotoxic T cells are CD4+. In some embodiments, the T cell of the present disclosure is CD4+ or CD8+.

The activation state of a T cell defines whether the T cell is "resting" (i.e., in the $G_o$ phase of the cell cycle) or "activated" to proliferate after an appropriate stimulus such as the recognition of its specific antigen, or by stimulation with OKT3 antibody, PHA or PMA, etc. The "phenotype" of the T cell (e.g., naive, central memory, effector memory, lytic effectors, help effectors (TH1 and TH2 cells), and regulatory effectors), describes the function the cell exerts when activated. A healthy donor has T cells of each of these phenotypes, and which are predominately in the resting state. A naive T cell will proliferate upon activation, and then differentiate into a memory T cell or an effector T cell. It can then assume the resting state again, until it gets activated the next time, to exert its new function and may change its phenotype again. An effector T cell will divide upon activation and antigen-specific effector function.

"Natural killer T cells" (NKT cells), not to be confused with natural killer cells of the innate immune system, bridge the adaptive immune system with the innate immune system. Unlike conventional T cells that recognize peptide antigens presented by major histocompatibility complex (WIC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

"Natural killer cells" ("NK cells") are a type of cytotoxic lymphocyte of the innate immune system. In some instances. NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

"Tumor antigen" as used herein refers to any antigenic substance produced, expressed or overexpressed in tumor cells. It may, for example, trigger an immune response in the host. Alternatively, for purposes of this disclosure, tumor antigens may be proteins that are expressed by both healthy and tumor cells but because they identify a certain tumor type, are a suitable therapeutic target. As described herein, in some aspects the tumor antigen can be CD64.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B cells, endothelial cells, activated T cells, and dendritic cells; or other molecules, naturally occurring or synthetic, such as purified MHC Class I molecules complexed to 2-microglobulin.

The term "culturing" refers to the in vitro maintenance, differentiation, and/or propagation of cells in suitable media. By "enriched" is meant a composition comprising cells present in a greater percentage of total cells than is found in the tissues where they are present in an organism.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

EXAMPLES

General Methods
Generation of CD64 Chimeric Antigen Receptor Constructs
CD64-directed chimeric antigen receptors (CARs) were constructed utilizing single-chain fragment of the variable region (scFv's) which binds to human CD64. One version of this CAR consisted of the scFv joined to the extracellular domain of CD28, which was contiguous with the transmembrane domain and intracellular signaling domain of the CD28 protein. The CD28 signaling domain was joined with the intracellular signaling domain of the CD3-zeta chain and collectively this formed the CD64-28z CAR. Another version of this CAR consisted of the scFv joined to the extracellular domain of CD8, which was contiguous with the CD8 transmembrane domain. The CD8 transmembrane domain was joined to the intracellular signaling domain of the 4-1BB costimulatory receptor. The 4-1BB signaling domain was joined with the intracellular signaling domain of the CD3-zeta chain, collectively forming the CD64-BBz CAR.

Generation of CD64 CAR T Cells
Lentivirus encoding the CAR transgene were produced through transient transfection of the Lenti-X 293T cell line (Takara Bio) with transfer plasmid and packaging plasmids (pRSV-Rev, pMDLg/pRRe and pMD2.G) using Lipofectamine 3000 (Life Technologies) in Opti-MEM (Thermo-Fisher). Media was replaced 6 hours after transfection and lentiviral supernatant was collected at 24- and 56-hours post-transfection, cleared by centrifugation at 2000G for 10 minutes, aliquoted and frozen at −80° C._Human T cells were thawed at $0.5 \times 10^6$ cells/mL and activated with a 3:1 ratio of Human T-expander CD3/CD28 Dynabeads per cell (Life Technologies) in AIM-V medium supplemented with 5% heat-inactivated FBS, 100 U/mL penicillin, 100 U/mL streptomycin, 5 mL GlutaMax™, 10 mM HEPES, and 40 IU/mL IL-2. T cells were transduced at an MOI of 2-10 by spinfection at 1000 g for 2 hours at 32° C. in the presence of 40 IU/mL IL-2 and 10 μg/mL protamine sulfate. Cells were incubated overnight at 37° C., and beads were removed the following day. CAR T cells were re-suspended at 0.5× $10^6$/mL and expanded in vitro in 100 IU/mL of IL-2 for 4 days. CAR expression was verified by flow cytometry. CAR T cells were then cryopreserved 8 days post-activation. CAR T cells were thawed one day prior to start of in vitro and in vivo assays.

In Vitro Testing of CD64 CAR T Cell Cytotoxicity Against AML Cell-Lines
The AML cell lines K562, MOLM14, and THP1 were stained with PE-conjugated anti-CD64 to demonstrate expression of CD64 on their surface. $10^5$ AML cell lines were co-incubated with $10^5$ CD64-28z CAR T cells or $10^5$ Mock T cells (which were activated and expanded but not transduced with the CAR). Co-incubations were carried out in 200 μL of media in wells of a 96-well plate. All co-incubations were performed in triplicate at 370 C, 10% $CO_2$ in a tissue culture incubator. 24 hours later, cells were collected from the co-incubations, stained with antibodies against CD3 and analyzed by flow cytometry. AML cells and T cells were distinguished from each other within the live cell gate based on CD3 staining (T cell marker) and either FSC (K562) or GFP expression (MOLM14 and THP1). Percentage of AML cell line within the live cell gate was quantified by flow cytometry and averaged across triplicate samples. Mann-Whitney Analysis was performed to determine statistical significance between CD64 CAR-treated and Mock T cell-treated groups.

In Vitro Testing of CD64 CAR T Cell Cytokine Production in Response to AML Cell-Lines $10^5$ K562 or THP1 cells were co-incubated with $10^5$ CD64-28z CAR T cells or $10^5$ CD19-28z CAR T cells (an irrelevant CAR targeting an antigen not expressed on either cell line). Additionally, $10^5$ CD64-28z CAR T cells or $10^5$ CD19-28z CAR T cells were added to wells with media only as negative controls. Co-incubations were carried out in 200 μL of media in wells of a 96-well plate, in triplicate for 24 hours at 37° C., 8% $CO_2$ in a tissue culture incubator. At the end of co-incubation, cells were pelleted by centrifugation at 300 g for 6 minutes and then supernatant was collected from all wells and analyzed by ELISA (R&D systems) to quantify secreted Interferon-Gamma (IFNG) and Interleukin-2 (IL-2). Quantification of each cytokine was averaged across triplicate samples and Mann-Whitney Analysis was performed to determine statistical significance between CD64-28z CAR and CD19-28z CAR T cell groups.

In Vivo Testing of CD64 CAR T Cells Against AML Cell-Lines

NOD/SCID/Gamma chain$^{null}$ (NSG) immunodeficient mice were inoculated with $10^6$ luciferase-expressing THP1 or MOLM14 cells via tail vein injection on Day −4. Engraftment of the AML cells was confirmed by intraperitoneal (ip) injection of D-luciferin followed by BLI on Xenogen In Vivo Imaging System (IVIS) on Day −1. Mice were injected via tail vein with of 3-5×$10^6$ CAR T cells or Mock T cells on Day 0. In some experiments, no treatment was administered on Day 0 as a negative control. At doses CD64-28z CAR T cells or were given no treatment. BLI was repeated once to twice weekly over the course of in vivo experiments to quantify leukemia burden. Mice were monitored 2-3 times per week for the development of predefined endpoint symptoms and were euthanized per institutional protocols upon reaching endpoint. Survival was recorded and statistically compared using Log-Rank Analysis.

In Vitro Testing of CD64 CAR T Cells Against Patient-Derived AML Samples

Cryopreserved patient-derived AML samples acquired from the University of Colorado Biorepository were thawed and cell viability and concentration was determined by Trypan-Blue exclusion. 400,000 patient-derived AML cells were plated with CD64 CAR T cells or an equivalent number of Mock T cells. CAR T cells were added at varying E:T ratios. Co-incubation of CAR T cells and AML cells was carried out at 37° C., 10% $CO_2$ in a tissue culture incubator for 24-48 hours, after which the cells from the co-incubation were collected, washed, and stained for viability (Fixable Viability Dye eFlour780, Invitrogen) and with fluorescently-labeled antibodies against: CD45-PeiCP-Cy5.5, CD3-BV605, CD34-BV421, and CD64-PE. Stained cells were analyzed on a Fortessa X-20 Flow cytometer (BD Biosciences). Live cells were analyzed for the ratio of AML cells ($CD45^{dim}/CD3^{neg}$) to T cells ($CD45^{bright}/CD3^{pos}$) and this ratio was normalized to mock-treated AML cells at each E:T ratio. AML cells were further analyzed for expression of CD34 and CD64. Statistical comparisons of Mock vs CAR (at either 24 and/or 48 hours) were performed using two-way ANOVA with Tukey's multiple comparison test.

Ex Vivo Depletion of Leukemia Stem Cells in Patient-Derived AML Samples by CD64 CAR T Cells Cryopreserved patient-derived AML samples acquired from the University of Colorado Biorepository were thawed and kept in culture at 37° C., 8% $CO_2$ in a tissue culture incubator. Cell viability and concentration was determined by trypan-blue exclusion. Patient-derived AML cells were co-incubated with CD64 CAR T cells at an E:T of 1:2 or an equivalent number of Mock T cells for 24 hours at 37° C., 10% $CO_2$ in a tissue culture incubator. T cells were depleted by antibody-mediated magnetic separation and $10^6$ AML cells were injected into NSG-S mice via tail vein. Mice were euthanized 6 weeks later. Bone marrow was collected from femurs, processed to a single cell suspension, red blood cells were lysed, and bone marrow cells were stained for viability (Fixable Viability Dye eFlour780, Invitrogen) and with fluorescently-labeled antibodies against: mouse CD45-BV786, human CD45-APC-R700, CD3-FITC, CD33-PE, and CD64-BV510. Human AML cells were defined as ($mCD45^{neg}/hCD45^{pos}/CD3^{neg}/CD33^{pos}/CD64^{+/-}$). Statistical comparisons between Mock and CAR T cell treatment were performed using Mann-Whitney Analysis.

Figure 1A:
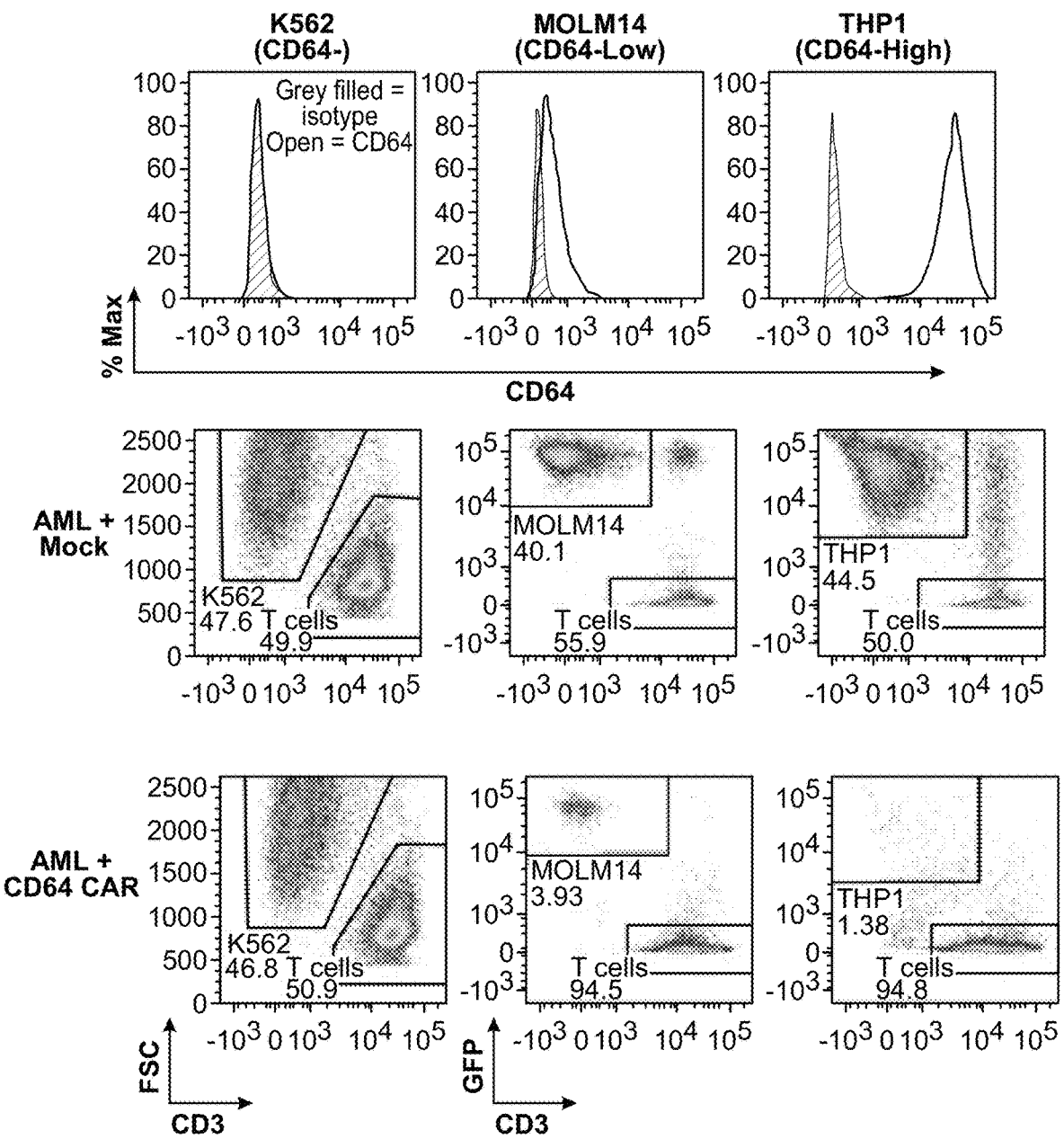
FIG. 1A-C is a series of graphs showing that CD64 CAR with a CD28 costimulatory domain and the m22 single chain fragment variable (scFv) (CD64-28z) T cells have antigen-dependent effector activity against AML cell lines. A) CD64 expression on AML cell lines K562 (CD64-negative), MOLM14 (CD64-low), and THP1 (CD64-high) used in downstream experiments (top). AML cell lines were co-incubated with either T cells from a healthy donor that were activated but not transduced (Mock, negative control) or with T cells transduced with a CD64 CAR containing a CD28 costimulatory domain (CD64 CAR). AML cells and T cells were co-incubated at a 1:1 ratio for 24 hours in triplicate and evaluated by flow cytometry. B) Quantification of the percentage of AML cells of remaining viable cells after the 24-hour coincubation using flow cytometry. The results demonstrate no reduction of the CD64-negative K652 cells by CD64 CAR T cells, but significant reduction of the CD64-low MOLM14 and CD64-high THP1 AML cells by CD64-28z CAR T cells (labeled as CD64 CAR). C) CD64-negative K562 cells and CD64-high THP1 cells were co-incubated with either CD19 CAR T cells (CD19-28z, irrelevant CAR used as a negative control) or with CD64 CAR T cells (CD64-28z) at a 1:1 ratio for 24 hours to measure antigen-dependent cytokine secretion from CD64-28z CAR T cells. CAR T cells were cultured alone as a negative control. All co-incubations/cultures were done in triplicate. After 24 hours, supernatant was collected from all wells and evaluated for cytokines by ELISA, demonstrating significant production of Interferon-gamma (IFNG) and Interleukin-2 (IL-2) by CD64-28z CAR T cells only in the presence of CD64+ AML cells. Statistical comparisons between CD64-28z and negative controls were performed using Mann-Whitney analysis.
Figure 1B:
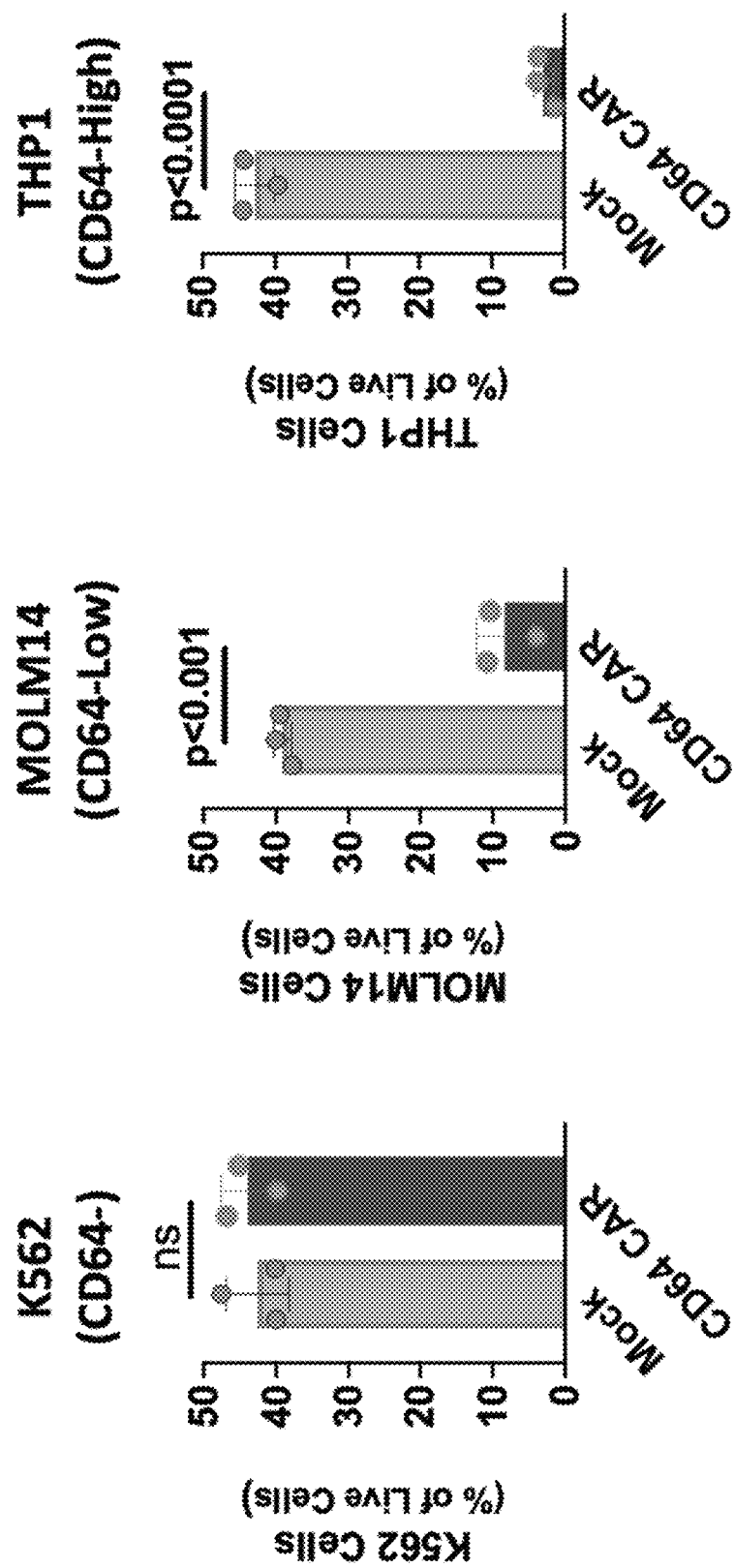
Figure 1C:
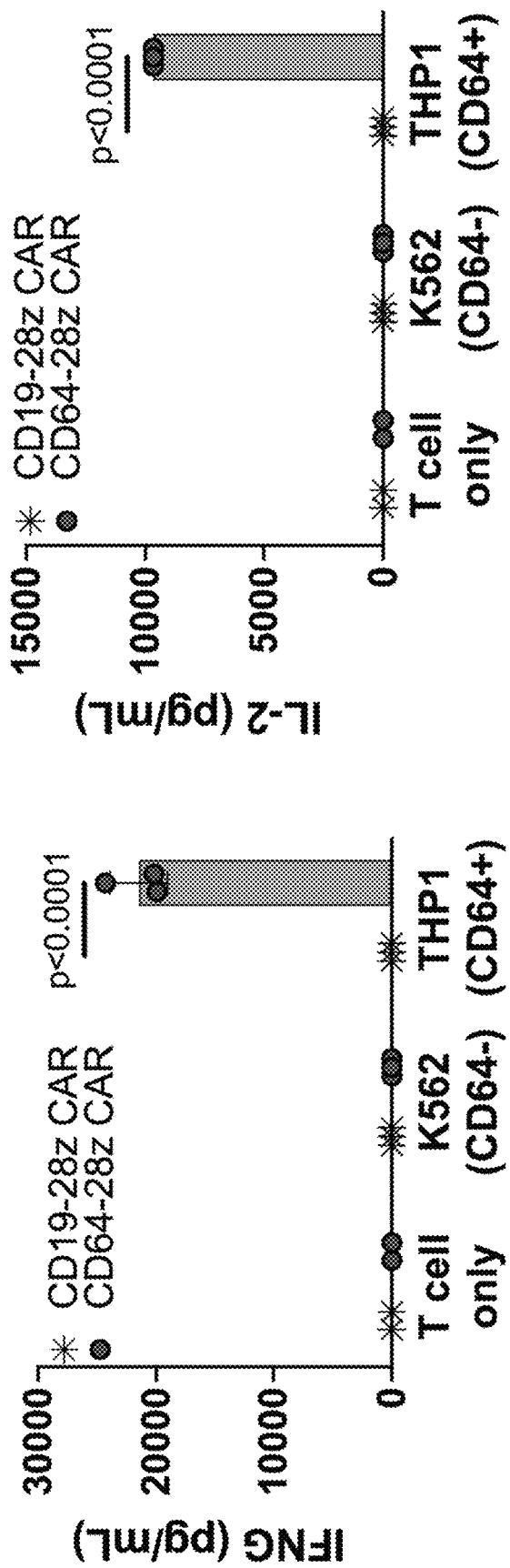

Example 1—CD64 CAR with a CD28 Costimulatory Domain (CD64-28z) T Cells Demonstrates Antigen-Dependent Effector Activity Against AML Cell Lines CD64-28z-m22 CAR T cells, generated from healthy donor T cells, demonstrated the ability to target CD64$^+$ AML cells lines in vitro after 24 hours co-incubation. Cytotoxicity of CD64-28z-m22 CAR T cells was evaluated by measuring residual AML cells by flow cytometry after co-incubation with either CAR T cells or Mock T cells. CD64-28z-m22 CAR T cells were able to significantly eliminate the CD64$^+$ cell lines, MOLM14, and THP1 (FIG. 1A-B). Cytotoxicity was completely dependent upon CD64 antigen expression, as the CD64-negative cell line, K562, was not targeted by CD64-28z-m22 CAR T cells as demonstrated by no change in the amount of residual K562 cells after co-incubation with CAR T cells relative to Mock T cells (FIG. 1A-B). There was a subtle decrease in cytotoxicity of CD64-28z-m22 CAR T cells against the CD64-low MOLM14 cells relative to the CD64-high THP1 cells, further supporting the activity of CD64-28z-m22 CAR T cells is dependent upon antigen expression on the target cells (FIG. 1A-B). CD64-28z-m22 CAR T cells also secrete the effector cytokines Interferon-Gamma (IFNG) and Interleukin-2 (IL-2) in response to CD64$^+$ cells (THP1), but not spontaneously (T cell only) or in response to CD64-negative (K562) cells (FIG. 1C). Without wishing to be bound by theory, these results demonstrate that the CD64-28z-m22 CAR is capable of recognizing CD64$^+$ AML cells and responding through cytotoxicity and cytokine production.

Example 2—CD64-28z-m22 CAR T Cells Demonstrate In Vivo Efficacy Against CD64$^+$ AML Cells Lines in Xenograft Models CD64-28z-m22 CAR T cells, generated from healthy donor T cells, demonstrate the ability to control AML progression in xenograft in vivo models. CD64-28z-m22

CAR T cells given to NSG mice engrafted with the CD64+ THP1 cell line demonstrated significant delay in leukemia progression and leukemia regression, ultimately significantly prolonging the survival of CAR-treated mice over untreated mice (FIG. 2A). Similarly, CD46-28z-m22 CAR T cells were able to eradicate CD64+ MOLM14 leukemia to undetectable levels and significantly prolonged the survival of mice beyond that of untreated mice (FIG. 2B).

Figure 3A:
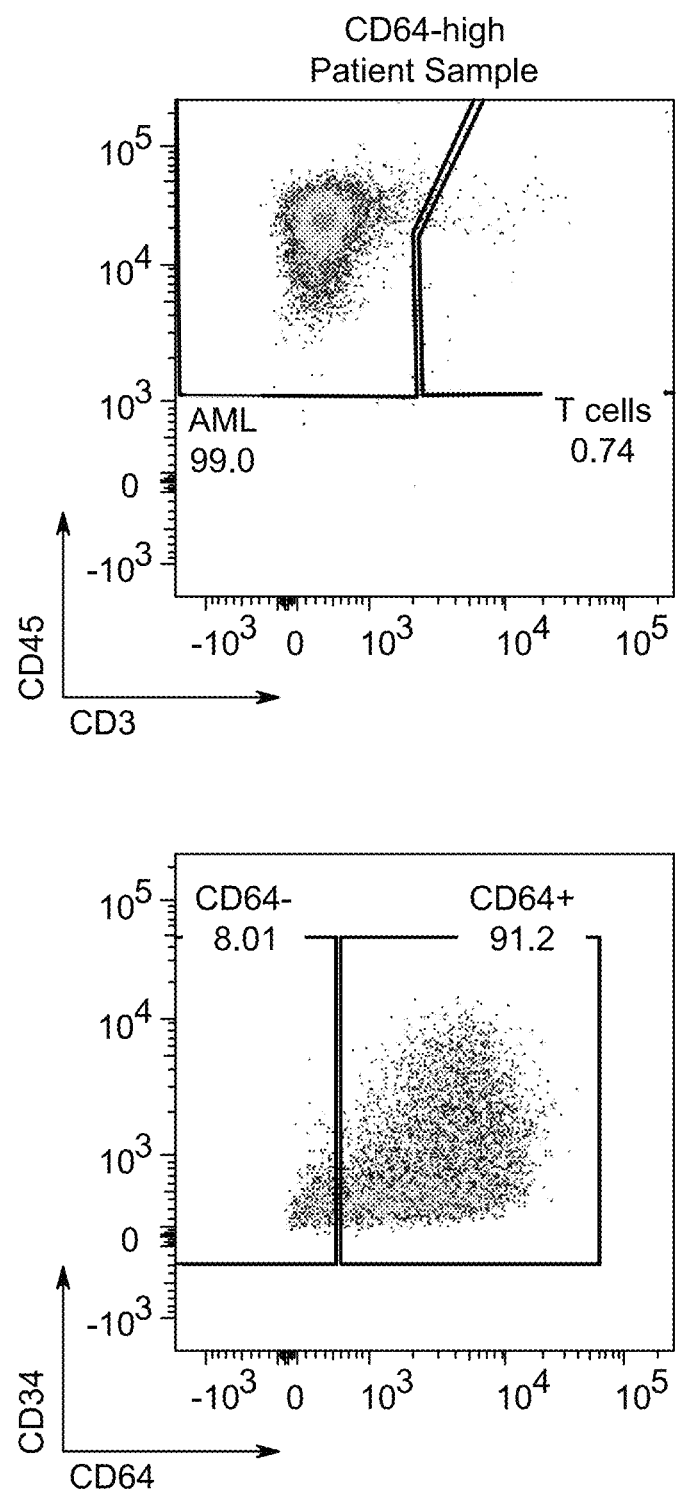
FIG. 3A-C is a series of graphs showing that CD64-28z CAR T cells (containing the m22 scFv) have cytotoxicity against patient-derived monocytic AML in vitro. A) CD64+ Monocytic AML cells with monocytic leukemia stem cells (mLSCs) were obtained from the University of Colorado Biorepository. B-C) Mock T cells or CD64-28z CAR T cells derived from the same healthy donor were co-incubated in vitro with patient AML cells in triplicate for 24 or 48 hours at different effector (T cell) to target (AML cells) ratios (E:T ratios). B) Co-incubation with CD64-28z CAR T cells resulted in a significant, dose-dependent depletion of live AML cells at all E:T ratios, as measured by flow cytometry. C) Flow cytometric evaluation of remaining AML cells at 24 and 48 hours demonstrates CD64-28z CAR T cells specifically deplete CD64+ AML cells significantly more than mock T cells at all E:T ratios. Depletion of CD64+ AML cells by CD64-28z CAR T cells occurs in a dose-dependent manner and increases from 24 hours to 48 hours at E:T ratios of 1:4 and 1:16, whereas all CD64+ AML cells are depleted within the first 24 hours at the 1:1 E:T ratio. Statistical comparisons using two-way ANOVA with Tukey's multiple comparison test. ns=not significant, *=p-value less than 0.001, **=p-value less than 0.0001.
Figure 3B:
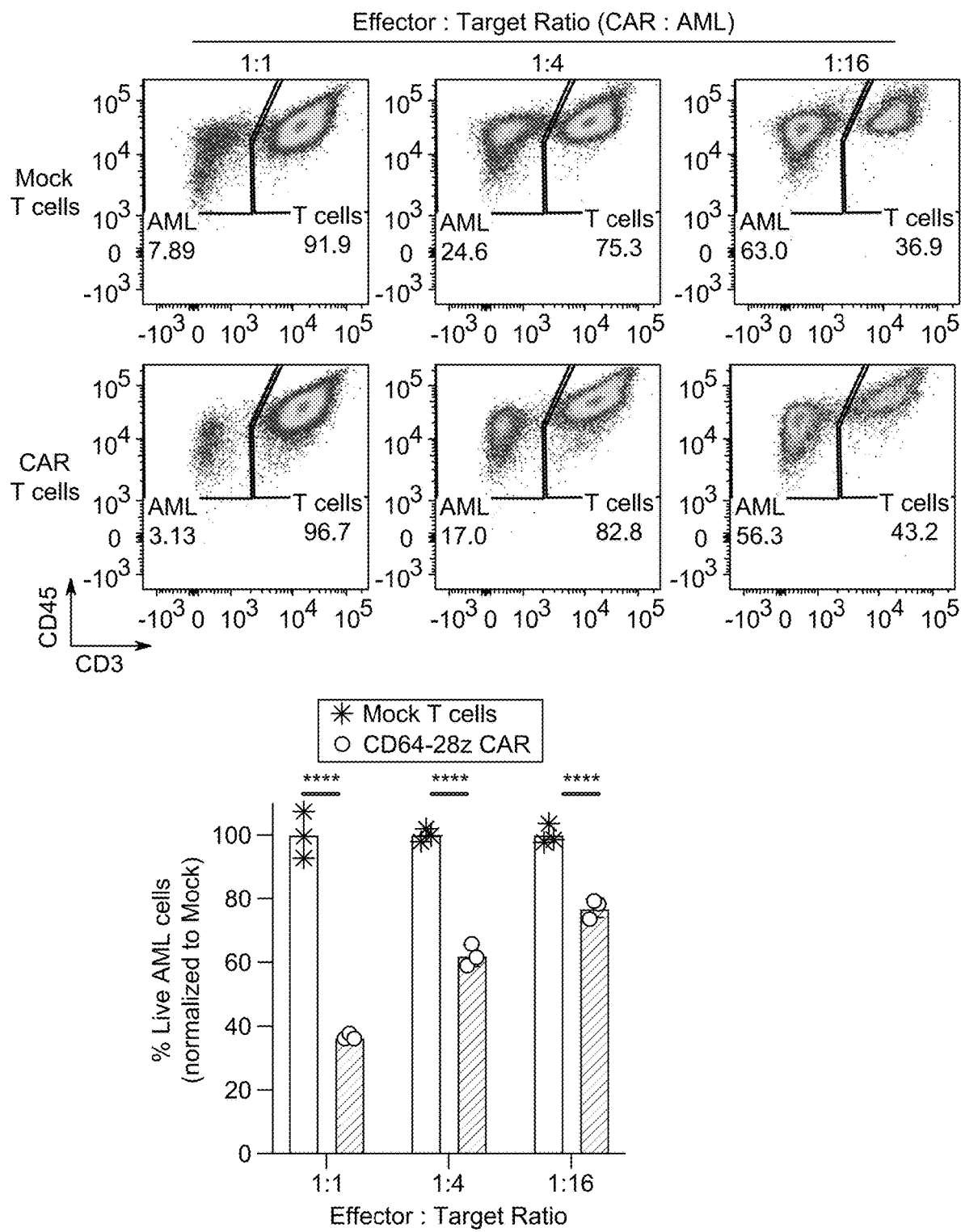
Figure 3C:
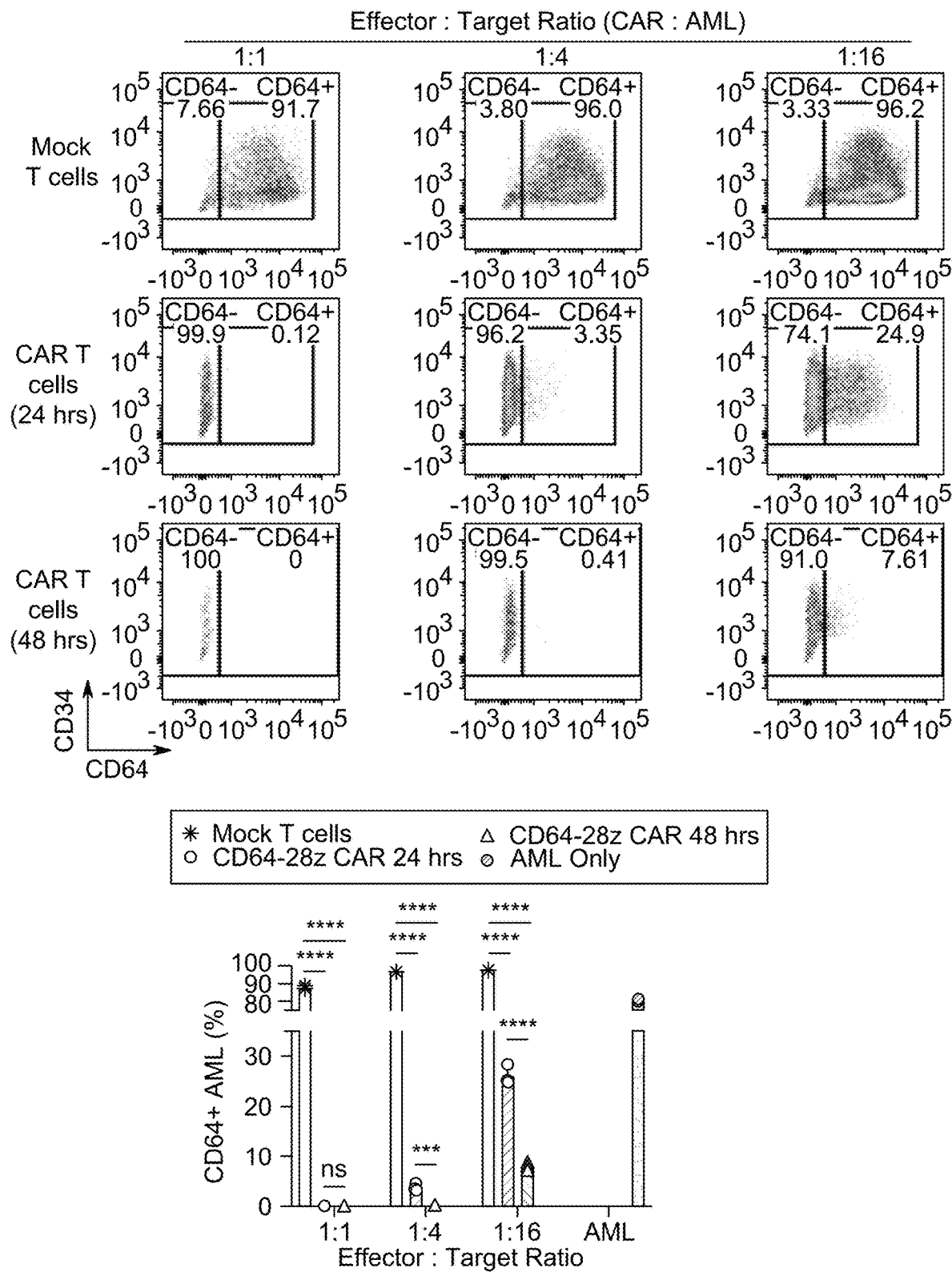
Figure 4A:
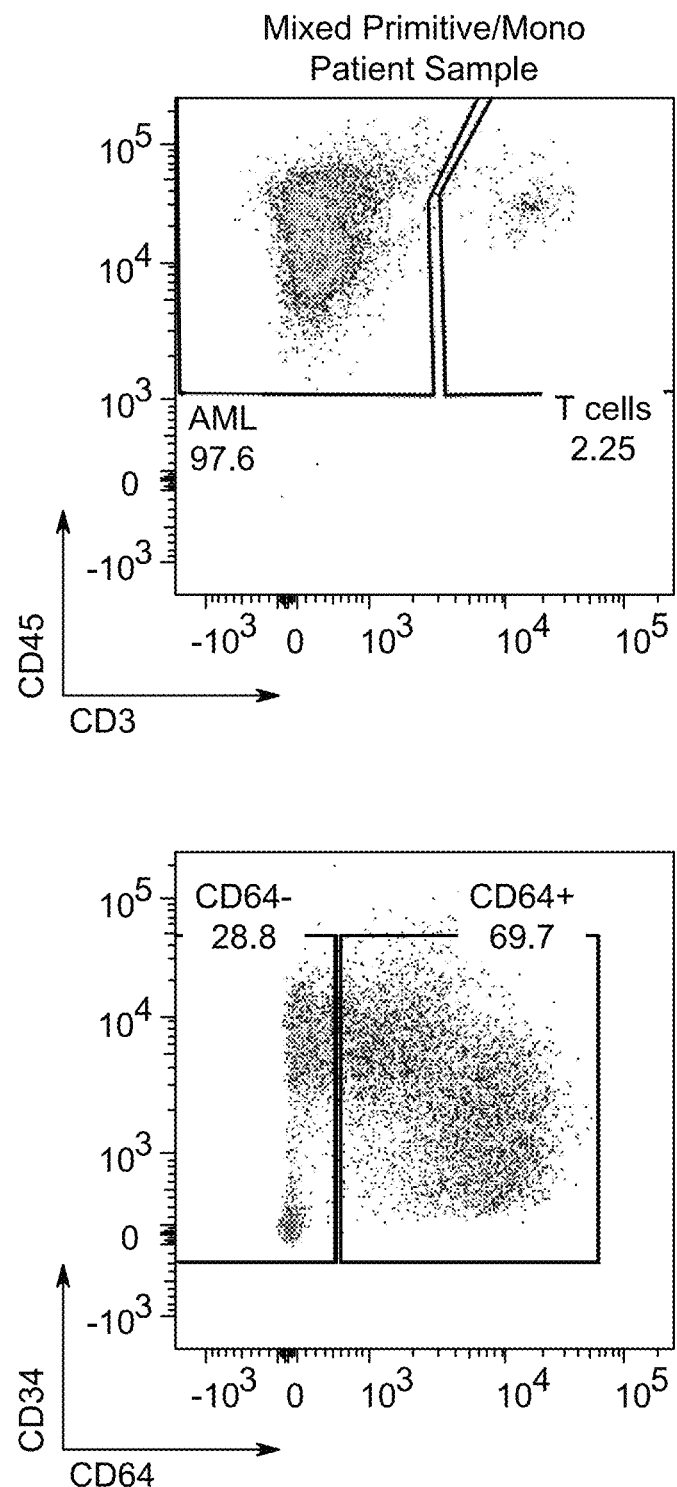
FIG. 4A-C is a series of graphs showing that CD64-28z CAR T cells (containing the m22 scFv) have cytotoxicity against patient-derived AML with mixed primitive and monocytic populations in vitro. A) Patient derived AML with a mixed population of CD64−(primitive) and CD64+ (monocytic) leukemia stem cells (LSCs) were obtained from the University of Colorado Biorepository. B-C) Mock T cells or CD64-28z CAR T cells derived from the same healthy donor were co-incubated with patient AML cells in vitro for 24 or 48 hours at different effector (T cell) to target (AML cells) ratios (E:T ratio) in triplicate. B) Co-incubation with CD64-28z CAR T cells resulted in a significant, dose-dependent depletion of live AML cells at all E:T ratios, as measured by flow cytometry. C) Flow cytometric evaluation of remaining AML cells at 24 and 48 hours demonstrates CD64-28z CAR T cells specifically deplete CD64+ AML cells significantly more than mock T cells at all E:T ratios. Depletion of CD64+ AML cells by CD64-28z CAR T cells occurs in a dose-dependent manner and increased from 24 hours to 48 hours for E:T ratios of 1:4 and 1:16, whereas all CD64+ AML cells were depleted within the first 24 hours at the 1:1 E:T ratio. Statistical comparisons using two-way ANOVA with Tukey's multiple comparison test. ns=not significant, *=p-value less than 0.05, ****=p-value less than 0.0001.
Figure 4B:
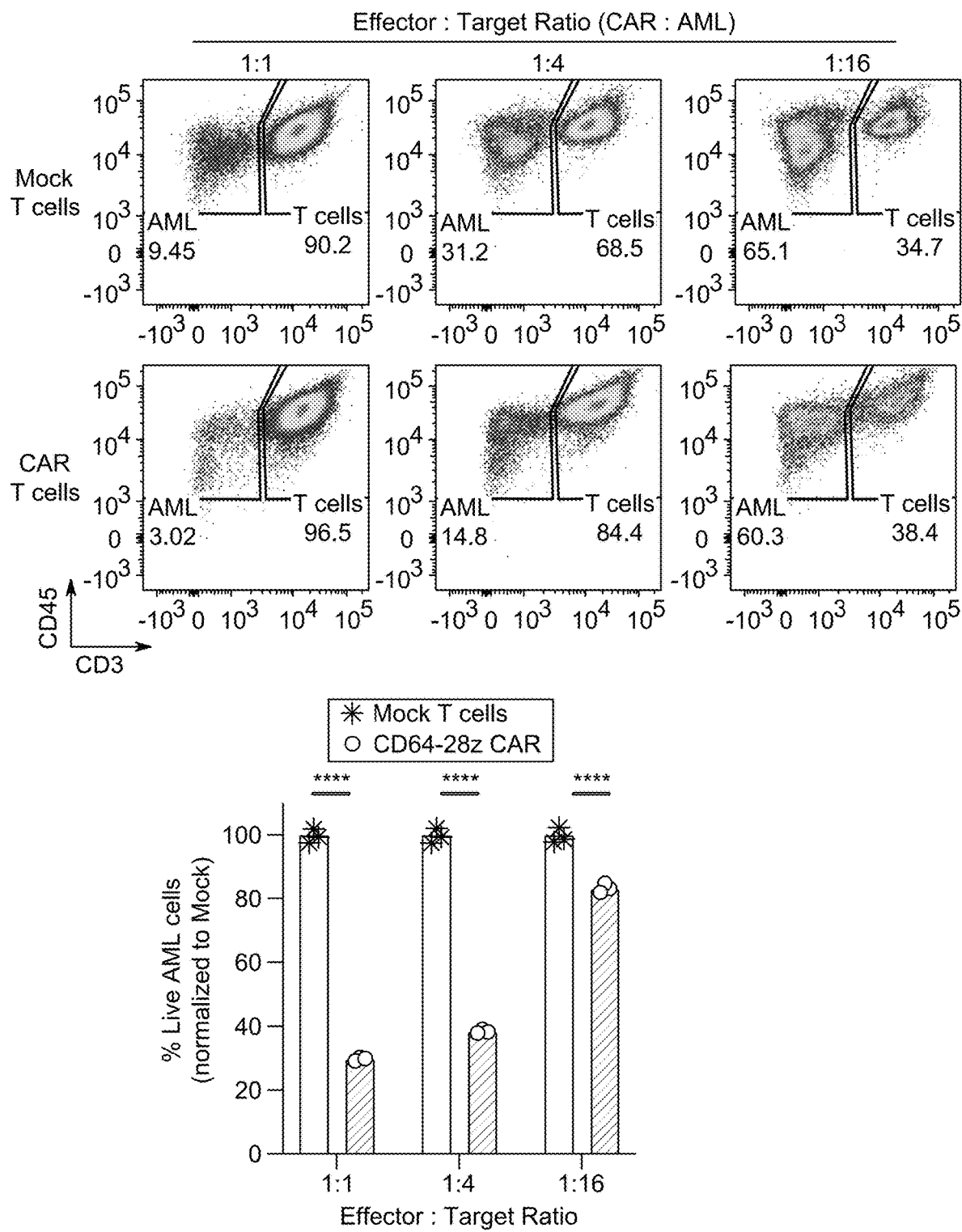
Figure 4C:
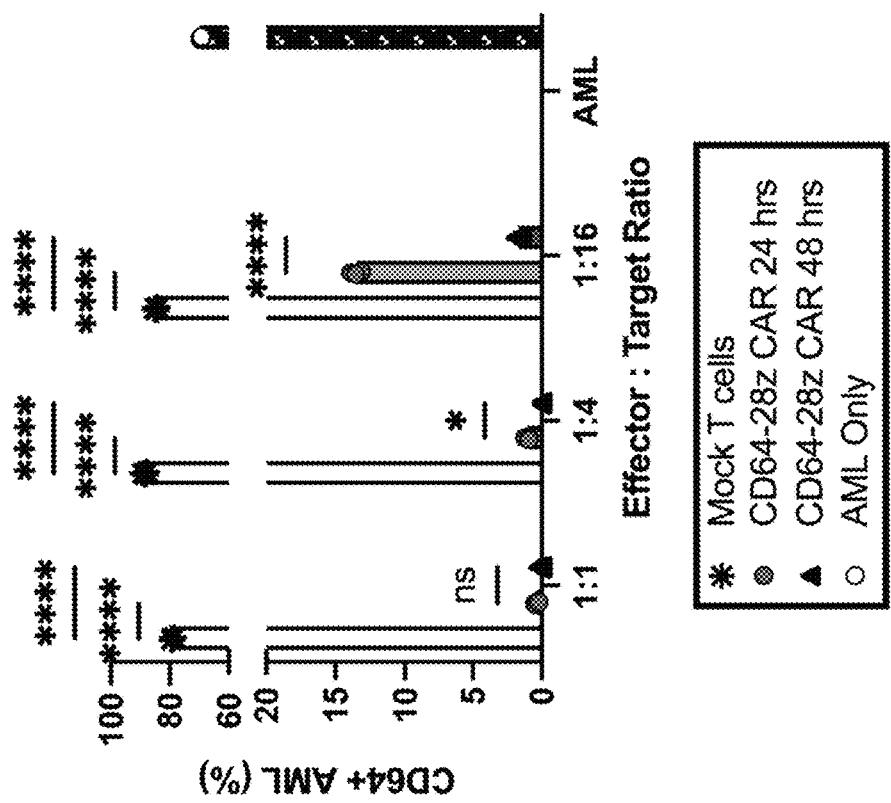
Figure 4C:
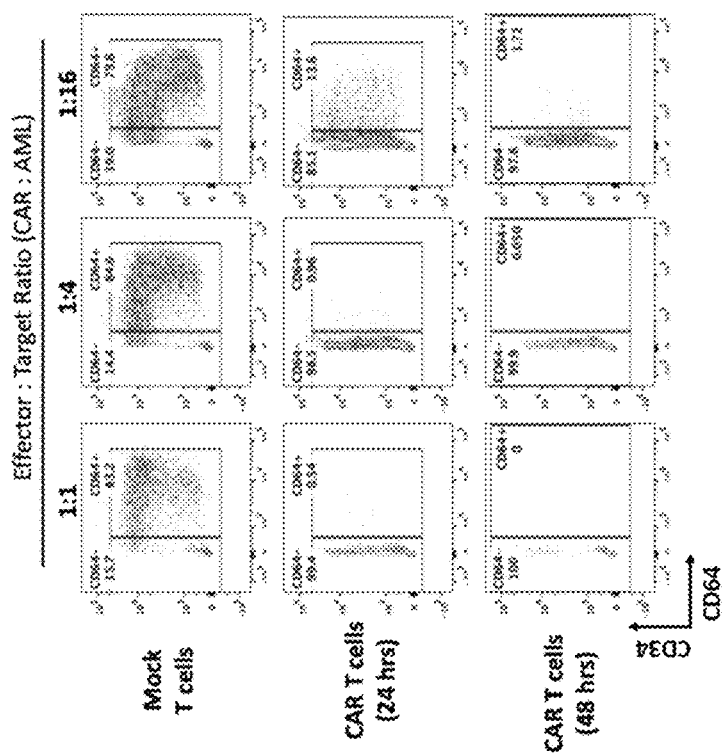

Example 3—CD64-28z-m22 CAR T Cells Demonstrate In Vitro Cytotoxicity Against Patient-Derived AML CD64-28z-m22 CAR T cells were tested for their ability to kill patient-derived AML that predominantly expressed CD64 (FIG. 3A). After 24 hours co-incubation, CD64-28z-m22 CAR T cells significantly reduced the amount of viable AML cells relative to mock T cells (FIG. 3B). In particular, CD64-28z-m22 CAR T cells eliminated the CD64+ cells within the AML, leading to virtually no detectable CD64+ at 24 hours at an E:T ratio of 1:1 and by 48 hours at the lower E:T of 1:4 (FIG. 3C). Even at E:T ratios as low as 1:16, there was significant reduction of both total AML and CD64+ AML at both 24 and 48 hours (FIG. 3B-C). Similar results were obtained when CD64-28z-m22 CAR T cells were co-incubated with patient-derived AML that contained both CD64+ and CD64- subpopulations (FIG. 4A) stemming from primitive (CD64-) and monocytic (CD64+) leukemia stem cell (LSC) populations, as previously described by Pei et. al., Cancer Discovery, 2020; 10(4):536-551. CD64-28z-m22 CAR T cells significantly reduced the number of viable AML cells in 24 hours, relative to Mock T cells (FIG. 4B). CD64-28z-m22 CAR T cells were found to also significantly deplete the CD64+ AML cells, with near complete elimination of CD64+ AML at 24 hours at E:T ratios of 1:1 and 1:4 and of E:T ratios as low as 1:16 at 48 hours (FIG. 4C). Without wishing to be bound by theory, these results demonstrate that the CD64-28z-m22 CAR shows effective cytotoxicity against patient-derived AML as well as AML cell lines (as demonstrated in FIG. 1A-B).

Example 4—CD64-28z-m22 CAR T Cells Deplete Monocytic Leukemic Stem Cells (mLSCs) from Patient-Derived AML Samples As monocytic leukemia stem cells (mLSCs) have been reported to drive resistance to common AML therapies, such as venetoclax and azacytidine, in patients (Pei et. al., Cancer Discovery, 2020; 10(4):536-551), the CD64-28z-m22 CAR was tested for its ability to specifically deplete mLSCs from patient-derived AML samples. As in vivo engraftment is the primary test of LSC activity, patient derived AML samples were first co-incubated with CD64-28z-m22 CAR T cells or Mock T cells at an E:T of 1:2 for 24 hours to allow for CAR T cell killing of the mLSC population. After 24 hours, T cells were depleted, and the remaining AML cells were inoculated into immunocompromised NSG-S mice. Leukemia engraftment was evaluated 6 weeks later and found to be significantly impaired after CAR T cell co-incubation relative to co-incubation with Mock T cells (FIG. 5A-D). Pre-treatment of the AML with CD64-28z-m22 CAR T cells resulted in decreased engraftment of the total AML population and the CD64+ AML population of patient-derived AML that was predominantly CD64+(FIG. 5A-B), suggesting the depletion of mLSCs prior to inoculation into the mice. Similarly, there was decreased engraftment of the total AML population and the CD64+ subpopulation of AML from a patient with mixed primitive/monocytic AML after co-incubation with CD64-28z-m22 CAR T cells (FIG. 5C-D). Without wishing to be bound by theory, these results demonstrate that CD64 CAR T cells can specifically deplete the monocytic leukemia stem cell population that has been implicated in patient relapses, particularly after treatment with venetoclax and azacitidine.

Example 5—CD64-BBz-m22 and CD64-28z-m22 CAR T Cells Demonstrate In Vivo Efficacy Against CD64+ AML Cells Lines in Xenograft Models CD64 CARs containing either a CD28 costimulatory domain (CD64-28z-m22) or a 4-1BB costimulatory domain (CD64-BBz-m22) were generated from T cells of two independent healthy donors and were tested for their ability to control the CD64+ MOLM14 AML cell line in xenograft models. Both CD64-28z-m22 and CD64-BBz-m22 CAR T cells significantly slowed leukemia progression and/or eliminated leukemia compared to Mock T cell treatment (FIG. 6A). The efficacy of CD64 CAR T cells was seen when CAR T cells were generated from different healthy T cell donors (FIG. 6A) and both CD64-28z-m22 and CD64-BBz-m22 CAR T cells significantly prolonged the survival of AML-bearing mice (FIG. 6B). Quantification of total bioluminescent flux per mouse demonstrated decreased leukemia burden in mice treated with CD64-28z-m22 and CD64-BBz-m22 CAR T cells as compared to mock treated mice (FIG. 6C). Without wishing to be bound by theory, these results demonstrate a significant survival advantageous of CD64-BBz-m22 CAR T cells relative to CD64-28z-m22 CAR T cells (FIG. 6B).

Example 6—CD64 CAR T Cells Demonstrate Efficacy Against Monocytic and Mixed Monocytic/Primitive AML The results in this Example re-present and expand on at least some of the results provided in other Examples.
CD64 Expression in AML Models
In order to assess the preclinical efficacy of the CD64 CAR, a variety of target leukemia models with varying levels of CD64 expression were utilized. AML cell lines with high, moderate, and negative CD64 expression to test CD64 CAR efficacy were employed. CD64 expression in three model cell lines was compared using flow cytometry with staining for CD64 (FIG. 7A). The CD64$^+$ cell line MOLM14 expressed a low-moderate level of CD64. The monocytic AML cell line, THP-1, expressed high levels of CD64. The K562 cell line was used as a negative control as it did not express CD64.

Figure 8A:
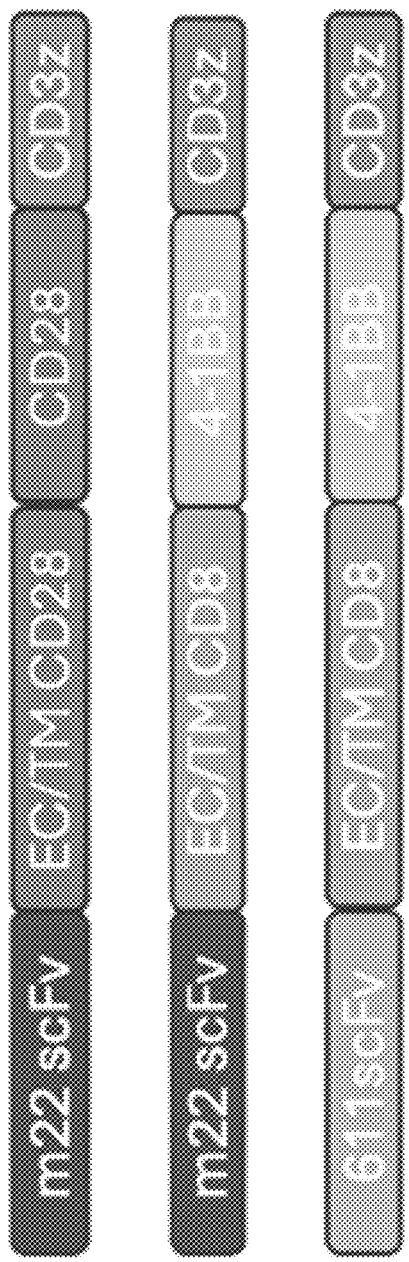

Primary AML samples with differing phenotypes, including monocytic (FAB M5) patient samples (AML04 and AML06 with uniformly high CD64 expression (CD64bright, CD34dim/-)) and mixed monocytic and primitive AML patient samples (AML03 and AML07, (CD64dim/-, CD34bright)), were used (FIG. 7B).
CD64 CAR Expression in Donor T-Cells
Human T cells were transduced with the CD64 CAR transgenes by lentiviral transduction following T cell activation with anti-CD3/CD28 T-Expander Dynabeads™ (Invitrogen) in the presence of IL-2 (R&D, 40 IU/mL). After transduction, the anti-CD3/CD28 Dynabeads™ were removed and T cells were expanded in the presence of IL-2 (100 IU/mL) for 5 days. Three different CAR constructs were tested. CD64-28-m22 included a scFv derived from the murine M22 antibody (which targets human CD64) attached to a portion of the extracellular domain of human CD28, the human CD28 transmembrane domain, and the human CD28 intracellular signaling domain inline with the human CD3-zeta signaling domain with all three ITAMs intact (FIG. 8A). CD64-BB-m22 included the same M22 scFv attached to a portion of the extracellular domain of human CD8a and the human CD8a transmembrane domain. This transmembrane domain was inline with the intracellular signaling domain of human 4-1BB and human CD3-zeta with all three ITAMs intact. CD64-BB-611 incorporated a scFv derived from the humanized anti-CD64 antibody, 611, attached to a portion of the extracellular domain of human CD8a and the human CD8α transmembrane domain. This transmembrane domain was in line with the intracellular signaling domain of human 4-1BB and human CD3-zeta with all three ITAMs intact.

Figure 8B:
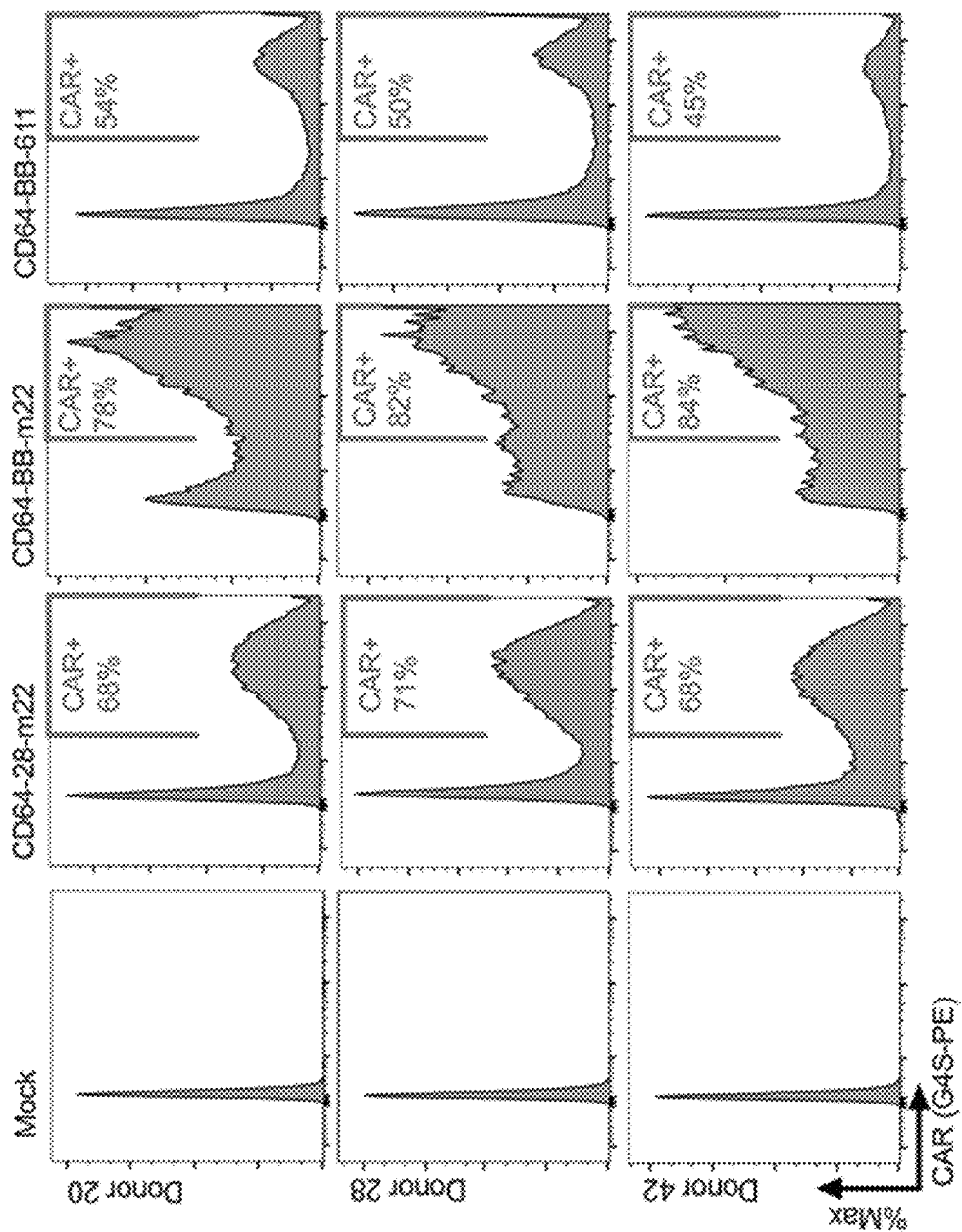

Healthy human donor T cells were successfully transduced with all CD64 CAR constructs. CAR molecules were consistently expressed across T cells from multiple healthy donors, as measured by flow cytometry using antibodies recognizing the G4S (SEQ ID NO: 422) linker of the CAR scFvs (FIG. 8B). In CAR+ populations transduced with a CAR construct incorporating a 4-1BB signaling domain, there was a skewing to a higher ratio of CD4 to CD8 T cells. There was a more balanced ratio of CD4 to CD8 seen in CAR+ populations transduced with a CAR incorporating the CD28 costimulatory domain (FIG. 8C).

Figures 8C, 8D:
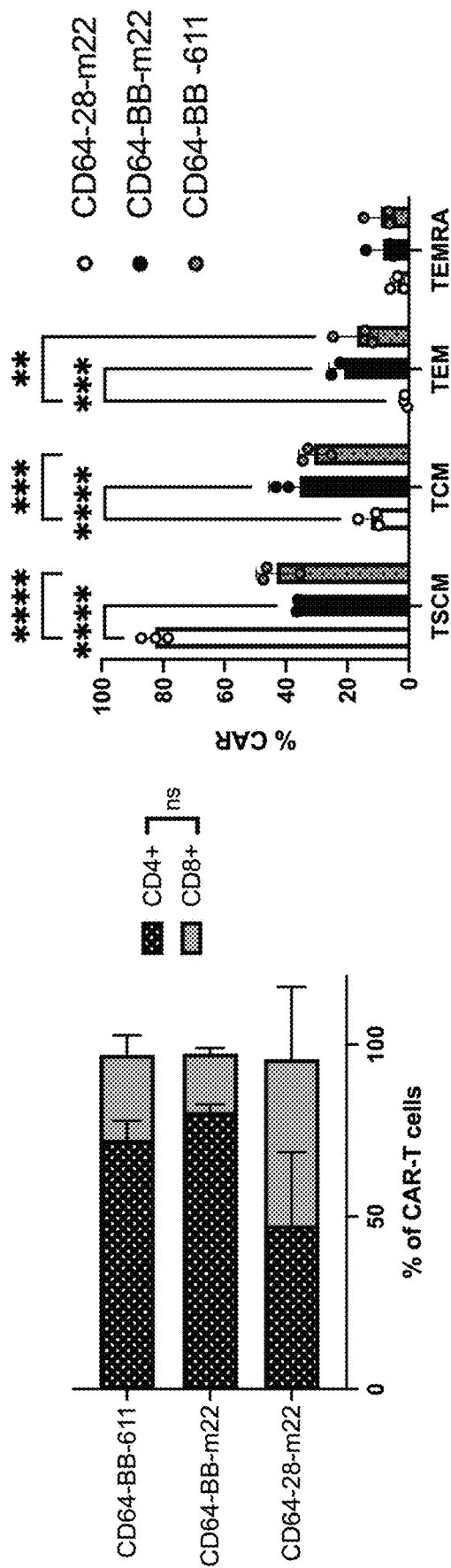

It was found that T cells transduced the CD64-28-m22 CAR predominantly had a phenotype consistent with T stem cell memory (TSCM) cells (CD62L+/CD45RA+/CD95+), whereas T cells transduced with either CD64-BB-m22 or CD64-BB-611 demonstrated a mixture of phenotypes consistent with TSCM, T central memory (TCM, CD62L+/CD45RA−/CD95+), and T effector memory (TEM, CD62L−/CD45RA−/CD95+) (FIG. 8D). These phenotypic trends were consistent across T cells from multiple healthy donors. Statistical analysis of three independent donors by two-way ANOVA with Turkey's multiple comparison test was performed.

CD64 CAR T Cell Cytotoxicity In Vitro

Figure 9B:
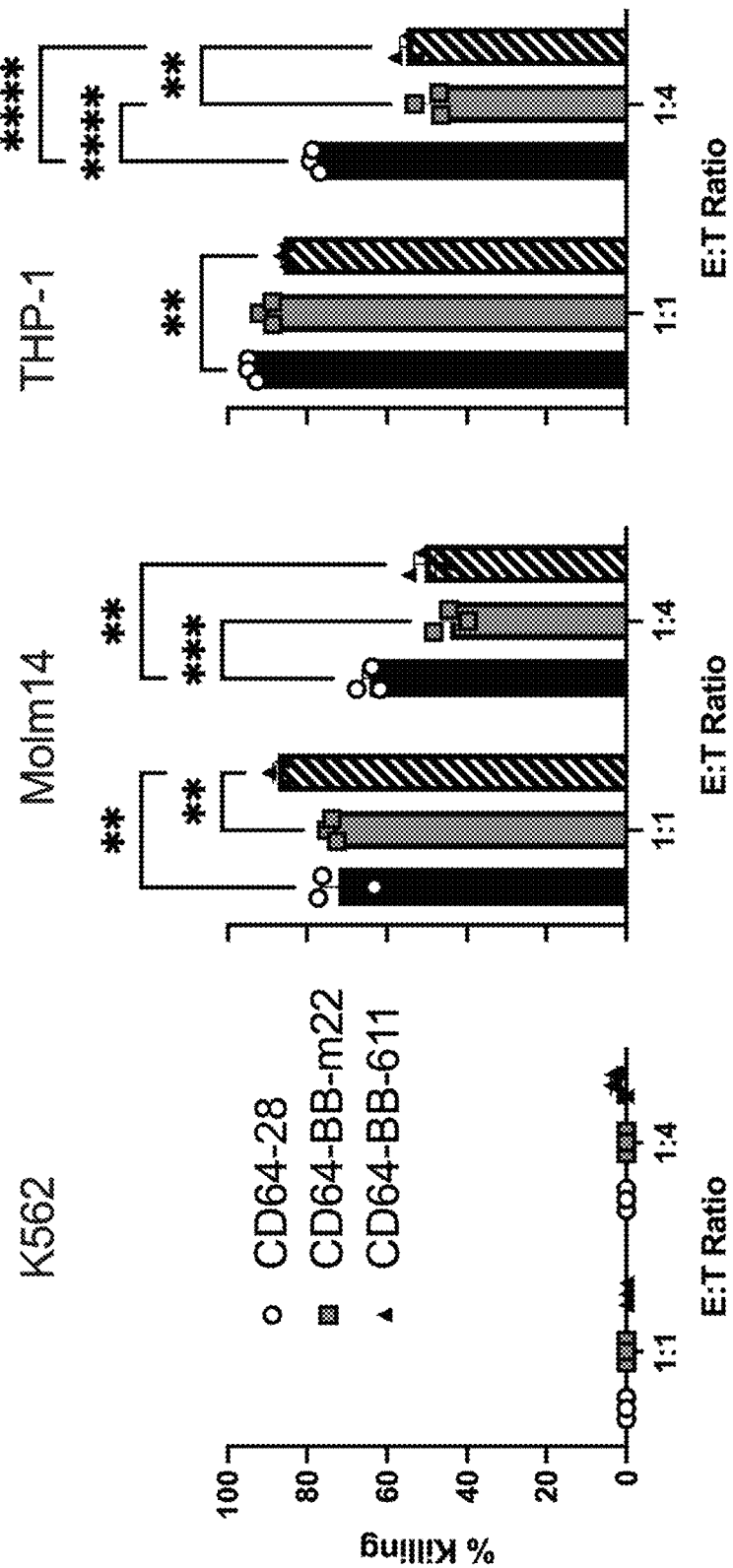

Efficacious CAR molecules are anticipated to elicit a cytotoxic response from CAR T cells upon engaging with antigen positive cells. To test the ability of the CD64 CAR constructs to elicit this effector function, CD64 CAR T cells were co-cultured with $1\times10^5$ cells from MOLM14 (CD64low), THP-1 (CD64high), and K562 (CD64 negative) AML cell lines. Cells were co-cultured overnight at an E:T ratio of 1:1 or 1:4. The following day, viable AML cells were quantified by flow cytometry. Untransduced T cells from the same T cell donor (Mock T cells) were used as a negative control. Reductions in the viable AML cell populations were observed when CD64+ AML cells were cultured with CD64-28-m22, CD64-BB-m22, and CD64-BB-611 CAR T cells (FIG. 9A). Killing of target cells from three replicates was quantified (FIG. 9B).

Figure 9C:
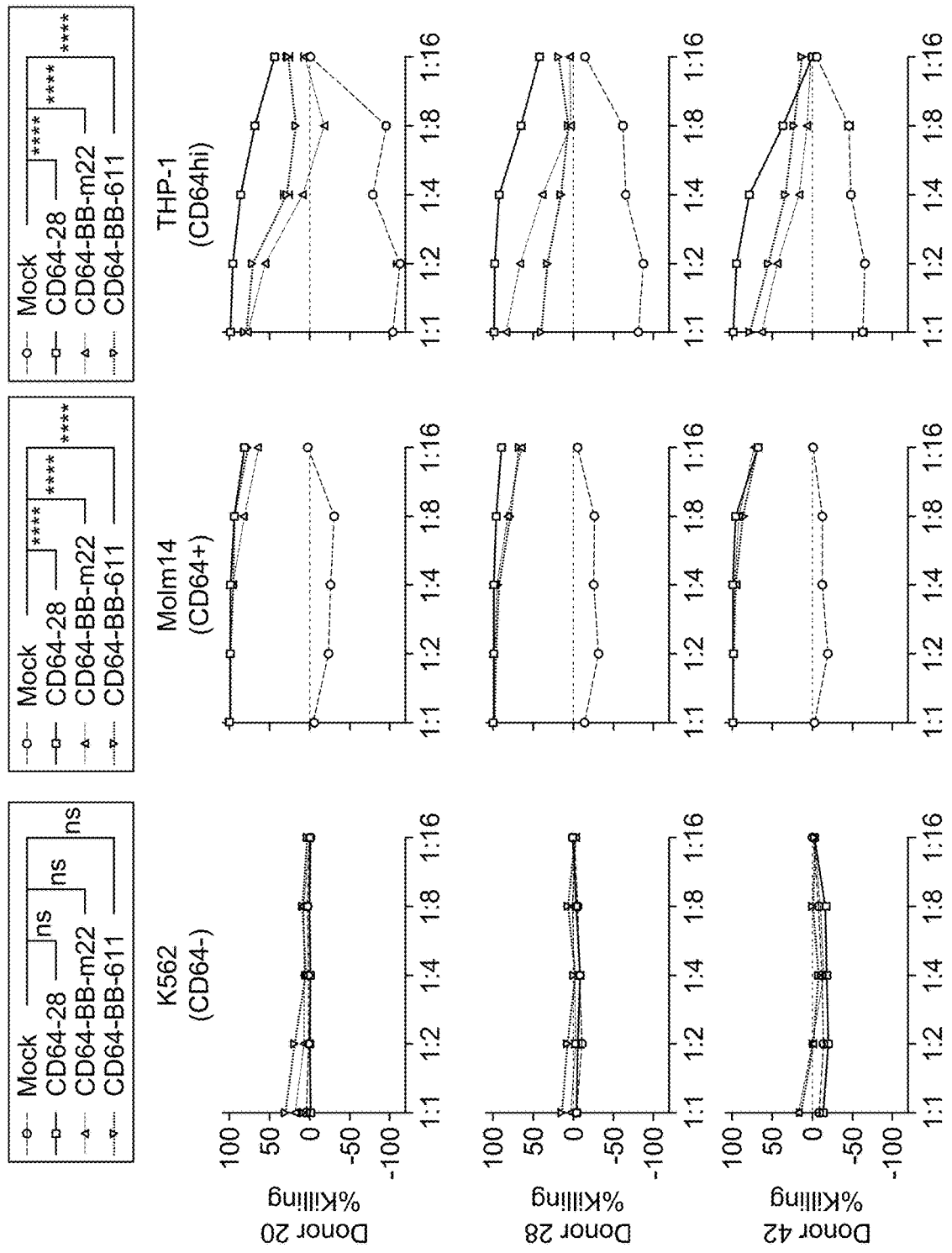

To further characterize the cytotoxicity of CD64 CAR T cells, a luciferase-based killing assay was used to test each of the CD64 CAR construct's ability to kill MOLM14, THP-1, and K562 cells. Cells were co-cultured with CD64-28-m22, CD64-BB-m22, or CD64-BB-611 CAR T cells from three independent donors overnight at a range of E:T ratios (FIG. 9C). CD64-28-m22 CAR T cells demonstrated significantly higher cytotoxicity against THP-1 cells across all donors and higher cytotoxicity against MOLM14 cells in two of three donors. Both CD64-BB-m22 and CD64-BB-611 showed effective killing against both THP-1 and MOLM14 cells (FIG. 9C), consistent with previous results (FIGS. 9A-9B). Importantly, no significant killing of CD64-negative K562 cells by any CD64 CAR constructs was observed, supporting the antigen-dependence and specificity of these CARs.

Figure 9D:
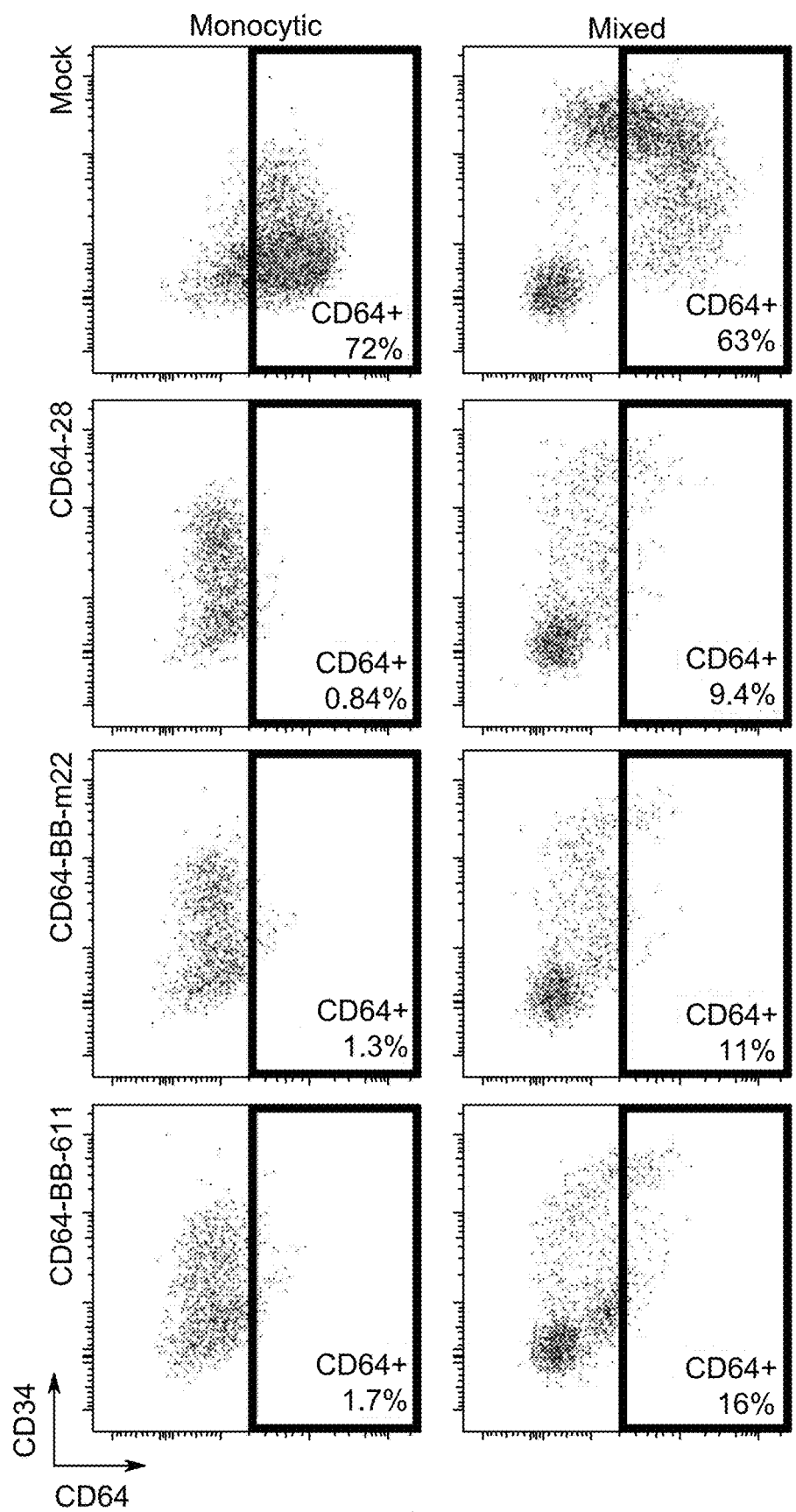
Figure 9E:
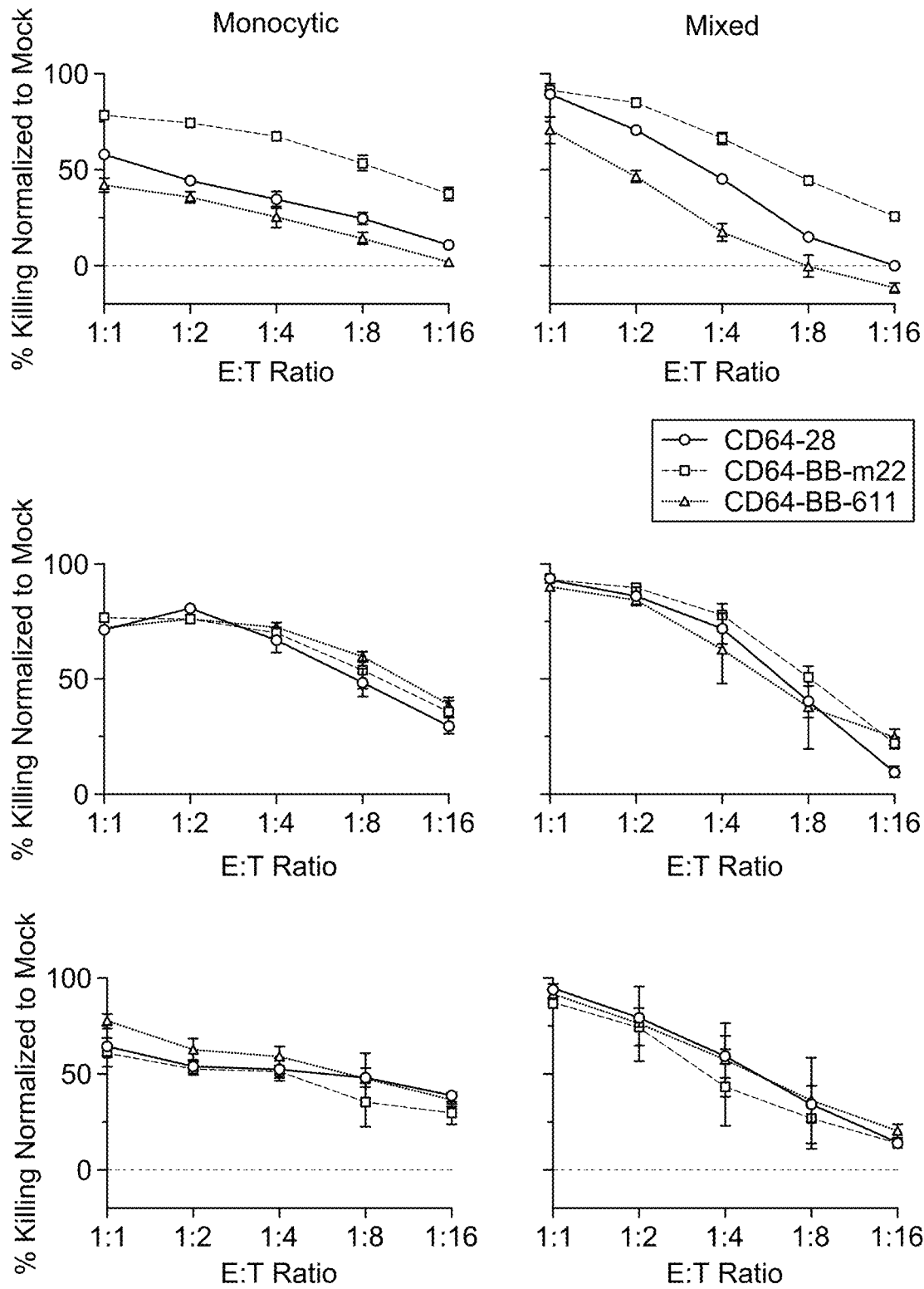

To test the CD64 CAR T cells against primary AML, CD64 CAR T cells were co-cultured with $1\times10^5$ patient-derived AML cells. Cells were co-cultured for 24 hours at various E:T ratios, and residual live AML cells were evaluated by flow cytometry. Patient-derived AML cells cultured with mock T cells showed a persistent CD64+ population, whereas each of the CD64 CAR T cell products reduced the CD64+ AML cells in a dose-dependent manner (FIGS. 9D-9E). CD64-28-m22, CD64-BB-m22, and CD64-BB-611 CAR T cells from multiple donors similarly eliminated CD64+ AML cells and showed killing of both monocytic and mixed monocytic/primitive AML patient cells (FIGS. 9D-9E). Collectively, these data demonstrate the cytotoxic function of CD64 CAR T cells against CD64-expressing AML cells.

Secretion of T-Cell Effector Cytokines

Figure 10A:
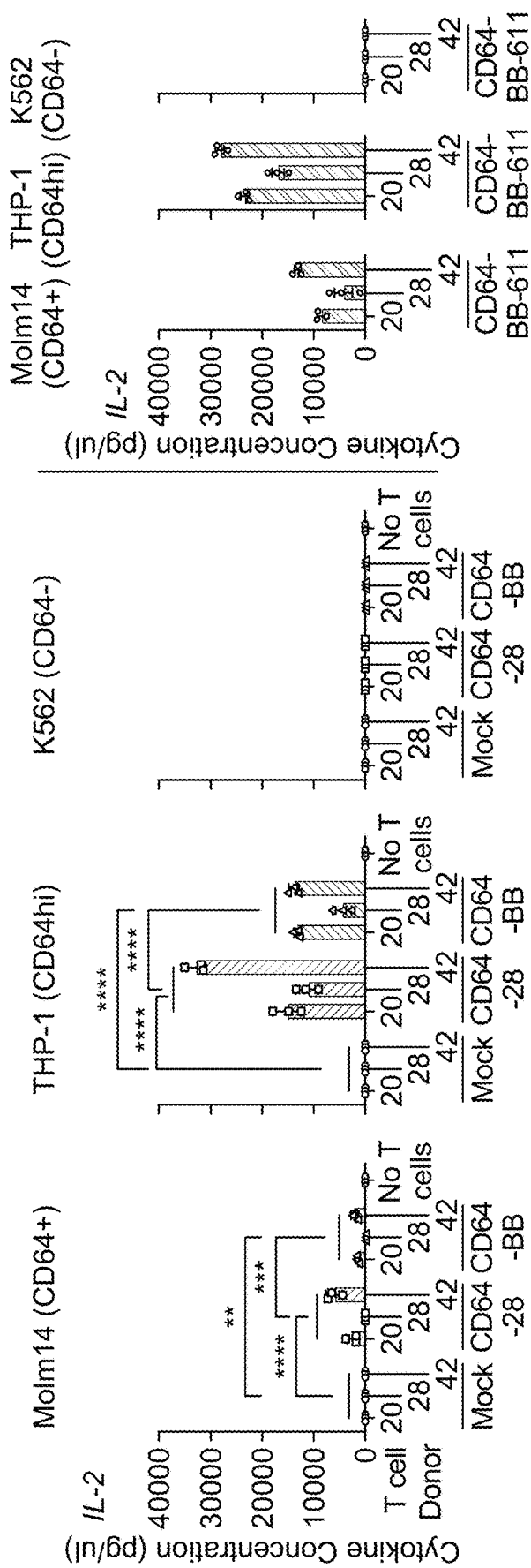
Figure 10B:
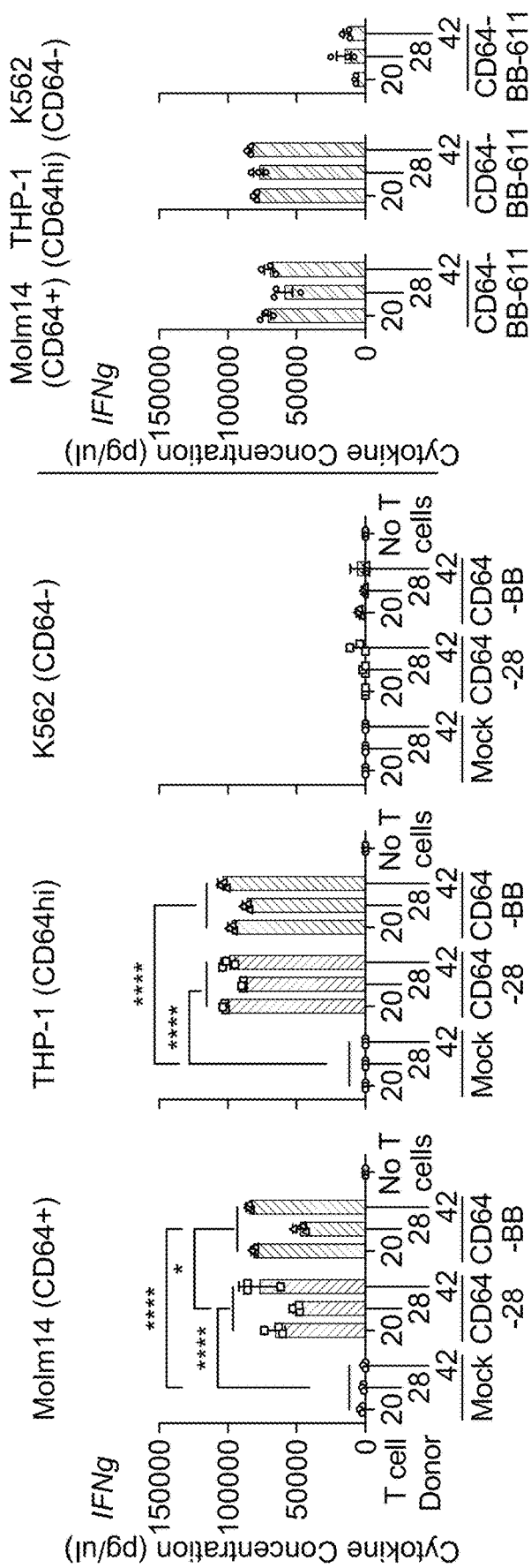
Figure 10C:
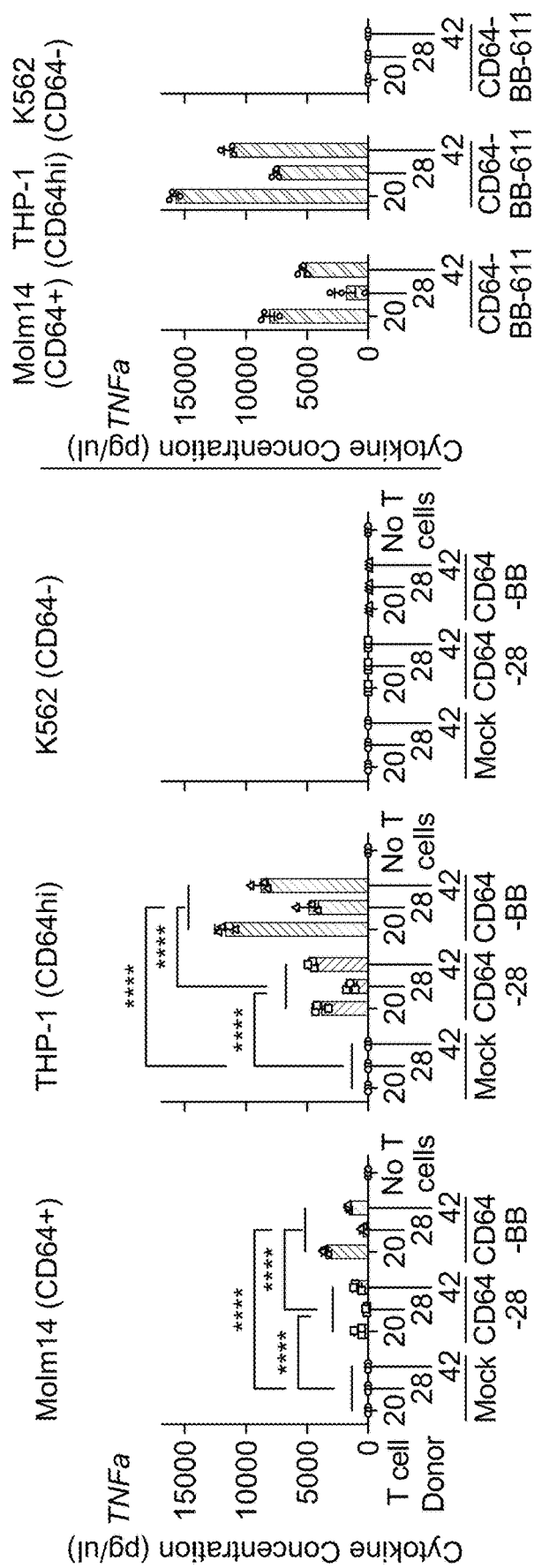

Upon antigen stimulation, CAR T cells initiate effector functions such as the secretion of cytokines and the release of cytotoxic granules targeting antigen positive cells. To test the ability of CD64 CAR molecules to elicit cytokine production from CAR transduced T cells, $1\times10^5$ CD64 CAR T cells (CD64-28-m22, CD64-BB-m22, or CD64-BB-611) were co-cultured with $1\times10^5$ cells from CD64 expressing cell lines (MOLM14 and THP-1) or $1\times10^5$ CD64+ cells from patient samples (monocytic and mixed monocytic/primitive primary AML). Cells were co-cultured for 24 hours and T cell effector cytokine (IL-2, IFNγ, and TNFα) production was measured by LegendPlex® assay (Biolegend) (FIGS. 10A-10F). Higher production of the canonical T cell effector cytokines IL-2, IFNγ, and TNFa was observed after stimulation with THP-1 cells (CD64high) relative to MOLM14 (CD64low) (FIGS. 10A-10C). No cytokine production was observed from mock T cells (untransduced T cells) co-cultured with THP-1 or MOLM14 cells. These results demonstrate that AML cell lines do not produce these cytokines, and transduction with a CD64 CAR was required for T cell release of these cytokines (FIGS. 10A-10C). Furthermore, CD64 CAR T cells did not demonstrate antigen-independent cytokine production as there was no cytokine production upon co-culture with the CD64-negative cell line, K562 (FIGS. 10A-10C). Despite the expected donor-to-donor variation in cytokine production that is common in CAR T cell products, increased IL-2 secretion by CD64-28-m22 CAR T cells was observed (FIG. 10A). A high level of IL-2 secretion by CD64-BB-611 CAR T cells was also observed in co-culture with CD64+ cell lines (FIG. 10A). Conversely, increased TNFa secretion from CD64-BB-m22 CAR T cells was observed (FIG. 10C). A high level of TNFa secretion by CD64-BB-611 CAR-T cells was also observed in co-culture with CD64+ cell lines (FIG. 10C). It was found that IFNγ was secreted in similar amounts from both of CD64-28-m22 and CD64-BB-m22 CAR T cell products in response to THP-1 cells and at a slightly higher level by CD64-BB-m22 CAR T cells in response to MOLM14 (FIG. 10B). A similarly high level of IFNγ secretion by CD64-BB-611 CAR-T cells was also observed in co-culture with CD64+ cell lines (FIG. 10B).

Figure 10D:
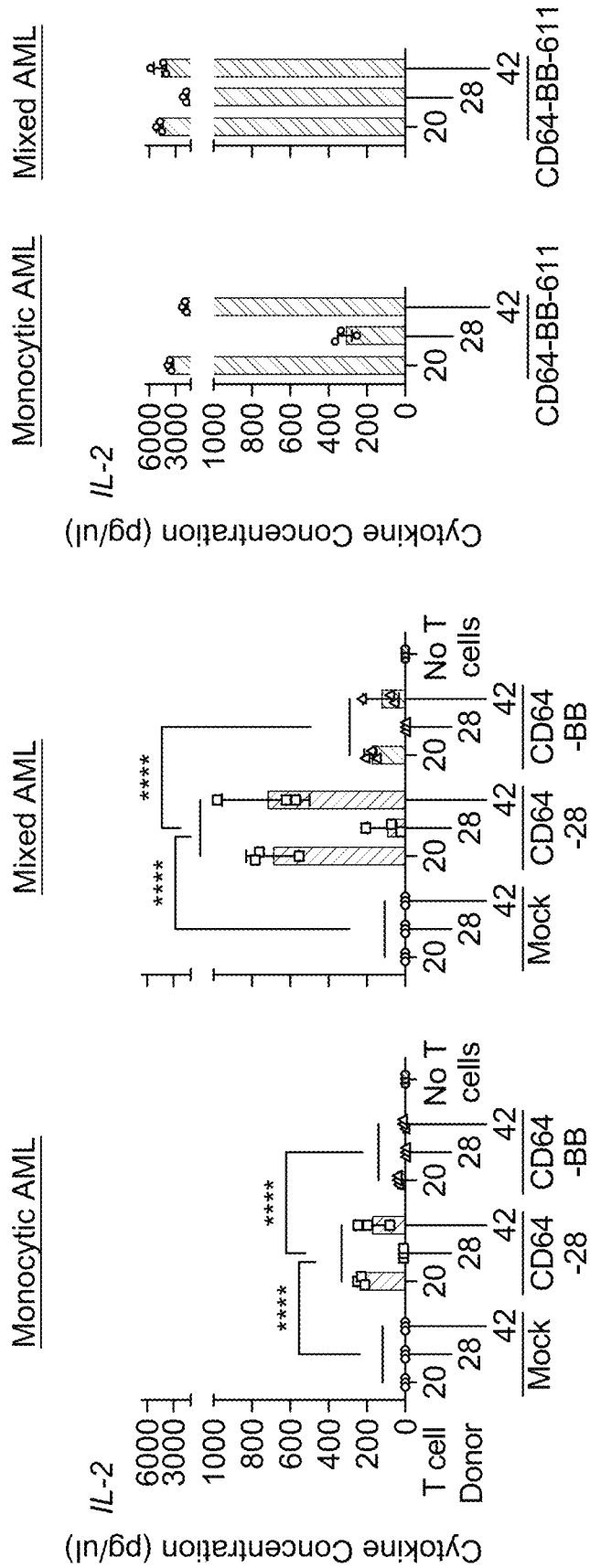
Figure 10E:
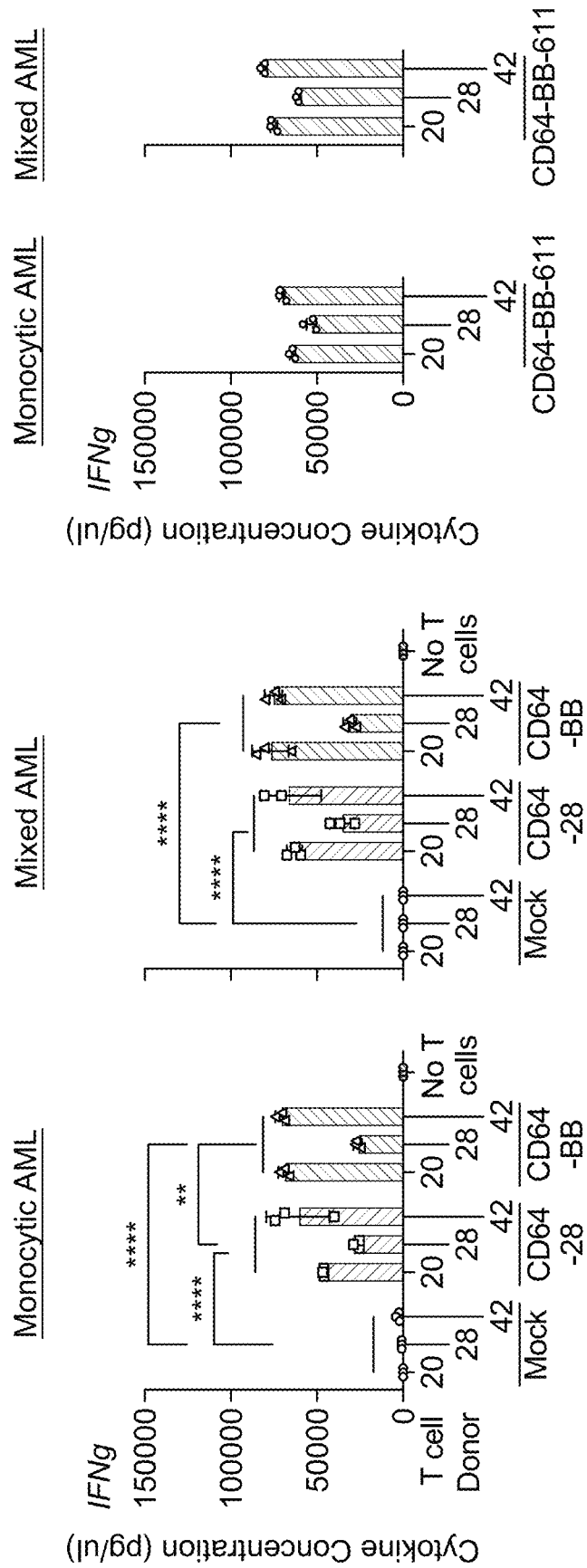
Figure 10F:
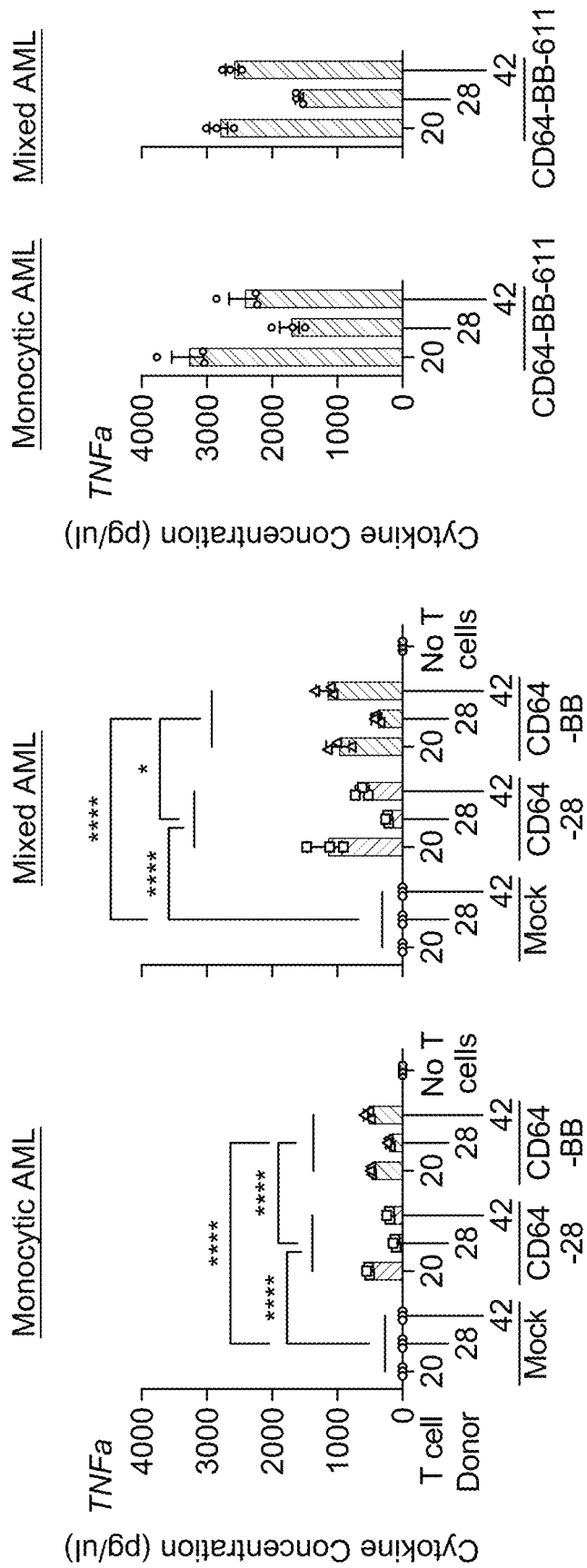

Upon co-culture with patient samples, CD64-28-m22 CAR T cells demonstrated the ability to produce significant amounts of IL-2, INFγ, and TNFα in response to both monocytic and mixed primitive/monocytic patient-derived AML samples (FIGS. 10D-10F). Similarly, CD64-BB-m22 CAR T cells secreted significant amounts of IFNγ and TNFα in response to both monocytic and mixed primitive/monocytic patient-derived AML cells (FIGS. 10E-10F). CD64-BB-611 CAR-T cells secreted particularly high levels of IL-2 and TNFα as well as comparably high levels of INFγ (FIGS. 10D-10F). All cytokine data was analyzed in triplicate using three independent T cell donors. Statistical analysis was conducted using two-way ANOVA with Turkey's multiple comparison test. Collectively, these data demonstrated that both CD64-28-m22, CD64-BB-m22, and CD64-BB-611 CARs elicited antigen-dependent cytokine production by transduced T cells in response to AML cells, supporting their effector function against leukemia expressing the target antigen.

Manufacturing of CD64 CAR T Cells

A concern with CAR T therapy for AML has been the fitness or ability to manufacture CAR T cells from patient-derived T cells. To address this concern, T cells from an AML patient sample biobank were transduced with CD64-BB-m22 CAR in parallel to healthy donor T cells.

Figure 11A:
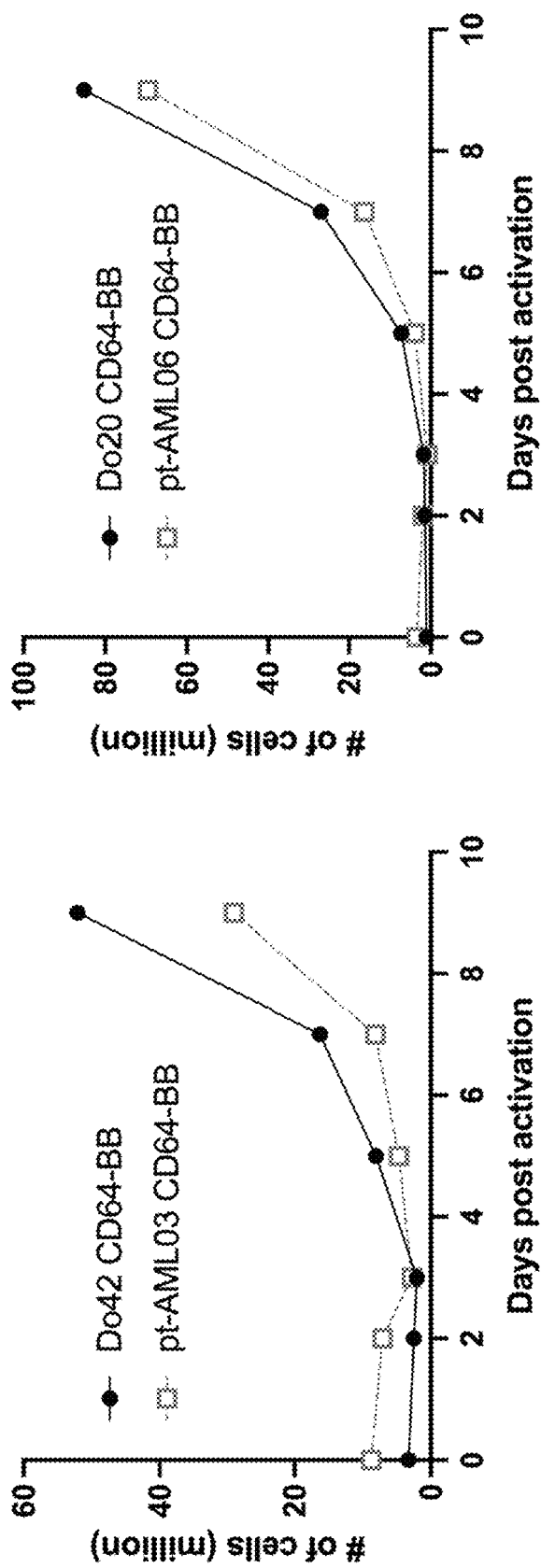
Figure 11B:
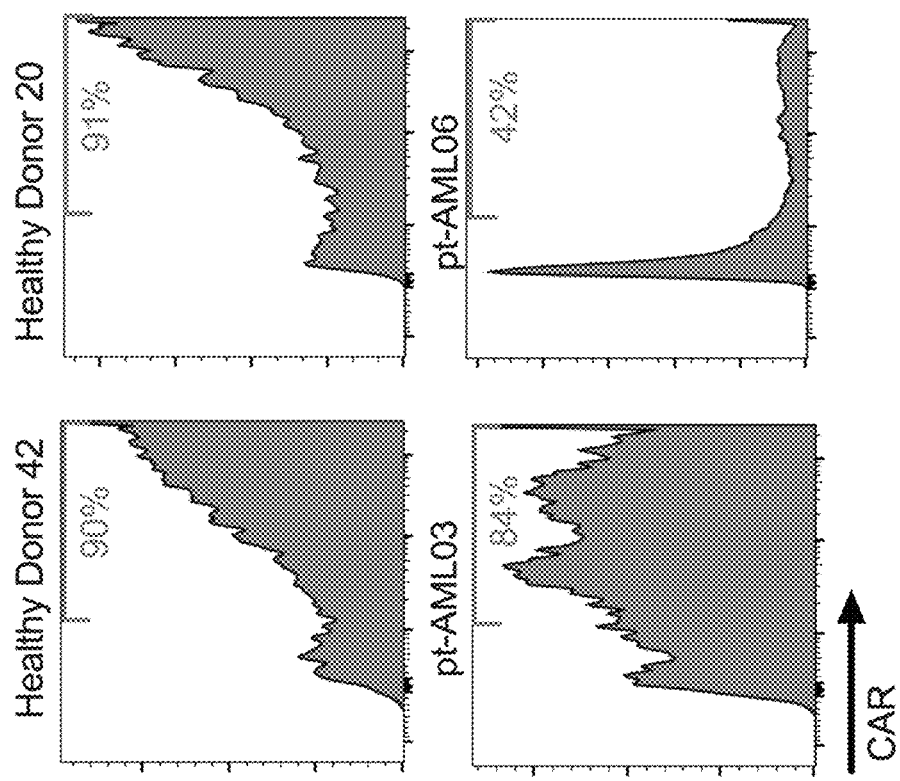

Patient-derived T cells proliferated similarly to healthy donor T cells during CAR T manufacturing (FIG. 11A). Patient derived T cells and healthy donor T cells were transduced with CAR with comparable efficiency in one donor but reduced efficiency in another (FIG. 11B). No significant difference in T cell proliferation was noted between patient-derived CD64-BB-m22 CAR T cells and healthy donor CD64-BB-m22 CAR T cells in co-culture with MOLM14 target leukemia cells (FIG. 11C).

Figure 11D:
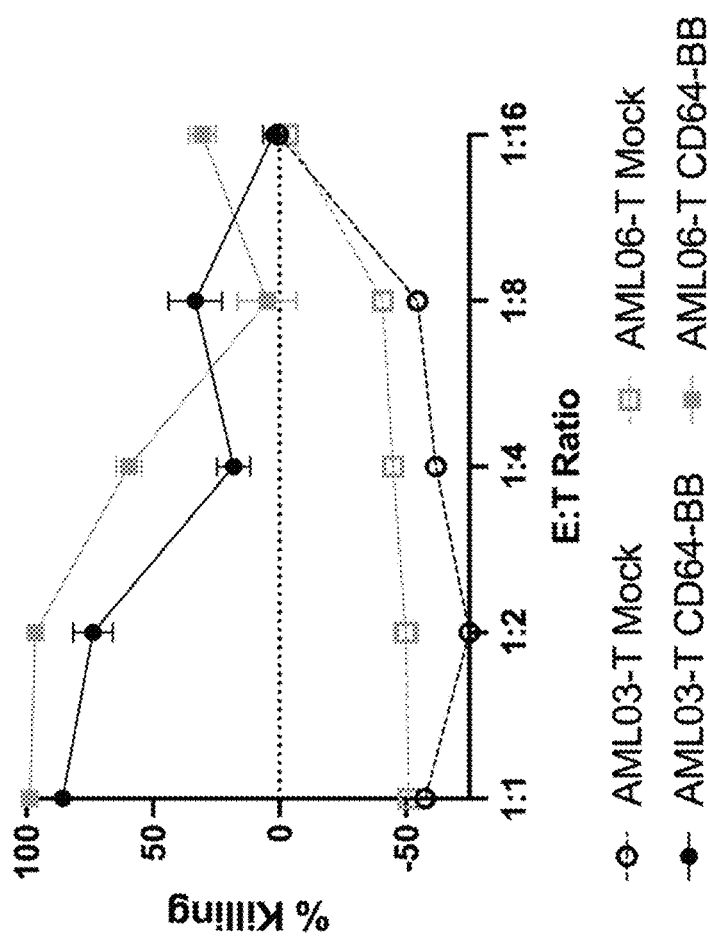
Figure 11C:
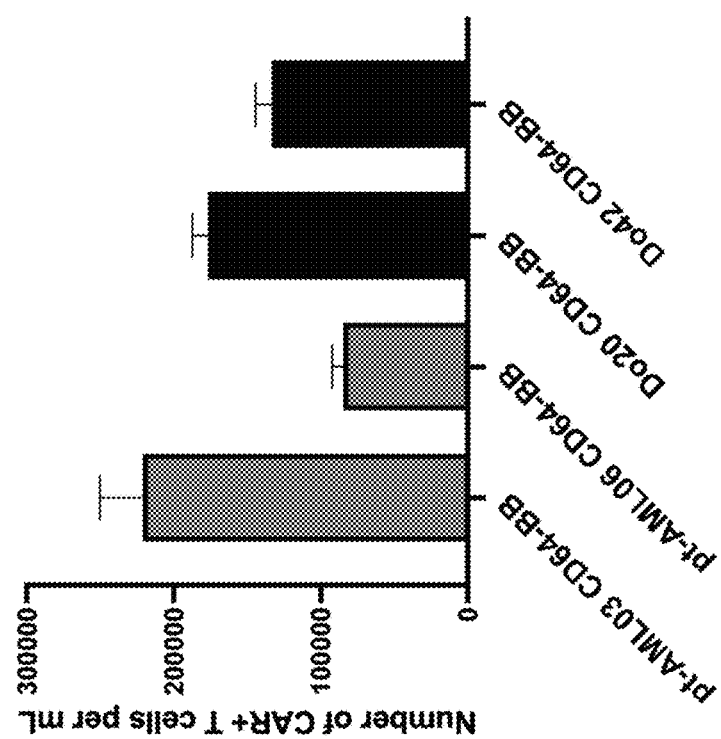
Figure 11E:
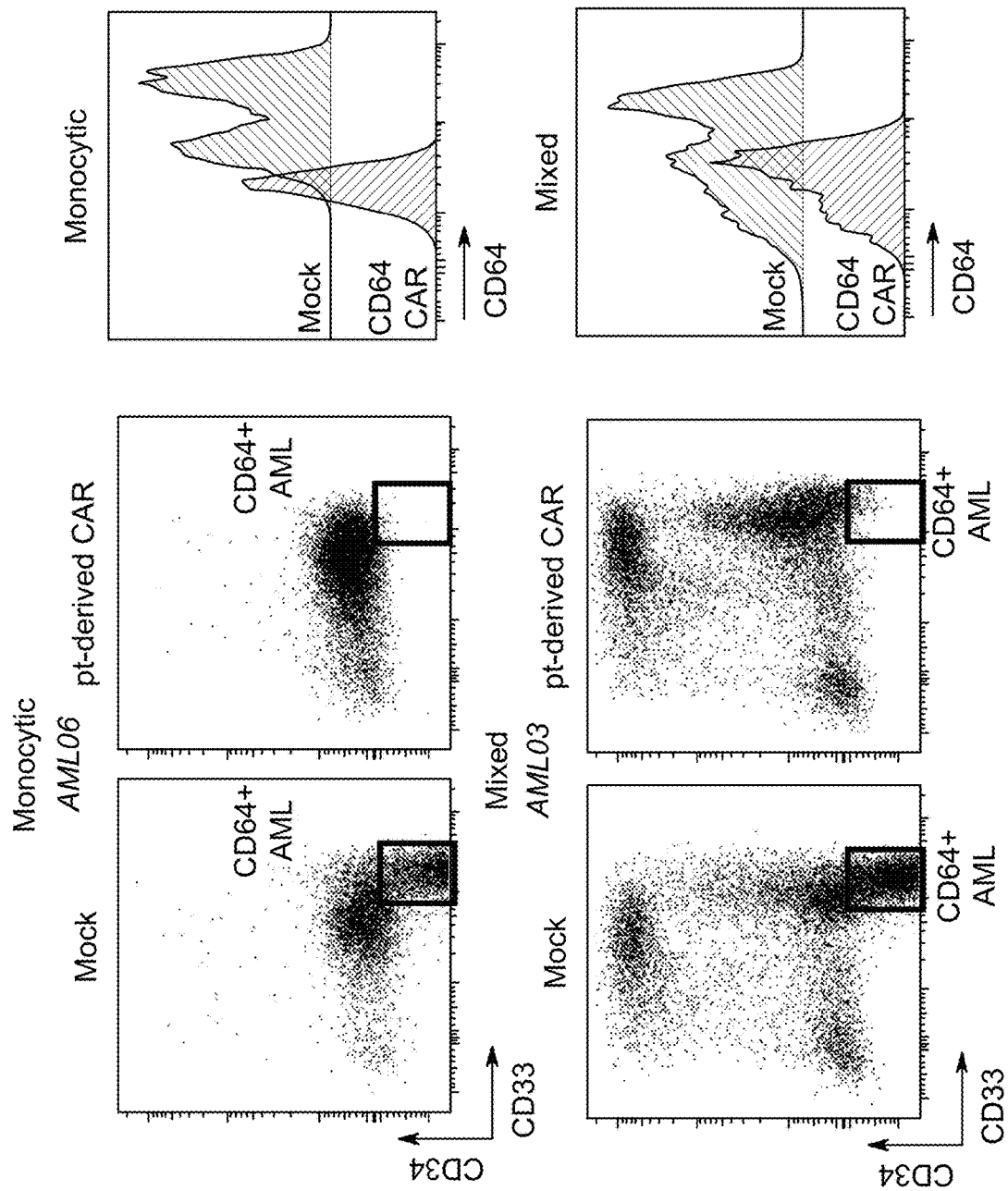

In a luciferase killing assay, it was shown that patient derived CD64-BB-m22 CAR T cells killed MOLM14 cells in a dose dependent manner, similar to the healthy donor-derived CD64-BB-m22 CAR T cells shown in FIG. 9C (FIG. 11D). Patient-derived CD64-BB-m22 CAR T cells were next cultured with their respective monocytic and mixed AML patient samples overnight. CD64-BB-m22 CAR T cells eliminated CD64+ AML cells in these patient samples (FIG. 11E). This data suggest that CD64 CAR T cells can be manufactured from patient derived T cells and are effective against CD64 expressing AML.

CAR T Cells in CD64 Leukemia Xenograft Models

Figure 12A:
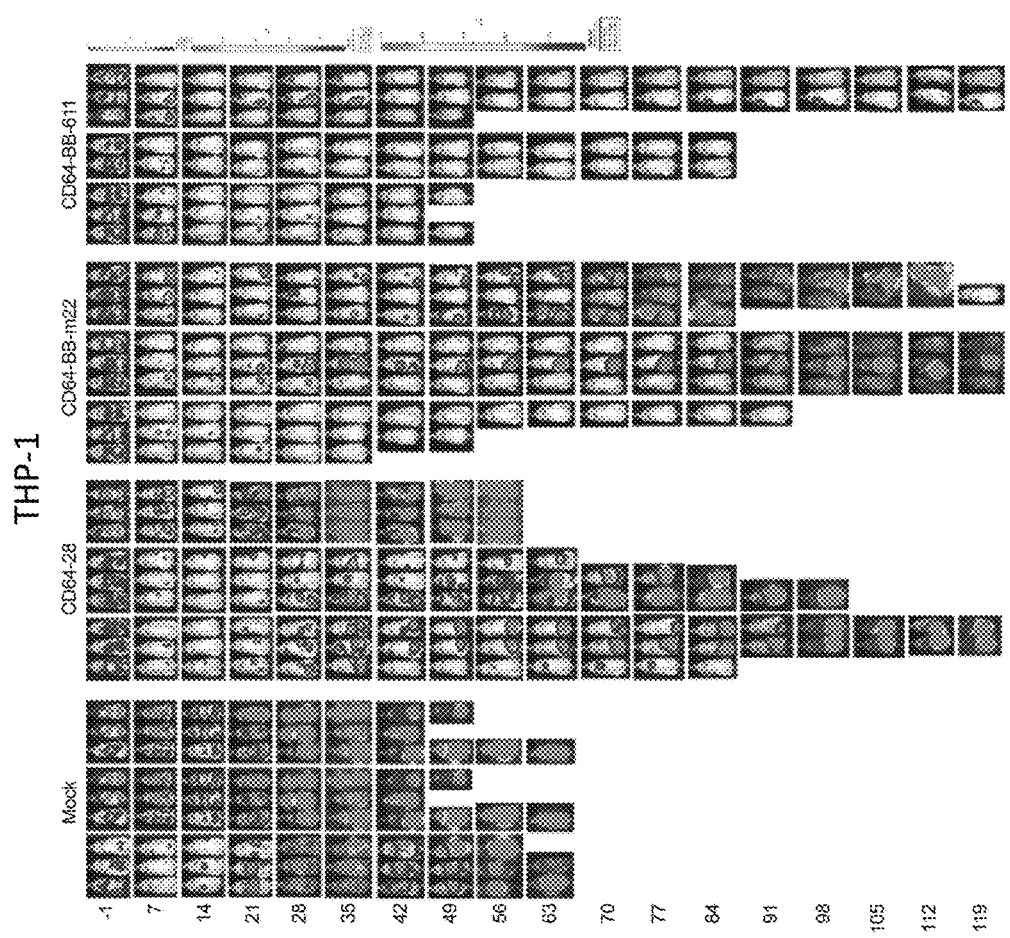
Figure 12B:
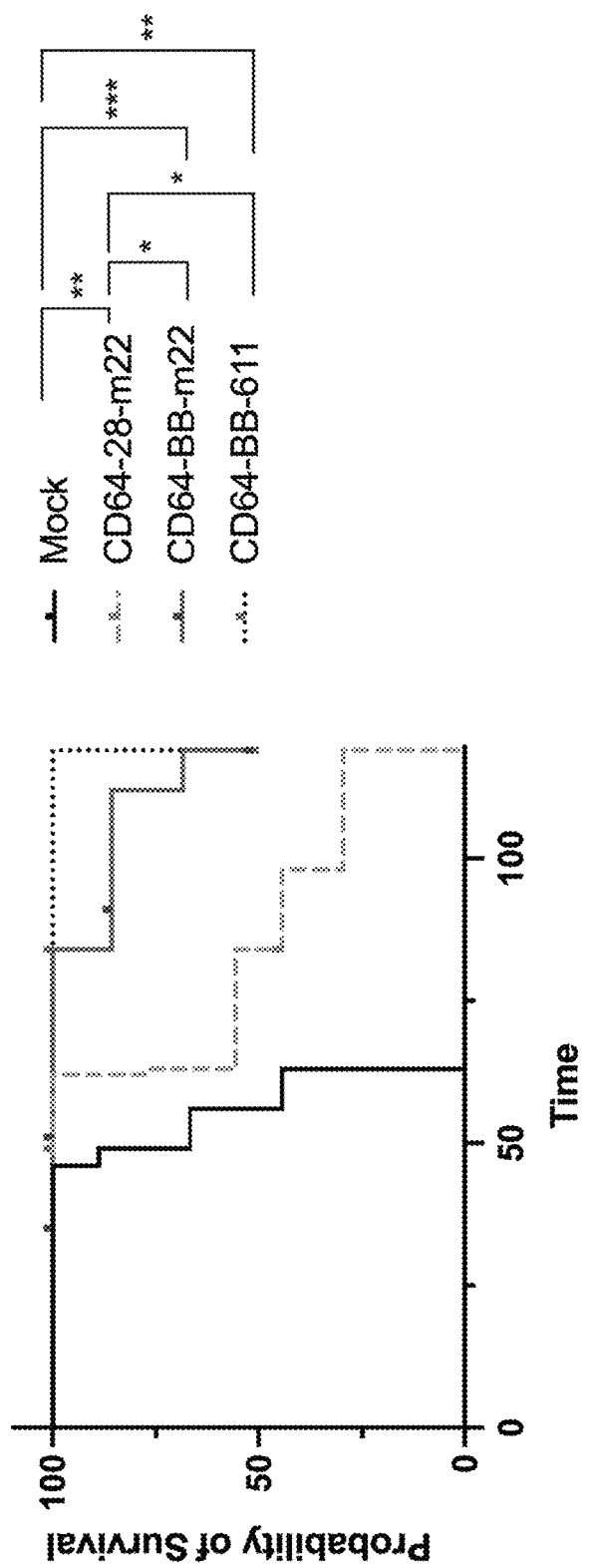
Figure 12C:
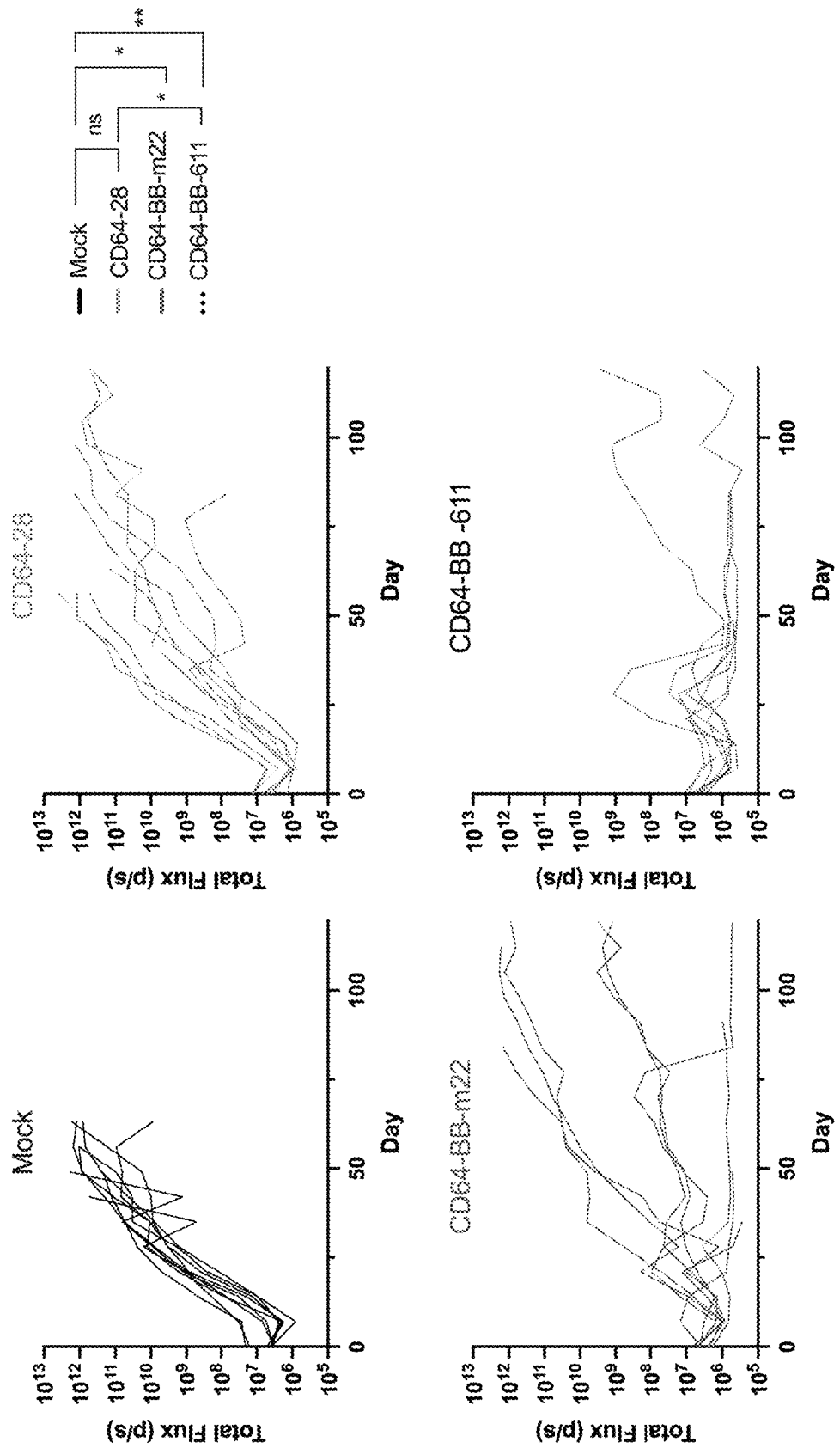

In vivo efficacy of CD64 CAR T cells was also assessed in mice engrafted with THP-1 (CD64high) leukemia cells, which produces a more resistant disease than MOLM14 in xenograft models. Mice were inoculated with $1 \times 10^6$ luciferase-positive THP1 cells by tail vein injection on day −4. Engraftment was confirmed by luciferase-based bioluminescent in vivo imaging on a Xenogen IVIS® platform on day 0. Mice were infused with $5 \times 10^6$ CD64 CAR$^+$ T cells or an equivalent number of mock T cells on day 0 and monitored by BLI weekly as described above in FIG. 6 (FIG. 12A). The experiment was replicated three times using CAR T cells manufactured from three independent human T cell donors. Mice treated with mock T cells all succumbed to leukemia progression by day 70 and none died of the expected complication of xenogeneic graft-versus-host disease (xGVHD) which leads to mice being euthanized due to predefined humane endpoints in the absence of detectable leukemia. This is a well-described complication of infusing human T cells into immunodeficient mice and was not related to the function of the CAR or the CAR T cells. CD64-BB-611 CAR T cells resulted in complete leukemia clearance in all 8 mice 14 days after treatment. None of these mice succumbed to leukemia and all deaths were due to xGVHD. Eight of the nine mice treated with CD64-28-m22 and three of nine treated with CD64-BB-m22 CAR T cells developed progressive leukemia. This data demonstrates that each of the CD64 CAR constructs has in vivo efficacy against established AML in xenograft models. Furthermore, the data demonstrates superior survival and leukemic clearance by CD64 CAR T cells that utilize a 4-1BB costimulatory domain, with the best leukemia control by CD64-BB-611 CAR T cells (FIG. 12B-12C).

Figure 12D:
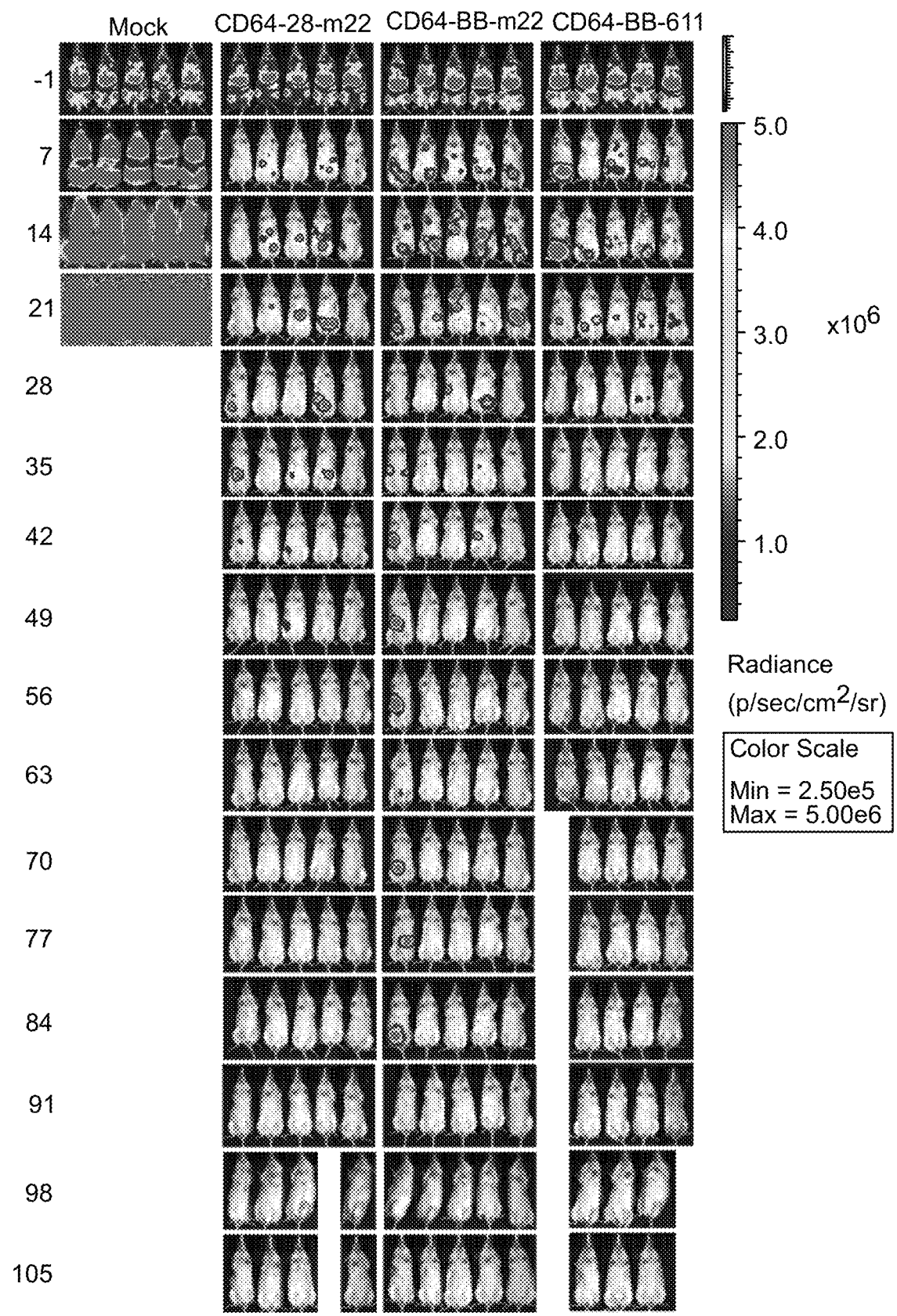
Figure 12E:
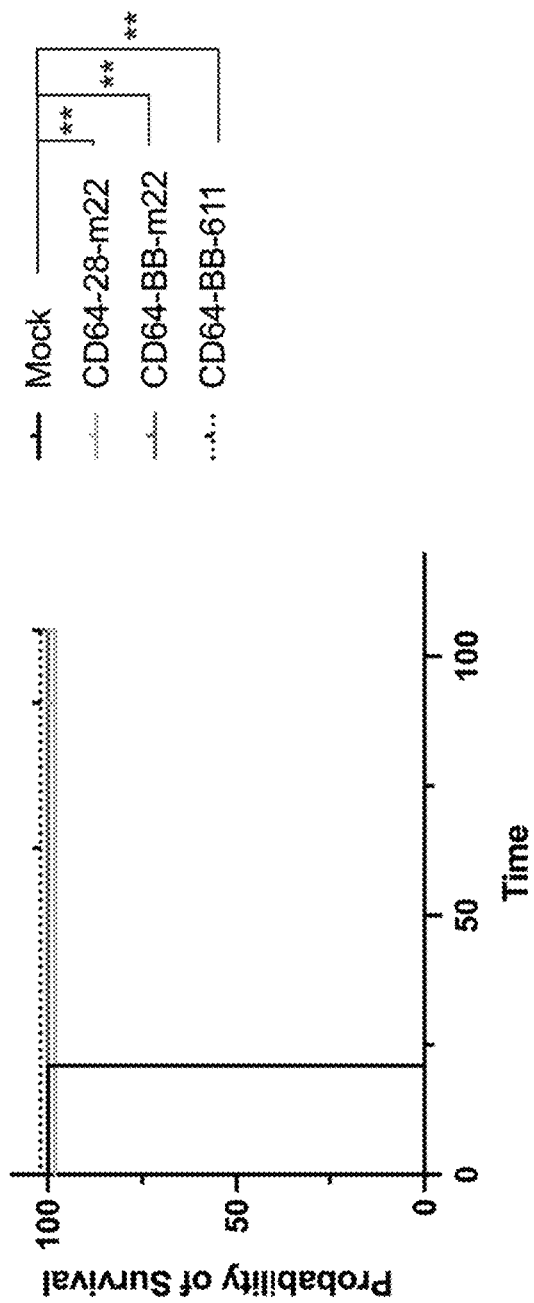
Figure 12F:
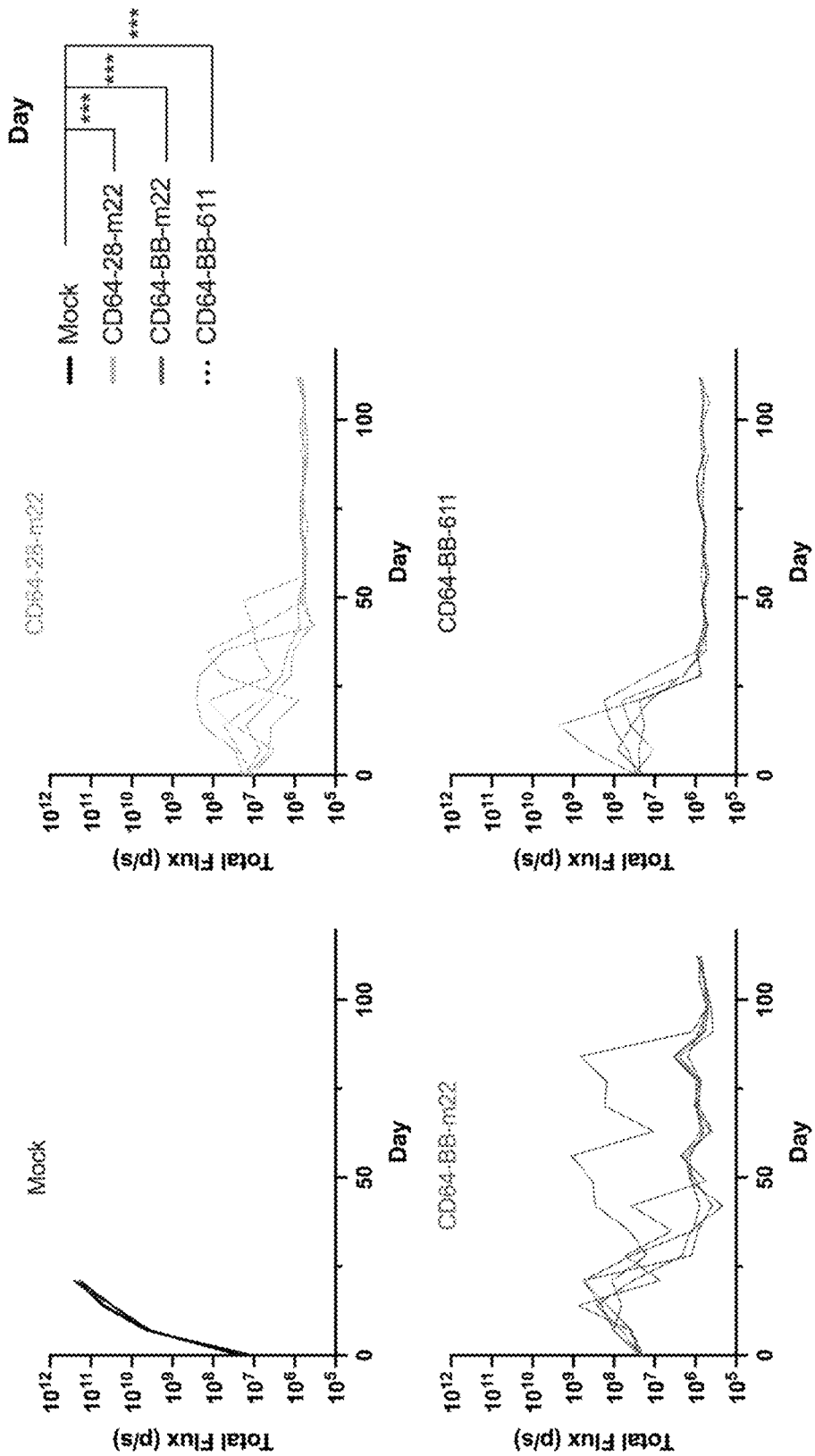

To assess the in vivo efficacy of CD64-BB-611 CAR T cells, NSG mice were engrafted with $1 \times 10^6$ luciferase-expressing MOLM14 cells on day −4. Leukemia engraftment was confirmed by luciferase-based BLI on day −1. On day 0, mice were treated with $3 \times 10^6$ CD64 CAR$^+$ T cells or an equivalent dose of mock T cells. Mice were subsequently imaged by BLI weekly to track leukemia burden (FIG. 12D). The experiment was replicated a third time as shown in FIG. 6A using T cells generated from a third healthy donor to include a comparison of CD64-BB-611 CAR T cells. By day 30, all 5 mice treated with untransduced control T cells had expired with leukemia. By day 91, all mice treated with CD64-28-m22, CD64-BB-m22, and CD64-BB-611 CAR T cells achieved a leukemia free state. All 5 mice treated with CD64-BB-611 had a complete clearance of leukemia as early as 35 days after CAR T administration, and no mice in this group died from leukemia progression. Leukemia free survival was 100% for all CD64 CAR-T cell treated mice (FIG. 12E). Quantification of total bioluminescent flux per mouse demonstrated decreased leukemia burden in mice treated with CD64-28-m22, CD64-BB-m22 and CD64-BB-611 CAR-T cells as compared to mock treated mice (FIG. 12F).

CD64 CAR T Cell Persistence in Xenograft Models

Figure 13A:
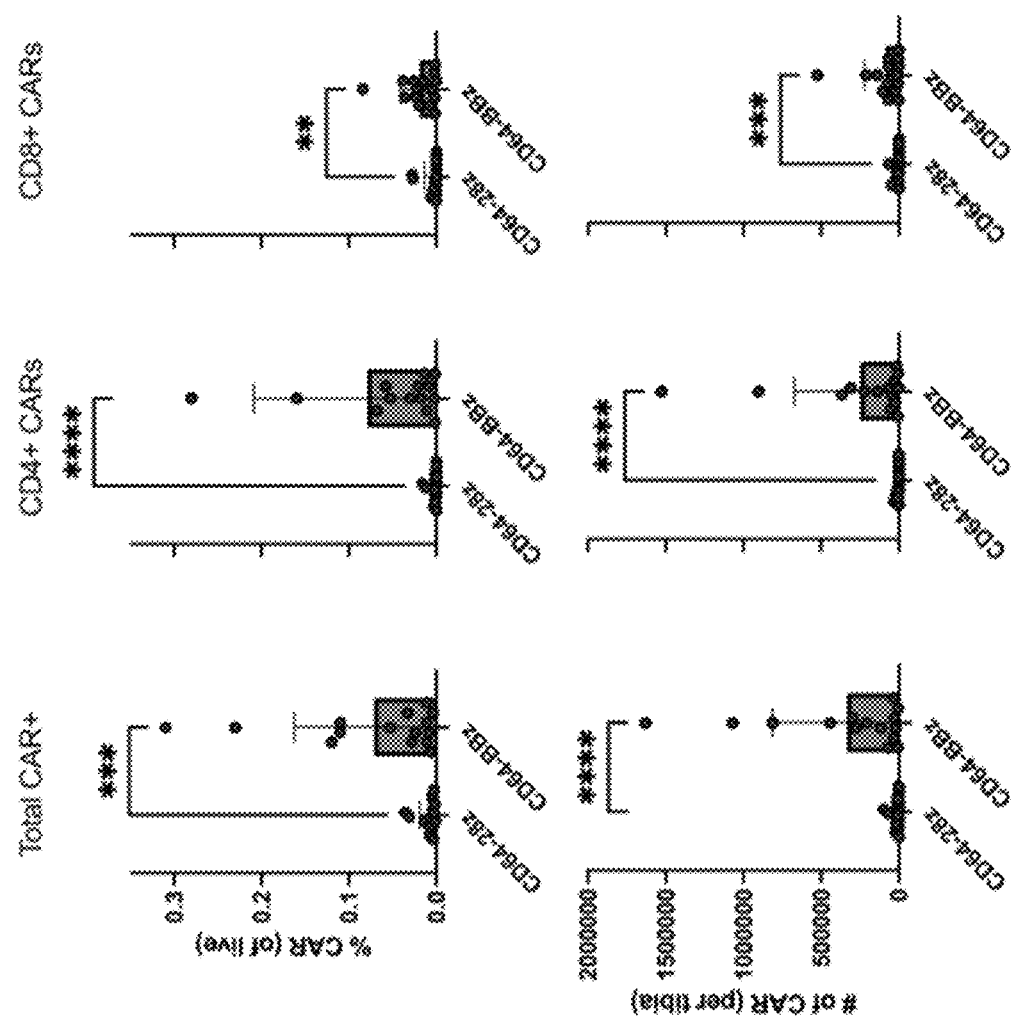
Figure 13C:
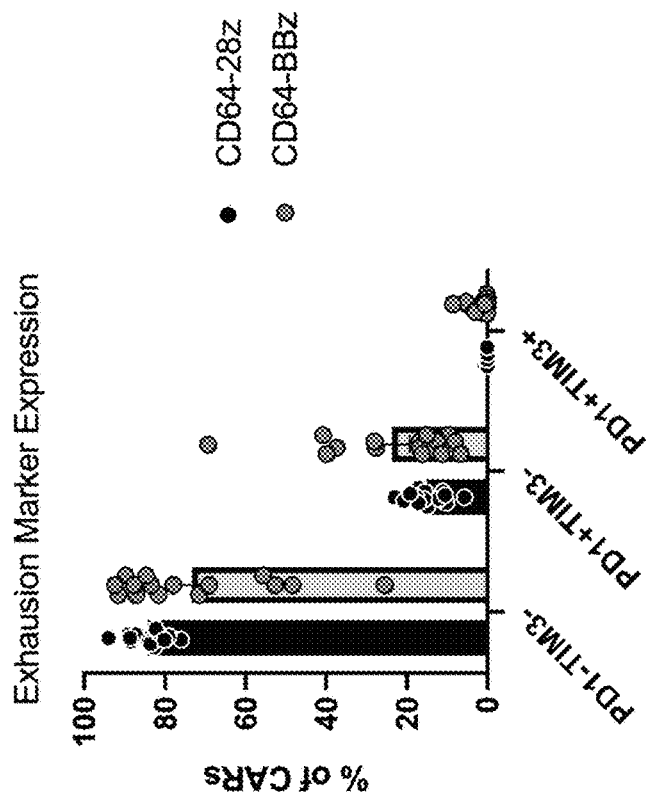
Figure 13B:
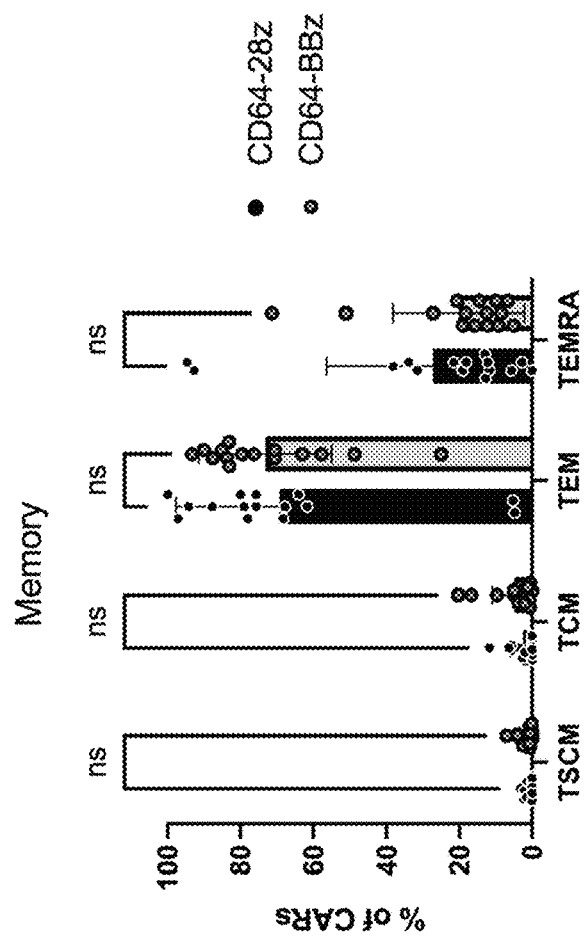

As persistence of CAR T cells has been shown to impact outcomes in lymphoid leukemias, the persistence of CD64 CAR T cells after clearance of MOLM14 leukemia was evaluated. NSG mice were engrafted with $1 \times 10^6$ MOLM14 cells at day −4. Mice were then treated with $5 \times 10^6$ CD64-28-m22 or CD64-BB-m22 CAR$^+$ T cells. At day 35, mice were euthanized and bone marrow was evaluated by flow cytometry to assess persistent CAR T cells. There was a significantly higher percentage and absolute number of CD64-BB-m22 CAR T cells in the marrow (mean 335,811 cells/tibia) after leukemia clearance as compared to CD64-28-m22 CAR T cells (15,148 cells/tibia; p<0.0001 by Mann-Whitney) (FIG. 13A). A similar pattern was observed in the CD4+ and CD8+ CAR T cell compartments (FIG. 13A). Phenotypically, the majority of persisting CAR T cells were T effector memory cells (TEM) with no difference observed between the CAR co-stimulatory domains (69% of CD64-28-m22 and 73% of CD64-BB-m22; p=0.95) (FIG. 13B). The remaining cells predominantly had a T effector memory with re-expression of CD45RA (TEMRA) phenotype (FIG. 13B). The majority of persisting CAR T cells did not express exhaustion markers (FIG. 13C). This data suggests that CD64 CAR T cells with 4-1BB co-stimulatory domains display an improved in vivo efficacy against monocytic AML and prolonged persistence of CAR T cells. Furthermore, CD64-BB-611 CAR T cells that incorporate a humanized binder showed the most in vivo efficacy against the monocytic THP-1 cell line.

Figure 13D:
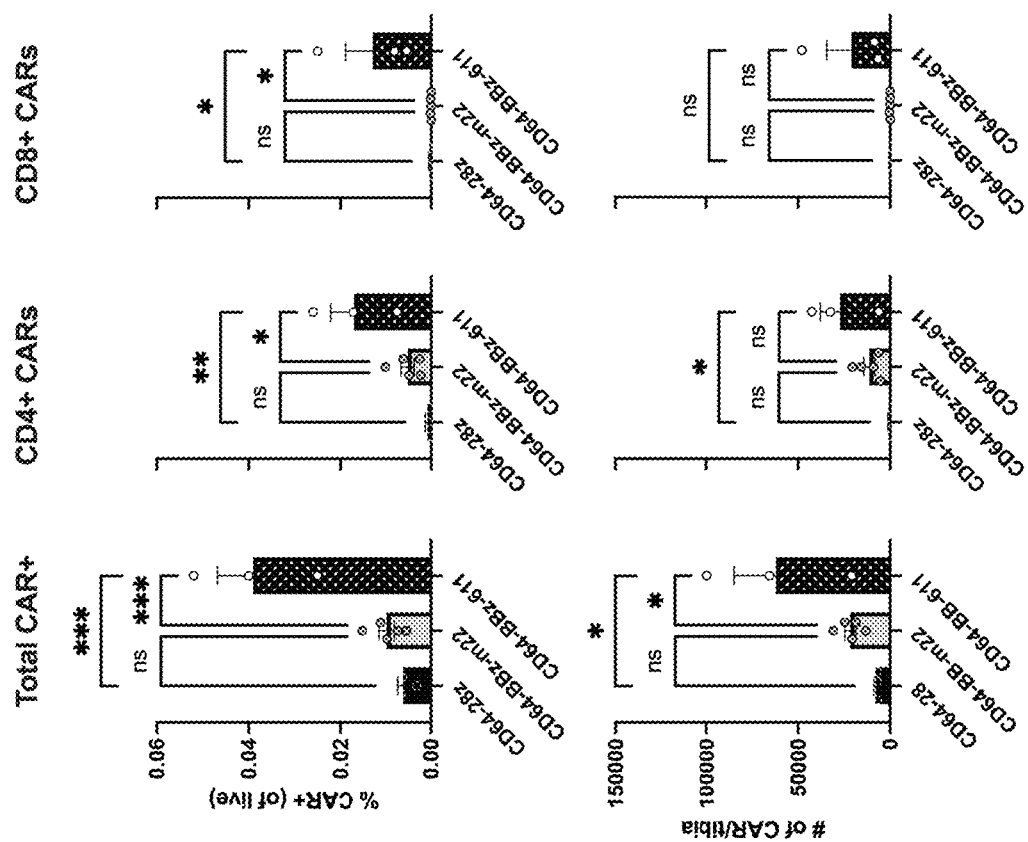
Figures 13E, 13F:
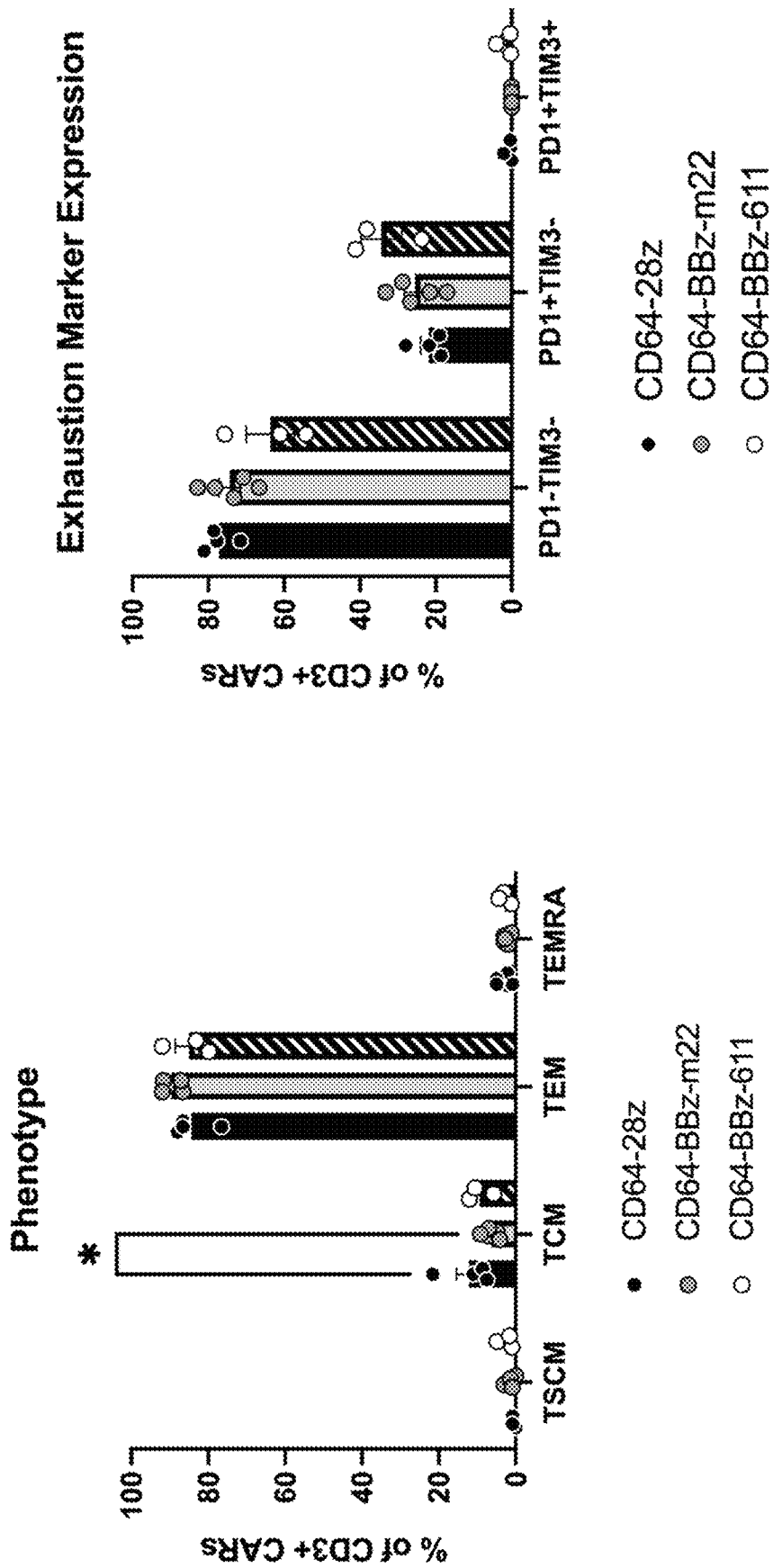

The previous experiment was repeated to include the CD64-BB-611 CAR and to investigate CAR T cell persistence and phenotype at a later time point after leukemia clearance. Mice cleared MOLM14 leukemia and were euthanized after 105 days. An average of 62,113 CD64-BB-611 CAR+ cells were detected per femur as compared to 7,992 CD64-28-m22 CAR+ cell per femur and 21,655 CD64-BB-m22 CAR+ cells per femur, suggesting further improvement in persistence with the CD64-BB-611 CAR construct over CD64-BB-m22 (FIG. 13D). CD64-BB-611 also produced TEM cells, and the majority of CD64 CAR T cells remained negative for exhaustion markers PD1 and TIM3 at this later time point (FIGS. 13E-13F).

CD64 CAR T Cell Toxicity Against Monocytes

Figure 14A:
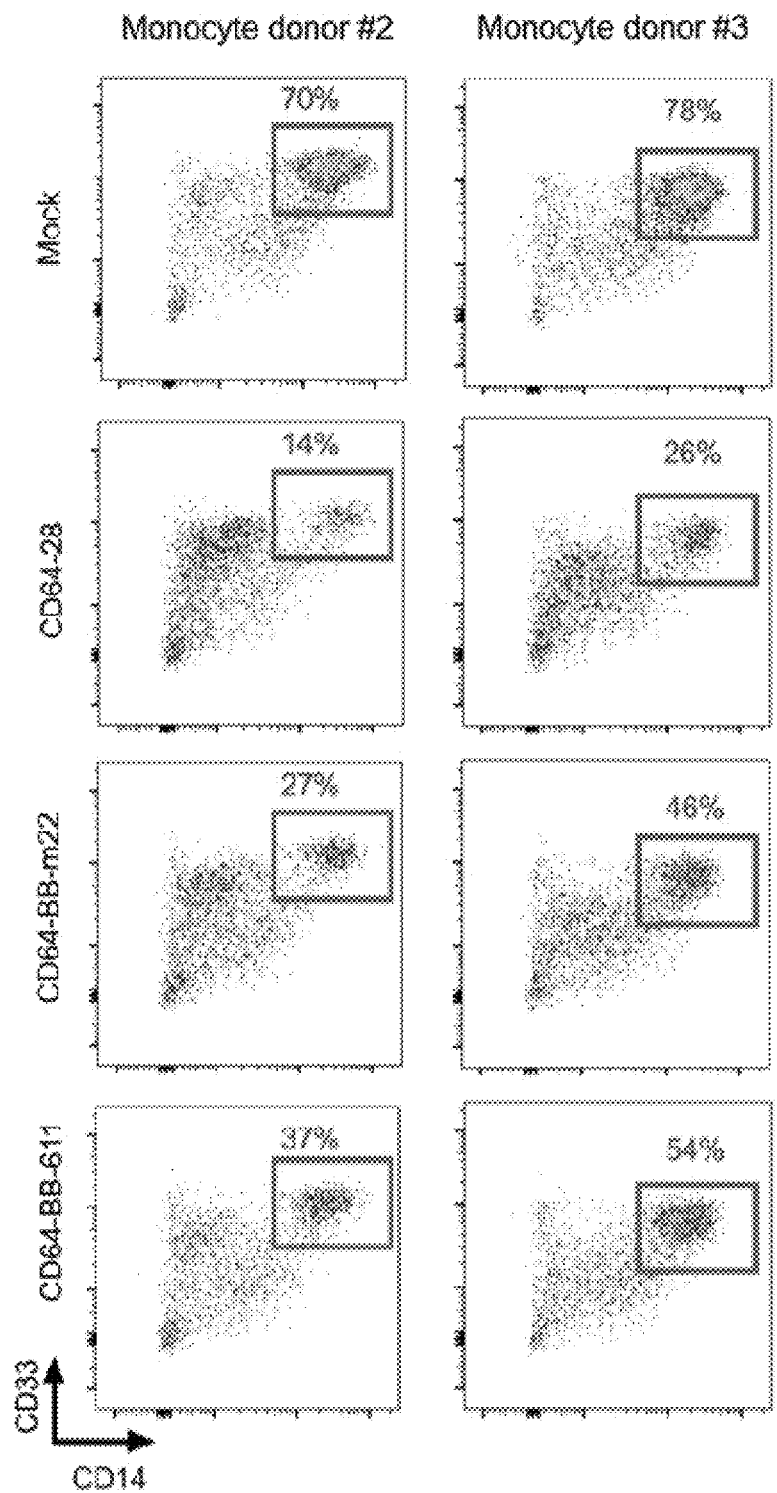
Figure 14B:
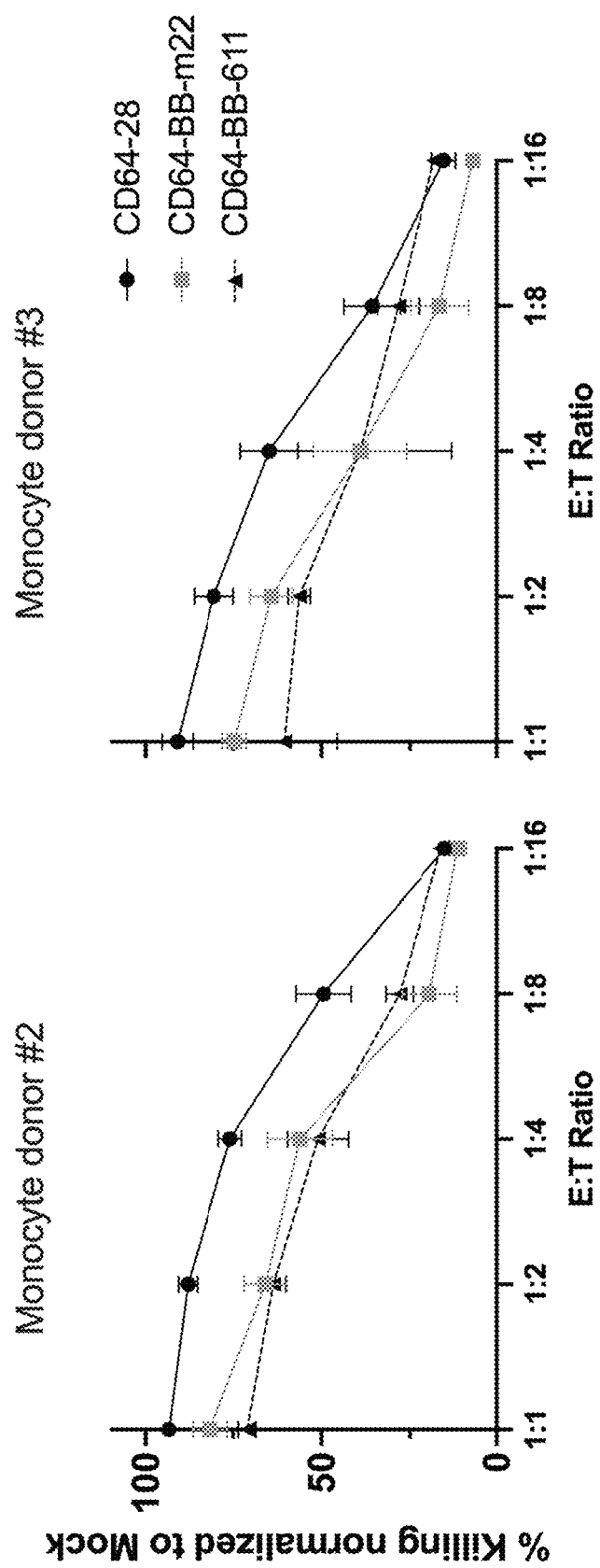
Figure 14C:
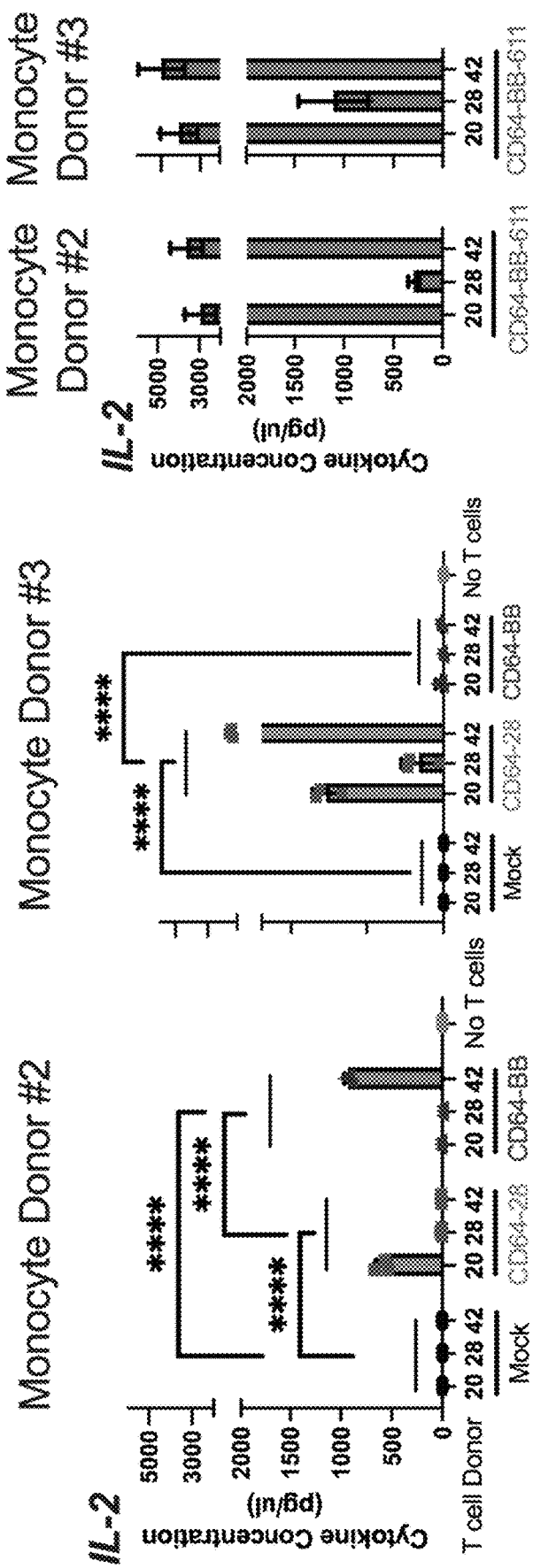
Figure 14D:
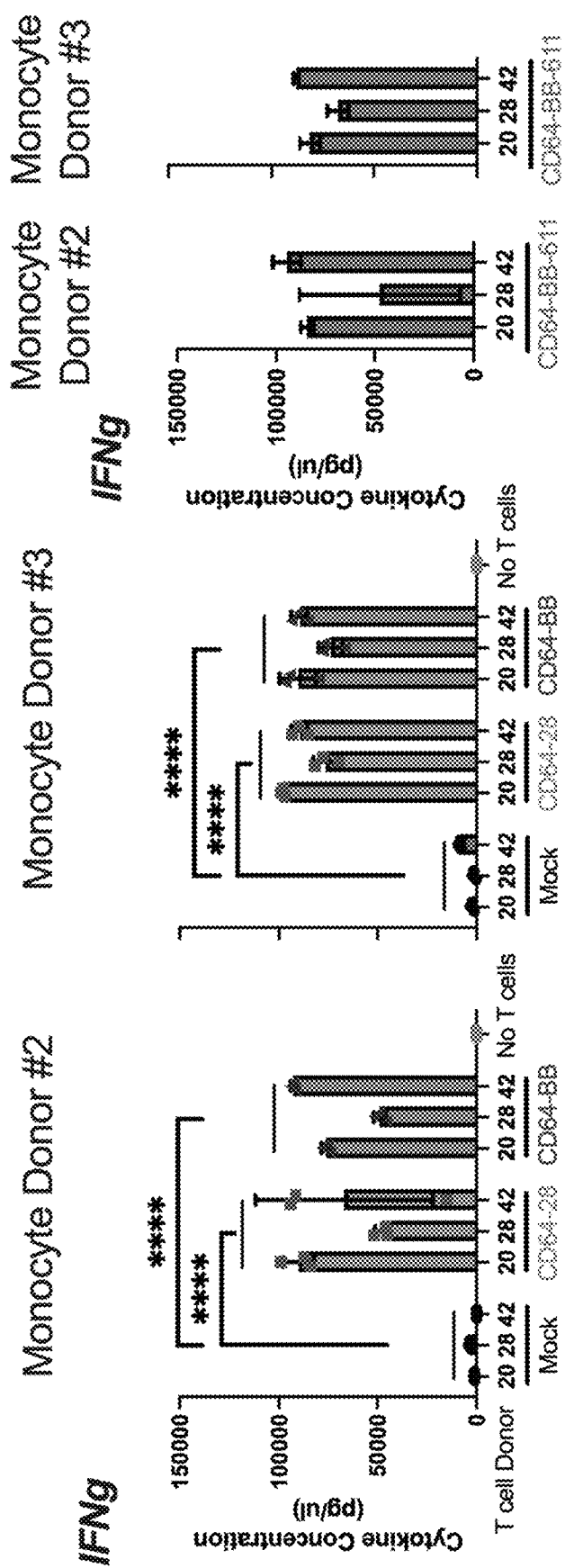
Figure 14E:
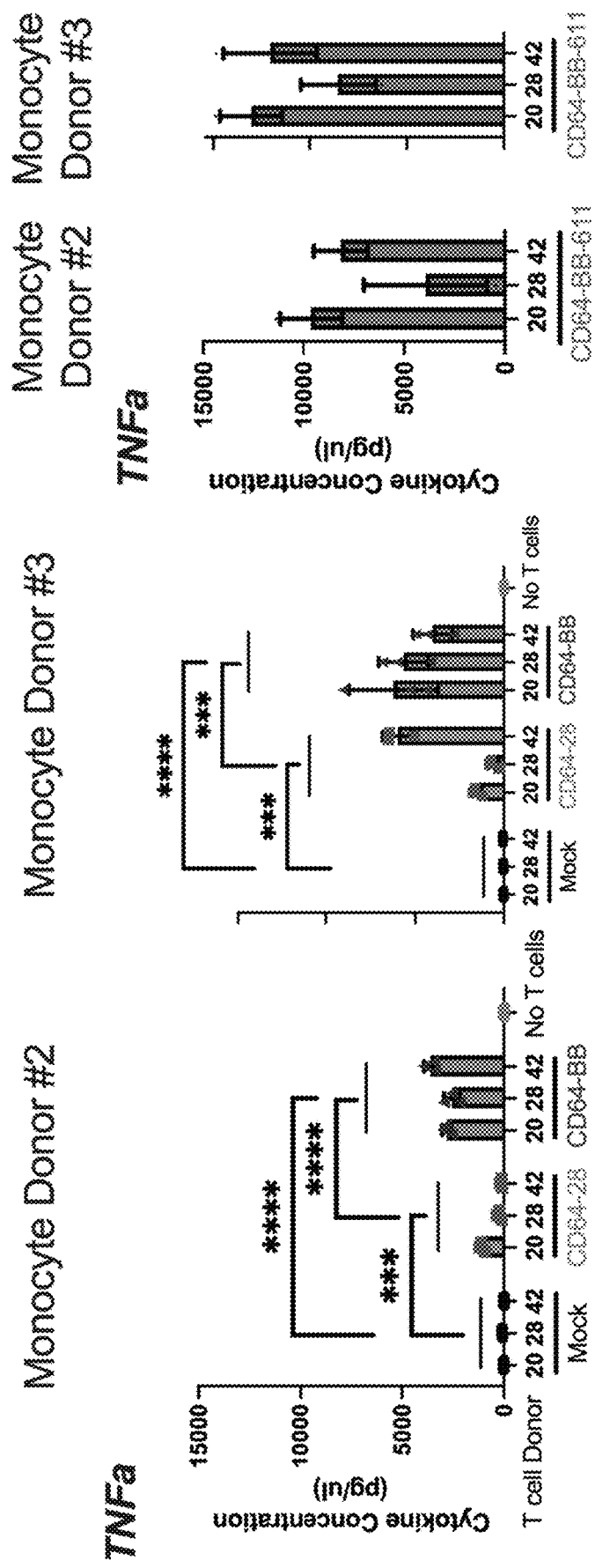

Given the known expression pattern of CD64 on monocytes and macrophages, CD64 CAR T cell treatment may result in depletion of these cell populations as an on-target/off-tumor toxicity. To test this, CD64 CAR-T cells from three different T cell donors were co-cultured with normal monocytes from two different, healthy blood donors. All CD64 CAR-T cells reduced viable populations of classic and non-classic CD14+ monocytes. CD64-28-m22 CAR T cells generated the greatest monocyte killing after 24 hours at a 1:2 E:T ratio (FIGS. 14A-14B). CD64 CAR-T cells produced IL-2, IFNγ, and TNFα effector cytokines after 24 hours of co-culture with normal monocytes (FIG. 14C) and showed a similar pattern of cytokine expression as was seen after co-culture with AML cells (FIGS. 10A-10F). Statistical analysis was performed using two-way ANOVA and Turkeys multiple comparison test. Thus, reduction of normal monocytes is an anticipated on-target/off-tumor toxicity of CD64 CAR T cell treatment. This may have further therapeutic potential to be harnessed in applications to deplete macrophages in the tumor microenvironment of other malignancies. Tumor associated macrophages (TAMs) have been shown to negatively impact cancer progression and prognosis by infiltrating the tumor microenvironment and driving a cytokine and growth facture milieu which promotes cancer cell division and metastasis, accelerates angiogenesis, supports maintenance of cancer stem cells, and produces an immunosuppressive effect through cytokine secretion and recruitment of suppressive regulatory T cells. (Li et al., J. Immunother. Cancer., 9(1):e001341 (2021) doi: 10.1 136/jitc-2020-001341. PMID: 33504575; DeNardo et al., Nat. Rev. Immunol., 19(6):369-382 (2019). doi: 10.1038/s41577-019-0127-6. PMID: 30718830; PMCID: PMC7339861). Methods of decreasing TAMs in the tumor microenvironment is an active area of study in clinical trials for a multitude of hematologic and solid tumors including AML, multiple myeloma, lymphomas, ovarian cancer, lung cancer, pancreatic cancer, sarcomas, colorectal cancer and in other malignancies including advanced/metastatic cancer of any origin. There is potential in harnessing the noted anti-monocyte/macrophage, on-target, off-tumor effect of CD64 CAR-T cell therapy to deplete these TAMs in various tumor types, in addition to the intended use in venetoclax relapsed/refractory AML, which is the primary subject of this discussion.

CD64 CAR T Cell and Ven/Aza Combination Therapy

Figure 15A:
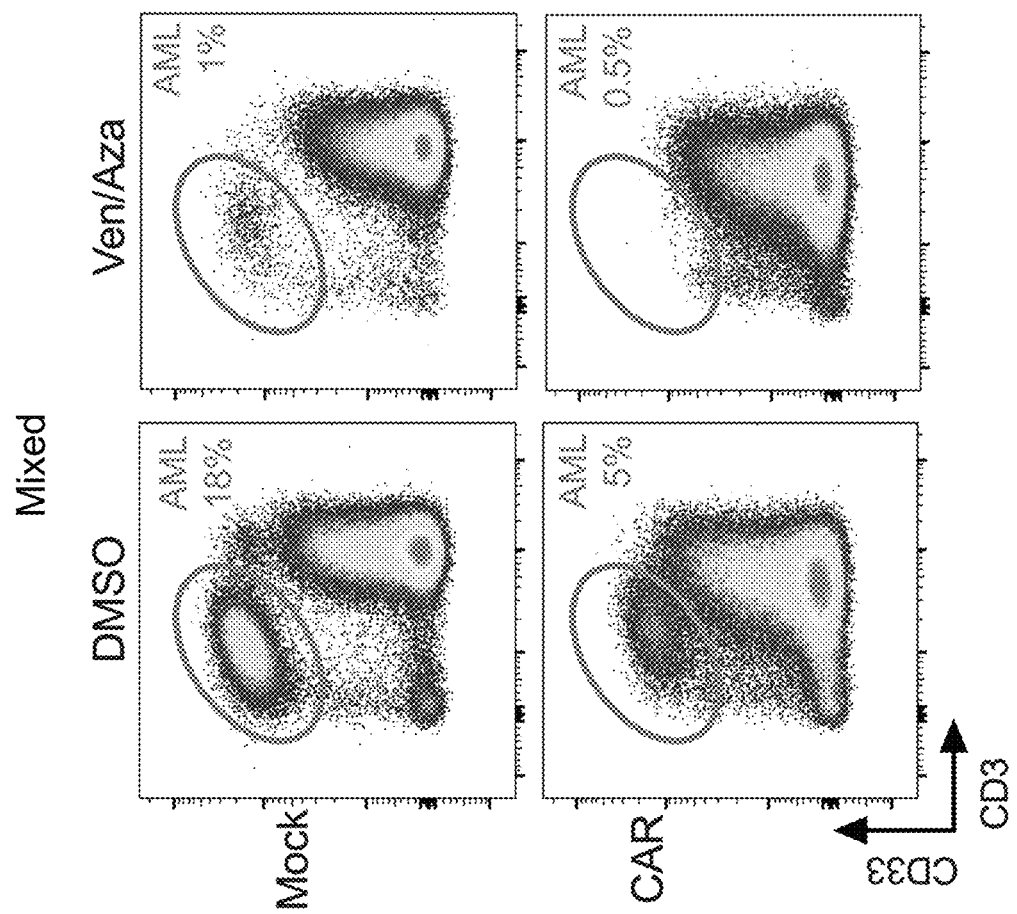
Figure 15B:
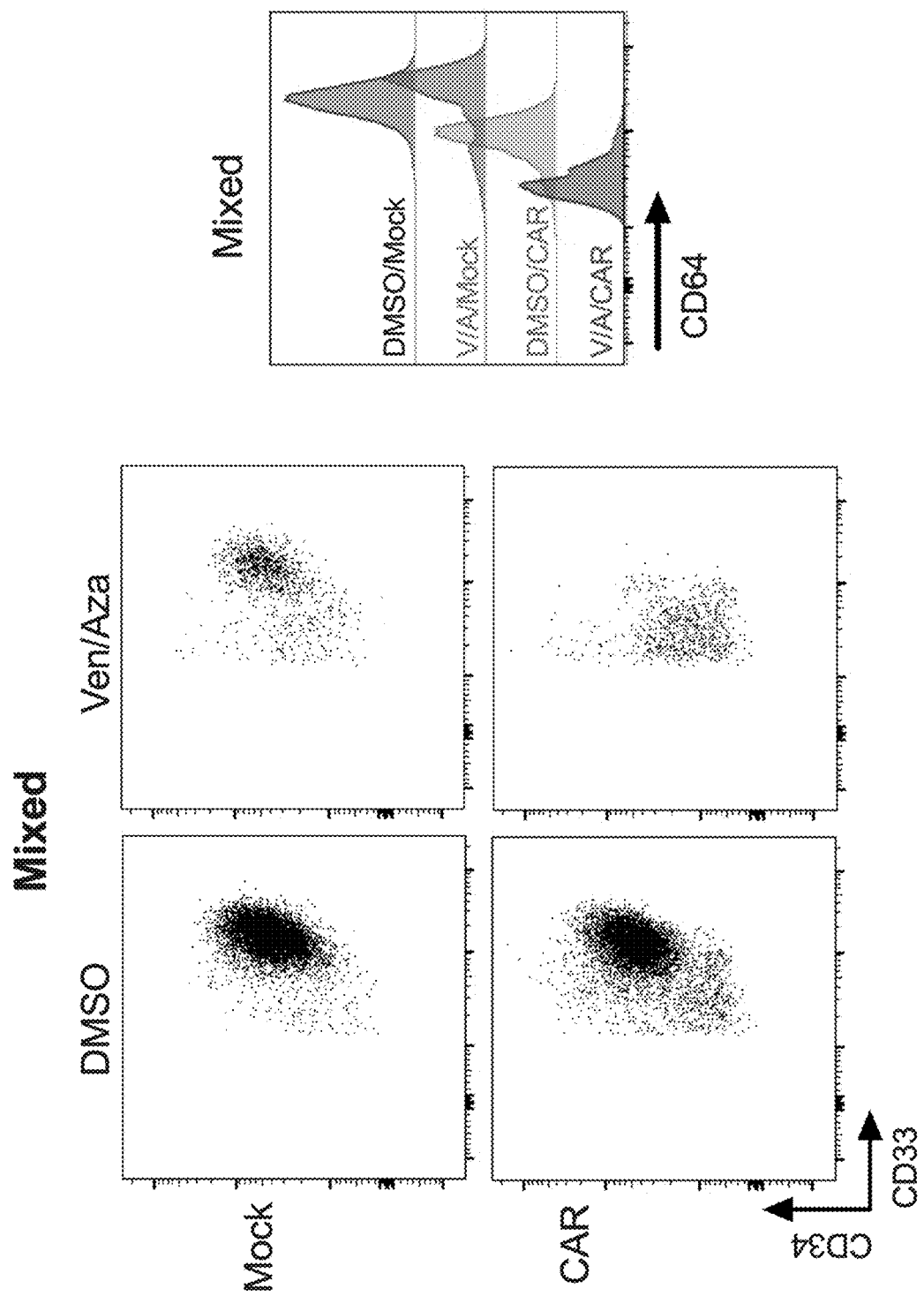
Figure 15C:
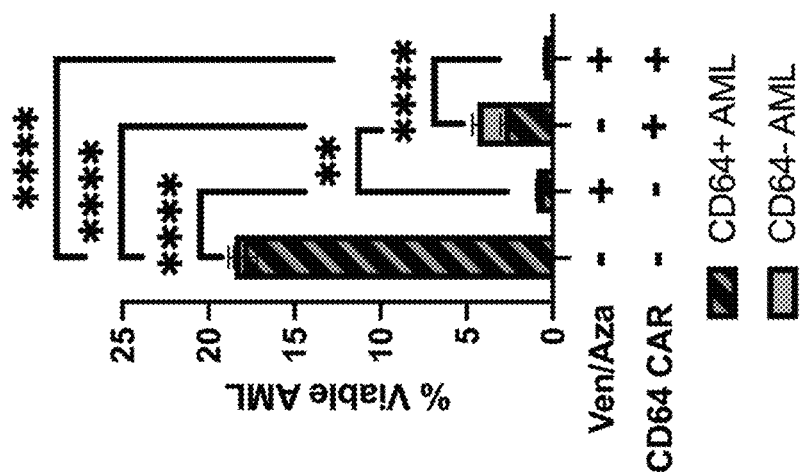
Figure 15D:
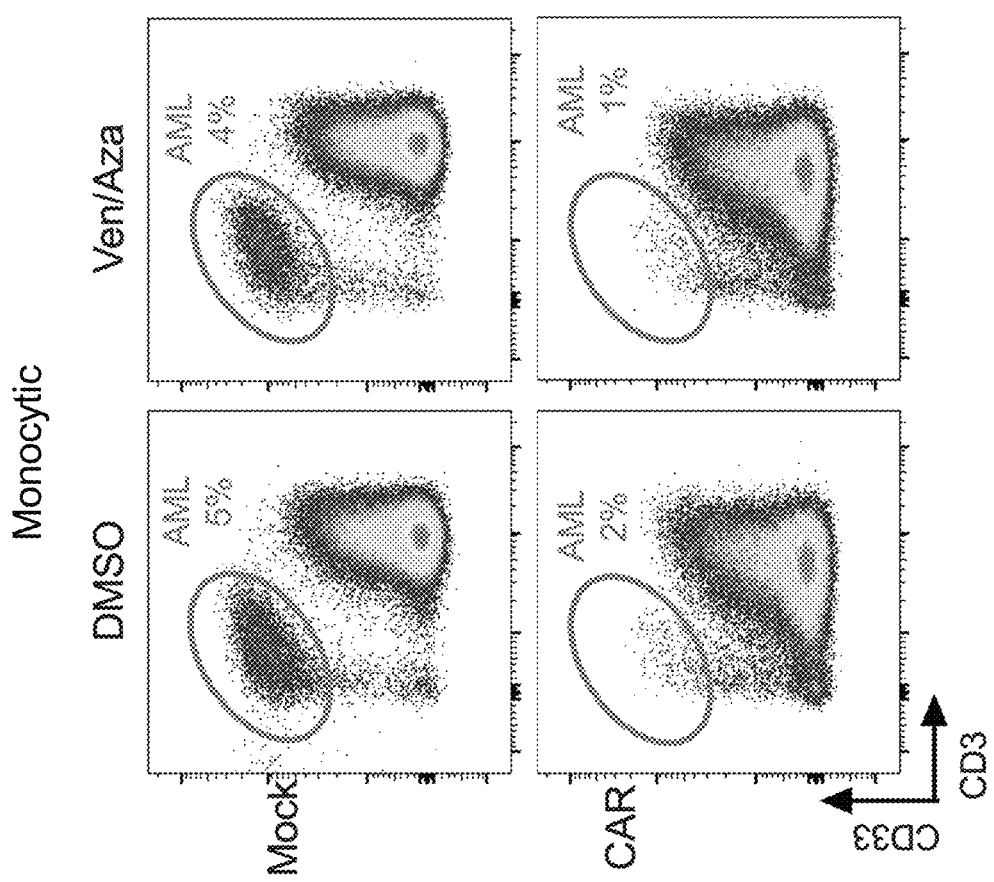
Figure 15E:
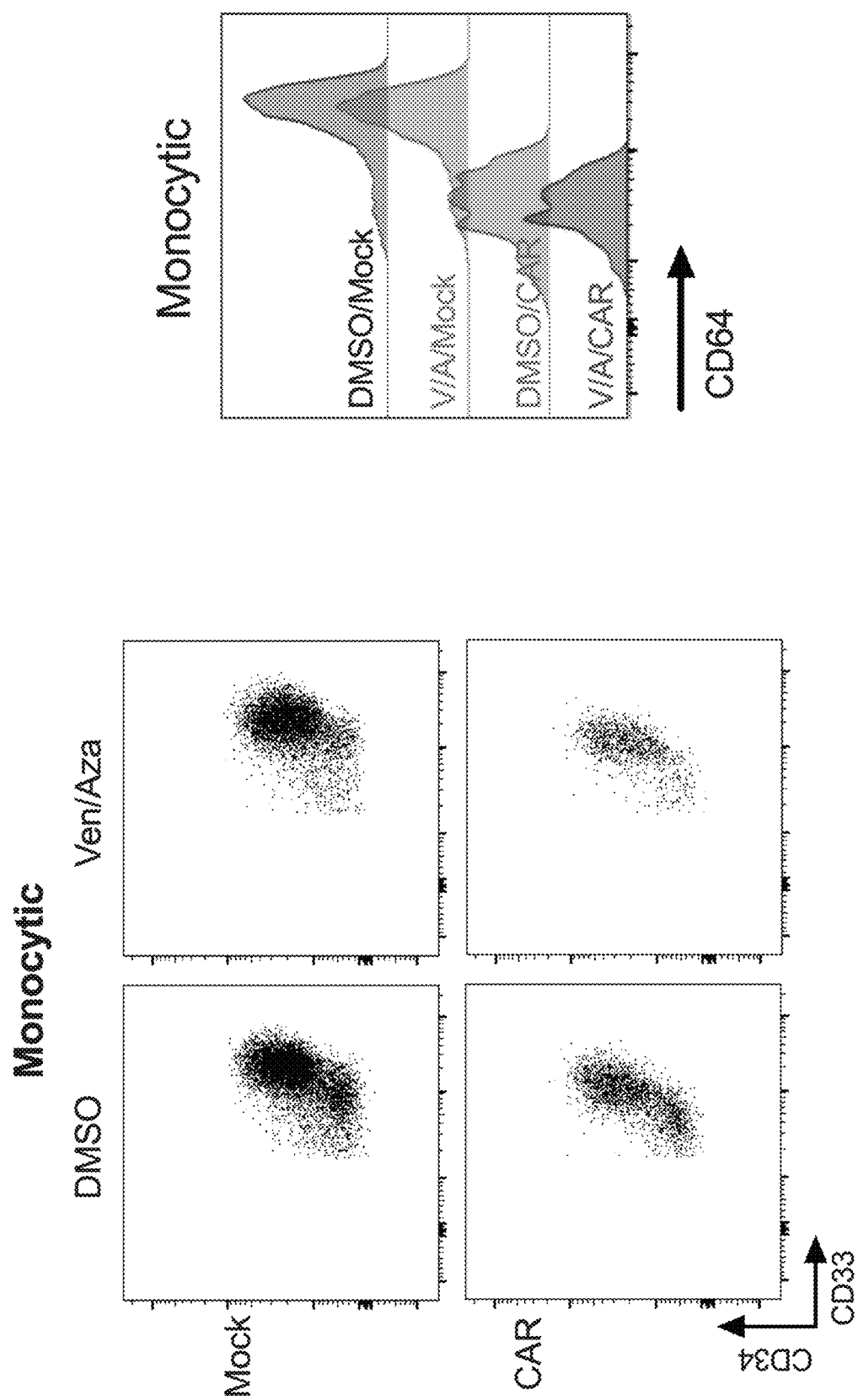
Figure 15F:
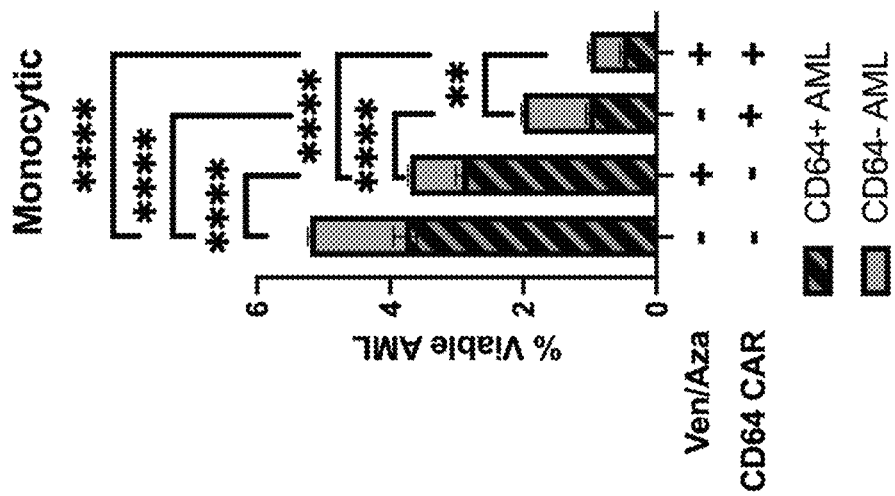

The effect of combining CD64 CAR-T cell therapy in series with ven/aza treatment on monocytic and mixed monocytic/primitive primary patient AML was assessed. Venetoclax with a hypomethylating agent, often azacitadine, is frequently used in standard of care AML therapy. Unfortunately, patients with monocytic AML are more likely to relapse after, or be initially refractory to, this combination. Monocytic or mixed AML patient samples ($1\times10^5$ cells per replicate) were thawed and cultured in vitro in IMDM media supplemented with BIT, FBS, BME, and LDL with supportive myeloid cytokines, FLT3, IL-3, and SCF at 10 ng/mL. Cells were treated for 48 hours with either 500 nM venetoclax in DMSO and 1.5 sM azacitadine in PBS or 500 nM DMSO alone as a control. 50,000 CD64-BB-m22 CAR-T cells or mock transduced T cells were then added, and culture was continued for an additional 48 hours. Following the 4 days of culture, viable AML cell number and CD64 expression was assessed by flow cytometry. Mixed monocytic/primitive AML was sensitive to ven/aza alone (21-fold reduction in viable AML cells compared to control, p<0.0001), but cells remaining at the end of treatment were highly CD64+(FIGS. 15A-15C), in line with results described previously (Pei, et. al., *Cancer Discovery* (2020)). Treatment with CD64-BB-m22 CAR-T cells alone decreased the number of viable AML cells (4.2-fold decrease in all AML) and nearly eliminated CD64+ AML. In sequence treatment with both ven/aza and CD64-BB-m22 CAR-T decreased viable AML by 34.25-fold and CD64+ AML by 353.5-fold (p<0.0001). Treating the monocytic AML patient sample with ven/aza did not significantly change AML cell viability (p=0.998) (FIG. 16D) or impactfully alter CD64 expression (FIGS. 15E-15F). Treating monocytic AML with CD64 CAR-T with or without ven/aza significantly decreased CD64+ AML by >40-fold (p<0.0001) (FIG. 15F). This data supports the efficacy of CD64 CAR-T therapy in primary monocytic AML and demonstrates the ability of ven/aza and CD64 CAR-T combination therapy to effectively target ven/aza resistant AML.

Example 7—Exemplary CD64-Binding Molecules

This Example provides the amino acid sequences of exemplary scFvs having the ability to bind CD64. The CDRs, linker, and framework sequences of each also are provided and delineated.

Anti-CD64 Clone #1

Full-Length scFV (SEQ ID NO: 1)

QVQLVEAGGGVVQPGRSLRLSCAASGFIFSGYGMHWVRQAPGKGLEWVT

VIWYDGSNKYYADSVKGRFTISRDNSKNTLYLQMNSLRAEDTAVYYC

ARDTGDRFFDYWGQGTLVTVSSGGGGSGGGGSGGGGSEIVLTQSPATLS

LSPGERATLSCRASQSVSSYLAWYQQKPGQAPRLLIYDASSRATGIPAR

FGGSGSGTDFTLTISSLEPEDFAVYYCQLRSNWPPYTFGQGTKLEIKTS

Vh Domain:

(SEQ ID NO: 31)

QVQLVEAGGGVVQPGRSLRLSCAASGFIFSGYGMHWVRQAPGKGLEWVT

VIWYDGSNKYYADSVKGRFTISRDNSKNTLYLQMNSLRAEDTAVYYC

ARDTGDRFFDYWGQGTLVTVSS

Framework Region 1 of VH Domain:

(SEQ ID NO: 27)

QVQLVEAGGGVVQPGRSLRLSCAA

CDR1 of VH Domain:

(SEQ ID NO: 24)

SGFIFSGYG

Framework Region 2 of VH Domain:

(SEQ ID NO: 28)

MHWVRQAPGKGLEWVTV

CDR2 of VH Domain:

```
                                    (SEQ ID NO: 25)
                        IWYDGSNK
```

Framework Region 3 of VH Domain:

```
                                            (SEQ ID NO: 29)
        YYADSVKGRFTISRDNSKNTLYLQMNSLRAEDTAVYYC
```

CDR3 of VH Domain:

```
                                    (SEQ ID NO: 26)
                        ARDTGDRFFDY
```

Framework Region 4 of VH Domain:

```
                                    (SEQ ID NO: 30)
                        WGQGTTVTVSS
```

In some cases, Framework Region 4 of VH domain can be WGQGTLVTV (SEQ ID NO:381) and/or an "SS" sequence can be added to the 5' end of a linker set forth in SEQ ID NO: 420.

Linker:

```
                                    (SEQ ID NO: 420)
                        GGGGSGGGGSGGGGS
```

VL Domain:

```
                                            (SEQ ID NO: 39)
EIVLTQSPATLSLSPGERATLSCRASQSVSSYLAWYQQKPGQAPRLLIY
DASSRATGIPARFGGSGSGTDFTLTISSLEPEDFAVYYCQLRSNWPPYT
FGQGTKLEIKTS
```

Framework Region 1 of VL Domain:

```
                                            (SEQ ID NO: 35)
                EIVLTQSPATLSLSPGERATLSCRAS
```

CDR1 of VL Domain:

```
                                    (SEQ ID NO: 32)
                        QSVSSY
```

Framework Region 2 of VL Domain:

```
                                    (SEQ ID NO: 36)
                        LAWYQQKPGQAPRLLIY
```

CDR2 of VL Domain:

```
                                    (SEQ ID NO: 33)
                        DAS
```

Framework Region 3 of VL Domain:

```
                                            (SEQ ID NO: 37)
                SRATGIPARFGGSGSGTDFTLTISSLEPEDFAVYYC
```

CDR3 of VL Domain:

```
                                    (SEQ ID NO: 34)
                        QLRSNWPPYT
```

Framework Region 4 of VL Domain:

```
                                    (SEQ ID NO: 38)
                        FGQGTKLEIKTS
```

In some cases, Framework Region 4 of VL domain can lack the 3' "TS" sequence:

```
                                    (SEQ ID NO: 382)
                        FGQGTKLEIK
```

Anti-CD64 Clone #2
Full-Length scFV

```
                                            (SEQ ID NO: 1)
QVQLVEAGGGVVQPGRSLRLSCAASGFIFSGYGMHWVRQAPGKGLEWVT
VIWYDGSNKYYADSVKGRFTISRDNSKNTLYLQMNSLRAEDTAVYYCA
RDTGDRFFDYWGQGTLVTVSSGGGGSGGGGSGGGGSEIVLTQSPATLSL
SPGERATLSCRASQSVSSYLAWYQQKPGQAPRLLIYDASSRATGIPAR
FGGSGSGTDFTLTISSLEPEDFAVYYCQLRSNWPPYTFGQGTKLEIKTS
```

VH Domain:

```
                                            (SEQ ID NO: 47)
QVQLVEAGGGVVQPGRSLRLSCAASGFIFSGYGMHWVRQAPGKGLEWVT
VIWYDGSNKYYADSVKGRFTISRDNSKNTLYLQMNSLRAEDTAVYYCA
RDTGDRFFDYWGQGTLVTVSS
```

Framework Region 1 of VH Domain:

```
                                            (SEQ ID NO: 43)
                QVQLVEAGGGVVQPGRSLRLSCAASGFIFS
```

CDR1 of VH Domain:

```
                                    (SEQ ID NO: 40)
                        GYGMH
```

Framework Region 2 of VH Domain:

```
                                    (SEQ ID NO: 44)
                        WVRQAPGKGLEWVT
```

CDR2 of VH Domain:

```
                                    (SEQ ID NO: 41)
                        VIWYDGSNKYYADSVKG
```

Framework Region 3 of VH Domain:

```
                                            (SEQ ID NO: 45)
                        FTISRDNSKNTLYLQMNSLRAEDTAVYYCAR
```

CDR3 of VH Domain:

(SEQ ID NO: 42)
DTGDRFFDY

Framework Region 4 of VH Domain:

(SEQ ID NO: 46)
WGQGTLVTVSS

In some cases, Framework Region 4 of VH domain can be WGQGTLVTV (SEQ ID NO:383) and/or an "SS" sequence can be added to the 5' end of a linker set forth in SEQ ID NO: 420.

Linker:

(SEQ ID NO: 420)
GGGGSGGGGSGGGGS

VL Domain:

(SEQ ID NO: 55)
EIVLTQSPATLSLSPGERATLSCRASQSVSSYLAWYQQKPGQAPRLLIYDASSRATGIPARFGGSGSGTDFTLTISSLEPEDFAVYYCQLRSNWPPYTFGQGTKLEIKTS

Framework Region 1 of VL Domain:

(SEQ ID NO: 51)
EIVLTQSPATLSLSPGERATLSC

CDR1 of VL Domain:

(SEQ ID NO: 48)
RASQSVSSYLA

Framework Region 2 of VL Domain:

(SEQ ID NO: 52)
WYQQKPGQAPRLLIY

CDR2 of VL Domain:

(SEQ ID NO: 49)
DASSRAT

Framework Region 3 of VL Domain:

(SEQ ID NO: 53)
GIPARFGGSGSGTDFTLTISSLEPEDFAVYYC

CDR3 of VL Domain:

(SEQ ID NO: 50)
QLRSNWPPYT

Framework Region 4 of VL Domain:

(SEQ ID NO: 54)
FGQGTKLEIKTS

In some cases, Framework Region 4 of VL domain can lack the 3' "TS" sequence:

(SEQ ID NO: 384)
FGQGTKLEIK

Anti-CD64 Clone #3
Full scFV (SEQ ID NO: 3)
EVQLVESGGGLVKPGGSLRLSCVASGFIFSDNYMYWVRQTPEKRLEWVATISDGGSYTYYPDSVKGRFTISRDNAKNNLYLQMSSLKSEDTAIYYCARGYYRYEGAMDYWGQGTSVTVSSGGGGSGGGGSGGGGSNIVMTQSPSSLAVSAGEKVTMSCKSSQSVLYSSNQKNYLAWYQQKPGQSPKLLIYWASTRESGVPDRFTGSGSGTDFTLTISSVQAEDLAVYYCHQYLSSWTFGGGTKLEIKTS VH Domain:

(SEQ ID NO: 385)
EVQLVESGGGLVKPGGSLRLSCVASGFIFSDNYMYWVRQTPEKRLEWVATISDGGSYTYYPDSVKGRFTISRDNAKNNLYLQMSSLKSEDTAIYYCARGYYRYEGAMDYWGQGTSVTVSS

Framework Region 1 of VH Domain:

(SEQ ID NO: 386)
EVQLVESGGGLVKPGGSLRLSCVAS

CDR1 of VH Domain:

(SEQ ID NO: 387)
GFIFSDNY

Framework Region 2 of VH Domain:

(SEQ ID NO: 388)
MYWVRQTPEKRLEWVAT

CDR2 of VH Domain:

(SEQ ID NO: 389)
ISDGGSYT

Framework Region 3 of VH Domain:

(SEQ ID NO: 390)
YYPDSVKGRFTISRDNAKNNLYLQMSSLKSEDTAIYYC

CDR3 of VH Domain:

(SEQ ID NO: 391)
ARGYYRYEGAMDY

Framework Region 4 of VH Domain:

(SEQ ID NO: 392)
WGQGTSVTVSS

In some cases, Framework Region 4 of VH domain can be WGQGTSVTV (SEQ ID NO:393) and/or an "SS" sequence can be added to the 5' end of a linker set forth in SEQ ID NO: 420.

Linker:

(SEQ ID NO: 420)
GGGGSGGGGSGGGGS

VL Domain:

(SEQ ID NO: 394)
NIVMTQSPSSLAVSAGEKVTMSCKSS<u>QSVLYSSNQKNY</u>LAWYQQKPGQ
SPKLLIY<u>WAS</u>TRESGVPDRFTGSGSGTDFTLTISSVQAEDLAVYYC
<u>HQYLSSWT</u>FGGGTKLEIKTS

Framework Region 1 of VL Domain:

(SEQ ID NO: 395)
NIVMTQSPSSLAVSAGEKVTMSCKSS

CDR1 of VL Domain:

(SEQ ID NO: 396)
QSVLYSSNQKNY

Framework Region 2 of VL Domain:

(SEQ ID NO: 397)
LAWYQQKPGQSPKLLIY

CDR2 of VL Domain:

(SEQ ID NO: 398)
WAS

Framework Region 3 of VL Domain:

(SEQ ID NO: 399)
TRESGVPDRFTGSGSGTDFTLTISSVQAEDLAVYYC

CDR3 of VL Domain:

(SEQ ID NO: 400)
HQYLSSWT

Framework Region 4 of VL Domain:

(SEQ ID NO: 401)
FGGGTKLEIKTS

In some cases, Framework Region 4 of VL domain can lack the 3' "TS" sequence:

(SEQ ID NO: 402)
FGGGTKLEIK

Anti-CD64 Clone #4
Full scFV (SEQ ID NO: 3)
EVQLVESGGGLVKPGGSLRLSCVASGFIFS<u>DNYMY</u>WVRQTPEKRLEWVA
<u>TISDGG</u>SYTYYPDSVKGRFTISRDNAKNNLYLQMSSLKSEDTAIYYCAR
<u>GYYRYEGAMDY</u>WGQGTSVTVSSGGGGSGGGGSGGGGSNIVMTQSPSSLAV
SAGEKVTMSC<u>KSSQSVLYSSNQKNYLA</u>WYQQKPGQSPKLLIY
<u>WASTRES</u>GVPDRFTGSGSGTDFTLTISSVQAEDLAVYYC<u>HQYLSSWT</u>FG
GGTKLEIKTS VH Domain:

(SEQ ID NO: 403)
EVQLVESGGGLVKPGGSLRLSCVASGFIFS<u>DNYMY</u>WVRQTPEKRLEWVA
<u>TISDGG</u>SYTYYPDSVKGRFTISRDNAKNNLYLQMSSLKSEDTAIYYCAR
<u>TISDGG</u>WGQGTSVTVSS

Framework Region 1 of VH Domain:

(SEQ ID NO: 404)
EVQLVESGGGLVKPGGSLRLSCVASGFIFS

CDR1 of VH Domain:

(SEQ ID NO: 405)
DNYMY

Framework Region 2 of VH Domain:

(SEQ ID NO: 406)
WVRQTPEKRLEWVA

CDR2 of VH Domain:

(SEQ ID NO: 407)
TISDGGSYTYYPDSVKG

Framework Region 3 of VH Domain:

(SEQ ID NO: 408)
RFTISRDNAKNNLYLQMSSLKSEDTAIYYCAR

CDR3 of VH Domain:

(SEQ ID NO: 409)
GYYRYEGAMDY

Framework Region 4 of VH Domain:

(SEQ ID NO: 410)
WGQGTSVTVSS

In some cases, Framework Region 4 of VH domain can be WGQGTSVTV (SEQ ID NO:411) and/or an "SS" sequence can be added to the 5' end of a linker set forth in SEQ ID NO: 420.

Linker:

(SEQ ID NO: 420)
GGGGSGGGGSGGGGS

VL Domain:

(SEQ ID NO: 412)
NIVMTQSPSSLAVSAGEKVTMSCKSSQSVLYSSNQKNYLAWYQQKPGQS
PKLLIYHQYLSSWTGVPDRFTGSGSGTDFTLTISSVQAEDLAVYYC
WASTRESFGGGTKLEIK

Framework Region 1 of VL Domain:

(SEQ ID NO: 413)
NIVMTQSPSSLAVSAGEKVTMSC

CDR1 of VL Domain:

(SEQ ID NO: 421)
KSSQSVLYSSNQKNYLA

Framework Region 2 of VL Domain:

(SEQ ID NO: 414)
WYQQKPGQSPKLLIY

CDR2 of VL Domain:

(SEQ ID NO: 415)
WASTRES

Framework Region 3 of VL Domain:

(SEQ ID NO: 416)
GVPDRFTGSGSGTDFTLTISSVQAEDLAVYYC

CDR3 of VL Domain:

(SEQ ID NO: 417)
HQYLSSWT

Framework Region 4 of VL Domain:

(SEQ ID NO: 418)
FGGGTKLEIKTS

In some cases, Framework Region 4 of VL domain can lack the 3' "TS" sequence:

(SEQ ID NO: 419)
FGGGTKLEIK

Anti-CD64 Clone #5
Full scFV (SEQ ID NO: 2)
QVQLVESGGGWQPGRSLRLSCSSSGFIFSDNYMYWVRQAPGKGLEWVAT
ISDGGSYTYYPDSVKGRFTISRDNSKNTLFLQMDSLRPEDTGVYFCARG
YYRYEGAMDYWGQGTPVTVSSGGGGSGGGGSGGGGSDIQLTQSPSSLSA
SVGDRVTITCKSSQSVLYSSNQKNYLAWYQQKPGKAPKLLIYWASTRES
GVPSRFSGSGSGTDFTFTISSLQPEDIATYYCHQYLSSWTFGQGTKLEI
KTS

---

SEQUENCE LISTING

```
Sequence total quantity: 422
SEQ ID NO: 1              moltype = AA  length = 243
FEATURE                   Location/Qualifiers
source                    1..243
                          mol_type = protein
                          organism = synthetic construct
SEQUENCE: 1
QVQLVEAGGG VVQPGRSLRL SCAASGFIFS GYGMHWVRQA PGKGLEWVTV IWYDGSNKYY   60
ADSVKGRFTI SRDNSKNTLY LQMNSLRAED TAVYYCARDT GDRFFDYWGQ GTLVTVSSGG  120
GGSGGGGSGG GGSEIVLTQS PATLSLSPGE RATLSCRASQ SVSSYLAWYQ QKPGQAPRLL  180
IYDASSRATG IPARFGGSGS GTDFTLTISS LEPEDFAVYY CQLRSNWPPY TFGQGTKLEI  240
KTS                                                                243

SEQ ID NO: 2              moltype = AA  length = 248
FEATURE                   Location/Qualifiers
source                    1..248
                          mol_type = protein
                          organism = synthetic construct
SEQUENCE: 2
QVQLVESGGG WQPGRSLRLS CSSSGFIFSD NYMYWVRQAP GKGLEWVATI SDGGSYTYYP   60
DSVKGRFTIS RDNSKNTLFL QMDSLRPEDT GVYFCARGYY RYEGAMDYWG QGTPVTVSSG  120
GGGSGGGGSG GGGSDIQLTQ SPSSLSASVG DRVTITCKSS QSVLYSSNQK NYLAWYQQKP  180
GKAPKLLIYW ASTRESGVPS RFSGSGSGTD FTFTISSLQP EDIATYYCHQ YLSSWTFGQG  240
TKLEIKTS                                                           248

SEQ ID NO: 3              moltype = AA  length = 249
FEATURE                   Location/Qualifiers
source                    1..249
                          mol_type = protein
                          organism = synthetic construct
SEQUENCE: 3
EVQLVESGGG LVKPGGSLRL SCVASGFIFS DNYMYWVRQT PEKRLEWVAT ISDGGSYTYY   60
```

```
PDSVKGRFTI SRDNAKNNLY LQMSSLKSED TAIYYCARGY YRYEGAMDYW GQGTSVTVSS   120
GGGGSGGGGS GGGGSNIVMT QSPSSLAVSA GEKVTMSCKS SQSVLYSSNQ KNYLAWYQQK   180
PGQSPKLLIY WASTRESGVP DRFTGSGSGT DFTLTISSVQ AEDLAVYYCH QYLSSWTFGG   240
GTKLEIKTS                                                          249

SEQ ID NO: 4            moltype = AA   length = 45
FEATURE                 Location/Qualifiers
source                  1..45
                        mol_type = protein
                        organism = Homo sapiens
SEQUENCE: 4
TTTPAPRPPT PAPTIASQPL SLRPEACRPA AGGAVHTRGL DFACD                   45

SEQ ID NO: 5            moltype = AA   length = 24
FEATURE                 Location/Qualifiers
source                  1..24
                        mol_type = protein
                        organism = Homo sapiens
SEQUENCE: 5
IYIWAPLAGT CGVLLLSLVI TLYC                                          24

SEQ ID NO: 6            moltype = AA   length = 42
FEATURE                 Location/Qualifiers
source                  1..42
                        mol_type = protein
                        organism = Homo sapiens
SEQUENCE: 6
KRGRKKLLYI FKQPFMRPVQ TTQEEDGCSC RFPEEEEGGC EL                      42

SEQ ID NO: 7            moltype = AA   length = 112
FEATURE                 Location/Qualifiers
source                  1..112
                        mol_type = protein
                        organism = Homo sapiens
SEQUENCE: 7
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR          112

SEQ ID NO: 8            moltype = AA   length = 39
FEATURE                 Location/Qualifiers
source                  1..39
                        mol_type = protein
                        organism = Homo sapiens
SEQUENCE: 8
IEVMYPPPYL DNEKSNGTII HVKGKHLCPS PLFPGPSKP                          39

SEQ ID NO: 9            moltype = AA   length = 27
FEATURE                 Location/Qualifiers
source                  1..27
                        mol_type = protein
                        organism = Homo sapiens
SEQUENCE: 9
FWVLVVVGGV LACYSLLVTV AFIIFWV                                       27

SEQ ID NO: 10           moltype = AA   length = 41
FEATURE                 Location/Qualifiers
source                  1..41
                        mol_type = protein
                        organism = Homo sapiens
SEQUENCE: 10
RSKRSRLLHS DYMNMTPRRP GPTRKHYQPY APPRDFAAYR S                       41

SEQ ID NO: 11           moltype = AA   length = 488
FEATURE                 Location/Qualifiers
source                  1..488
                        mol_type = protein
                        organism = synthetic construct
SEQUENCE: 11
MALPVTALLL PLALLLHAAR PQVQLVEAGG GVVQPGRSLR LSCAASGFIF SGYGMHWVRQ    60
APGKGLEWVT VIWYDGSNKY YADSVKGRFT ISRDNSKNTL YLQMNSLRAE DTAVYYCARD   120
TGDRFFDYWG QGTLVTVSSG GGGSGGGGS GGGGSEIVLTQ SPATLSLSPG ERATLSCRAS   180
QSVSSYLAWY QQKPGQAPRL LIYDASSRAT GIPARFGGSG SGTDFTLTIS SLEPEDFAVY   240
YCQLRSNWPP YTFGQGTKLE IKTSTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELSRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 12           moltype = AA   length = 493
```

```
FEATURE                 Location/Qualifiers
source                  1..493
                        mol_type = protein
                        organism = synthetic construct
SEQUENCE: 12
MALPVTALLL PLALLLHAAR PQVQLVESGG GWQPGRSLRL SCSSSGFIFS DNYMYWVRQA    60
PGKGLEWVAT ISDGGSYTYY PDSVKGRFTI SRDNSKNTLF LQMDSLRPED TGVYFCARGY   120
YRYEGAMDYW GQGTPVTVSS GGGGSGGGGS GGGGSDIQLT QSPSSLSASV GDRVTITCKS   180
SQSVLYSSNQ KNYLAWYQQK PGKAPKLLIY WASTRESGVP SRFSGSGSGT DFTFTISSLQ   240
PEDIATYYCH QYLSSWTFGQ GTKLEIKTST TTPAPRPPTP APTIASQPLS LRPEACRPAA   300
GGAVHTRGLD FACDIYIWAP LAGTCGVLLL SLVITLYCKR GRKKLLYIFK QPFMRPVQTT   360
QEEDGCSCRF PEEEEGGCEL SRVKFSRSAD APAYQQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPR                                                     493

SEQ ID NO: 13           moltype = AA   length = 494
FEATURE                 Location/Qualifiers
source                  1..494
                        mol_type = protein
                        organism = synthetic construct
SEQUENCE: 13
MALPVTALLL PLALLLHAAR PEVQLVESGG GLVKPGGSLR LSCVASGFIF SDNYMYWVRQ    60
TPEKRLEWVA TISDGGSYTY YPDSVKGRFT ISRDNAKNNL YLQMSSLKSE DTAIYYCARG   120
YYRYEGAMDY WGQGTSVTVS SGGGGSGGGG SGGGGSNIVM TQSPSSLAVS AGEKVTMSCK   180
SSQSVLYSSN QKNYLAWYQQ KPGQSPKLLI YWASTRESGV PDRFTGSGSG TDFTLTISSV   240
QAEDLAVYYC HQYLSSWTFG GGTKLEIKTS TTTPAPRPPT PAPTIASQPL SLRPEACRPA   300
AGGAVHTRGL DFACDIYIWA PLAGTCGVLL LSLVITLYCK RGRKKLLYIF KQPFMRPVQT   360
TQEEDGCSCR FPEEEEGGCE LSRVKFSRSA DAPAYQQGQN QLYNELNLGR REEYDVLDKR   420
RGRDPEMGGK PRRKNPQEGL YNELQKDKMA EAYSEIGMKG ERRRGKGHDG LYQGLSTATK   480
DTYDALHMQA LPPR                                                    494

SEQ ID NO: 14           moltype = AA   length = 487
FEATURE                 Location/Qualifiers
source                  1..487
                        mol_type = protein
                        organism = synthetic construct
SEQUENCE: 14
MALPVTALLL PLALLLHAAR PQVQLVEAGG GVVQPGRSLR LSCAASGFIF SGYGMHWVRQ    60
APGKGLEWVT VIWYDGSNKY YADSVKGRFT ISRDNSKNTL YLQMNSLRAE DTAVYYCARD   120
TGDRFFDYWG QGTLVTVSSG GGGSGGGGSG GGGSEIVLTQ SPATLSLSPG ERATLSCRAS   180
QSVSSYLAWY QQKPGQAPRL LIYDASSRAT GIPARFGGSG SGTDFTLTIS SLEPEDFAVY   240
YCQLRSNWPP YTFGQGTKLE IKTSGAAAIE VMYPPPYLDN EKSNGTIIHV KGKHLCPSPL   300
FPGPSKPFWV LVVVGGVLAC YSLLVTVAFI IFWVRSKRSR LLHSDYMNMT PRRPGPTRKH   360
YQPYAPPRDF AAYRSVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                            487

SEQ ID NO: 15           moltype = AA   length = 492
FEATURE                 Location/Qualifiers
source                  1..492
                        mol_type = protein
                        organism = synthetic construct
SEQUENCE: 15
MALPVTALLL PLALLLHAAR PQVQLVESGG GWQPGRSLRL SCSSSGFIFS DNYMYWVRQA    60
PGKGLEWVAT ISDGGSYTYY PDSVKGRFTI SRDNSKNTLF LQMDSLRPED TGVYFCARGY   120
YRYEGAMDYW GQGTPVTVSS GGGGSGGGGS GGGGSDIQLT QSPSSLSASV GDRVTITCKS   180
SQSVLYSSNQ KNYLAWYQQK PGKAPKLLIY WASTRESGVP SRFSGSGSGT DFTFTISSLQ   240
PEDIATYYCH QYLSSWTFGQ GTKLEIKTSG AAAIEVMYPP PYLDNEKSNG TIIHVKGKHL   300
CPSPLFPGPS KPFWVLVVVG GVLACYSLLV TVAFIIFWVR SKRSRLLHSD YMNMTPRRPG   360
PTRKHYQPYA PPRDFAAYRS RVKFSRSADA PAYQQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                      492

SEQ ID NO: 16           moltype = AA   length = 493
FEATURE                 Location/Qualifiers
source                  1..493
                        mol_type = protein
                        organism = synthetic construct
SEQUENCE: 16
MALPVTALLL PLALLLHAAR PEVQLVESGG GLVKPGGSLR LSCVASGFIF SDNYMYWVRQ    60
TPEKRLEWVA TISDGGSYTY YPDSVKGRFT ISRDNAKNNL YLQMSSLKSE DTAIYYCARG   120
YYRYEGAMDY WGQGTSVTVS SGGGGSGGGG SGGGGSNIVM TQSPSSLAVS AGEKVTMSCK   180
SSQSVLYSSN QKNYLAWYQQ KPGQSPKLLI YWASTRESGV PDRFTGSGSG TDFTLTISSV   240
QAEDLAVYYC HQYLSSWTFG GGTKLEIKTS GAAAIEVMYP PPYLDNEKSN GTIIHVKGKH   300
LCPSPLFPGP SKPFWVLVVV GGVLACYSLL VTVAFIIFWV RSKRSRLLHS DYMNMTPRRP   360
GPTRKHYQPY APPRDFAAYR SRVKFSRSAD APAYQQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPR                                                     493
```

```
SEQ ID NO: 17          moltype = DNA   length = 1467
FEATURE                Location/Qualifiers
source                 1..1467
                       mol_type = other DNA
                       organism = synthetic construct
SEQUENCE: 17
atggctttgc ctgttacagc tctgctgctg cccctggctc tgcttctgca tgctgctaga   60
cctcaggtga agctggttga agctggtggc ggagttgtgc agcctggcag atctctgaga  120
ctgagctgtg ccgccagcgg cttcatcttt agcggctatg gcatgcactg ggtccgacag  180
gcacctggca aaggcctgga atgggtcacc gtgatttggt acgacggcag caacaagtac  240
tacgccgaca gcgtgaaggg cagattcacc atcagccggg acaacagcaa gaaccccctg  300
tacctgcaga tgaacagcct gagagccgag gacaccgccg tgtactactg tgccagagac  360
accggcgaca gattcttcga ctattgggggc cagggcaccc tcgtgacagt ttcttctggc  420
ggcggaggat ctggcggagg tggaagcgga ggcggtggat ctgaaatcgt gctgacacag  480
agccccgcca cactgtcact ttctccaggc gaaagagcca cactgagctg cagagcctct  540
cagagcgtgt cctcttacct ggcctggtat cagcagaagc ctggacaggc tccccggctg  600
ctgatctacg atgcttctag cagagctaca ggcatcccccg ccagatttgg cggctctggc  660
tctggcactg atttcacccct gaccataagc agcctgagcc tgaggactt tgccgtgtat  720
tattgccagc tgcggagcaa ctggcctcct tacacatttg gccaggggac caagctggaa  780
atcaagacta gtaccaccac accagctcct cggccaccta ctccagctcc aacaattgcc  840
agccagcctc tgtctctgag gcccgaagct tgtagacctg ctgctggcgg agccgtgcat  900
acaagaggac tggatttcgc ctgcgacatc tacatctggg ccccctctgg tgaacatgt  960
ggcgtgctgc tgctcagcct ggtcatcacc ctgtactgca agcggggcag aaagaagctg 1020
ctgtacatct tcaagcagcc cttcatgcgc cccgtgcaga ccacacaaga ggaagatggc 1080
tgctcctgca gattccccga ggaagaagaa ggcggctgcg agctgtctag agtgaagttc 1140
agcagaagcg ccgacgctcc tgcctatcag cagggacaga atcagctgta caacgagctg 1200
aacctgggcg gcagaagaga gtacgacgtg ctggacaaga agagggcag ggaccctgag 1260
atgggcggca gcccagaag aaagaaccct caagaggggcc tgtataatga gctgcagaaa 1320
gacaagatgc cgaggccta cagcgagatc ggaatgaagg gcgaacgcag aagaggaaag 1380
ggccacgacg gactgtatca gggcctgagc acagccacca aggacaccta tgatgccctg 1440
cacatgcagg cactgcctcc aagatga                                      1467

SEQ ID NO: 18          moltype = DNA   length = 1464
FEATURE                Location/Qualifiers
source                 1..1464
                       mol_type = other DNA
                       organism = synthetic construct
SEQUENCE: 18
atggctttgc ctgttacagc tctgctgctg cccctggctc tgcttctgca tgctgctaga   60
cctcaggtgc agctggttga agctggtggc ggagttgtgc agcctggcag atctctgaga  120
ctgagctgtg ccgccagcgg cttcatcttt agcggctatg gcatgcactg ggtccgacag  180
gcacctggca aaggcctgga atgggtcacc gtgatttggt acgacggcag caacaagtac  240
tacgccgaca gcgtgaaggg cagattcacc atcagccggg acaacagcaa gaaccccctg  300
tacctgcaga tgaacagcct gagagccgag gacaccgccg tgtactactg tgccagagac  360
accggcgaca gattcttcga ctattgggggc cagggcaccc tcgtgacagt ttcttctggc  420
ggcggaggat ctggcggagg tggaagcgga ggcggtggat ctgaaatcgt gctgacacag  480
agccccgcca cactgtcact ttctccaggc gaaagagcca cactgagctg cagagcctct  540
cagagcgtgt cctcttacct ggcctggtat cagcagaagc ctggacaggc tccccggctg  600
ctgatctacg atgcttctag cagagctaca ggcatcccccg ccagatttgg cggctctggc  660
tctggcactg atttcacccct gaccataagc agcctgaac ctgaggactt tgccgtgtat  720
tattgccagc tgcggagcaa ctggcctcct tacacatttg gccaggggac caagctggaa  780
atcaagacta gtggcgccgc tgctattgaa gtgatgtacc ctcctcctta cctggacaac  840
gagaagtcca acggcaccat catccacgtg aagggcaagc acctgtgtcc ttctccactg  900
ttcccccgga ctagcaagcc tttctgggtg tcgttgttg ttggcggcgt gctggcctgt  960
tatttcctgc tggttaccgt ggccttcatc atctttttggg tccgaagcaa gcggagccgg 1020
ctgctgcaca gcgactacat gaacatgacc cctagacgcc ccggaccaac cagaaagcac 1080
taccagcctt acgctcctcc tagagacttc gccgcctacc ggtctagagt gaagttcagc 1140
agatccgccg acgctcctgc ctatcagcag ggacagaacc agctgtacaa cgagctgaac 1200
ctggggagaa gagaagagta cgacgtgctg gacaagcgga gaggcagaga tcctgagatg 1260
ggcggcaagc ccagacggaa gaatcctcaa gagggcctgt ataatgagct gcagaaagac 1320
aagatggccg aggcctacag cgagatcgga atgaagggcg agcgcagaag aggcaaggga 1380
cacgatggac tgtaccaggg cctgagcacc gccaccaagg ataccatga tgccctgcac 1440
atgcaggccc tgcctccaag atga                                         1464

SEQ ID NO: 19          moltype = DNA   length = 1482
FEATURE                Location/Qualifiers
source                 1..1482
                       mol_type = other DNA
                       organism = synthetic construct
SEQUENCE: 19
atggctttgc ctgttacagc tctgctgctg cccctggctc tgcttctgca tgctgctaga   60
cctcaggtga gctggtgga atctggcgga ggatggcagc tggcagaag cctgagactg  120
agctgtagca gcagcggctt catcttcagc gacaactaca tgtactgggt ccgacaggcc  180
cctggcaaag gccttgaatg ggtcgccaca atctcgtacg gcggcagcta cacctactat  240
cccgactctg tgaagggcag attcaccatc agccgggaca acagcaagaa taccctgttc  300
ctgcagatgg acagcctgcg gcctgaagat accggcgtgt actttttgcg cagaggctac  360
tacagatacg gggcgccat ggactattgg ggccagggaa cacctgtgac cgttctagc  420
ggcggaggtg gaagcggagg cggaggtagt ggtggtgggcg atctgacat tcagctgaca  480
cagagcccta gcagcctgtc tgcctctgtg ggcgacagag tgaccatcac atgcaagagc  540
```

```
agccagagcg tgctgtactc cagcaaccag aagaactacc tggcctggta tcagcagaag    600
cccggcaagg ctcctaagct gctgatctac tgggccagca ccagagaaag cggcgtgcca    660
agcagatttt ctggcagcgg ctctggcacc gacttcaccc tcaccataag ctccctgcag    720
cctgaggaca ttgccaccta ctactgccac cagtacctga gcagctggac cttttggccag   780
ggcaccaagc tggaaatcaa gactagtacc accacaccag ctcctcggcc acctactcca    840
gctccaacaa ttgccagcca gcctctgtct ctgaggcccg aagcttgtag acctgctgct    900
ggcggagccg tgcatacaag aggactggat ttcgcctgcg acatctacat ctgggcccct    960
ctggctggaa catgtggcgt gctgctgctc agcctggtca tcaccctgta ctgcaagcgg   1020
ggcagaaaga agctgctgta catcttcaag cagcccttca tgcggcccgt gcagaccaca   1080
caaggaagg atggctgctc ctgcagattc cccgaggaag aagaaggcgg ctgcgagctg   1140
tctagagtga agttcagcag aagcgccgac gctcctgcct atcagcaggg acagaatcag   1200
ctgtacaacg agctgaacct gggggcgcaga gaagagtacg acgtgctgga caagagaaga   1260
ggcagggacc ctgagatggg cggcaagccc agaagaaaga accctcaaga gggcctgtat   1320
aatgagctgc agaaagacaa gatggccgag gcctacagcg agatcggaat gaagggcgaa   1380
cgcagaagag gaaagggcca cgacggactg tatcagggcc tgagcacagc caccaaggac   1440
acctatgatg ccctgcacat gcaggcactg cctccaagat ga                      1482

SEQ ID NO: 20           moltype = DNA  length = 1479
FEATURE                 Location/Qualifiers
source                  1..1479
                        mol_type = other DNA
                        organism = synthetic construct
SEQUENCE: 20
atggctttgc ctgttacagc tctgctgctg cccctggctc tgcttctgca tgctgctaga     60
cctcaggtgc agctggtgga atctggcgga ggatggcagc tggcagaag cctgagactg    120
agctgtagca gcagcggctt catcttcagc gacaactaca tgtactgc ccgacaggcc     180
cctggcaaag gccttgaatg ggtcgccaca atctctgacg gcggcagcta cacctactat    240
cccgactctg tgaagggcag attcaccatc agccgggaca acagcaagaa taccctgttc    300
ctgcagatgc acagcctgcg gcctgaagat accggcgtgt acttttgcgc cagaggctac    360
tacagatacg agggcgccat ggactattgg ggccagggca cactgtgcc cgtttctagt    420
ggcggaggtg aagcggagg cggaggtagt ggtggtggcg gatctgacat tcagctgaca    480
cagagcccta gcagcctgtc tgcctctgtg gcgacagag tgaccatcac atgcaagagc    540
agccagagcg tgctgtactc cagcaaccag aagaactacc tggcctggta tcagcagaag    600
cccggcaagg ctcctaagct gctgatctac tgggccagca ccagagaaag cggcgtgcca    660
agcagatttt ctggcagcgg ctctggcacc gacttcaccc tcaccataag ctccctgcag    720
cctgaggaca ttgccaccta ctactgccac cagtacctga gcagctggac cttttggccag   780
ggcaccaagc tggaaatcaa gactagtggc gccgctgcta ttgaagtgat gtaccctcct    840
ccttacctgg acaacgagaa gtccaacggc accatcatcc acgtgaaggg caagcacctg    900
tgtccttctc cactgttccc cggacctagc aagccttttc gggtgctcgt tgttgttggc    960
ggcgtgctgg cctgttattc cctgctggtt accgtggcct tcatcatctt tgggtccga   1020
agcaagcgga gccggctgct gcacagcgac tacatgaaca tgacccctag acggcccgga   1080
ccaaccgaaa gcactacca gccttacgct cctcctagag acttcgccgc ctaccggtct   1140
agagtgaagt tcagcagatc cgccgacgct cctgcctatc agcagggaca gaaccagctg   1200
tacaacgagc tgaacctggg gagaagagaa gagtacgacg tgctggacaa gcggagaggc   1260
agagatcctg agatgggcgg caagcccaga cggaagaatc ctcaaaggg cctgtataat   1320
gagctgcaga agacaagat ggccgaggcc tacagcgaga tcggaatgaa gggcgagcgc    1380
agaagaggca agggacacga tggactgtac caggcctga gcaccgccac caaggatacc   1440
tatgatgccc tgcacatgca ggccctgcct ccaagatga                         1479

SEQ ID NO: 21           moltype = DNA  length = 1485
FEATURE                 Location/Qualifiers
source                  1..1485
                        mol_type = other DNA
                        organism = synthetic construct
SEQUENCE: 21
atggctctgc tgttacagc tctgctgctg cctctggctc tgcttctgca tgccgctaga     60
cctgaggtgc agctggttga atctggcggc ggacttgtga gcctggcgg atctctgaga    120
ctgagctgtg tggccagcgg cttcatcttc agcgacaact acatgtactg ggtccgacag    180
acccctgaga agcggctgga atgggtcgcc acaatctctg atggcggcag ctacacctac    240
tatcccgaca gcgtgaaggg cagattcacc atcagccggg acaacgccaa gaacaacctg    300
tacctgcaga tgagcagcct gaagtccgag gacaccgcca tctactactg cgccagaggc    360
tactacagat acgagggcgc catggactat tggggccagg gaacaagcgt gacagtgtct    420
agcggaggcg gaggatcagg tggcggtgga tctggcggtg gcggctctaa tatcgtgatg    480
acacagagcc ctagcagcct ggctgtgtct gccggcgaga agtgaccat gagctgcaag    540
agcagccaga gcgtgctgta ctccagcaac cagaagaact acctggcctg gtatcagcag    600
aagcccggac agtctcccaa gctgctgatc tactgggcca gcaccagaga aagcggcgtg    660
cccgatagat ctcaggcag cggctctggc accgacttca ccctgacaat cagctctgtg    720
caggccgagg atctggccgt gtactactgt caccagtacc tgagcagctg gaccttttgc    780
ggaggcacca agctggaaat caagactagt accaccacac cagctcctcg gccacctact    840
ccagctccaa caattgccag ccagcctctg tctctgaggc cgaagcttg tagacctgct    900
gctggcggag ccgtgcatac aagaggactg gattcgcct gcgacatcta catctgggcc    960
cctctggctg gaacatgtgg cgtgctgctg ctcagcctgg tcatcaccct gtactgcaag   1020
cggggcagaa agaagctgct gtacatcttc aagcagcct tcatgcggcc cgtgcagacc   1080
acacaagatg gctgctcctg cagattcccc gaggaagaag aaggcggctg cgagctgcga   1140
ctgtctagag tgaagttcag cagaagcgcc gacgctcctg cctatcagca gggacagaat   1200
cagctgtaca acgagctgaa cctgggggc gagaagagt acgacgtgct ggacaagaga    1260
agaggcaggg acctgagat gggcggcaag cccagaagaa gaaccctca gagggcctg   1320
tataatgagc tgcagaaaga caagatggcc gaggcctaca gcgagatcgg aatgaaggg   1380
gaacgcagaa gaggaaaggg ccacgacgga ctgtatcagg gcctgagcac agccaccaag   1440
```

-continued

```
gacacctatg atgccctgca catgcaggca ctgcctccaa gatga                     1485

SEQ ID NO: 22          moltype = DNA   length = 1482
FEATURE                Location/Qualifiers
source                 1..1482
                       mol_type = other DNA
                       organism = synthetic construct
SEQUENCE: 22
atggctctgc ctgttacagc tctgctgctg cctctggctc tgcttctgca tgccgctaga     60
cctgaggtgc agctggttga atctggcggc ggacttgtga agcctggcgg atctctgaga    120
ctgagctgtg tggccagcgg cttcatcttc agcgacaact acatgtactg ggtccgacag    180
accctgaga agcggctgga atgggtcgcc acaatctctg atggcggcag ctacacctac     240
tatccccgaca gcgtgaaggg cagattcacc atcagccggg acaacgccaa gaacaacctg    300
tacctgcaga tgagcagcct gaagtccgag gacaccgcca tctactactg cgccagaggc    360
tactacagat acgagggcgc catggactat gggggccagg aacaagcgt gacagtgtct     420
agcggaggcg gaggatcagg tggcggtgga tctggcggtg gcggctctaa tatcgtgatg    480
acacagagcc ctagcagcct ggctgtgtct gccggcgaga agtgaccat gagctgcaag     540
agcagccaga gcgtgctgta ctccagcaac cagaagaact acctggcctg gtatcagcag    600
aagcccggac agtctcccaa gctgctgatc tactgggcca gcaccagaga agcggcgtg    660
cccgatagat tcacaggcag cggctctggc accgacttca ccctgacaat cagctctgtg    720
caggccgagg atctggccgt gtactactgt caccagtacc tgagcagctg gacctttggc    780
ggaggcacca agctggaaat caagactagt ggcgccgctc ctattgaagt gatgtaccct    840
cctccttacc tggacaacga gaagtccaac ggcaccatca tccacgtgaa gggcaagcac    900
ctgtgtcctt ctccactgtt ccccggacct agcaagcctt ctgggtgct cgttgttgtt     960
ggcggcgtgc tggcctgtta ttccctgctg gttaccgtgg ccttcatcat ctttgggtc    1020
cgaagcaagc ggagccggct gctgcacagc gactacatga acatgacccc tagacggccc    1080
ggaccaacca gaaagcacta ccagccttac gctcctccta gagacttcgc cgcctaccgg    1140
tctagagtga agttcagcag atccgccgac gctcctgcct atcagcaggg acagaaccag    1200
ctgtacaacg agctgaacct ggggagaaga gaagagtacg acgtgctgga caagcggaga    1260
ggcagagatc ctgagatggg cggcaagccc agacggaaga atcctcaaga gggcctgtat    1320
aatgagctgc agaaagacaa gatggccgag gcctacagcg agatcggaat gaagggcgcc    1380
cgcagaagag caagggaca cgatggactg taccagggcc tgagcaccgc caccaaggat    1440
acctatgatg ccctgcacat gcaggccctg cctccaagat ga                      1482

SEQ ID NO: 23          moltype = AA   length = 21
FEATURE                Location/Qualifiers
source                 1..21
                       mol_type = protein
                       organism = Homo sapiens
SEQUENCE: 23
MALPVTALLL PLALLLHAAR P                                               21

SEQ ID NO: 24          moltype = AA   length = 9
FEATURE                Location/Qualifiers
source                 1..9
                       mol_type = protein
                       organism = synthetic construct
SEQUENCE: 24
SGFIFSGYG                                                              9

SEQ ID NO: 25          moltype = AA   length = 8
FEATURE                Location/Qualifiers
source                 1..8
                       mol_type = protein
                       organism = synthetic construct
SEQUENCE: 25
IWYDGSNK                                                               8

SEQ ID NO: 26          moltype = AA   length = 11
FEATURE                Location/Qualifiers
source                 1..11
                       mol_type = protein
                       organism = synthetic construct
SEQUENCE: 26
ARDTGDRFFD Y                                                          11

SEQ ID NO: 27          moltype = AA   length = 24
FEATURE                Location/Qualifiers
source                 1..24
                       mol_type = protein
                       organism = synthetic construct
SEQUENCE: 27
QVQLVEAGGG VVQPGRSLRL SCAA                                            24

SEQ ID NO: 28          moltype = AA   length = 17
FEATURE                Location/Qualifiers
source                 1..17
                       mol_type = protein
                       organism = synthetic construct
```

```
SEQUENCE: 28
MHWVRQAPGK GLEWVTV                                                              17

SEQ ID NO: 29           moltype = AA  length = 38
FEATURE                 Location/Qualifiers
source                  1..38
                        mol_type = protein
                        organism = synthetic construct
SEQUENCE: 29
YYADSVKGRF TISRDNSKNT LYLQMNSLRA EDTAVYYC                                        38

SEQ ID NO: 30           moltype = AA  length = 11
FEATURE                 Location/Qualifiers
source                  1..11
                        mol_type = protein
                        organism = synthetic construct
SEQUENCE: 30
WGQGTTVTVS S                                                                    11

SEQ ID NO: 31           moltype = AA  length = 118
FEATURE                 Location/Qualifiers
source                  1..118
                        mol_type = protein
                        organism = synthetic construct
SEQUENCE: 31
QVQLVEAGGG VVQPGRSLRL SCAASGFIFS GYGMHWVRQA PGKGLEWVTV IWYDGSNKYY                60
ADSVKGRFTI SRDNSKNTLY LQMNSLRAED TAVYYCARDT GDRFFDYWGQ GTLVTVSS                 118

SEQ ID NO: 32           moltype = AA  length = 6
FEATURE                 Location/Qualifiers
source                  1..6
                        mol_type = protein
                        organism = synthetic construct
SEQUENCE: 32
QSVSSY                                                                          6

SEQ ID NO: 33           moltype =    length =
SEQUENCE: 33
000

SEQ ID NO: 34           moltype = AA  length = 10
FEATURE                 Location/Qualifiers
source                  1..10
                        mol_type = protein
                        organism = synthetic construct
SEQUENCE: 34
QLRSNWPPYT                                                                      10

SEQ ID NO: 35           moltype = AA  length = 26
FEATURE                 Location/Qualifiers
source                  1..26
                        mol_type = protein
                        organism = synthetic construct
SEQUENCE: 35
EIVLTQSPAT LSLSPGERAT LSCRAS                                                    26

SEQ ID NO: 36           moltype = AA  length = 17
FEATURE                 Location/Qualifiers
source                  1..17
                        mol_type = protein
                        organism = synthetic construct
SEQUENCE: 36
LAWYQQKPGQ APRLLIY                                                              17

SEQ ID NO: 37           moltype = AA  length = 36
FEATURE                 Location/Qualifiers
source                  1..36
                        mol_type = protein
                        organism = synthetic construct
SEQUENCE: 37
SRATGIPARF GGSGSGTDFT LTISSLEPED FAVYYC                                          36

SEQ ID NO: 38           moltype = AA  length = 12
FEATURE                 Location/Qualifiers
source                  1..12
                        mol_type = protein
                        organism = synthetic construct
SEQUENCE: 38
FGQGTKLEIK TS                                                                   12
```

```
SEQ ID NO: 39            moltype = AA  length = 110
FEATURE                  Location/Qualifiers
source                   1..110
                         mol_type = protein
                         organism = synthetic construct
SEQUENCE: 39
EIVLTQSPAT LSLSPGERAT LSCRASQSVS SYLAWYQQKP GQAPRLLIYD ASSRATGIPA     60
RFGGSGSGTD FTLTISSLEP EDFAVYYCQL RSNWPPYTFG QGTKLEIKTS               110

SEQ ID NO: 40            moltype = AA  length = 5
FEATURE                  Location/Qualifiers
source                   1..5
                         mol_type = protein
                         organism = synthetic construct
SEQUENCE: 40
GYGMH                                                                  5

SEQ ID NO: 41            moltype = AA  length = 17
FEATURE                  Location/Qualifiers
source                   1..17
                         mol_type = protein
                         organism = synthetic construct
SEQUENCE: 41
VIWYDGSNKY YADSVKG                                                    17

SEQ ID NO: 42            moltype = AA  length = 9
FEATURE                  Location/Qualifiers
source                   1..9
                         mol_type = protein
                         organism = synthetic construct
SEQUENCE: 42
DTGDRFFDY                                                              9

SEQ ID NO: 43            moltype = AA  length = 30
FEATURE                  Location/Qualifiers
source                   1..30
                         mol_type = protein
                         organism = synthetic construct
SEQUENCE: 43
QVQLVEAGGG VVQPGRSLRL SCAASGFIFS                                      30

SEQ ID NO: 44            moltype = AA  length = 14
FEATURE                  Location/Qualifiers
source                   1..14
                         mol_type = protein
                         organism = synthetic construct
SEQUENCE: 44
WVRQAPGKGL EWVT                                                       14

SEQ ID NO: 45            moltype = AA  length = 31
FEATURE                  Location/Qualifiers
source                   1..31
                         mol_type = protein
                         organism = synthetic construct
SEQUENCE: 45
FTISRDNSKN TLYLQMNSLR AEDTAVYYCA R                                    31

SEQ ID NO: 46            moltype = AA  length = 11
FEATURE                  Location/Qualifiers
source                   1..11
                         mol_type = protein
                         organism = synthetic construct
SEQUENCE: 46
WGQGTLVTVS S                                                          11

SEQ ID NO: 47            moltype = AA  length = 118
FEATURE                  Location/Qualifiers
source                   1..118
                         mol_type = protein
                         organism = synthetic construct
SEQUENCE: 47
QVQLVEAGGG VVQPGRSLRL SCAASGFIFS GYGMHWVRQA PGKGLEWVTV IWYDGSNKYY     60
ADSVKGRFTI SRDNSKNTLY LQMNSLRAED TAVYYCARDT GDRFFDYWGQ GTLVTVSS     118

SEQ ID NO: 48            moltype = AA  length = 11
FEATURE                  Location/Qualifiers
source                   1..11
                         mol_type = protein
```

```
                                organism = synthetic construct
SEQUENCE: 48
RASQSVSSYL A                                                            11

SEQ ID NO: 49           moltype = AA  length = 7
FEATURE                 Location/Qualifiers
source                  1..7
                        mol_type = protein
                        organism = synthetic construct
SEQUENCE: 49
DASSRAT                                                                 7

SEQ ID NO: 50           moltype = AA  length = 10
FEATURE                 Location/Qualifiers
source                  1..10
                        mol_type = protein
                        organism = synthetic construct
SEQUENCE: 50
QLRSNWPPYT                                                              10

SEQ ID NO: 51           moltype = AA  length = 23
FEATURE                 Location/Qualifiers
source                  1..23
                        mol_type = protein
                        organism = synthetic construct
SEQUENCE: 51
EIVLTQSPAT LSLSPGERAT LSC                                               23

SEQ ID NO: 52           moltype = AA  length = 15
FEATURE                 Location/Qualifiers
source                  1..15
                        mol_type = protein
                        organism = synthetic construct
SEQUENCE: 52
WYQQKPGQAP RLLIY                                                        15

SEQ ID NO: 53           moltype = AA  length = 32
FEATURE                 Location/Qualifiers
source                  1..32
                        mol_type = protein
                        organism = synthetic construct
SEQUENCE: 53
GIPARFGGSG SGTDFTLTIS SLEPEDFAVY YC                                     32

SEQ ID NO: 54           moltype = AA  length = 12
FEATURE                 Location/Qualifiers
source                  1..12
                        mol_type = protein
                        organism = synthetic construct
SEQUENCE: 54
FGQGTKLEIK TS                                                           12

SEQ ID NO: 55           moltype = AA  length = 110
FEATURE                 Location/Qualifiers
source                  1..110
                        mol_type = protein
                        organism = synthetic construct
SEQUENCE: 55
EIVLTQSPAT LSLSPGERAT LSCRASQSVS SYLAWYQQKP GQAPRLLIYD ASSRATGIPA        60
RFGGSGSGTD FTLTISSLEP EDFAVYYCQL RSNWPPYTFG QGTKLEIKTS                   110

SEQ ID NO: 56           moltype = AA  length = 9
FEATURE                 Location/Qualifiers
source                  1..9
                        mol_type = protein
                        organism = synthetic construct
SEQUENCE: 56
TGFIFSGYG                                                               9

SEQ ID NO: 57           moltype = AA  length = 9
FEATURE                 Location/Qualifiers
source                  1..9
                        mol_type = protein
                        organism = synthetic construct
SEQUENCE: 57
CGFIFSGYG                                                               9

SEQ ID NO: 58           moltype = AA  length = 9
FEATURE                 Location/Qualifiers
```

```
                          -continued source                   1..9
                         mol_type = protein
                         organism = synthetic construct
SEQUENCE: 58
GGFIFSGYG                                                                9

SEQ ID NO: 59            moltype = AA   length = 9
FEATURE                  Location/Qualifiers
source                   1..9
                         mol_type = protein
                         organism = synthetic construct
SEQUENCE: 59
SSFIFSGYG                                                                9

SEQ ID NO: 60            moltype = AA   length = 9
FEATURE                  Location/Qualifiers
source                   1..9
                         mol_type = protein
                         organism = synthetic construct
SEQUENCE: 60
SCFIFSGYG                                                                9

SEQ ID NO: 61            moltype = AA   length = 9
FEATURE                  Location/Qualifiers
source                   1..9
                         mol_type = protein
                         organism = synthetic construct
SEQUENCE: 61
SQFIFSGYG                                                                9

SEQ ID NO: 62            moltype = AA   length = 9
FEATURE                  Location/Qualifiers
source                   1..9
                         mol_type = protein
                         organism = synthetic construct
SEQUENCE: 62
SNFIFSGYG                                                                9

SEQ ID NO: 63            moltype = AA   length = 9
FEATURE                  Location/Qualifiers
source                   1..9
                         mol_type = protein
                         organism = synthetic construct
SEQUENCE: 63
STFIFSGYG                                                                9

SEQ ID NO: 64            moltype = AA   length = 9
FEATURE                  Location/Qualifiers
source                   1..9
                         mol_type = protein
                         organism = synthetic construct
SEQUENCE: 64
SGWIFSGYG                                                                9

SEQ ID NO: 65            moltype = AA   length = 9
FEATURE                  Location/Qualifiers
source                   1..9
                         mol_type = protein
                         organism = synthetic construct
SEQUENCE: 65
SGFIWSGYG                                                                9

SEQ ID NO: 66            moltype = AA   length = 9
FEATURE                  Location/Qualifiers
source                   1..9
                         mol_type = protein
                         organism = synthetic construct
SEQUENCE: 66
SGWIWSGYG                                                                9

SEQ ID NO: 67            moltype = AA   length = 9
FEATURE                  Location/Qualifiers
source                   1..9
                         mol_type = protein
                         organism = synthetic construct
SEQUENCE: 67
SGPIFSGYG                                                                9

SEQ ID NO: 68            moltype = AA   length = 9
```

-continued

```
FEATURE                 Location/Qualifiers
source                  1..9
                        mol_type = protein
                        organism = synthetic construct
SEQUENCE: 68
SGFIPSGYG                                                                      9

SEQ ID NO: 69           moltype = AA   length = 9
FEATURE                 Location/Qualifiers
source                  1..9
                        mol_type = protein
                        organism = synthetic construct
SEQUENCE: 69
SGPIPSGYG                                                                      9

SEQ ID NO: 70           moltype = AA   length = 9
FEATURE                 Location/Qualifiers
source                  1..9
                        mol_type = protein
                        organism = synthetic construct
SEQUENCE: 70
SGYIFSGYG                                                                      9

SEQ ID NO: 71           moltype = AA   length = 9
FEATURE                 Location/Qualifiers
source                  1..9
                        mol_type = protein
                        organism = synthetic construct
SEQUENCE: 71
SGFIYSGYG                                                                      9

SEQ ID NO: 72           moltype = AA   length = 9
FEATURE                 Location/Qualifiers
source                  1..9
                        mol_type = protein
                        organism = synthetic construct
SEQUENCE: 72
SGYIYSGYG                                                                      9

SEQ ID NO: 73           moltype = AA   length = 9
FEATURE                 Location/Qualifiers
source                  1..9
                        mol_type = protein
                        organism = synthetic construct
SEQUENCE: 73
SGFLFSGYG                                                                      9

SEQ ID NO: 74           moltype = AA   length = 9
FEATURE                 Location/Qualifiers
source                  1..9
                        mol_type = protein
                        organism = synthetic construct
SEQUENCE: 74
SGFVFSGYG                                                                      9

SEQ ID NO: 75           moltype = AA   length = 9
FEATURE                 Location/Qualifiers
source                  1..9
                        mol_type = protein
                        organism = synthetic construct
SEQUENCE: 75
SGFAFSGYG                                                                      9

SEQ ID NO: 76           moltype = AA   length = 9
FEATURE                 Location/Qualifiers
source                  1..9
                        mol_type = protein
                        organism = synthetic construct
SEQUENCE: 76
SGFMFSGYG                                                                      9

SEQ ID NO: 77           moltype = AA   length = 9
FEATURE                 Location/Qualifiers
source                  1..9
                        mol_type = protein
                        organism = synthetic construct
SEQUENCE: 77
SGFIFTGYG                                                                      9
```

```
SEQ ID NO: 78           moltype = AA   length = 9
FEATURE                 Location/Qualifiers
source                  1..9
                        mol_type = protein
                        organism = synthetic construct
SEQUENCE: 78
SGFIFCGYG                                                                9

SEQ ID NO: 79           moltype = AA   length = 9
FEATURE                 Location/Qualifiers
source                  1..9
                        mol_type = protein
                        organism = synthetic construct
SEQUENCE: 79
SGFIFGGYG                                                                9

SEQ ID NO: 80           moltype = AA   length = 9
FEATURE                 Location/Qualifiers
source                  1..9
                        mol_type = protein
                        organism = synthetic construct
SEQUENCE: 80
SGFIFSSYG                                                                9

SEQ ID NO: 81           moltype = AA   length = 9
FEATURE                 Location/Qualifiers
source                  1..9
                        mol_type = protein
                        organism = synthetic construct
SEQUENCE: 81
SGFIFSCYG                                                                9

SEQ ID NO: 82           moltype = AA   length = 9
FEATURE                 Location/Qualifiers
source                  1..9
                        mol_type = protein
                        organism = synthetic construct
SEQUENCE: 82
SGFIFSTYG                                                                9

SEQ ID NO: 83           moltype = AA   length = 9
FEATURE                 Location/Qualifiers
source                  1..9
                        mol_type = protein
                        organism = synthetic construct
SEQUENCE: 83
SGFIFSQYG                                                                9

SEQ ID NO: 84           moltype = AA   length = 9
FEATURE                 Location/Qualifiers
source                  1..9
                        mol_type = protein
                        organism = synthetic construct
SEQUENCE: 84
SGFIFSNYG                                                                9

SEQ ID NO: 85           moltype = AA   length = 9
FEATURE                 Location/Qualifiers
source                  1..9
                        mol_type = protein
                        organism = synthetic construct
SEQUENCE: 85
SGFIFSGYS                                                                9

SEQ ID NO: 86           moltype = AA   length = 9
FEATURE                 Location/Qualifiers
source                  1..9
                        mol_type = protein
                        organism = synthetic construct
SEQUENCE: 86
SGFIFSGYC                                                                9

SEQ ID NO: 87           moltype = AA   length = 9
FEATURE                 Location/Qualifiers
source                  1..9
                        mol_type = protein
                        organism = synthetic construct
SEQUENCE: 87
SGFIFSGYT                                                                9
```

| | | |
|---|---|---|
| SEQ ID NO: 88<br>FEATURE<br>source | moltype = AA   length = 9<br>Location/Qualifiers<br>1..9<br>mol_type = protein<br>organism = synthetic construct | |
| SEQUENCE: 88<br>SGFIFSGYQ | | 9 |
| SEQ ID NO: 89<br>FEATURE<br>source | moltype = AA   length = 9<br>Location/Qualifiers<br>1..9<br>mol_type = protein<br>organism = synthetic construct | |
| SEQUENCE: 89<br>SGFIFSGYN | | 9 |
| SEQ ID NO: 90<br>FEATURE<br>source | moltype = AA   length = 9<br>Location/Qualifiers<br>1..9<br>mol_type = protein<br>organism = synthetic construct | |
| SEQUENCE: 90<br>SGFIFSGFG | | 9 |
| SEQ ID NO: 91<br>FEATURE<br>source | moltype = AA   length = 9<br>Location/Qualifiers<br>1..9<br>mol_type = protein<br>organism = synthetic construct | |
| SEQUENCE: 91<br>SGFIFSGSG | | 9 |
| SEQ ID NO: 92<br>FEATURE<br>source | moltype = AA   length = 9<br>Location/Qualifiers<br>1..9<br>mol_type = protein<br>organism = synthetic construct | |
| SEQUENCE: 92<br>SGFIFSGTG | | 9 |
| SEQ ID NO: 93<br>FEATURE<br>source | moltype = AA   length = 8<br>Location/Qualifiers<br>1..8<br>mol_type = protein<br>organism = synthetic construct | |
| SEQUENCE: 93<br>LWYDGSNK | | 8 |
| SEQ ID NO: 94<br>FEATURE<br>source | moltype = AA   length = 8<br>Location/Qualifiers<br>1..8<br>mol_type = protein<br>organism = synthetic construct | |
| SEQUENCE: 94<br>VWYDGSNK | | 8 |
| SEQ ID NO: 95<br>FEATURE<br>source | moltype = AA   length = 8<br>Location/Qualifiers<br>1..8<br>mol_type = protein<br>organism = synthetic construct | |
| SEQUENCE: 95<br>AWYDGSNK | | 8 |
| SEQ ID NO: 96<br>FEATURE<br>source | moltype = AA   length = 8<br>Location/Qualifiers<br>1..8<br>mol_type = protein<br>organism = synthetic construct | |
| SEQUENCE: 96<br>IFYDGSNK | | 8 |
| SEQ ID NO: 97<br>FEATURE<br>source | moltype = AA   length = 8<br>Location/Qualifiers<br>1..8<br>mol_type = protein<br>organism = synthetic construct | |
| SEQUENCE: 97 | | |

```
IPYDGSNK                                                                          8

SEQ ID NO: 98           moltype = AA  length = 8
FEATURE                 Location/Qualifiers
source                  1..8
                        mol_type = protein
                        organism = synthetic construct
SEQUENCE: 98
IHYDGSNK                                                                          8

SEQ ID NO: 99           moltype = AA  length = 8
FEATURE                 Location/Qualifiers
source                  1..8
                        mol_type = protein
                        organism = synthetic construct
SEQUENCE: 99
IWFDGSNK                                                                          8

SEQ ID NO: 100          moltype = AA  length = 8
FEATURE                 Location/Qualifiers
source                  1..8
                        mol_type = protein
                        organism = synthetic construct
SEQUENCE: 100
IWSDGSNK                                                                          8

SEQ ID NO: 101          moltype = AA  length = 8
FEATURE                 Location/Qualifiers
source                  1..8
                        mol_type = protein
                        organism = synthetic construct
SEQUENCE: 101
IWTDGSNK                                                                          8

SEQ ID NO: 102          moltype = AA  length = 8
FEATURE                 Location/Qualifiers
source                  1..8
                        mol_type = protein
                        organism = synthetic construct
SEQUENCE: 102
IWYEGSNK                                                                          8

SEQ ID NO: 103          moltype = AA  length = 8
FEATURE                 Location/Qualifiers
source                  1..8
                        mol_type = protein
                        organism = synthetic construct
SEQUENCE: 103
IWYNGSNK                                                                          8

SEQ ID NO: 104          moltype = AA  length = 8
FEATURE                 Location/Qualifiers
source                  1..8
                        mol_type = protein
                        organism = synthetic construct
SEQUENCE: 104
IWYDSSNK                                                                          8

SEQ ID NO: 105          moltype = AA  length = 8
FEATURE                 Location/Qualifiers
source                  1..8
                        mol_type = protein
                        organism = synthetic construct
SEQUENCE: 105
IWYDTSNK                                                                          8

SEQ ID NO: 106          moltype = AA  length = 8
FEATURE                 Location/Qualifiers
source                  1..8
                        mol_type = protein
                        organism = synthetic construct
SEQUENCE: 106
IWYDCSNK                                                                          8

SEQ ID NO: 107          moltype = AA  length = 8
FEATURE                 Location/Qualifiers
source                  1..8
                        mol_type = protein
                        organism = synthetic construct
```

```
SEQUENCE: 107
IWYDNSNK                                                                          8

SEQ ID NO: 108          moltype = AA  length = 8
FEATURE                 Location/Qualifiers
source                  1..8
                        mol_type = protein
                        organism = synthetic construct
SEQUENCE: 108
IWYDQSNK                                                                          8

SEQ ID NO: 109          moltype = AA  length = 8
FEATURE                 Location/Qualifiers
source                  1..8
                        mol_type = protein
                        organism = synthetic construct
SEQUENCE: 109
IWYDGCNK                                                                          8

SEQ ID NO: 110          moltype = AA  length = 8
FEATURE                 Location/Qualifiers
source                  1..8
                        mol_type = protein
                        organism = synthetic construct
SEQUENCE: 110
IWYDGTNK                                                                          8

SEQ ID NO: 111          moltype = AA  length = 8
FEATURE                 Location/Qualifiers
source                  1..8
                        mol_type = protein
                        organism = synthetic construct
SEQUENCE: 111
IWYDGGNK                                                                          8

SEQ ID NO: 112          moltype = AA  length = 8
FEATURE                 Location/Qualifiers
source                  1..8
                        mol_type = protein
                        organism = synthetic construct
SEQUENCE: 112
IWYDGNNK                                                                          8

SEQ ID NO: 113          moltype = AA  length = 8
FEATURE                 Location/Qualifiers
source                  1..8
                        mol_type = protein
                        organism = synthetic construct
SEQUENCE: 113
IWYDGQNK                                                                          8

SEQ ID NO: 114          moltype = AA  length = 8
FEATURE                 Location/Qualifiers
source                  1..8
                        mol_type = protein
                        organism = synthetic construct
SEQUENCE: 114
IWYDGSQK                                                                          8

SEQ ID NO: 115          moltype = AA  length = 8
FEATURE                 Location/Qualifiers
source                  1..8
                        mol_type = protein
                        organism = synthetic construct
SEQUENCE: 115
IWYDGSGK                                                                          8

SEQ ID NO: 116          moltype = AA  length = 8
FEATURE                 Location/Qualifiers
source                  1..8
                        mol_type = protein
                        organism = synthetic construct
SEQUENCE: 116
IWYDGSSK                                                                          8

SEQ ID NO: 117          moltype = AA  length = 8
FEATURE                 Location/Qualifiers
source                  1..8
                        mol_type = protein
```

```
                                             -continued organism = synthetic construct
SEQUENCE: 117
IWYDGSCK                                                                    8

SEQ ID NO: 118         moltype = AA  length = 8
FEATURE                Location/Qualifiers
source                 1..8
                       mol_type = protein
                       organism = synthetic construct
SEQUENCE: 118
IWYDGSTK                                                                    8

SEQ ID NO: 119         moltype = AA  length = 8
FEATURE                Location/Qualifiers
source                 1..8
                       mol_type = protein
                       organism = synthetic construct
SEQUENCE: 119
IWYDGSNR                                                                    8

SEQ ID NO: 120         moltype = AA  length = 8
FEATURE                Location/Qualifiers
source                 1..8
                       mol_type = protein
                       organism = synthetic construct
SEQUENCE: 120
IWYDGSNH                                                                    8

SEQ ID NO: 121         moltype = AA  length = 11
FEATURE                Location/Qualifiers
source                 1..11
                       mol_type = protein
                       organism = synthetic construct
SEQUENCE: 121
VRDTGDRFFD Y                                                               11

SEQ ID NO: 122         moltype = AA  length = 11
FEATURE                Location/Qualifiers
source                 1..11
                       mol_type = protein
                       organism = synthetic construct
SEQUENCE: 122
LRDTGDRFFD Y                                                               11

SEQ ID NO: 123         moltype = AA  length = 11
FEATURE                Location/Qualifiers
source                 1..11
                       mol_type = protein
                       organism = synthetic construct
SEQUENCE: 123
IRDTGDRFFD Y                                                               11

SEQ ID NO: 124         moltype = AA  length = 11
FEATURE                Location/Qualifiers
source                 1..11
                       mol_type = protein
                       organism = synthetic construct
SEQUENCE: 124
AKDTGDRFFD Y                                                               11

SEQ ID NO: 125         moltype = AA  length = 11
FEATURE                Location/Qualifiers
source                 1..11
                       mol_type = protein
                       organism = synthetic construct
SEQUENCE: 125
AHDTGDRFFD Y                                                               11

SEQ ID NO: 126         moltype = AA  length = 11
FEATURE                Location/Qualifiers
source                 1..11
                       mol_type = protein
                       organism = synthetic construct
SEQUENCE: 126
ARETGDRFFD Y                                                               11

SEQ ID NO: 127         moltype = AA  length = 11
FEATURE                Location/Qualifiers
source                 1..11
```

```
                        mol_type = protein
                        organism = synthetic construct
SEQUENCE: 127
ARDSGDRFFD Y                                                              11

SEQ ID NO: 128          moltype = AA   length = 11
FEATURE                 Location/Qualifiers
source                  1..11
                        mol_type = protein
                        organism = synthetic construct
SEQUENCE: 128
ARDCGDRFFD Y                                                              11

SEQ ID NO: 129          moltype = AA   length = 11
FEATURE                 Location/Qualifiers
source                  1..11
                        mol_type = protein
                        organism = synthetic construct
SEQUENCE: 129
ARDYGDRFFD Y                                                              11

SEQ ID NO: 130          moltype = AA   length = 11
FEATURE                 Location/Qualifiers
source                  1..11
                        mol_type = protein
                        organism = synthetic construct
SEQUENCE: 130
ARDTQDRFFD Y                                                              11

SEQ ID NO: 131          moltype = AA   length = 11
FEATURE                 Location/Qualifiers
source                  1..11
                        mol_type = protein
                        organism = synthetic construct
SEQUENCE: 131
ARDTCDRFFD Y                                                              11

SEQ ID NO: 132          moltype = AA   length = 11
FEATURE                 Location/Qualifiers
source                  1..11
                        mol_type = protein
                        organism = synthetic construct
SEQUENCE: 132
ARDTTDRFFD Y                                                              11

SEQ ID NO: 133          moltype = AA   length = 11
FEATURE                 Location/Qualifiers
source                  1..11
                        mol_type = protein
                        organism = synthetic construct
SEQUENCE: 133
ARDTSDRFFD Y                                                              11

SEQ ID NO: 134          moltype = AA   length = 11
FEATURE                 Location/Qualifiers
source                  1..11
                        mol_type = protein
                        organism = synthetic construct
SEQUENCE: 134
ARDTGERFFD Y                                                              11

SEQ ID NO: 135          moltype = AA   length = 11
FEATURE                 Location/Qualifiers
source                  1..11
                        mol_type = protein
                        organism = synthetic construct
SEQUENCE: 135
ARDTGDKFFD Y                                                              11

SEQ ID NO: 136          moltype = AA   length = 11
FEATURE                 Location/Qualifiers
source                  1..11
                        mol_type = protein
                        organism = synthetic construct
SEQUENCE: 136
ARDTGDHFFD Y                                                              11

SEQ ID NO: 137          moltype = AA   length = 11
FEATURE                 Location/Qualifiers
```

| | | |
|---|---|---|
| source | 1..11<br>mol_type = protein<br>organism = synthetic construct | |
| SEQUENCE: 137<br>ARDTGDRWFD Y | | 11 |
| SEQ ID NO: 138<br>FEATURE<br>source | moltype = AA   length = 11<br>Location/Qualifiers<br>1..11<br>mol_type = protein<br>organism = synthetic construct | |
| SEQUENCE: 138<br>ARDTGDRPFD Y | | 11 |
| SEQ ID NO: 139<br>FEATURE<br>source | moltype = AA   length = 11<br>Location/Qualifiers<br>1..11<br>mol_type = protein<br>organism = synthetic construct | |
| SEQUENCE: 139<br>ARDTGDRYFD Y | | 11 |
| SEQ ID NO: 140<br>FEATURE<br>source | moltype = AA   length = 11<br>Location/Qualifiers<br>1..11<br>mol_type = protein<br>organism = synthetic construct | |
| SEQUENCE: 140<br>ARDTGDRFWD Y | | 11 |
| SEQ ID NO: 141<br>FEATURE<br>source | moltype = AA   length = 11<br>Location/Qualifiers<br>1..11<br>mol_type = protein<br>organism = synthetic construct | |
| SEQUENCE: 141<br>ARDTGDRFPD Y | | 11 |
| SEQ ID NO: 142<br>FEATURE<br>source | moltype = AA   length = 11<br>Location/Qualifiers<br>1..11<br>mol_type = protein<br>organism = synthetic construct | |
| SEQUENCE: 142<br>ARDTGDRFYD Y | | 11 |
| SEQ ID NO: 143<br>FEATURE<br>source | moltype = AA   length = 11<br>Location/Qualifiers<br>1..11<br>mol_type = protein<br>organism = synthetic construct | |
| SEQUENCE: 143<br>ARDTGDRFFE Y | | 11 |
| SEQ ID NO: 144<br>FEATURE<br>source | moltype = AA   length = 11<br>Location/Qualifiers<br>1..11<br>mol_type = protein<br>organism = synthetic construct | |
| SEQUENCE: 144<br>ARDTGDRFFD T | | 11 |
| SEQ ID NO: 145<br>FEATURE<br>source | moltype = AA   length = 11<br>Location/Qualifiers<br>1..11<br>mol_type = protein<br>organism = synthetic construct | |
| SEQUENCE: 145<br>ARDTGDRFFD S | | 11 |
| SEQ ID NO: 146<br>FEATURE<br>source | moltype = AA   length = 11<br>Location/Qualifiers<br>1..11<br>mol_type = protein<br>organism = synthetic construct | |
| SEQUENCE: 146<br>ARDTGDRFFD F | | 11 |
| SEQ ID NO: 147 | moltype = AA   length = 6 | |

```
FEATURE            Location/Qualifiers
source             1..6
                   mol_type = protein
                   organism = synthetic construct
SEQUENCE: 147
GSVSSY                                                                    6

SEQ ID NO: 148     moltype = AA  length = 6
FEATURE            Location/Qualifiers
source             1..6
                   mol_type = protein
                   organism = synthetic construct
SEQUENCE: 148
NSVSSY                                                                    6

SEQ ID NO: 149     moltype = AA  length = 6
FEATURE            Location/Qualifiers
source             1..6
                   mol_type = protein
                   organism = synthetic construct
SEQUENCE: 149
QTVSSY                                                                    6

SEQ ID NO: 150     moltype = AA  length = 6
FEATURE            Location/Qualifiers
source             1..6
                   mol_type = protein
                   organism = synthetic construct
SEQUENCE: 150
QCVSSY                                                                    6

SEQ ID NO: 151     moltype = AA  length = 6
FEATURE            Location/Qualifiers
source             1..6
                   mol_type = protein
                   organism = synthetic construct
SEQUENCE: 151
QYVSSY                                                                    6

SEQ ID NO: 152     moltype = AA  length = 6
FEATURE            Location/Qualifiers
source             1..6
                   mol_type = protein
                   organism = synthetic construct
SEQUENCE: 152
QSASSY                                                                    6

SEQ ID NO: 153     moltype = AA  length = 6
FEATURE            Location/Qualifiers
source             1..6
                   mol_type = protein
                   organism = synthetic construct
SEQUENCE: 153
QSLSSY                                                                    6

SEQ ID NO: 154     moltype = AA  length = 6
FEATURE            Location/Qualifiers
source             1..6
                   mol_type = protein
                   organism = synthetic construct
SEQUENCE: 154
QSISSY                                                                    6

SEQ ID NO: 155     moltype = AA  length = 6
FEATURE            Location/Qualifiers
source             1..6
                   mol_type = protein
                   organism = synthetic construct
SEQUENCE: 155
QSMSSY                                                                    6

SEQ ID NO: 156     moltype = AA  length = 6
FEATURE            Location/Qualifiers
source             1..6
                   mol_type = protein
                   organism = synthetic construct
SEQUENCE: 156
QSVTSY                                                                    6
```

-continued

| SEQ ID NO: 157<br>FEATURE<br>source | moltype = AA   length = 6<br>Location/Qualifiers<br>1..6<br>mol_type = protein<br>organism = synthetic construct | |
|---|---|---|
| SEQUENCE: 157<br>QSVCSY | | 6 |
| SEQ ID NO: 158<br>FEATURE<br>source | moltype = AA   length = 6<br>Location/Qualifiers<br>1..6<br>mol_type = protein<br>organism = synthetic construct | |
| SEQUENCE: 158<br>QSVYSY | | 6 |
| SEQ ID NO: 159<br>FEATURE<br>source | moltype = AA   length = 6<br>Location/Qualifiers<br>1..6<br>mol_type = protein<br>organism = synthetic construct | |
| SEQUENCE: 159<br>QSVSTY | | 6 |
| SEQ ID NO: 160<br>FEATURE<br>source | moltype = AA   length = 6<br>Location/Qualifiers<br>1..6<br>mol_type = protein<br>organism = synthetic construct | |
| SEQUENCE: 160<br>QSVSCY | | 6 |
| SEQ ID NO: 161<br>FEATURE<br>source | moltype = AA   length = 6<br>Location/Qualifiers<br>1..6<br>mol_type = protein<br>organism = synthetic construct | |
| SEQUENCE: 161<br>QSVSYY | | 6 |
| SEQ ID NO: 162<br>FEATURE<br>source | moltype = AA   length = 6<br>Location/Qualifiers<br>1..6<br>mol_type = protein<br>organism = synthetic construct | |
| SEQUENCE: 162<br>QSVSSS | | 6 |
| SEQ ID NO: 163<br>FEATURE<br>source | moltype = AA   length = 6<br>Location/Qualifiers<br>1..6<br>mol_type = protein<br>organism = synthetic construct | |
| SEQUENCE: 163<br>QSVSST | | 6 |
| SEQ ID NO: 164<br>FEATURE<br>source | moltype = AA   length = 6<br>Location/Qualifiers<br>1..6<br>mol_type = protein<br>organism = synthetic construct | |
| SEQUENCE: 164<br>QSVSSF | | 6 |
| SEQ ID NO: 165<br>SEQUENCE: 165<br>000 | moltype =    length = | |
| SEQ ID NO: 166<br>SEQUENCE: 166<br>000 | moltype =    length = | |
| SEQ ID NO: 167<br>SEQUENCE: 167<br>000 | moltype =    length = | |
| SEQ ID NO: 168<br>SEQUENCE: 168<br>000 | moltype =    length = | |

| | | |
|---|---|---|
| SEQ ID NO: 169<br>SEQUENCE: 169<br>000 | moltype =     length = | |
| SEQ ID NO: 170<br>SEQUENCE: 170<br>000 | moltype =     length = | |
| SEQ ID NO: 171<br>SEQUENCE: 171<br>000 | moltype =     length = | |
| SEQ ID NO: 172<br>SEQUENCE: 172<br>000 | moltype =     length = | |
| SEQ ID NO: 173<br>FEATURE<br>source<br>SEQUENCE: 173<br>NLRSNWPPYT | moltype = AA   length = 10<br>Location/Qualifiers<br>1..10<br>mol_type = protein<br>organism = synthetic construct | 10 |
| SEQ ID NO: 174<br>FEATURE<br>source<br>SEQUENCE: 174<br>PLRSNWPPYT | moltype = AA   length = 10<br>Location/Qualifiers<br>1..10<br>mol_type = protein<br>organism = synthetic construct | 10 |
| SEQ ID NO: 175<br>FEATURE<br>source<br>SEQUENCE: 175<br>QIRSNWPPYT | moltype = AA   length = 10<br>Location/Qualifiers<br>1..10<br>mol_type = protein<br>organism = synthetic construct | 10 |
| SEQ ID NO: 176<br>FEATURE<br>source<br>SEQUENCE: 176<br>QVRSNWPPYT | moltype = AA   length = 10<br>Location/Qualifiers<br>1..10<br>mol_type = protein<br>organism = synthetic construct | 10 |
| SEQ ID NO: 177<br>FEATURE<br>source<br>SEQUENCE: 177<br>QARSNWPPYT | moltype = AA   length = 10<br>Location/Qualifiers<br>1..10<br>mol_type = protein<br>organism = synthetic construct | 10 |
| SEQ ID NO: 178<br>FEATURE<br>source<br>SEQUENCE: 178<br>QLKSNWPPYT | moltype = AA   length = 10<br>Location/Qualifiers<br>1..10<br>mol_type = protein<br>organism = synthetic construct | 10 |
| SEQ ID NO: 179<br>FEATURE<br>source<br>SEQUENCE: 179<br>QLHSNWPPYT | moltype = AA   length = 10<br>Location/Qualifiers<br>1..10<br>mol_type = protein<br>organism = synthetic construct | 10 |
| SEQ ID NO: 180<br>FEATURE<br>source<br>SEQUENCE: 180 | moltype = AA   length = 10<br>Location/Qualifiers<br>1..10<br>mol_type = protein<br>organism = synthetic construct | |

QLRTNWPPYT                                                                          10

SEQ ID NO: 181          moltype = AA  length = 10
FEATURE                 Location/Qualifiers
source                  1..10
                        mol_type = protein
                        organism = synthetic construct SEQUENCE: 181
QLRCNWPPYT                                                                          10

SEQ ID NO: 182          moltype = AA  length = 10
FEATURE                 Location/Qualifiers
source                  1..10
                        mol_type = protein
                        organism = synthetic construct SEQUENCE: 182
QLRYNWPPYT                                                                          10

SEQ ID NO: 183          moltype = AA  length = 10
FEATURE                 Location/Qualifiers
source                  1..10
                        mol_type = protein
                        organism = synthetic construct SEQUENCE: 183
QLRSQWPPYT                                                                          10

SEQ ID NO: 184          moltype = AA  length = 10
FEATURE                 Location/Qualifiers
source                  1..10
                        mol_type = protein
                        organism = synthetic construct SEQUENCE: 184
QLRSNFPPYT                                                                          10

SEQ ID NO: 185          moltype = AA  length = 10
FEATURE                 Location/Qualifiers
source                  1..10
                        mol_type = protein
                        organism = synthetic construct SEQUENCE: 185
QLRSNYPPYT                                                                          10

SEQ ID NO: 186          moltype = AA  length = 10
FEATURE                 Location/Qualifiers
source                  1..10
                        mol_type = protein
                        organism = synthetic construct SEQUENCE: 186
QLRSNPPPYT                                                                          10

SEQ ID NO: 187          moltype = AA  length = 10
FEATURE                 Location/Qualifiers
source                  1..10
                        mol_type = protein
                        organism = synthetic construct SEQUENCE: 187
QLRSNWFPYT                                                                          10

SEQ ID NO: 188          moltype = AA  length = 10
FEATURE                 Location/Qualifiers
source                  1..10
                        mol_type = protein
                        organism = synthetic construct SEQUENCE: 188
QLRSNWQPYT                                                                          10

SEQ ID NO: 189          moltype = AA  length = 10
FEATURE                 Location/Qualifiers
source                  1..10
                        mol_type = protein
                        organism = synthetic construct SEQUENCE: 189
QLRSNWNPYT                                                                          10

SEQ ID NO: 190          moltype = AA  length = 10
FEATURE                 Location/Qualifiers
source                  1..10
                        mol_type = protein
                        organism = synthetic construct

```
SEQUENCE: 190
QLRSNWPWYT                                                                    10

SEQ ID NO: 191         moltype = AA  length = 10
FEATURE                Location/Qualifiers
source                 1..10
                       mol_type = protein
                       organism = synthetic construct
SEQUENCE: 191
QLRSNWWPYT                                                                    10

SEQ ID NO: 192         moltype = AA  length = 10
FEATURE                Location/Qualifiers
source                 1..10
                       mol_type = protein
                       organism = synthetic construct
SEQUENCE: 192
QLRSNWPNYT                                                                    10

SEQ ID NO: 193         moltype = AA  length = 10
FEATURE                Location/Qualifiers
source                 1..10
                       mol_type = protein
                       organism = synthetic construct
SEQUENCE: 193
QLRSNWPQYT                                                                    10

SEQ ID NO: 194         moltype = AA  length = 10
FEATURE                Location/Qualifiers
source                 1..10
                       mol_type = protein
                       organism = synthetic construct
SEQUENCE: 194
QLRSNWPPTT                                                                    10

SEQ ID NO: 195         moltype = AA  length = 10
FEATURE                Location/Qualifiers
source                 1..10
                       mol_type = protein
                       organism = synthetic construct
SEQUENCE: 195
QLRSNWPPST                                                                    10

SEQ ID NO: 196         moltype = AA  length = 10
FEATURE                Location/Qualifiers
source                 1..10
                       mol_type = protein
                       organism = synthetic construct
SEQUENCE: 196
QLRSNWPPFT                                                                    10

SEQ ID NO: 197         moltype = AA  length = 10
FEATURE                Location/Qualifiers
source                 1..10
                       mol_type = protein
                       organism = synthetic construct
SEQUENCE: 197
QLRSNWPPYS                                                                    10

SEQ ID NO: 198         moltype = AA  length = 10
FEATURE                Location/Qualifiers
source                 1..10
                       mol_type = protein
                       organism = synthetic construct
SEQUENCE: 198
QLRSNWPPYC                                                                    10

SEQ ID NO: 199         moltype = AA  length = 10
FEATURE                Location/Qualifiers
source                 1..10
                       mol_type = protein
                       organism = synthetic construct
SEQUENCE: 199
QLRSNWPPYY                                                                    10

SEQ ID NO: 200         moltype = AA  length = 5
FEATURE                Location/Qualifiers
source                 1..5
                       mol_type = protein
```

```
                       organism = synthetic construct
SEQUENCE: 200
SYGMH                                                                    5

SEQ ID NO: 201         moltype = AA   length = 5
FEATURE                Location/Qualifiers
source                 1..5
                       mol_type = protein
                       organism = synthetic construct
SEQUENCE: 201
CYGMH                                                                    5

SEQ ID NO: 202         moltype = AA   length = 5
FEATURE                Location/Qualifiers
source                 1..5
                       mol_type = protein
                       organism = synthetic construct
SEQUENCE: 202
TYGMH                                                                    5

SEQ ID NO: 203         moltype = AA   length = 5
FEATURE                Location/Qualifiers
source                 1..5
                       mol_type = protein
                       organism = synthetic construct
SEQUENCE: 203
QYGMH                                                                    5

SEQ ID NO: 204         moltype = AA   length = 5
FEATURE                Location/Qualifiers
source                 1..5
                       mol_type = protein
                       organism = synthetic construct
SEQUENCE: 204
NYGMH                                                                    5

SEQ ID NO: 205         moltype = AA   length = 5
FEATURE                Location/Qualifiers
source                 1..5
                       mol_type = protein
                       organism = synthetic construct
SEQUENCE: 205
GYSMH                                                                    5

SEQ ID NO: 206         moltype = AA   length = 5
FEATURE                Location/Qualifiers
source                 1..5
                       mol_type = protein
                       organism = synthetic construct
SEQUENCE: 206
GYCMH                                                                    5

SEQ ID NO: 207         moltype = AA   length = 5
FEATURE                Location/Qualifiers
source                 1..5
                       mol_type = protein
                       organism = synthetic construct
SEQUENCE: 207
GYTMH                                                                    5

SEQ ID NO: 208         moltype = AA   length = 5
FEATURE                Location/Qualifiers
source                 1..5
                       mol_type = protein
                       organism = synthetic construct
SEQUENCE: 208
GYQMH                                                                    5

SEQ ID NO: 209         moltype = AA   length = 5
FEATURE                Location/Qualifiers
source                 1..5
                       mol_type = protein
                       organism = synthetic construct
SEQUENCE: 209
GYNMH                                                                    5

SEQ ID NO: 210         moltype = AA   length = 5
FEATURE                Location/Qualifiers
source                 1..5
```

```
                        mol_type = protein
                        organism = synthetic construct
SEQUENCE: 210
GFGMH                                                                   5

SEQ ID NO: 211          moltype = AA   length = 5
FEATURE                 Location/Qualifiers
source                  1..5
                        mol_type = protein
                        organism = synthetic construct
SEQUENCE: 211
GSGMH                                                                   5

SEQ ID NO: 212          moltype = AA   length = 5
FEATURE                 Location/Qualifiers
source                  1..5
                        mol_type = protein
                        organism = synthetic construct
SEQUENCE: 212
GTGMH                                                                   5

SEQ ID NO: 213          moltype = AA   length = 5
FEATURE                 Location/Qualifiers
source                  1..5
                        mol_type = protein
                        organism = synthetic construct
SEQUENCE: 213
GYGIH                                                                   5

SEQ ID NO: 214          moltype = AA   length = 5
FEATURE                 Location/Qualifiers
source                  1..5
                        mol_type = protein
                        organism = synthetic construct
SEQUENCE: 214
GYGLH                                                                   5

SEQ ID NO: 215          moltype = AA   length = 5
FEATURE                 Location/Qualifiers
source                  1..5
                        mol_type = protein
                        organism = synthetic construct
SEQUENCE: 215
GYGVH                                                                   5

SEQ ID NO: 216          moltype = AA   length = 5
FEATURE                 Location/Qualifiers
source                  1..5
                        mol_type = protein
                        organism = synthetic construct
SEQUENCE: 216
GYGAH                                                                   5

SEQ ID NO: 217          moltype = AA   length = 5
FEATURE                 Location/Qualifiers
source                  1..5
                        mol_type = protein
                        organism = synthetic construct
SEQUENCE: 217
GYGCH                                                                   5

SEQ ID NO: 218          moltype = AA   length = 5
FEATURE                 Location/Qualifiers
source                  1..5
                        mol_type = protein
                        organism = synthetic construct
SEQUENCE: 218
GYGMK                                                                   5

SEQ ID NO: 219          moltype = AA   length = 5
FEATURE                 Location/Qualifiers
source                  1..5
                        mol_type = protein
                        organism = synthetic construct
SEQUENCE: 219
GYGMR                                                                   5

SEQ ID NO: 220          moltype = AA   length = 5
FEATURE                 Location/Qualifiers
```

```
source                    1..5
                          mol_type = protein
                          organism = synthetic construct
SEQUENCE: 220
GYGMP                                                                      5

SEQ ID NO: 221            moltype = AA   length = 17
FEATURE                   Location/Qualifiers
source                    1..17
                          mol_type = protein
                          organism = synthetic construct
SEQUENCE: 221
LIWYDGSNKY YADSVKG                                                        17

SEQ ID NO: 222            moltype = AA   length = 17
FEATURE                   Location/Qualifiers
source                    1..17
                          mol_type = protein
                          organism = synthetic construct
SEQUENCE: 222
IIWYDGSNKY YADSVKG                                                        17

SEQ ID NO: 223            moltype = AA   length = 17
FEATURE                   Location/Qualifiers
source                    1..17
                          mol_type = protein
                          organism = synthetic construct
SEQUENCE: 223
AIWYDGSNKY YADSVKG                                                        17

SEQ ID NO: 224            moltype = AA   length = 17
FEATURE                   Location/Qualifiers
source                    1..17
                          mol_type = protein
                          organism = synthetic construct
SEQUENCE: 224
MIWYDGSNKY YADSVKG                                                        17

SEQ ID NO: 225            moltype = AA   length = 17
FEATURE                   Location/Qualifiers
source                    1..17
                          mol_type = protein
                          organism = synthetic construct
SEQUENCE: 225
VLWYDGSNKY YADSVKG                                                        17

SEQ ID NO: 226            moltype = AA   length = 17
FEATURE                   Location/Qualifiers
source                    1..17
                          mol_type = protein
                          organism = synthetic construct
SEQUENCE: 226
VVWYDGSNKY YADSVKG                                                        17

SEQ ID NO: 227            moltype = AA   length = 17
FEATURE                   Location/Qualifiers
source                    1..17
                          mol_type = protein
                          organism = synthetic construct
SEQUENCE: 227
VAWYDGSNKY YADSVKG                                                        17

SEQ ID NO: 228            moltype = AA   length = 17
FEATURE                   Location/Qualifiers
source                    1..17
                          mol_type = protein
                          organism = synthetic construct
SEQUENCE: 228
VMWYDGSNKY YADSVKG                                                        17

SEQ ID NO: 229            moltype = AA   length = 18
FEATURE                   Location/Qualifiers
source                    1..18
                          mol_type = protein
                          organism = synthetic construct
SEQUENCE: 229
VILWYDGSNK YYADSVKG                                                       18

SEQ ID NO: 230            moltype = AA   length = 18
```

```
FEATURE               Location/Qualifiers
source                1..18
                      mol_type = protein
                      organism = synthetic construct
SEQUENCE: 230
VIVWYDGSNK YYADSVKG                                                     18

SEQ ID NO: 231        moltype = AA  length = 18
FEATURE               Location/Qualifiers
source                1..18
                      mol_type = protein
                      organism = synthetic construct
SEQUENCE: 231
VIAWYDGSNK YYADSVKG                                                     18

SEQ ID NO: 232        moltype = AA  length = 18
FEATURE               Location/Qualifiers
source                1..18
                      mol_type = protein
                      organism = synthetic construct
SEQUENCE: 232
VIIFYDGSNK YYADSVKG                                                     18

SEQ ID NO: 233        moltype = AA  length = 18
FEATURE               Location/Qualifiers
source                1..18
                      mol_type = protein
                      organism = synthetic construct
SEQUENCE: 233
VIIPYDGSNK YYADSVKG                                                     18

SEQ ID NO: 234        moltype = AA  length = 18
FEATURE               Location/Qualifiers
source                1..18
                      mol_type = protein
                      organism = synthetic construct
SEQUENCE: 234
VIIHYDGSNK YYADSVKG                                                     18

SEQ ID NO: 235        moltype = AA  length = 18
FEATURE               Location/Qualifiers
source                1..18
                      mol_type = protein
                      organism = synthetic construct
SEQUENCE: 235
VIIWFDGSNK YYADSVKG                                                     18

SEQ ID NO: 236        moltype = AA  length = 18
FEATURE               Location/Qualifiers
source                1..18
                      mol_type = protein
                      organism = synthetic construct
SEQUENCE: 236
VIIWSDGSNK YYADSVKG                                                     18

SEQ ID NO: 237        moltype = AA  length = 18
FEATURE               Location/Qualifiers
source                1..18
                      mol_type = protein
                      organism = synthetic construct
SEQUENCE: 237
VIIWTDGSNK YYADSVKG                                                     18

SEQ ID NO: 238        moltype = AA  length = 18
FEATURE               Location/Qualifiers
source                1..18
                      mol_type = protein
                      organism = synthetic construct
SEQUENCE: 238
VIIWYEGSNK YYADSVKG                                                     18

SEQ ID NO: 239        moltype = AA  length = 18
FEATURE               Location/Qualifiers
source                1..18
                      mol_type = protein
                      organism = synthetic construct
SEQUENCE: 239
VIIWYNGSNK YYADSVKG                                                     18
```

```
SEQ ID NO: 240           moltype = AA   length = 18
FEATURE                  Location/Qualifiers
source                   1..18
                         mol_type = protein
                         organism = synthetic construct
SEQUENCE: 240
VIIWYDSSNK YYADSVKG                                                   18

SEQ ID NO: 241           moltype = AA   length = 18
FEATURE                  Location/Qualifiers
source                   1..18
                         mol_type = protein
                         organism = synthetic construct
SEQUENCE: 241
VIIWYDTSNK YYADSVKG                                                   18

SEQ ID NO: 242           moltype = AA   length = 18
FEATURE                  Location/Qualifiers
source                   1..18
                         mol_type = protein
                         organism = synthetic construct
SEQUENCE: 242
VIIWYDCSNK YYADSVKG                                                   18

SEQ ID NO: 243           moltype = AA   length = 18
FEATURE                  Location/Qualifiers
source                   1..18
                         mol_type = protein
                         organism = synthetic construct
SEQUENCE: 243
VIIWYDNSNK YYADSVKG                                                   18

SEQ ID NO: 244           moltype = AA   length = 18
FEATURE                  Location/Qualifiers
source                   1..18
                         mol_type = protein
                         organism = synthetic construct
SEQUENCE: 244
VIIWYDQSNK YYADSVKG                                                   18

SEQ ID NO: 245           moltype = AA   length = 18
FEATURE                  Location/Qualifiers
source                   1..18
                         mol_type = protein
                         organism = synthetic construct
SEQUENCE: 245
VIIWYDGCNK YYADSVKG                                                   18

SEQ ID NO: 246           moltype = AA   length = 18
FEATURE                  Location/Qualifiers
source                   1..18
                         mol_type = protein
                         organism = synthetic construct
SEQUENCE: 246
VIIWYDGTNK YYADSVKG                                                   18

SEQ ID NO: 247           moltype = AA   length = 18
FEATURE                  Location/Qualifiers
source                   1..18
                         mol_type = protein
                         organism = synthetic construct
SEQUENCE: 247
VIIWYDGGNK YYADSVKG                                                   18

SEQ ID NO: 248           moltype = AA   length = 18
FEATURE                  Location/Qualifiers
source                   1..18
                         mol_type = protein
                         organism = synthetic construct
SEQUENCE: 248
VIIWYDGNNK YYADSVKG                                                   18

SEQ ID NO: 249           moltype = AA   length = 18
FEATURE                  Location/Qualifiers
source                   1..18
                         mol_type = protein
                         organism = synthetic construct
SEQUENCE: 249
VIIWYDGQNK YYADSVKG                                                   18
```

```
SEQ ID NO: 250           moltype = AA  length = 18
FEATURE                  Location/Qualifiers
source                   1..18
                         mol_type = protein
                         organism = synthetic construct
SEQUENCE: 250
VIIWYDGSQK YYADSVKG                                                  18

SEQ ID NO: 251           moltype = AA  length = 18
FEATURE                  Location/Qualifiers
source                   1..18
                         mol_type = protein
                         organism = synthetic construct
SEQUENCE: 251
VIIWYDGSGK YYADSVKG                                                  18

SEQ ID NO: 252           moltype = AA  length = 18
FEATURE                  Location/Qualifiers
source                   1..18
                         mol_type = protein
                         organism = synthetic construct
SEQUENCE: 252
VIIWYDGSSK YYADSVKG                                                  18

SEQ ID NO: 253           moltype = AA  length = 18
FEATURE                  Location/Qualifiers
source                   1..18
                         mol_type = protein
                         organism = synthetic construct
SEQUENCE: 253
VIIWYDGSCK YYADSVKG                                                  18

SEQ ID NO: 254           moltype = AA  length = 18
FEATURE                  Location/Qualifiers
source                   1..18
                         mol_type = protein
                         organism = synthetic construct
SEQUENCE: 254
VIIWYDGSTK YYADSVKG                                                  18

SEQ ID NO: 255           moltype = AA  length = 18
FEATURE                  Location/Qualifiers
source                   1..18
                         mol_type = protein
                         organism = synthetic construct
SEQUENCE: 255
VIIWYDGSNR YYADSVKG                                                  18

SEQ ID NO: 256           moltype = AA  length = 18
FEATURE                  Location/Qualifiers
source                   1..18
                         mol_type = protein
                         organism = synthetic construct
SEQUENCE: 256
VIIWYDGSNH YYADSVKG                                                  18

SEQ ID NO: 257           moltype = AA  length = 17
FEATURE                  Location/Qualifiers
source                   1..17
                         mol_type = protein
                         organism = synthetic construct
SEQUENCE: 257
VIWYDGSNKS YADSVKG                                                   17

SEQ ID NO: 258           moltype = AA  length = 17
FEATURE                  Location/Qualifiers
source                   1..17
                         mol_type = protein
                         organism = synthetic construct
SEQUENCE: 258
VIWYDGSNKT YADSVKG                                                   17

SEQ ID NO: 259           moltype = AA  length = 17
FEATURE                  Location/Qualifiers
source                   1..17
                         mol_type = protein
                         organism = synthetic construct
SEQUENCE: 259
```

```
VIWYDGSNKF YADSVKG                                                            17

SEQ ID NO: 260          moltype = AA  length = 17
FEATURE                 Location/Qualifiers
source                  1..17
                        mol_type = protein
                        organism = synthetic construct SEQUENCE: 260
VIWYDGSNKY SADSVKG                                                            17

SEQ ID NO: 261          moltype = AA  length = 17
FEATURE                 Location/Qualifiers
source                  1..17
                        mol_type = protein
                        organism = synthetic construct SEQUENCE: 261
VIWYDGSNKY TADSVKG                                                            17

SEQ ID NO: 262          moltype = AA  length = 17
FEATURE                 Location/Qualifiers
source                  1..17
                        mol_type = protein
                        organism = synthetic construct SEQUENCE: 262
VIWYDGSNKY FADSVKG                                                            17

SEQ ID NO: 263          moltype = AA  length = 17
FEATURE                 Location/Qualifiers
source                  1..17
                        mol_type = protein
                        organism = synthetic construct SEQUENCE: 263
VIWYDGSNKY YVDSVKG                                                            17

SEQ ID NO: 264          moltype = AA  length = 17
FEATURE                 Location/Qualifiers
source                  1..17
                        mol_type = protein
                        organism = synthetic construct SEQUENCE: 264
VIWYDGSNKY YLDSVKG                                                            17

SEQ ID NO: 265          moltype = AA  length = 17
FEATURE                 Location/Qualifiers
source                  1..17
                        mol_type = protein
                        organism = synthetic construct SEQUENCE: 265
VIWYDGSNKY YIDSVKG                                                            17

SEQ ID NO: 266          moltype = AA  length = 17
FEATURE                 Location/Qualifiers
source                  1..17
                        mol_type = protein
                        organism = synthetic construct SEQUENCE: 266
VIWYDGSNKY YMDSVKG                                                            17

SEQ ID NO: 267          moltype = AA  length = 17
FEATURE                 Location/Qualifiers
source                  1..17
                        mol_type = protein
                        organism = synthetic construct SEQUENCE: 267
VIWYDGSNKY YAESVKG                                                            17

SEQ ID NO: 268          moltype = AA  length = 17
FEATURE                 Location/Qualifiers
source                  1..17
                        mol_type = protein
                        organism = synthetic construct SEQUENCE: 268
VIWYDGSNKY YADCVKG                                                            17

SEQ ID NO: 269          moltype = AA  length = 17
FEATURE                 Location/Qualifiers
source                  1..17
                        mol_type = protein
                        organism = synthetic construct
```

```
SEQUENCE: 269
VIWYDGSNKY YADTVKG                                                     17

SEQ ID NO: 270          moltype = AA  length = 17
FEATURE                 Location/Qualifiers
source                  1..17
                        mol_type = protein
                        organism = synthetic construct
SEQUENCE: 270
VIWYDGSNKY YADSAKG                                                     17

SEQ ID NO: 271          moltype = AA  length = 17
FEATURE                 Location/Qualifiers
source                  1..17
                        mol_type = protein
                        organism = synthetic construct
SEQUENCE: 271
VIWYDGSNKY YADSLKG                                                     17

SEQ ID NO: 272          moltype = AA  length = 17
FEATURE                 Location/Qualifiers
source                  1..17
                        mol_type = protein
                        organism = synthetic construct
SEQUENCE: 272
VIWYDGSNKY YADSIKG                                                     17

SEQ ID NO: 273          moltype = AA  length = 17
FEATURE                 Location/Qualifiers
source                  1..17
                        mol_type = protein
                        organism = synthetic construct
SEQUENCE: 273
VIWYDGSNKY YADSMKG                                                     17

SEQ ID NO: 274          moltype = AA  length = 17
FEATURE                 Location/Qualifiers
source                  1..17
                        mol_type = protein
                        organism = synthetic construct
SEQUENCE: 274
VIWYDGSNKY YADSVRG                                                     17

SEQ ID NO: 275          moltype = AA  length = 17
FEATURE                 Location/Qualifiers
source                  1..17
                        mol_type = protein
                        organism = synthetic construct
SEQUENCE: 275
VIWYDGSNKY YADSVHG                                                     17

SEQ ID NO: 276          moltype = AA  length = 17
FEATURE                 Location/Qualifiers
source                  1..17
                        mol_type = protein
                        organism = synthetic construct
SEQUENCE: 276
VIWYDGSNKY YADSVKS                                                     17

SEQ ID NO: 277          moltype = AA  length = 17
FEATURE                 Location/Qualifiers
source                  1..17
                        mol_type = protein
                        organism = synthetic construct
SEQUENCE: 277
VIWYDGSNKY YADSVKT                                                     17

SEQ ID NO: 278          moltype = AA  length = 17
FEATURE                 Location/Qualifiers
source                  1..17
                        mol_type = protein
                        organism = synthetic construct
SEQUENCE: 278
VIWYDGSNKY YADSVKC                                                     17

SEQ ID NO: 279          moltype = AA  length = 9
FEATURE                 Location/Qualifiers
source                  1..9
                        mol_type = protein
```

```
SEQUENCE: 279
ETGDRFFDY                                                                     9

SEQ ID NO: 280          moltype = AA   length = 9
FEATURE                 Location/Qualifiers
source                  1..9
                        mol_type = protein
                        organism = synthetic construct
SEQUENCE: 280
DSGDRFFDY                                                                     9

SEQ ID NO: 281          moltype = AA   length = 9
FEATURE                 Location/Qualifiers
source                  1..9
                        mol_type = protein
                        organism = synthetic construct
SEQUENCE: 281
DCGDRFFDY                                                                     9

SEQ ID NO: 282          moltype = AA   length = 9
FEATURE                 Location/Qualifiers
source                  1..9
                        mol_type = protein
                        organism = synthetic construct
SEQUENCE: 282
DYGDRFFDY                                                                     9

SEQ ID NO: 283          moltype = AA   length = 9
FEATURE                 Location/Qualifiers
source                  1..9
                        mol_type = protein
                        organism = synthetic construct
SEQUENCE: 283
DTQDRFFDY                                                                     9

SEQ ID NO: 284          moltype = AA   length = 9
FEATURE                 Location/Qualifiers
source                  1..9
                        mol_type = protein
                        organism = synthetic construct
SEQUENCE: 284
DTCDRFFDY                                                                     9

SEQ ID NO: 285          moltype = AA   length = 9
FEATURE                 Location/Qualifiers
source                  1..9
                        mol_type = protein
                        organism = synthetic construct
SEQUENCE: 285
DTTDRFFDY                                                                     9

SEQ ID NO: 286          moltype = AA   length = 9
FEATURE                 Location/Qualifiers
source                  1..9
                        mol_type = protein
                        organism = synthetic construct
SEQUENCE: 286
DTSDRFFDY                                                                     9

SEQ ID NO: 287          moltype = AA   length = 9
FEATURE                 Location/Qualifiers
source                  1..9
                        mol_type = protein
                        organism = synthetic construct
SEQUENCE: 287
DTGERFFDY                                                                     9

SEQ ID NO: 288          moltype = AA   length = 9
FEATURE                 Location/Qualifiers
source                  1..9
                        mol_type = protein
                        organism = synthetic construct
SEQUENCE: 288
DTGDKFFDY                                                                     9

SEQ ID NO: 289          moltype = AA   length = 9
FEATURE                 Location/Qualifiers
source                  1..9
```

```
                              mol_type = protein
                              organism = synthetic construct
SEQUENCE: 289
DTGDHFFDY                                                              9

SEQ ID NO: 290                moltype = AA   length = 9
FEATURE                       Location/Qualifiers
source                        1..9
                              mol_type = protein
                              organism = synthetic construct
SEQUENCE: 290
DTGDRWFDY                                                              9

SEQ ID NO: 291                moltype = AA   length = 9
FEATURE                       Location/Qualifiers
source                        1..9
                              mol_type = protein
                              organism = synthetic construct
SEQUENCE: 291
DTGDRPFDY                                                              9

SEQ ID NO: 292                moltype = AA   length = 9
FEATURE                       Location/Qualifiers
source                        1..9
                              mol_type = protein
                              organism = synthetic construct
SEQUENCE: 292
DTGDRYFDY                                                              9

SEQ ID NO: 293                moltype = AA   length = 9
FEATURE                       Location/Qualifiers
source                        1..9
                              mol_type = protein
                              organism = synthetic construct
SEQUENCE: 293
DTGDRFWDY                                                              9

SEQ ID NO: 294                moltype = AA   length = 9
FEATURE                       Location/Qualifiers
source                        1..9
                              mol_type = protein
                              organism = synthetic construct
SEQUENCE: 294
DTGDRFPDY                                                              9

SEQ ID NO: 295                moltype = AA   length = 9
FEATURE                       Location/Qualifiers
source                        1..9
                              mol_type = protein
                              organism = synthetic construct
SEQUENCE: 295
DTGDRFYDY                                                              9

SEQ ID NO: 296                moltype = AA   length = 9
FEATURE                       Location/Qualifiers
source                        1..9
                              mol_type = protein
                              organism = synthetic construct
SEQUENCE: 296
DTGDRFFEY                                                              9

SEQ ID NO: 297                moltype = AA   length = 9
FEATURE                       Location/Qualifiers
source                        1..9
                              mol_type = protein
                              organism = synthetic construct
SEQUENCE: 297
DTGDRFFDT                                                              9

SEQ ID NO: 298                moltype = AA   length = 9
FEATURE                       Location/Qualifiers
source                        1..9
                              mol_type = protein
                              organism = synthetic construct
SEQUENCE: 298
DTGDRFFDS                                                              9

SEQ ID NO: 299                moltype = AA   length = 9
FEATURE                       Location/Qualifiers
```

```
source                      1..9
                            mol_type = protein
                            organism = synthetic construct
SEQUENCE: 299
DTGDRFFDF                                                                        9

SEQ ID NO: 300              moltype = AA   length = 11
FEATURE                     Location/Qualifiers
source                      1..11
                            mol_type = protein
                            organism = synthetic construct
SEQUENCE: 300
KASQSVSSYL A                                                                    11

SEQ ID NO: 301              moltype = AA   length = 11
FEATURE                     Location/Qualifiers
source                      1..11
                            mol_type = protein
                            organism = synthetic construct
SEQUENCE: 301
HASQSVSSYL A                                                                    11

SEQ ID NO: 302              moltype = AA   length = 11
FEATURE                     Location/Qualifiers
source                      1..11
                            mol_type = protein
                            organism = synthetic construct
SEQUENCE: 302
RVSQSVSSYL A                                                                    11

SEQ ID NO: 303              moltype = AA   length = 11
FEATURE                     Location/Qualifiers
source                      1..11
                            mol_type = protein
                            organism = synthetic construct
SEQUENCE: 303
RLSQSVSSYL A                                                                    11

SEQ ID NO: 304              moltype = AA   length = 11
FEATURE                     Location/Qualifiers
source                      1..11
                            mol_type = protein
                            organism = synthetic construct
SEQUENCE: 304
RISQSVSSYL A                                                                    11

SEQ ID NO: 305              moltype = AA   length = 11
FEATURE                     Location/Qualifiers
source                      1..11
                            mol_type = protein
                            organism = synthetic construct
SEQUENCE: 305
RMSQSVSSYL A                                                                    11

SEQ ID NO: 306              moltype = AA   length = 11
FEATURE                     Location/Qualifiers
source                      1..11
                            mol_type = protein
                            organism = synthetic construct
SEQUENCE: 306
RATQSVSSYL A                                                                    11

SEQ ID NO: 307              moltype = AA   length = 11
FEATURE                     Location/Qualifiers
source                      1..11
                            mol_type = protein
                            organism = synthetic construct
SEQUENCE: 307
RACQSVSSYL A                                                                    11

SEQ ID NO: 308              moltype = AA   length = 11
FEATURE                     Location/Qualifiers
source                      1..11
                            mol_type = protein
                            organism = synthetic construct
SEQUENCE: 308
RAYQSVSSYL A                                                                    11

SEQ ID NO: 309              moltype = AA   length = 11
```

```
                           -continued

FEATURE                Location/Qualifiers
source                 1..11
                       mol_type = protein
                       organism = synthetic construct
SEQUENCE: 309
RASGSVSSYL A                                                         11

SEQ ID NO: 310         moltype = AA   length = 11
FEATURE                Location/Qualifiers
source                 1..11
                       mol_type = protein
                       organism = synthetic construct
SEQUENCE: 310
RASNSVSSYL A                                                         11

SEQ ID NO: 311         moltype = AA   length = 11
FEATURE                Location/Qualifiers
source                 1..11
                       mol_type = protein
                       organism = synthetic construct
SEQUENCE: 311
RASQTVSSYL A                                                         11

SEQ ID NO: 312         moltype = AA   length = 11
FEATURE                Location/Qualifiers
source                 1..11
                       mol_type = protein
                       organism = synthetic construct
SEQUENCE: 312
RASQCVSSYL A                                                         11

SEQ ID NO: 313         moltype = AA   length = 11
FEATURE                Location/Qualifiers
source                 1..11
                       mol_type = protein
                       organism = synthetic construct
SEQUENCE: 313
RASQYVSSYL A                                                         11

SEQ ID NO: 314         moltype = AA   length = 11
FEATURE                Location/Qualifiers
source                 1..11
                       mol_type = protein
                       organism = synthetic construct
SEQUENCE: 314
RASQSASSYL A                                                         11

SEQ ID NO: 315         moltype = AA   length = 11
FEATURE                Location/Qualifiers
source                 1..11
                       mol_type = protein
                       organism = synthetic construct
SEQUENCE: 315
RASQSLSSYL A                                                         11

SEQ ID NO: 316         moltype = AA   length = 11
FEATURE                Location/Qualifiers
source                 1..11
                       mol_type = protein
                       organism = synthetic construct
SEQUENCE: 316
RASQSISSYL A                                                         11

SEQ ID NO: 317         moltype = AA   length = 11
FEATURE                Location/Qualifiers
source                 1..11
                       mol_type = protein
                       organism = synthetic construct
SEQUENCE: 317
RASQSMSSYL A                                                         11

SEQ ID NO: 318         moltype = AA   length = 11
FEATURE                Location/Qualifiers
source                 1..11
                       mol_type = protein
                       organism = synthetic construct
SEQUENCE: 318
RASQSVTSYL A                                                         11
```

| | | |
|---|---|---|
| SEQ ID NO: 319<br>FEATURE<br>source | moltype = AA  length = 11<br>Location/Qualifiers<br>1..11<br>mol_type = protein<br>organism = synthetic construct | |
| SEQUENCE: 319<br>RASQSVCSYL A | | 11 |
| SEQ ID NO: 320<br>FEATURE<br>source | moltype = AA  length = 11<br>Location/Qualifiers<br>1..11<br>mol_type = protein<br>organism = synthetic construct | |
| SEQUENCE: 320<br>RASQSVYSYL A | | 11 |
| SEQ ID NO: 321<br>FEATURE<br>source | moltype = AA  length = 11<br>Location/Qualifiers<br>1..11<br>mol_type = protein<br>organism = synthetic construct | |
| SEQUENCE: 321<br>RASQSVSTYL A | | 11 |
| SEQ ID NO: 322<br>FEATURE<br>source | moltype = AA  length = 11<br>Location/Qualifiers<br>1..11<br>mol_type = protein<br>organism = synthetic construct | |
| SEQUENCE: 322<br>RASQSVSCYL A | | 11 |
| SEQ ID NO: 323<br>FEATURE<br>source | moltype = AA  length = 11<br>Location/Qualifiers<br>1..11<br>mol_type = protein<br>organism = synthetic construct | |
| SEQUENCE: 323<br>RASQSVSYYL A | | 11 |
| SEQ ID NO: 324<br>FEATURE<br>source | moltype = AA  length = 11<br>Location/Qualifiers<br>1..11<br>mol_type = protein<br>organism = synthetic construct | |
| SEQUENCE: 324<br>RASQSVSSSL A | | 11 |
| SEQ ID NO: 325<br>FEATURE<br>source | moltype = AA  length = 11<br>Location/Qualifiers<br>1..11<br>mol_type = protein<br>organism = synthetic construct | |
| SEQUENCE: 325<br>RASQSVSSTL A | | 11 |
| SEQ ID NO: 326<br>FEATURE<br>source | moltype = AA  length = 11<br>Location/Qualifiers<br>1..11<br>mol_type = protein<br>organism = synthetic construct | |
| SEQUENCE: 326<br>RASQSVSSFL A | | 11 |
| SEQ ID NO: 327<br>FEATURE<br>source | moltype = AA  length = 11<br>Location/Qualifiers<br>1..11<br>mol_type = protein<br>organism = synthetic construct | |
| SEQUENCE: 327<br>RASQSVSSYI A | | 11 |
| SEQ ID NO: 328<br>FEATURE<br>source | moltype = AA  length = 11<br>Location/Qualifiers<br>1..11<br>mol_type = protein<br>organism = synthetic construct | |
| SEQUENCE: 328<br>RASQSVSSYV A | | 11 |

| | | |
|---|---|---|
| SEQ ID NO: 329<br>FEATURE<br>source | moltype = AA  length = 11<br>Location/Qualifiers<br>1..11<br>mol_type = protein<br>organism = synthetic construct | |
| SEQUENCE: 329<br>RASQSVSSYA A | | 11 |
| SEQ ID NO: 330<br>FEATURE<br>source | moltype = AA  length = 11<br>Location/Qualifiers<br>1..11<br>mol_type = protein<br>organism = synthetic construct | |
| SEQUENCE: 330<br>RASQSVSSYM A | | 11 |
| SEQ ID NO: 331<br>FEATURE<br>source | moltype = AA  length = 11<br>Location/Qualifiers<br>1..11<br>mol_type = protein<br>organism = synthetic construct | |
| SEQUENCE: 331<br>RASQSVSSYL V | | 11 |
| SEQ ID NO: 332<br>FEATURE<br>source | moltype = AA  length = 11<br>Location/Qualifiers<br>1..11<br>mol_type = protein<br>organism = synthetic construct | |
| SEQUENCE: 332<br>RASQSVSSYL L | | 11 |
| SEQ ID NO: 333<br>FEATURE<br>source | moltype = AA  length = 11<br>Location/Qualifiers<br>1..11<br>mol_type = protein<br>organism = synthetic construct | |
| SEQUENCE: 333<br>RASQSVSSYL I | | 11 |
| SEQ ID NO: 334<br>FEATURE<br>source | moltype = AA  length = 11<br>Location/Qualifiers<br>1..11<br>mol_type = protein<br>organism = synthetic construct | |
| SEQUENCE: 334<br>RASQSVSSYL M | | 11 |
| SEQ ID NO: 335<br>FEATURE<br>source | moltype = AA  length = 7<br>Location/Qualifiers<br>1..7<br>mol_type = protein<br>organism = synthetic construct | |
| SEQUENCE: 335<br>EASSRAT | | 7 |
| SEQ ID NO: 336<br>FEATURE<br>source | moltype = AA  length = 7<br>Location/Qualifiers<br>1..7<br>mol_type = protein<br>organism = synthetic construct | |
| SEQUENCE: 336<br>DVSSRAT | | 7 |
| SEQ ID NO: 337<br>FEATURE<br>source | moltype = AA  length = 7<br>Location/Qualifiers<br>1..7<br>mol_type = protein<br>organism = synthetic construct | |
| SEQUENCE: 337<br>DLSSRAT | | 7 |
| SEQ ID NO: 338<br>FEATURE<br>source | moltype = AA  length = 7<br>Location/Qualifiers<br>1..7<br>mol_type = protein<br>organism = synthetic construct | |
| SEQUENCE: 338 | | |

|  |  | -continued |
|---|---|---|
| DISSRAT | | 7 |

SEQ ID NO: 339　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 339
DMSSRAT　　　　　　　　　　　　　　　　　　　　　　　　　　　　　　　　　7

SEQ ID NO: 340　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 340
DATSRAT　　　　　　　　　　　　　　　　　　　　　　　　　　　　　　　　　7

SEQ ID NO: 341　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 341
DACSRAT　　　　　　　　　　　　　　　　　　　　　　　　　　　　　　　　　7

SEQ ID NO: 342　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 342
DAYSRAT　　　　　　　　　　　　　　　　　　　　　　　　　　　　　　　　　7

SEQ ID NO: 343　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 343
DASTRAT　　　　　　　　　　　　　　　　　　　　　　　　　　　　　　　　　7

SEQ ID NO: 344　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 344
DASCRAT　　　　　　　　　　　　　　　　　　　　　　　　　　　　　　　　　7

SEQ ID NO: 345　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 345
DASYRAT　　　　　　　　　　　　　　　　　　　　　　　　　　　　　　　　　7

SEQ ID NO: 346　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 346
DASSKAT　　　　　　　　　　　　　　　　　　　　　　　　　　　　　　　　　7

SEQ ID NO: 347　　moltype = AA　length = 7
FEATURE　　　　　Location/Qualifiers
source　　　　　　1..7
　　　　　　　　　mol_type = protein
　　　　　　　　　organism = synthetic construct
SEQUENCE: 347
DASSHAT　　　　　　　　　　　　　　　　　　　　　　　　　　　　　　　　　7

SEQ ID NO: 348　　moltype = AA　length = 7
FEATURE　　　　　Location/Qualifiers
source　　　　　　1..7
　　　　　　　　　mol_type = protein
　　　　　　　　　organism = synthetic construct

```
SEQUENCE: 348
DASSRVT                                                                    7

SEQ ID NO: 349          moltype = AA  length = 7
FEATURE                 Location/Qualifiers
source                  1..7
                        mol_type = protein
                        organism = synthetic construct
SEQUENCE: 349
DASSRLT                                                                    7

SEQ ID NO: 350          moltype = AA  length = 7
FEATURE                 Location/Qualifiers
source                  1..7
                        mol_type = protein
                        organism = synthetic construct
SEQUENCE: 350
DASSRIT                                                                    7

SEQ ID NO: 351          moltype = AA  length = 7
FEATURE                 Location/Qualifiers
source                  1..7
                        mol_type = protein
                        organism = synthetic construct
SEQUENCE: 351
DASSRAS                                                                    7

SEQ ID NO: 352          moltype = AA  length = 7
FEATURE                 Location/Qualifiers
source                  1..7
                        mol_type = protein
                        organism = synthetic construct
SEQUENCE: 352
DASSRAC                                                                    7

SEQ ID NO: 353          moltype = AA  length = 7
FEATURE                 Location/Qualifiers
source                  1..7
                        mol_type = protein
                        organism = synthetic construct
SEQUENCE: 353
DASSRAY                                                                    7

SEQ ID NO: 354          moltype = AA  length = 10
FEATURE                 Location/Qualifiers
source                  1..10
                        mol_type = protein
                        organism = synthetic construct
SEQUENCE: 354
NLRSNWPPYT                                                                10

SEQ ID NO: 355          moltype = AA  length = 10
FEATURE                 Location/Qualifiers
source                  1..10
                        mol_type = protein
                        organism = synthetic construct
SEQUENCE: 355
PLRSNWPPYT                                                                10

SEQ ID NO: 356          moltype = AA  length = 10
FEATURE                 Location/Qualifiers
source                  1..10
                        mol_type = protein
                        organism = synthetic construct
SEQUENCE: 356
QIRSNWPPYT                                                                10

SEQ ID NO: 357          moltype = AA  length = 10
FEATURE                 Location/Qualifiers
source                  1..10
                        mol_type = protein
                        organism = synthetic construct
SEQUENCE: 357
QVRSNWPPYT                                                                10

SEQ ID NO: 358          moltype = AA  length = 10
FEATURE                 Location/Qualifiers
source                  1..10
                        mol_type = protein
```

```
                                    -continued

SEQUENCE: 358
QARSNWPPYT                                                                  10

SEQ ID NO: 359          moltype = AA   length = 10
FEATURE                 Location/Qualifiers
source                  1..10
                        mol_type = protein
                        organism = synthetic construct
SEQUENCE: 359
QLKSNWPPYT                                                                  10

SEQ ID NO: 360          moltype = AA   length = 10
FEATURE                 Location/Qualifiers
source                  1..10
                        mol_type = protein
                        organism = synthetic construct
SEQUENCE: 360
QLHSNWPPYT                                                                  10

SEQ ID NO: 361          moltype = AA   length = 10
FEATURE                 Location/Qualifiers
source                  1..10
                        mol_type = protein
                        organism = synthetic construct
SEQUENCE: 361
QLRTNWPPYT                                                                  10

SEQ ID NO: 362          moltype = AA   length = 10
FEATURE                 Location/Qualifiers
source                  1..10
                        mol_type = protein
                        organism = synthetic construct
SEQUENCE: 362
QLRCNWPPYT                                                                  10

SEQ ID NO: 363          moltype = AA   length = 10
FEATURE                 Location/Qualifiers
source                  1..10
                        mol_type = protein
                        organism = synthetic construct
SEQUENCE: 363
QLRYNWPPYT                                                                  10

SEQ ID NO: 364          moltype = AA   length = 10
FEATURE                 Location/Qualifiers
source                  1..10
                        mol_type = protein
                        organism = synthetic construct
SEQUENCE: 364
QLRSQWPPYT                                                                  10

SEQ ID NO: 365          moltype = AA   length = 10
FEATURE                 Location/Qualifiers
source                  1..10
                        mol_type = protein
                        organism = synthetic construct
SEQUENCE: 365
QLRSNFPPYT                                                                  10

SEQ ID NO: 366          moltype = AA   length = 10
FEATURE                 Location/Qualifiers
source                  1..10
                        mol_type = protein
                        organism = synthetic construct
SEQUENCE: 366
QLRSNYPPYT                                                                  10

SEQ ID NO: 367          moltype = AA   length = 10
FEATURE                 Location/Qualifiers
source                  1..10
                        mol_type = protein
                        organism = synthetic construct
SEQUENCE: 367
QLRSNPPPYT                                                                  10

SEQ ID NO: 368          moltype = AA   length = 10
FEATURE                 Location/Qualifiers
source                  1..10
```

```
SEQUENCE: 368
QLRSNWFPYT                                                                    10

SEQ ID NO: 369           moltype = AA  length = 10
FEATURE                  Location/Qualifiers
source                   1..10
                         mol_type = protein
                         organism = synthetic construct
SEQUENCE: 369
QLRSNWQPYT                                                                    10

SEQ ID NO: 370           moltype = AA  length = 10
FEATURE                  Location/Qualifiers
source                   1..10
                         mol_type = protein
                         organism = synthetic construct
SEQUENCE: 370
QLRSNWNPYT                                                                    10

SEQ ID NO: 371           moltype = AA  length = 10
FEATURE                  Location/Qualifiers
source                   1..10
                         mol_type = protein
                         organism = synthetic construct
SEQUENCE: 371
QLRSNWPWYT                                                                    10

SEQ ID NO: 372           moltype = AA  length = 10
FEATURE                  Location/Qualifiers
source                   1..10
                         mol_type = protein
                         organism = synthetic construct
SEQUENCE: 372
QLRSNWWPYT                                                                    10

SEQ ID NO: 373           moltype = AA  length = 10
FEATURE                  Location/Qualifiers
source                   1..10
                         mol_type = protein
                         organism = synthetic construct
SEQUENCE: 373
QLRSNWPNYT                                                                    10

SEQ ID NO: 374           moltype = AA  length = 10
FEATURE                  Location/Qualifiers
source                   1..10
                         mol_type = protein
                         organism = synthetic construct
SEQUENCE: 374
QLRSNWPQYT                                                                    10

SEQ ID NO: 375           moltype = AA  length = 10
FEATURE                  Location/Qualifiers
source                   1..10
                         mol_type = protein
                         organism = synthetic construct
SEQUENCE: 375
QLRSNWPPTT                                                                    10

SEQ ID NO: 376           moltype = AA  length = 10
FEATURE                  Location/Qualifiers
source                   1..10
                         mol_type = protein
                         organism = synthetic construct
SEQUENCE: 376
QLRSNWPPST                                                                    10

SEQ ID NO: 377           moltype = AA  length = 10
FEATURE                  Location/Qualifiers
source                   1..10
                         mol_type = protein
                         organism = synthetic construct
SEQUENCE: 377
QLRSNWPPFT                                                                    10

SEQ ID NO: 378           moltype = AA  length = 10
FEATURE                  Location/Qualifiers
```

```
source                  1..10
                        mol_type = protein
                        organism = synthetic construct
SEQUENCE: 378
QLRSNWPPYS                                                                10

SEQ ID NO: 379          moltype = AA   length = 10
FEATURE                 Location/Qualifiers
source                  1..10
                        mol_type = protein
                        organism = synthetic construct
SEQUENCE: 379
QLRSNWPPYC                                                                10

SEQ ID NO: 380          moltype = AA   length = 10
FEATURE                 Location/Qualifiers
source                  1..10
                        mol_type = protein
                        organism = synthetic construct
SEQUENCE: 380
QLRSNWPPYY                                                                10

SEQ ID NO: 381          moltype = AA   length = 9
FEATURE                 Location/Qualifiers
source                  1..9
                        mol_type = protein
                        organism = synthetic construct
SEQUENCE: 381
WGQGTLVTV                                                                  9

SEQ ID NO: 382          moltype = AA   length = 10
FEATURE                 Location/Qualifiers
source                  1..10
                        mol_type = protein
                        organism = synthetic construct
SEQUENCE: 382
FGQGTKLEIK                                                                10

SEQ ID NO: 383          moltype = AA   length = 9
FEATURE                 Location/Qualifiers
source                  1..9
                        mol_type = protein
                        organism = synthetic construct
SEQUENCE: 383
WGQGTLVTV                                                                  9

SEQ ID NO: 384          moltype = AA   length = 10
FEATURE                 Location/Qualifiers
source                  1..10
                        mol_type = protein
                        organism = synthetic construct
SEQUENCE: 384
FGQGTKLEIK                                                                10

SEQ ID NO: 385          moltype = AA   length = 120
FEATURE                 Location/Qualifiers
source                  1..120
                        mol_type = protein
                        organism = synthetic construct
SEQUENCE: 385
EVQLVESGGG LVKPGGSLRL SCVASGFIFS DNYMYWVRQT PEKRLEWVAT ISDGGSYTYY          60
PDSVKGRFTI SRDNAKNNLY LQMSSLKSED TAIYYCARGY YRYEGAMDYW GQGTSVTVSS         120

SEQ ID NO: 386          moltype = AA   length = 25
FEATURE                 Location/Qualifiers
source                  1..25
                        mol_type = protein
                        organism = synthetic construct
SEQUENCE: 386
EVQLVESGGG LVKPGGSLRL SCVAS                                               25

SEQ ID NO: 387          moltype = AA   length = 8
FEATURE                 Location/Qualifiers
source                  1..8
                        mol_type = protein
                        organism = synthetic construct
SEQUENCE: 387
GFIFSDNY                                                                   8
```

```
SEQ ID NO: 388          moltype = AA   length = 17
FEATURE                 Location/Qualifiers
source                  1..17
                        mol_type = protein
                        organism = synthetic construct
SEQUENCE: 388
MYWVRQTPEK RLEWVAT                                                      17

SEQ ID NO: 389          moltype = AA   length = 8
FEATURE                 Location/Qualifiers
source                  1..8
                        mol_type = protein
                        organism = synthetic construct
SEQUENCE: 389
ISDGGSYT                                                                 8

SEQ ID NO: 390          moltype = AA   length = 38
FEATURE                 Location/Qualifiers
source                  1..38
                        mol_type = protein
                        organism = synthetic construct
SEQUENCE: 390
YYPDSVKGRF TISRDNAKNN LYLQMSSLKS EDTAIYYC                                38

SEQ ID NO: 391          moltype = AA   length = 13
FEATURE                 Location/Qualifiers
source                  1..13
                        mol_type = protein
                        organism = synthetic construct
SEQUENCE: 391
ARGYYRYEGA MDY                                                          13

SEQ ID NO: 392          moltype = AA   length = 11
FEATURE                 Location/Qualifiers
source                  1..11
                        mol_type = protein
                        organism = synthetic construct
SEQUENCE: 392
WGQGTSVTVS S                                                            11

SEQ ID NO: 393          moltype = AA   length = 9
FEATURE                 Location/Qualifiers
source                  1..9
                        mol_type = protein
                        organism = synthetic construct
SEQUENCE: 393
WGQGTSVTV                                                                9

SEQ ID NO: 394          moltype = AA   length = 114
FEATURE                 Location/Qualifiers
source                  1..114
                        mol_type = protein
                        organism = synthetic construct
SEQUENCE: 394
NIVMTQSPSS LAVSAGEKVT MSCKSSQSVL YSSNQKNYLA WYQQKPGQSP KLLIYWASTR        60
ESGVPDRFTG SGSGTDFTLT ISSVQAEDLA VYYCHQYLSS WTFGGGTKLE IKTS             114

SEQ ID NO: 395          moltype = AA   length = 26
FEATURE                 Location/Qualifiers
source                  1..26
                        mol_type = protein
                        organism = synthetic construct
SEQUENCE: 395
NIVMTQSPSS LAVSAGEKVT MSCKSS                                            26

SEQ ID NO: 396          moltype = AA   length = 12
FEATURE                 Location/Qualifiers
source                  1..12
                        mol_type = protein
                        organism = synthetic construct
SEQUENCE: 396
QSVLYSSNQK NY                                                           12

SEQ ID NO: 397          moltype = AA   length = 17
FEATURE                 Location/Qualifiers
source                  1..17
                        mol_type = protein
                        organism = synthetic construct
SEQUENCE: 397
```

```
LAWYQQKPGQ SPKLLIY                                                          17

SEQ ID NO: 398          moltype =    length =
SEQUENCE: 398
000

SEQ ID NO: 399          moltype = AA   length = 36
FEATURE                 Location/Qualifiers
source                  1..36
                        mol_type = protein
                        organism = synthetic construct
SEQUENCE: 399
TRESGVPDRF TGSGSGTDFT LTISSVQAED LAVYYC                                     36

SEQ ID NO: 400          moltype = AA   length = 8
FEATURE                 Location/Qualifiers
source                  1..8
                        mol_type = protein
                        organism = synthetic construct
SEQUENCE: 400
HQYLSSWT                                                                    8

SEQ ID NO: 401          moltype = AA   length = 12
FEATURE                 Location/Qualifiers
source                  1..12
                        mol_type = protein
                        organism = synthetic construct
SEQUENCE: 401
FGGGTKLEIK TS                                                               12

SEQ ID NO: 402          moltype = AA   length = 10
FEATURE                 Location/Qualifiers
source                  1..10
                        mol_type = protein
                        organism = synthetic construct
SEQUENCE: 402
FGGGTKLEIK                                                                  10

SEQ ID NO: 403          moltype = AA   length = 120
FEATURE                 Location/Qualifiers
source                  1..120
                        mol_type = protein
                        organism = synthetic construct
SEQUENCE: 403
EVQLVESGGG LVKPGGSLRL SCVASGFIFS DNYMYWVRQT PEKRLEWVAT ISDGGSYTYY           60
PDSVKGRFTI SRDNAKNNLY LQMSSLKSED TAIYYCARGY YRYEGAMDYW GQGTSVTVSS          120

SEQ ID NO: 404          moltype = AA   length = 30
FEATURE                 Location/Qualifiers
source                  1..30
                        mol_type = protein
                        organism = synthetic construct
SEQUENCE: 404
EVQLVESGGG LVKPGGSLRL SCVASGFIFS                                            30

SEQ ID NO: 405          moltype = AA   length = 5
FEATURE                 Location/Qualifiers
source                  1..5
                        mol_type = protein
                        organism = synthetic construct
SEQUENCE: 405
DNYMY                                                                       5

SEQ ID NO: 406          moltype = AA   length = 14
FEATURE                 Location/Qualifiers
source                  1..14
                        mol_type = protein
                        organism = synthetic construct
SEQUENCE: 406
WVRQTPEKRL EWVA                                                             14

SEQ ID NO: 407          moltype = AA   length = 17
FEATURE                 Location/Qualifiers
source                  1..17
                        mol_type = protein
                        organism = synthetic construct
SEQUENCE: 407
TISDGGSYTY YPDSVKG                                                          17
```

| | | |
|---|---|---|
| SEQ ID NO: 408<br>FEATURE<br>source | moltype = AA  length = 32<br>Location/Qualifiers<br>1..32<br>mol_type = protein<br>organism = synthetic construct | |
| SEQUENCE: 408<br>RFTISRDNAK NNLYLQMSSL KSEDTAIYYC AR | | 32 |
| SEQ ID NO: 409<br>FEATURE<br>source | moltype = AA  length = 11<br>Location/Qualifiers<br>1..11<br>mol_type = protein<br>organism = synthetic construct | |
| SEQUENCE: 409<br>GYYRYEGAMD Y | | 11 |
| SEQ ID NO: 410<br>FEATURE<br>source | moltype = AA  length = 11<br>Location/Qualifiers<br>1..11<br>mol_type = protein<br>organism = synthetic construct | |
| SEQUENCE: 410<br>WGQGTSVTVS S | | 11 |
| SEQ ID NO: 411<br>FEATURE<br>source | moltype = AA  length = 9<br>Location/Qualifiers<br>1..9<br>mol_type = protein<br>organism = synthetic construct | |
| SEQUENCE: 411<br>WGQGTSVTV | | 9 |
| SEQ ID NO: 412<br>FEATURE<br>source | moltype = AA  length = 112<br>Location/Qualifiers<br>1..112<br>mol_type = protein<br>organism = synthetic construct | |
| SEQUENCE: 412<br>NIVMTQSPSS LAVSAGEKVT MSCKSSQSVL YSSNQKNYLA WYQQKPGQSP KLLIYWASTR<br>ESGVPDRFTG SGSGTDFTLT ISSVQAEDLA VYYCHQYLSS WTFGGGTKLE IK | | 60<br>112 |
| SEQ ID NO: 413<br>FEATURE<br>source | moltype = AA  length = 23<br>Location/Qualifiers<br>1..23<br>mol_type = protein<br>organism = synthetic construct | |
| SEQUENCE: 413<br>NIVMTQSPSS LAVSAGEKVT MSC | | 23 |
| SEQ ID NO: 414<br>FEATURE<br>source | moltype = AA  length = 15<br>Location/Qualifiers<br>1..15<br>mol_type = protein<br>organism = synthetic construct | |
| SEQUENCE: 414<br>WYQQKPGQSP KLLIY | | 15 |
| SEQ ID NO: 415<br>FEATURE<br>source | moltype = AA  length = 7<br>Location/Qualifiers<br>1..7<br>mol_type = protein<br>organism = synthetic construct | |
| SEQUENCE: 415<br>WASTRES | | 7 |
| SEQ ID NO: 416<br>FEATURE<br>source | moltype = AA  length = 32<br>Location/Qualifiers<br>1..32<br>mol_type = protein<br>organism = synthetic construct | |
| SEQUENCE: 416<br>GVPDRFTGSG SGTDFTLTIS SVQAEDLAVY YC | | 32 |
| SEQ ID NO: 417<br>FEATURE<br>source | moltype = AA  length = 8<br>Location/Qualifiers<br>1..8<br>mol_type = protein<br>organism = synthetic construct | |
| SEQUENCE: 417 | | |

```
HQYLSSWT                                                                      8

SEQ ID NO: 418         moltype = AA  length = 12
FEATURE                Location/Qualifiers
source                 1..12
                       mol_type = protein
                       organism = synthetic construct
SEQUENCE: 418
FGGGTKLEIK TS                                                                12

SEQ ID NO: 419         moltype = AA  length = 10
FEATURE                Location/Qualifiers
source                 1..10
                       mol_type = protein
                       organism = synthetic construct
SEQUENCE: 419
FGGGTKLEIK                                                                   10

SEQ ID NO: 420         moltype = AA  length = 15
FEATURE                Location/Qualifiers
source                 1..15
                       mol_type = protein
                       organism = synthetic construct
SEQUENCE: 420
GGGGSGGGGS GGGGS                                                             15

SEQ ID NO: 421         moltype = AA  length = 17
FEATURE                Location/Qualifiers
source                 1..17
                       mol_type = protein
                       organism = synthetic construct
SEQUENCE: 421
KSSQSVLYSS NQKNYLA                                                           17

SEQ ID NO: 422         moltype = AA  length = 5
FEATURE                Location/Qualifiers
source                 1..5
                       mol_type = protein
                       organism = synthetic construct
SEQUENCE: 422
GGGGS                                                                         5
```

What is claimed is:

1. A polypeptide comprising:
   a) a first domain comprising SEQ ID NO: 1;
   b) a second domain comprising an amino acid sequence of SEQ ID NO: 4;
   c) a third domain comprising an amino acid sequence of SEQ ID NO: 5;
   d) a fourth domain comprising an amino acid sequence of SEQ ID NO: 6; and
   e) a fifth domain comprising an amino acid sequence of SEQ ID NO: 7.

2. The polypeptide of claim 1, wherein said first domain further comprises an amino acid sequence of SEQ ID NO: 23.

3. The polypeptide of claim 1, wherein said polypeptide comprises an amino acid sequence of SEQ ID NO: 11.

4. A nucleic acid molecule comprising a nucleic acid sequence encoding a polypeptide, wherein said polypeptide comprises:
   a) a first domain comprising SEQ ID NO: 1;
   b) a second domain comprising an amino acid sequence of SEQ ID NO: 4;
   c) a third domain comprising an amino acid sequence of SEQ ID NO: 5;
   d) a fourth domain comprising an amino acid sequence of SEQ ID NO: 6; and
   e) a fifth domain comprising an amino acid sequence of SEQ ID NO: 7.

5. The nucleic acid molecule of claim 4, wherein said first domain further comprises an amino acid sequence of SEQ ID NO: 23.

6. The nucleic acid molecule of claim 4, wherein said polypeptide comprises an amino acid sequence of SEQ ID NO: 11.

7. The nucleic acid molecule of claim 4, wherein said nucleic acid molecule comprises a nucleic acid sequence of SEQ ID NO: 17.

8. A population of cells comprising nucleic acid encoding a polypeptide, wherein said polypeptide comprises:
   a) a first domain comprising SEQ ID NO: 1;
   b) a second domain comprising an amino acid sequence of SEQ ID NO: 4;
   c) a third domain comprising an amino acid sequence of SEQ ID NO: 5;
   d) a fourth domain comprising an amino acid sequence of SEQ ID NO: 6; and
   e) a fifth domain comprising an amino acid sequence of SEQ ID NO: 7.

9. The population of cells of claim 8, wherein said first domain further comprises an amino acid sequence of SEQ ID NO: 23.

10. The population of cells of claim 8, wherein said polypeptide comprises an amino acid sequence of SEQ ID NO: 11.

11. The population of cells of claim 8, wherein said nucleic acid comprises a nucleic acid sequence of SEQ ID NO: 17.

12. The population of cells of claim 8, wherein said population comprises immune cells.

13. The population of cells of claim 12, wherein said immune cells are T-cells or Natural Killer (NK) cells.

14. The population of cells of claim 8, wherein said population comprises T-cells.

15. The population of cells of claim 8, wherein said population comprises NK cells.

16. A method of treating acute myeloid leukemia (AML) in a mammal, wherein said method comprises administering, to said mammal, a population of cells comprising nucleic acid encoding a polypeptide, wherein said polypeptide comprises:
   a) a first domain comprising SEQ ID NO: 1;
   b) a second domain comprising an amino acid sequence of SEQ ID NO: 4;
   c) a third domain comprising an amino acid sequence of SEQ ID NO: 5;
   d) a fourth domain comprising an amino acid sequence of SEQ ID NO: 6; and
   e) a fifth domain comprising an amino acid sequence of SEQ ID NO: 7.

17. The method of claim 16, wherein said mammal is a human.

18. The method of claim 16, wherein said first domain further comprises an amino acid sequence of SEQ ID NO: 23.

19. The method of claim 16, wherein said polypeptide comprises an amino acid sequence of SEQ ID NO: 11.

20. The method of claim 16, wherein said nucleic acid comprises a nucleic acid sequence of SEQ ID NO: 17.

21. The method of claim 16, wherein said population comprises immune cells.

22. The method of claim 21, wherein said immune cells are T-cells or Natural Killer (NK) cells.

23. The method of claim 16, wherein said population comprises T-cells.

24. The method of claim 16, wherein said mammal comprises a population of AML cells that are $CD64^+$.

25. The method of claim 16, wherein said mammal comprises a population of monocytic leukemia stem cells (mLSCs).

26. The method of claim 16, wherein said mammal has been previously administered at least one AML-targeting therapy.

27. The method of claim 26, wherein said mammal relapsed after treatment with said at least one AML-targeting therapy, or wherein said mammal is resistant to treatment with said at least one AML-targeting therapy.

28. The method of claim 16, wherein said mammal has been previously administered a combination of venetoclax and azacitidine.

29. The method of claim 28, wherein said mammal relapsed after treatment with said combination.

30. The method of claim 28, wherein said mammal is resistant to treatment with said combination.

* * * * *